United States Patent
Beechem et al.

(10) Patent No.: US 10,093,974 B2
(45) Date of Patent: *Oct. 9, 2018

(54) METHODS AND APPARATUS FOR SINGLE MOLECULE SEQUENCING USING ENERGY TRANSFER DETECTION

(71) Applicant: Life Technologies Corporation, Carlsbad, CA (US)

(72) Inventors: Joseph Beechem, Eugene, OR (US); Theo Nikiforov, Carlsbad, CA (US); Vi-En Choong, Carlsbad, CA (US); Xinzhan Peng, Carlsbad, CA (US); Guobin Luo, Oceanside, CA (US); Cheng-Yao Chen, San Diego, CA (US); Michael Previte, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/621,341

(22) Filed: Jun. 13, 2017

(65) Prior Publication Data
US 2017/0283868 A1    Oct. 5, 2017

Related U.S. Application Data

(60) Division of application No. 14/584,829, filed on Dec. 29, 2014, now Pat. No. 9,695,471, which is a division
(Continued)

(51) Int. Cl.
*C12N 9/12* (2006.01)
*C12Q 1/6869* (2018.01)
(Continued)

(52) U.S. Cl.
CPC ........... *C12Q 1/6869* (2013.01); *C07H 19/20* (2013.01); *C12N 9/1241* (2013.01);
(Continued)

(58) Field of Classification Search
None
See application file for complete search history.

(56) References Cited

U.S. PATENT DOCUMENTS

| 4,658,649 A | 4/1987 | Brook |
| 5,001,050 A | 3/1991 | Blanco et al. |

(Continued)

FOREIGN PATENT DOCUMENTS

| EP | 0272007 | 6/1988 |
| EP | 0272007 | 3/1992 |

(Continued)

OTHER PUBLICATIONS

Agard et al., "A Strain-Promoted [3 +2]Azide-Alkyne Cycloaddition for Covalent Modification of Biomolecules in Living Systems", *J. Am. Chem Soc.* vol. 126(46), 2004, pp. 15046-15047.

(Continued)

*Primary Examiner* — Richard G Hutson
(74) *Attorney, Agent, or Firm* — Life Technologies Corporation; Karen Zachow

(57) ABSTRACT

Provided herein are systems and methods for nucleotide incorporation reactions. The systems comprise polymerases having altered nucleotide incorporation kinetics and are linked to an energy transfer donor moiety, and nucleotide molecules linked with at least one energy transfer acceptor moiety. The donor and acceptor moieties undergo energy transfer when the polymerase and nucleotide are proximal to each other during nucleotide binding and/or nucleotide incorporation. As the donor and acceptor moieties undergo energy transfer, they generate an energy transfer signal which can be associated with nucleotide binding or incorporation. Detecting a time sequence of the generated signals, or the change in the signals, can be used to determine the
(Continued)

order of the incorporated nucleotides, and can therefore be used to deduce the sequence of the target molecule.

12 Claims, 14 Drawing Sheets

Specification includes a Sequence Listing.

Related U.S. Application Data of application No. 13/562,159, filed on Jul. 30, 2012, now Pat. No. 8,999,674, which is a continuation of application No. 12/748,168, filed on Mar. 26, 2010, now abandoned.

(60) Provisional application No. 61/307,356, filed on Feb. 23, 2010, provisional application No. 61/299,917, filed on Jan. 29, 2010, provisional application No. 61/299,919, filed on Jan. 29, 2010, provisional application No. 61/293,616, filed on Jan. 8, 2010, provisional application No. 61/293,618, filed on Jan. 8, 2010, provisional application No. 61/289,388, filed on Dec. 22, 2009, provisional application No. 61/263,974, filed on Nov. 24, 2009, provisional application No. 61/245,457, filed on Sep. 24, 2009, provisional application No. 61/242,771, filed on Sep. 15, 2009, provisional application No. 61/184,770, filed on Jun. 5, 2009, provisional application No. 61/164,324, filed on Mar. 27, 2009.

(51) Int. Cl.
*C07H 19/20* (2006.01)
*G01N 21/64* (2006.01)
*G01N 33/58* (2006.01)
*C12N 9/96* (2006.01)
*C12Q 1/6818* (2018.01)

(52) U.S. Cl.
CPC .......... *C12N 9/1252* (2013.01); *C12N 9/96* (2013.01); *C12Q 1/6818* (2013.01); *G01N 21/6428* (2013.01); *G01N 33/582* (2013.01); *C12Y 207/07* (2013.01); *C12Y 207/07007* (2013.01); *G01N 2021/6432* (2013.01)

(56) References Cited

U.S. PATENT DOCUMENTS

| | | |
|---|---|---|
| 5,151,507 A | 9/1992 | Hobbs et al. |
| 5,188,934 A | 2/1993 | Menchen et al. |
| 5,198,543 A | 3/1993 | Blanco et al. |
| 5,322,785 A | 6/1994 | Comb et al. |
| 5,473,060 A | 12/1995 | Gryaznov et al. |
| 5,510,270 A | 4/1996 | Fodor et al. |
| 5,558,991 A | 9/1996 | Trainor |
| 5,576,204 A | 11/1996 | Blanco et al. |
| 5,599,695 A | 2/1997 | Pease et al. |
| 5,707,804 A | 1/1998 | Mathies et al. |
| 5,723,584 A | 3/1998 | Schatz |
| 5,831,070 A | 11/1998 | Pease et al. |
| 5,874,239 A | 2/1999 | Schatz |
| 5,932,433 A | 8/1999 | Schatz |
| 6,087,095 A | 7/2000 | Rosenthal et al. |
| 6,207,229 B1 | 3/2001 | Bawendi et al. |
| 6,221,592 B1 | 4/2001 | Schwartz et al. |
| 6,255,083 B1 | 7/2001 | Williams |
| 6,294,136 B1 | 9/2001 | Schwartz |
| 6,316,230 B1 | 11/2001 | Egholm et al. |
| 6,322,901 B1 | 11/2001 | Bawendi et al. |
| 6,399,304 B1 | 6/2002 | Kilger et al. |
| 6,399,335 B1 | 6/2002 | Kao et al. |
| 6,423,551 B1 | 7/2002 | Weiss et al. |
| 6,524,829 B1 | 2/2003 | Seeger |
| 6,627,424 B1 | 9/2003 | Wang |
| 6,635,163 B1 | 10/2003 | Han et al. |
| 6,664,079 B2 | 12/2003 | Ju et al. |
| 6,815,064 B2 | 11/2004 | Treadway et al. |
| 6,818,395 B1 | 11/2004 | Quake et al. |
| 6,849,411 B2 | 2/2005 | Knapp et al. |
| 6,864,626 B1 | 3/2005 | Weiss et al. |
| 6,911,345 B2 | 6/2005 | Quake et al. |
| 6,955,855 B2 | 10/2005 | Naasaniad |
| 6,960,437 B2 | 11/2005 | Enzelberger et al. |
| 6,982,146 B1 | 1/2006 | Schneider et al. |
| 7,033,762 B2 | 4/2006 | Nelson et al. |
| 7,033,764 B2 | 4/2006 | Korlach et al. |
| 7,041,812 B2 | 5/2006 | Kumar et al. |
| 7,052,839 B2 | 5/2006 | Nelson et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,078,499 B2 | 7/2006 | Odedra et al. |
| 7,125,671 B2 | 10/2006 | Sood et al. |
| 7,198,847 B2 | 4/2007 | Naasani |
| 7,205,048 B2 | 4/2007 | Naasani |
| 7,211,414 B2 | 5/2007 | Hardin et al. |
| 7,214,428 B2 | 5/2007 | Naasani |
| 7,217,562 B2 | 5/2007 | Cao et al. |
| 7,223,541 B2 | 5/2007 | Fuller et al. |
| 7,223,568 B2 | 5/2007 | Kondow et al. |
| 7,229,799 B2 | 6/2007 | Williams |
| 7,244,566 B2 | 7/2007 | Sood et al. |
| 7,244,602 B2 | 7/2007 | Frey et al. |
| 7,256,019 B2 | 8/2007 | Sood et al. |
| 7,264,934 B2 | 9/2007 | Fuller |
| 7,270,951 B1 | 9/2007 | Stemple et al. |
| 7,276,720 B2 | 10/2007 | Ulmer |
| 7,329,492 B2 | 2/2008 | Hardin et al. |
| 7,345,159 B2 | 3/2008 | Ju et al. |
| 7,361,466 B2 | 4/2008 | Korlach et al. |
| 7,368,086 B2 | 5/2008 | Naasani |
| 7,393,640 B2 | 7/2008 | Kumar et al. |
| 7,405,281 B2 | 7/2008 | Xu et al. |
| 7,416,844 B2 | 8/2008 | Korlach et al. |
| 7,427,673 B2 | 9/2008 | Balasubramanian et al. |
| 7,452,698 B2 | 11/2008 | Sood et al. |
| 7,456,954 B2 | 11/2008 | Weiss et al. |
| 7,485,424 B2 | 2/2009 | Korlach et al. |
| 7,501,245 B2 | 3/2009 | Quake et al. |
| 7,521,541 B2 | 4/2009 | Eigenbrot et al. |
| 7,541,444 B2 | 6/2009 | Milton et al. |
| 7,553,949 B2 | 6/2009 | Lee et al. |
| 7,599,059 B2 | 10/2009 | Laurence et al. |
| 7,611,907 B2 | 11/2009 | Dickson et al. |
| 7,668,697 B2 | 2/2010 | Volkov et al. |
| 7,670,770 B2 | 3/2010 | Chou et al. |
| 7,745,116 B2 | 6/2010 | Williams |
| 7,928,038 B2 | 4/2011 | Menchen et al. |
| 8,058,414 B2 | 11/2011 | Menchen et al. |
| 8,603,792 B2 | 12/2013 | Nikiforov et al. |
| 8,999,674 B2 | 4/2015 | Beechem et al. |
| 9,695,471 B2 | 7/2017 | Beechem et al. |
| 2002/0115092 A1 | 8/2002 | Rebek et al. |
| 2002/0132259 A1 | 9/2002 | Wagner et al. |
| 2002/0197611 A1 | 12/2002 | Chagovetz |
| 2003/0044781 A1 | 3/2003 | Korlach et al. |
| 2003/0064366 A1 | 4/2003 | Hardin et al. |
| 2003/0087300 A1 | 5/2003 | Knapp et al. |
| 2003/0092005 A1 | 5/2003 | Levene et al. |
| 2004/0048300 A1 | 3/2004 | Sood et al. |
| 2004/0152119 A1 | 8/2004 | Sood et al. |
| 2004/0197800 A1 | 10/2004 | Borns |
| 2004/0197843 A1 | 10/2004 | Chou et al. |
| 2004/0244827 A1 | 12/2004 | Hatsukaiwa et al. |
| 2005/0003464 A1 | 1/2005 | Tibbe et al. |
| 2005/0042633 A1 | 2/2005 | Williams |
| 2005/0164255 A1 | 7/2005 | Korlach et al. |
| 2005/0244827 A1 | 11/2005 | Olsson et al. |
| 2005/0266424 A1 | 12/2005 | Hardin et al. |
| 2006/0003383 A1 | 1/2006 | Graham |
| 2006/0057565 A1 | 3/2006 | Ju et al. |

(56) References Cited

U.S. PATENT DOCUMENTS

| | | |
|---|---|---|
| 2006/0063264 A1 | 3/2006 | Turner et al. |
| 2006/0078937 A1 | 4/2006 | Korlach |
| 2006/0176479 A1 | 8/2006 | Laurence et al. |
| 2006/0177495 A1 | 8/2006 | Allen et al. |
| 2006/0275806 A1 | 12/2006 | Schwartz et al. |
| 2007/0009980 A1 | 1/2007 | Graham |
| 2007/0020772 A1 | 1/2007 | Cao et al. |
| 2007/0072196 A1 | 3/2007 | Xu et al. |
| 2007/0109536 A1 | 5/2007 | Weiss et al. |
| 2007/0111350 A1 | 5/2007 | Weiss et al. |
| 2007/0116868 A1 | 5/2007 | Weiss et al. |
| 2007/0128133 A1 | 6/2007 | Eid et al. |
| 2007/0161028 A1 | 7/2007 | Schwartz et al. |
| 2007/0172819 A1 | 7/2007 | Hardin et al. |
| 2007/0172858 A1 | 7/2007 | Hardin et al. |
| 2007/0172859 A1 | 7/2007 | Hardin et al. |
| 2007/0172860 A1 | 7/2007 | Hardin et al. |
| 2007/0172861 A1 | 7/2007 | Hardin et al. |
| 2007/0172862 A1 | 7/2007 | Hardin et al. |
| 2007/0172863 A1 | 7/2007 | Hardin et al. |
| 2007/0172864 A1 | 7/2007 | Gao et al. |
| 2007/0172865 A1 | 7/2007 | Hardin et al. |
| 2007/0172866 A1 | 7/2007 | Hardin et al. |
| 2007/0172867 A1 | 7/2007 | Hardin et al. |
| 2007/0172868 A1 | 7/2007 | Hardin et al. |
| 2007/0172869 A1 | 7/2007 | Hardin et al. |
| 2007/0184475 A1 | 8/2007 | Hardin et al. |
| 2007/0196846 A1 | 8/2007 | Hanzel et al. |
| 2007/0250274 A1 | 10/2007 | Volkov et al. |
| 2007/0275395 A1 | 11/2007 | Hardin et al. |
| 2007/0292679 A1 | 12/2007 | Pellerite et al. |
| 2007/0292867 A1 | 12/2007 | Hardin et al. |
| 2008/0009100 A1 | 1/2008 | Davison |
| 2008/0091005 A1 | 4/2008 | Wang et al. |
| 2008/0108082 A1 | 5/2008 | Rank et al. |
| 2008/0131952 A1 | 6/2008 | Wu et al. |
| 2008/0132692 A1 | 6/2008 | Wu et al. |
| 2008/0176316 A1 | 7/2008 | Eid et al. |
| 2008/0176761 A1 | 7/2008 | Menchen et al. |
| 2008/0213910 A1 | 9/2008 | Jogikalmath |
| 2008/0219888 A1 | 9/2008 | Lawson et al. |
| 2008/0219890 A1 | 9/2008 | Lawson et al. |
| 2008/0261833 A1 | 10/2008 | Stemmer |
| 2008/0274905 A1 | 11/2008 | Greene |
| 2008/0293071 A1 | 11/2008 | Gelfand et al. |
| 2009/0024331 A1 | 1/2009 | Tomaney et al. |
| 2009/0029385 A1 | 1/2009 | Christians et al. |
| 2009/0047699 A1 | 2/2009 | Graham |
| 2009/0061447 A1 | 3/2009 | Schneider |
| 2009/0081686 A1 | 3/2009 | Wu et al. |
| 2009/0176233 A1 | 7/2009 | Clark et al. |
| 2009/0275036 A1 | 11/2009 | Hardin et al. |
| 2009/0286245 A1 | 11/2009 | Bjornson et al. |
| 2009/0298075 A1 | 12/2009 | Travers et al. |
| 2009/0305248 A1 | 12/2009 | Lander et al. |
| 2009/0305278 A1 | 12/2009 | Hardin et al. |
| 2010/0216122 A1 | 8/2010 | Hardin et al. |
| 2010/0255463 A1 | 10/2010 | Hardin et al. |
| 2010/0255464 A1 | 10/2010 | Hardin et al. |
| 2010/0255487 A1 | 10/2010 | Beechem et al. |
| 2010/0261185 A1 | 10/2010 | Nikiforov |
| 2010/0304367 A1 | 12/2010 | Hardin et al. |
| 2010/0317005 A1 | 12/2010 | Hardin et al. |
| 2010/0330570 A1 | 12/2010 | Vander Horn et al. |
| 2011/0003343 A1 | 1/2011 | Nikiforov et al. |
| 2011/0014604 A1 | 1/2011 | Hardin et al. |
| 2011/0014612 A1 | 1/2011 | Hendricks et al. |
| 2011/0021383 A1 | 1/2011 | Hardin et al. |
| 2011/0059436 A1 | 3/2011 | Hardin et al. |
| 2011/0184163 A1 | 7/2011 | Hardin et al. |
| 2011/0220844 A1 | 9/2011 | Tulsky et al. |
| 2011/0226995 A1 | 9/2011 | Tulsky et al. |
| 2011/0281740 A1 | 11/2011 | Beechem et al. |
| 2011/0306079 A1 | 12/2011 | Tulsky et al. |
| 2012/0322057 A1 | 12/2012 | Hendricks et al. |
| 2012/0329042 A1 | 12/2012 | Beechem et al. |
| 2013/0005020 A1 | 1/2013 | Peris et al. |
| 2013/0040363 A1 | 2/2013 | Nikiforov et al. |
| 2013/0102050 A1 | 4/2013 | Hardin et al. |

FOREIGN PATENT DOCUMENTS

| | | |
|---|---|---|
| EP | 1681356 | 7/2006 |
| WO | 1990/007576 | 7/1990 |
| WO | 1991/001087 | 2/1991 |
| WO | 91/05060 | 4/1991 |
| WO | 91/06678 | 5/1991 |
| WO | 1998/022615 | 5/1998 |
| WO | 1998/031834 | 7/1998 |
| WO | 1999/053034 | 12/1999 |
| WO | 2000/017330 | 3/2000 |
| WO | 2000/036151 | 6/2000 |
| WO | 2000/036152 | 6/2000 |
| WO | 2000/067698 | 11/2000 |
| WO | 2000/070073 | 11/2000 |
| WO | 2002/004680 | 1/2002 |
| WO | 2002/044425 | 6/2002 |
| WO | 2007/070642 | 6/2007 |
| WO | 2008/030115 | 3/2008 |
| WO | 2008/069973 | 6/2008 |
| WO | 2008/154317 | 12/2008 |
| WO | 2009/017678 | 2/2009 |
| WO | 2009/091847 | 7/2009 |
| WO | 2010/002939 | 1/2010 |
| WO | 2010/039897 | 4/2010 |
| WO | 2010/040111 | 4/2010 |
| WO | 2010/048580 | 4/2010 |
| WO | 2010/048581 | 4/2010 |
| WO | 2010/096084 | 8/2010 |
| WO | 2010/111674 | 9/2010 |
| WO | 2010/111686 | 9/2010 |
| WO | 2010/111690 | 9/2010 |
| WO | 2011/111691 | 9/2010 |
| WO | 2010/151714 | 12/2010 |
| WO | 2011/038158 | 3/2011 |
| WO | 2010/111686 | 5/2011 |
| WO | 2011/078897 | 6/2011 |

OTHER PUBLICATIONS

Ahn et al., "DNA Polymerase Beta: Structure-Fidelity Relationship from Pre-Steady-State Kinetic Analyses of All Possible Correct and Incorrect Base Pairs for Wild Type and R283A Mutant", *Biochemistry*, 36, 1997, 1100-1107.

Akerman et al., "Nanocrystal targeting in vivo", *Proceedings of the National Academy of Sciences (PNAS)* vol. 99, No. 20, Oct. 1, 2002, 12617-12621.

Arenkov et al., "Protein Microchips: Use for Immunoassay and Enzymatic Reactions", *Analytical Biochemistry*, vol. 278, 2000, 123-131.

Arion et al., "HIV resistance to zidovudine: the role of pyrophosphorolysis", *Drug Resistance Updates*, vol. 2, No. 2, Apr. 1999, 91-95.

Arkin et al., "An algorithm for protein engineering: Simulations of recursive ensemble mutadenesis", *PNAS USA*; vol. 89, 1992, pp. 7811-7815.

Arzumanov et al., "γ-Phosphate-substituted 2'-Deoxynucleoside 5'-Triphosphates as Substrates for DNA Polymerases", *J. Biol. Chem.*, vol. 27(140), 1996, pp. 24389-24394.

Bakhtina et al., "Contribution of the Reverse Rate of the Conformational Step to Polymerase B Fidelity", *Biochem.*, vol. 48, 2009, 3197-3208.

Barone et al., "Novel Nucleoside Triphosphate Analogs for The Enzymatic Labeling of Nucleic Acids", *Nucleosides Nucleotides & Nucleic Acids*, 20(4-7), 2001, 1141-1145.

Barone et al., "Photolithographic Synthesis of High-Density Oligonucleotide Probe Arrays", *Nucleosides, Nucleotides & Nucleic Acids*, vol. 20, Nos. 4-7, 2001, 525-531.

Beattie et al., "Hybridization of DNA targets to glass-tethered oligonucleotide probes", *Mol. Biotechnology*, vol. 4(3), 1995, pp. 213-225.

(56) References Cited

OTHER PUBLICATIONS

Berman et al., "Structures of phi 29 DNA polymerase complexed with substrate: the mechanism of translocation in B-family polymerases", *The EMBO Journal*, vol. 26, 2007, 3494-3505.

Bernad et al., "Structural and functional relationships between prokaryotic and eukaryotic DNA polymerases", *The EMBO Journal*, vol. 6 No. 13, 1987, 4219-4225.

Blanco et al., "A general structure for DNA-dependent DNA polymerases", *Gene*, vol. 100, Elsevier Science Publishers B.V., 1991, 27-38.

Blasco et al., "Phi29 D A polymerase active site. Residue ASP249 of conserved amino acid motif "Dx2SLYP" is critical for synthetic activities", *The Journal of Biological Chemistry*, vol. 268 No. 32, Nov. 15, 1993, 24106-24113.

Blasco, "Phi29 DNA polymerase active site. Mutants in conserved residues Tyr254 and Tyr390 are affected in dNTP binding", *The Journal of Biological Chemistry*, vol. 267 No. 27, Sep. 25, 1992, 19427-19434.

Blasco et al., "Primer terminus stabi 1 ization at the phi29 DNA polymer ase active site. Mutational analysis of conserved motif KXY", *The Journal of Biological Chemistry*. vol. 270 No. 6, Feb. 10, 1995, 2735-2740.

Blasco et al., "Phi29 DNA Polymerase Active Site", *The Journal of Biological Chemistry*, vol. 268, No. 22,, 1993, 16763-16770.

Bouizar et al., "Purification and Characterization of Calcitonin Receptors in Rat Kidney Membranes by Covalent Cross-Linking Techniques.", *European Journal of Biochemistry*, vol. 155, No. 1, 1986, 141-147.

Bowers et al., "Virtual terminator nucleotides for next-generation DNA sequencing", *Nature Methods*, vol. 6, No. 8, 2009, 593-595.

Braslavsky et al., "Sequence information can be obtained from single DNA molecules", *Proc. Natl. Acad. Sci.*, vol. 100( 7), 2003, pp. 3960-3964.

Brinkley, "A Brief Survey of Methods for Preparing Protein Conjugates with Dyes, Haptens, and Cross-Linking Reagents", *Bioconjugate Chemistry*, vol. 3, No. 1, 1992, 2-13.

Browning et al., "Studies on the Differing Effects of the Tumor Necrosis Factor and Lymphotoxin on the Growth of Several Human Tumor Lines", *Journal of Immunology*, vol. 143, No. 6, 1989, 1859-1867.

Brustad et al., "A General and Efficient Method for the Site-Specific Dual-Labeling of Proteins for Single Molecule Fluorescence Resonance Energy Transfer", *J. Am. Chem. Soc.*, 130, 2008, 17664-17665.

Calogero et al., "In vivo recombination and the production of hybrid genes", *FEMS Microbiology Letters* , vol. 97, 1992, pp. 41-44.

Campbell et al., "A homogeneous immunoassay for cyclic nucleotides based on chemiluminescence energy transfer", *Biochem. J.*, vol. 216, 1983, pp. 185-194.

Caren et al., "Efficient Sampling of Protein Sequence Space for Multiple Mutants", *Bio/Technology*, vol. 12, 1994, pp. 517-520.

Caspar et al., "Photochemistry of Ru(bpy)3 2+. Solvent Effects", *J. Am. Chem. Soc.*, 105, 1983, 5583.

Caspar et al., "Application of the Energy Gap Law to Nonradiative, Excited-State Decay", *J. Phys. Chem.*, vol. 87, No. 6, 1983, pp. 952-957.

Castro et al., "Nucleic acid polymerases use a general acid for nucleotidyl transfer", *Nature Structural & Molecular Biology*, vol. 16 No. 2, 2009, 212-218.

Cha, Taewoon et al., "Enzymatic activity on a chip: The critical role of protein orientation", *Proteomics*, vol. 5, 2005, 416-419.

Cha et al., "Immobilization of oriented protein molecules on poly-(ethylene glycol)-coated Si(111)", *Proteomics*, vol. 4 2004, 1965-1976.

Choi et al., "Nature Biotechnology", *vol. 25, No. 10*, Oct. 2007, pp. 1165-1170.

Chrisey et al., "Covalent attachment of synthetic DNA to self-assembled monolayer films", *Nucleic Acid Research*, vol. 24, No. 15, 1996, pp. 3031-3039.

Clapp et al., "Fluorescence Resonance Energy Transfer Between Quantum Dot Donars and Dye-Labeled Protein Acceptors", *J. Am. Chem. Soc.*, 126, 2004, 301-310.

Clapp et al., "Capping of CdSe-ZnS quantum dots with DHLA and subsequent conjugation with proteins", *Nature Protocols*, vol. 1 No. 3, 2006, 1258-1266.

Cull et al., "Screening for receptor ligands using large libraries of peptides linked to the C terminus of the lac repressor", *Proc. Natl. Acad. Sci. USA*, vol. 89, 1992, pp. 1865-1869.

Cwirla et al., "Peptides on phage: A vast library of peptides for identifying ligands" *PNAS*, vol. 87, 1990, pp. 6378-6382.

Dafni et al., "Overexpression of Vascular Endothelial Growth Factor 165 Drives Peritumor Interstitial Convection and Induces Lymphatic Drain: Magnetic Resonance Imaging, Confocal Microscopy, and Histological Tracking of Triple-labeled Albumin", *Cancer Research*. vol. 62, No.15, Nov. 15, 2002, pp. 6731-6739.

Dawson et al., "Synthesis of Native Proteins by Chemical Ligation", *Annu. Rev. Biochem.*, 69:, 2000, 923-960.

Dawson et al., "Synthesis of Proteins by Native Chemical Ligation", *Science*, vol. 266, 1994, 776-779.

De Graaf et al., "Nonnatural Amino Acids for Site-Specific Protein Conjugation", *Bioconjugate Chem.*, vol. 20, No. 7, 2009, 1281-1295.

De Vega et al., "Primer-terminus stabilization at the 3'-5' exonuclease active site of Phi29 DNA polymerase. Involvement of two amino acid residues highly conserved in proofreading DNA polymerases", *The EMBO Journal*, vol. 15 No. 5, 1996, 1182-1192.

Decher et al., "Buildup of ultrathin multilayer films by a self-assembly process: III. Consecutively alternating adsorption of anionic and cationic polyelectrolytes on charged surfaces", *Thin Solid Films*, vol. 210-211, Part 2, 1992, pp. 831-835.

Delagrave et al., "Recursive ensemble mutagenesis", *Protein Engineering*, vol. 6, No. 3, 1993, 327-331.

Delagrave et al., "Searching Sequence Space to Engineer Proteins: Exponential Ensemble Mutagenesis", *Bio/Technology*, vol. 11, 1993, pp. 1548-1552.

Derfus et al., "Nano Letters.", *vol. 4. No. I*, Dec. 10, 2003, pp. 11-18.

Deuschl et al., "Construction and optimization of a family of genetically encoded metabolite sensors by semirational protein engineering", *Protein Science*, vol. 14, Iss. 9, 14 2005, 2304-2314.

Dilgimen et al., "Water-soluble covalent conjugates of bovine serum albumin with anionic poly(N-isopropyl-acrylamide) and their immunogenicity", *Biomaterials*, 22, 2001, 2383-2392.

Dos Remedios et al., "Fluorescence Resonance Energy Transfer Spectroscopy is a Reliable "Ruler" for Measuring Structural Changes in Proteins", *Journal of Structural Biology*, vol. 115, 1995, pp. 175-185.

Drosopoulos et al., "Virtues of being faithful: Can we limit the genetic variation in Human Immunodeficiency Virus", *J. Molecular Medicine*, vol. 76 (9), Aug. 1998, pp. 604-612.

Dryden et al., "Nucleoside triphosphate-dependent restriction enzymes", *Nucleic Acids Research*, vol. 29, No. 18, 2001, 3728-3741.

Eigen et al., "The fifth Paul Ehrlich lecture virus strains as models of molecular evolution", *Medicinal Research Reviews*, vol. 13, No. 4 (XP000430626), Jul. 1993, 385-398.

Eschenmoser, "Chemical Etiology of Nucleic Acid Structure", *Science*, vol. 284, 1999, 2118-2124.

Fasman, "UV Spectral Characteristics and Acidic Dissociation Constants of 280 Alkyl Bases. Nucleosides and Nucleotides", *Practical Handbook of Biochemistry and Molecular Biology*, CRC Press, Boca Raton, FL, 1989, pp. 385-394.

Fazio et al., "DNA Curtains and Nanoscale Curtain Rods: High-Throughput Tools for Single Molecule Imaging", *Langmuir*, vol. 24, 2008, 10524-10531.

Ferrero et al., "Biocatalytic Selective Modifications of Conventional Nucleosides, Carbocyclic Nucleosides, and C-Nucleosides", *Chem. Rev.*, vol. 100, No. 12, 2000, 4319-4348.

Flemer et al., "Strategies for the Solid-Phase Diversification of Poly-L-proline-Type II Peptide Mimic Scaffolds and Peptide Scaffolds Through Guanidinylation", *J. Org. Chem.*. vol. 73, 2008, 7593-7602.

Forster, "Intermolecular energy migration and fluorescence", *Annalen der Physik*, vol. 437(1-2), 1948, 55-75.

(56) References Cited

OTHER PUBLICATIONS

Fu et al., "Sequencing double-stranded DNA by strand displacement", *Nucleic Acids Research*, vol. 25 (3), Feb. 1997, pp. 677-679.
Furey et al., "Use of Fluorescence Resonance Energy Transfer to Investigate the Conformation of DNA Substrates Bound to the Klenow Fragment", *Biochemistry*, vol. 37, No. 9, 1998, 2979-2990.
GE, "UPA, a universal protein array system for quantitative detection of protein-protein, protein-DNA, protein-RNA and protein-ligand interaction", *Nucleic Acids Research*, vol. 28(2), 2000, pp. i-vii.
Ghadessy et al., "Generic expansion of the substrate spectrum of a DNA polymerase by directed evolution", *Nature Biotech.*. vol. 22. No. 6. 2004, 755-759.
Gheorghe et al., "Combination of Perfluoroalkyl and Triazole Moieties: A New Recovery Strategy for TEMPT", *Organic Letters*, vol. 10, No. 19, 2008, 4171-4174.
Givens et al., "New Photoactivated Protecting Groups", *J. Am. Chem. Soc.*. vol. 119, 1997, pp. 8369-8370.
Goldman et al., "An Algorithmically Optimized Combinatorial Library Screened by Digital Imaging Spectroscopy", *Bio/Technology*, vol. 10 1992, pp. 1557-1561.
Goldman et al., "Luminescent Quantum Dot-Adaptor Protein-Antibody Conjugates for Use in Fluoroimmunoassays", *phys. stat. sol. (b)* 229, No. 1, 2002, 407-414.
Goldman et al., "Avidin: A Natural Bridge for Quantum Dot-Antibody Conjugates", *J. Am.Chem. Soc.*. 124, 2002, 6378-6382.
Goldman et al., "Conjugation of Luminescent Quantum Dots with Antibodies Using an Engineered Adaptor Protein to Provide New Reagents for Fluoroimmunoassays", *Anal. Chem.*. 74, 2002, 841-847.
Goldman et al., "Self-assembled luminescent CdSe-ZnS quantum dot bioconjugates prepared using engineered poly-histidine terminated proteins", *Analytica Chimica Acta*, 534, 2005, 63-67.
Gram et al., "In vitro selection and affinity maturation of antibodies from a naive combinatorial immunoglobulin library", *PNAS*, vol. 89, 1992, pp. 3576-3580.
Guo et al., "Direct fluorescence analysis of genetic polymorphisms by hybridization with oligonucleotide arrays on glass supports", *Nucleic Acids Research*, vol. 22, No. 24, 1994, 5456-5465.
Ha et al., "Initiation and re-initiation of DNA unwinding by the *Escherichia coli* Rep helicase", *Nature*, vol. 419, 2002, 638-641.
Haab et al., "Protein microarrays for highly parallel detection and quantitation of specific proteins and antibodies in complex solutions", *Genome Biology*, vol. 2, No. 2, 2001, 1-13.
Hainfeld et al., "Ni-NTA-Gold Clusters Target His-Tagged Proteins", *Journal of Structural Biology*, 127, 1999, 185-198.
Han et al., "Quantum-dot-tagged Microbeads for Multiplexed Optical Coding of Biomolecules,", *Nature Biotechnology*, vol. 19, Jul. 2001, 631-635.
Harris et al., "Single-Molecule DNA Sequencing of a Viral Genome", *Science*, vol. 320, 2008, 106-109.
Hermes et al., "Searching sequence space by definably random mutagenesis: Improving the catalytic potency of an enzyme", *PNAS*, vol. 87, 1990, pp. 696-700.
Howarth et al., "Targeting quantum dots to surface proteins in living cells with biotin ligase", *PNAS*, vol. 102, No. 21, 2005, 7583-7588.
Jaiswal et al., "Use of quantum dots for live cell imaging", *Nature Methods*, vol. 1, No. 1, 2004, 71-78.
Jares-Erijman et al., "FRET imaging", *Nature Biotechnology*, vol. 21, No. 11, 2003, 1387-1395.
Jauffred et al., "Three-Dimensional Optical Control of Individual Quantum Dots", *Nano Letter*, vol. 8, No. 10, 2008, 3376-3380.
Jeong et al., "Structure-activity relationships of .beta.-D-(2S,5R)- and .alpha.-D-(2S,5S)-1,3-oxathiolanyl nucleosides as potential anti-HIV agents", *J. Med. Chem.*. vol. 36, 1993, pp. 2627-2638.
Jewett et al., "Rapid Cu-Free Click Chemistry with Readily Synthesized Biarylazacyclooctynones", *J. Am. Chem. Soc.*. 132, 2010, 3688-3690.
Johnson et al., "Insights into the Mechanism and Catalysis of the Native Chemical Ligation Reaction", *J. Am. Chem. Soc.* 128, 2006, 6640-6646.
Johnson, "Rapid kinetic analysis of mechanochemical adenosinetriphosphatases", *Methods Enzymol.*, vol. 134, 1986, pp. 677-705.
Joos et al., "Covalent Attachment of Hybridizable Oligonucleotides to Glass Supports", *Analytical Biochem.*, vol. 247(1), 1997, pp. 96-101.
Joshi et al., "ATP Synthase Complex from Bovine Heart Mitochondria", *Journal of Biological Chemistry*, vol. 265, No. 24, 1990, 14518-14525.
Jung et al., "Crosslinking of platelet glycoprotein Ib by N-succinimidyl(4-azidophenyldithio)propionate and 3,3'-dithiobis(sulfosuccinimidyl propionate)", *Biochimica et Biophysica Acta*, vol. 761, No. 2, 1983, 152-162.
Kamiya et al., "Extension of the Applicable Range of Fluorescein: A Fluorescein-Based Probe for Western Blot Analysis", *Agnew. Chem. Int. Ed.*, vol. 44, 2005, 5439-5441.
Kamtekar et al., "The phi29 DNA polymerase:protein-primer structure suggests a model for the initiation to elongation transition", *EMBO Journal*, vol. 25, No. 6, 2006, 1335-1343.
Kim et al., "1,3-Dioxolanylpurine nucleosides (2R,4R) and (2R,4S) with selective anti-HIV-1 activity in human lymphocytes", *J. Med. Chem.*. vol. 36, No. 1, 1993, 30-37.
Kiyonaka et al., "Semi-wet peptide/protein array using supramolecular hydrogel", *Nature Materials*, vol. 3, 2004, 58-64.
Kumar et al., "Inhibition of T7 RNA Polymerase: Transcription Initiation and Transition from Initiation to Elongation Are Inhibited by T7 Lysozyme via a Ternary Complex with RNA Polymerase and Promoter DNA", *Biochemistry*, vol. 36, No. 45, 1997, pp. 13954-13962.
Kumar et al., "Terminal Phosphate Labeled Nucleotides: Synthesis, Applications, and Linker Effect on Incorporation by DNA Polymerases", *Nucleosides, Nucleotides and Nucleic Acids*, vol. 24, Nos. 5-7, 2005, 401-408.
Kunkel, "DNA replication fidelity", *Journal of Biological Chemistry*, vol. 267, No. 26, Sep. 15, 1992, 18251-18254.
Laitala et al., "Homogeneous Assay Based on Anti-Stokes' Shift Time-Resolved Fluorescence Resonance Energy-Transfer Measurement", *Analytical Chem.*, vol. 77, 2005, 1483-1487.
Lakowicz, "Energy Transfer", *Principles of Fluorescence Spectroscopy, 2nd Ed. Plenum Publishing Corp.*, New York, NY, 1999, 367-394.
Lamture et al., "Direct detection of nucleic acid hybridization on the surface of a charge coupled device", *Nucleic Acids Research*, vol. 22(11), 1994, pp. 2121-2125.
Liu et al., "Genetic incorporation of unnatural amino acids into proteins in mammalian cells", *Nature Methods*, vol. 4, No. 3, 2007, 239-244.
Lundberg et al., "High-fidelity amplification using a thermostabile DNA polymerase isolated from Pyrococcus furiosus", *Gene*, vol. 108, Elsevier Science Publishers B.V.,, 1991, 1-6.
Mac Beath et al., "Printing Proteins as Microarrays for High-Throughput Function Determination", *Science*, vol. 289, 2000, 1760-1763.
Marshall, "Rules for the visible absorption spectra of halogenated Fluorescein dyes", *Histochemical Journal*, vol. 7, 1975, pp. 299-303.
Martinez et al., "Acyclic nucleoside triphosphate analogs as terminators in biocatalytic DNA replication", *Bioorganic & Medicinal Chemistry Letters*, vol. 7(23), 1997, pp. 3013-3016.
Martinez et al., "An allylic/acyclic adenosine nucleoside triphosphate for termination of DNA synthesis by DNA template-dependent polymerases", *Nucleic Acids Research*, vol. 27, No. 5, 1999, 1271-1274.
Matayoshi et al., "Novel Fluorogenic Substrates for Assaying Retroviral Proteases by Resonance Energy Transfer", *Science*, vol. 247, Feb. 23, 1990, pp. 954-958.
Mathis, "Probing molecular interactions with homogeneous techniques based on rare earth cryptates and fluorescence energy transfer", *Clin. Chem.*, vol. 41, No. 9, 1995, pp. 1391-1397.
Matsumoto et al., "Genbank Accession No. M33144", 1993.

(56) References Cited

OTHER PUBLICATIONS

Mattoussi et al., "Bioconjugation of Highly Luminescent Colloidal CdSe—ZnS Quantum Dots with an Engineered Two-Domain Recombinant Protein", *Phys. Status Solido B-Basic Res.*, 224, No. 1, 2001, 277-283.
Mattoussi et al., "Self-Assembly of CdSe—ZnS Quantum Dot Bioconjugates Using an Engineered Recombinant Protein", *J Am Chem Soc*, vol. 122, No. 49, Nov. 22, 2000, 12142-12150.
McCafferty et al., "Phage antibodies: filamentous phage displaying antibody variable domains", *Nature*, vol. 348, Dec. 6, 1990, 552-554.
Medintz et al., "A fluorescence resonance energy transfer-derived structure of a quantum dot-protein bioconjugate nanoassembly" *Proceedings of the National Academy of Sciences (PNAS)*, 101(26), 2004, 9612-9617.
Medintz et al., "Self-assembled nanoscale biosensors based on quantum dot FRET donors", *Nature Materials*, vol. 2, 2003, 630-638.
Megiatto et al., "General Method for Synthesis of Functionalized Macrocycles and Catenanes Utilizing "Click" Chemistry", *J. Am. Chem. Soc.*, vol. 130, 2008, 12872-12873.
Meijer et al., "Phi29 Family of Phages", *Microbiology and Molecular Biology Reviews*, vol. 65, No. 2, 2001, 261-287.
Meisel et al., "Type III restriction enzymes need two inversely oriented recognition sites for DNA cleavage", *Nature*, vol. 355, 1992, 467-469.
Moll et al., "Designed heterodimerizing leucine zippers with a ranger of pIs and stabilities up to 10-15 M", *Protein Science*, vol. 10, 2001, 649-655.
Motre et al., "Enhancing helicase-dependent amplification by fusing the helicase with the DNA polymerase", *Gene*, 420:, 2008, 17-22.
Murray, "Type I Restriction Systems: Sophisticated Molecular Machines (a Legacy of Bertani and Weigle)", *Microbiology and Molecular Biology Reviews*, vol. 64, No. 2, 2000, 412-434.
Nakaji-Hirabayashi et al., "Oriented immobilization of epidermal growth factor onto culture substrates for the selective expansion of neural stem cells", *Biomaterials*, vol. 28, No. 24, 2007, 3517-3529.
Nakanishi et al., "Recent Advances in Controlled Immobilization of Proteins onto the Surface of the Solid Substrate and Its Possible Application to Proteomics", *Current Proteomics*, vol. 5, 2008, 161-175.
Ngo et al., "The Protein Folding Problem and Tertiary Structure Predict ion", Merz et al. (ed.), Birkhauser, Boston, MA, 1994, pp. 433 and 492-495.
Oliphant et al., "Cloning of random-sequence oligodeoxynucleotides", *Gene*, vol. 44, Iss. 2-3, 1986, 177-183.
Park et al., "Characterization of the Cell Surface Receptor for a Multi-Lineage Colony-Stimulating Factor (CSF-2alpha)", *Journal of Biological Chemistry*, vol. 261, No. 1, 1986, 205-210.
Park et al., "New Photoactivated Protecting Groups. 6. p-Hydroxyphenacyl: A Phototrigger for Chemical and Biochemical Probes1,2", *J. Am. Chem. Soc.*, vol. 119, No. 10, 1997, 2453-2463.
Patel et al., "Pre-Steady-State Kinetic Analysis of Processive DNA Replication Including Complete Characterization of an Exonuclease-Deficient Mutant", *Biochemistry*, 30 1991, 511-525.
PCT/US01/21811, International Search Report, dated May 12, 2003, 6 Pages.
PCT/US01/45819, nternational Search Report, dated Jun. 2, 2003, 6 Pages.
PCT/US2010/028952, International Search Report and Written Opinion, dated Mar. 23, 2011, 11 Pages.
PCT/US2010/028967, International Search Report and Written Opinion, dated Mar. 18, 2011, 10 Pages.
PCT/US2010/028972, International Search Report and Written Opinion, dated Jan. 21, 2011, 13 Pages.
PCT/US2010/028974, International Search Report and Written Opinion, dated Jan. 26, 2011, 13 Pages.
PCT/US2010/050406, International Search Report and Written Opinion, dated Feb. 21, 2011, 14 Pages.

Pease et al., "Light-Generated Oligonucleotide Arrays for Rapid DNA Sequence Analysis", *Proc. Natl. Acad. Sci.*, vol. 91, May 1994, 5022-5026.
Pecenkova, et al., "DNA Polymerase (Early Protein GP2)", *UniProt Accession Q37882*, Dec. 1998, 1-2.
Pecenkova et al., "Bacteriophage B103: complete DNA sequence of its genome and relationship to other Bacillus phages", *Gene*, 199, 1997, 157-163.
Pingoud et al., "Structure and function of type II restriction endonucleases", *Nucleic Acids Research*, vol. 29, No. 18, 2001, 3705-3727.
Piston et al., "Fluorescent protein FRET: the good, the bad and the ugly", *Trends Biochem. Sci.*, vol. 32, No. 9, 2007, 407-414.
Qu et al., "Alternative Routes Toward High Quality CdSe Nanocrystals", *Nano Letters*, vol. 1, No. 6, 2001, 333-337.
Rao et al., "Oriented Immobilization of Proteins", *Mikrochim. Acta.* vol. 128, 1998, 127-143.
Richard et al., "7-Hydroxycoumarin-Hemicyanine Hybrids: A New Class of Far-Red Emitting Fluorogenic Dyes", *Organic Letters*, vol. 10, 2008, 4175-4178.
Rienitz et al., "On the fidelity of DNA polymerase alpha: the influence of alpha-thio dNTPs, Mn2+ and mismatch repair", *Nucleic Acids Research*, vol. 13, No. 15, 1985, 5685-5695.
Roettger et al., "Mismatched and Matched dNTP Incorporation by DNA Polymerase # Proceed via Analogous Kinetic Pathways", *Biochemistry*, vol. 47, No. 37 2008, 9718-9727.
Rogers et al., "Immobilization of Oligonucleotides onto a Glass Support via Disulfide Bonds: A Method for Preparation of DNA Microarrays", *Analytical Biochemistry*, vol. 266, 1999, 23-30.
Ronaghi et al., "Real-time DNA Sequencing Using Detection of Pyrophosphate Release", *Anal Biochem*, vol. 242(1), 1996, pp. 84-89.
Rothwell et al., "Structure and Mechanism of DNA Polymerases", *Advances in Protein Chemistry*, vol. 71, 2005, 401-440.
Sapsford et al., "Materials for Fluorescence Resonance Energy Transfer Analysis: Beyond Traditional Donor-Acceptor Combinations", *Angew. Chem. Int. Ed.*, vol. 45, 2006, 4562-4588.
Sarkez et al., "A Fluorescence-based Assay for Analysis of Biotinylated Proteins and Nucleic Acids", *Biophysical Society 48th Annual Meeting*, Feb. 14, 2004, 1-6.
Schlageck et al., "Spectroscopic techniques for study of phosphodiester bond formation by *Escherichia coil* RNA polymerase", *Journal of Biological Chemistry*, vol. 254, No. 23, Dec. 10, 1979, 12074-12077.
Schmitt et al., "Kinetics of Formation and Functional Properties of Conjugates Prepared by Dry-State Incubation of Beta-Lactoglobulin/Acacia Gum Electrostatic Complexes", *J. Agric. Food Chem.*, 53, 2005, 9089-9099.
Schwartz et al., "Separation of Yeast Chromosome-Sized DNAs by Pulsed Field Gradient Gel Electrophoresis", *Cell*, vol. 37, 1984, 67-75.
Scott et al., "Searching for Peptide Ligands with an Epitope Library", *Science*, vol. 249, 1990, 386-390.
Selvin, "Fluorescence Resonance Energy Transfer", *Methods in Enzymology*, vol. 246, 1995, 300-334.
Shao et al., "Unprotected Peptides as Building Blocks for the Synthesis of Peptide Dendrimers with Oxime, Hydrazone, and Thiazolidine Linkages", *J. Am. Chem. Soc.*, vol. 117, No. 14, 1995, 3893-3899.
Smith et al., "Orthogonal Site-Specific Protein Modification by Engineering Reversible Thiol Protection Mechanisms", *Protein Science*, vol. 14, 2005, 64-73.
Soengas et al., "Site-directed mutagenesis at the Exo III motif of Phi29 DNA polymerase; overlapping structural domains for the 3'-5' exonuclease and strand-displacement activities", *The EMBO Journal*, vol. 1 1 no. 1 1, 1992, 4227-4237.
Sood et al., "Terminal Phosphaye-Labeled Nucleotides with Improved Substrate Properties for Homogeneous Nucleic Acid Assays", *J. Am. Chem. Soc.*, vol. 127, No. 8, 2005, 2394-2395.
Steitz, "DNA Polymerases: Structural Diversity and Common Mechanisms", *The Journal of Biological Chemistry*, vol. 274, No. 25, 1999, 17395-17398.

(56) References Cited

OTHER PUBLICATIONS

Stryer, "Fluorescence Energy Transfer as a Spectroscopic Ruler", *Annual Review of Biochemistry*, vol. 47, Jul. 1978, 819-846.
Sun et al., "Surface-Enhanced Raman Scattering Based Nonfluorescent Probe for Multiplex Detection", *Analytical Chemistry*, vol. 79, No. 11, 2007, 3981-3988.
Tolbert et al., "Conjugation of Glycopeptide Thioesters to Expressed Protein Fragments", *Methods in Molecular Biology, Bioconjugation Protocols: Strategies and Methods*, vol. 283, 2004, 255-266.
Tominaga et al., "An enzymatic strategy for site-specific immobilization of functional proteins using microbial transglutaminase", *Enzyme and Microbial Technology*, vol. 35, Iss. 6-7, 2004, 613-618.
Truniger et al., "Phi29 DNA polymerase residue Leu384, highly conserved in motif B of eukaryotic type DNA replicases, is involved in nucleotide insert ion fidelity", *The Journal of Biological Chemistry*, vol. 278 No. 35, Jun. 12, 2003, pp. 33482-33491.
Truniger et al., "Two positively charged residues of phi29 DNA polymerase conserved in protein-primed DNA polymerases, are involved in stabil isation of the incoming nucleotide", *Journal of Molecular Biology*, vol. 335 No. 2, Jan. 9, 2004, pp. 481-494.
Tsai et al., "A New Paradigm for DNA Polymerase Specificity", *Biochemistry*, vol. 45, No. 32, 2006, 9675-9687.
Tsang et al., "Copper-1,10-phenanthroline induces internucleosomal DNA fragmentation in HepG2 cells, resulting from direct oxidation by the hydroxyl radical", *Biochem. J.*, vol. 317, 1996, 13-16.
Tyagi et al., "Multicolor molecular beacons for allele discrimination", *Nature Biotechnology*, vol. 16, 1998, 49-53.
Tyagi, "Taking DNA probes into a protein world", *Nature Biotechnology*, vol. 14, 1996-947-948.
Vallina-Garcia et al., "Oriented immbilisation of anti-pneumolysin Fab through a histidine tag for electrochemical immunosensors", *Biosensors and Bioelectronics*, vol. 23, Iss. 2, 2007, 210-217.
Watkins et al., "Detection of Intensity Change Points in Time-Resolved Single-Molecule Measurements", *J. Phys. Chem. B.*, vol. 109(1), 2005, 617-628.
Werts, "Mechanically Linked Polyrotaxanes: A Stepwise Approach", *Macromolecules*, vol. 36 Iss. 19, 2003, 7004-7013.
Wetmur, "DNA probes: applications of the principles of nucleic acid hybridization", *Crit. Rev. Biochem. Mol. Biol.*, vol. 26, Nos. 3-4, 1991, 227-259.
Williams et al., "An artificial processivity clamp made with streptavidin facilitates oriented attachment of polymerase-DNA complexes to surfaces", *Nucleic Acid Research*. vol. 36. No. 18., Aug. 22, 2008, pp. e121.
Wong et al., "An induced-fit kinetic mechanism for DNA replication fidelity: direct measurement by single-turnover kinetics", *Biochemistry*, vol. 30, No. 2, Jan. 1991, 526-537.
Wu et al., "Synthesis and Properties of Adenosine-5'-triphosphoro-gamma-1-(5-sulfonic acid)naphthyl Ethylamidate: A Fluorescent Nucleotide Substrate for DNA-Dependent RNA Polymerase from *Escherichia coli*", *Archives of Biochemistry and Biophysics*, vol. 246, No. 2, 1986, 564-571.
Wu et al., "Resonance Energy Transfer: Methods and Applications", *Analytical Biochemistry*, vol. 218, No. 1, 1994, 1-13.
Xia et al., "Photolabile 'Caged' Fatty Acids Containing A 1-(2'-Nitrophenyl)-1,2-Ethanediol Moiety", *Bioorganic & Medicinal Chemistry Letters*, vol. 7, Iss. 10, 1997, 1243-1248.
Xu et al., "Imaging interactions with bioluminescence resonance energy transfer (BRET) in plant and mammalian cells and tissues", *Proc. Natl. Acad. Sci.*, vol. 96, 1999, 151-156.
Yarbrough et al., "Synthesis and properties of fluorescent nucleotide substrates for DNA-dependent RNA polymerases", *Journal of Biological Chemistry*, vol. 254, No. 23, Dec. 10, 1979, 12069-12073.
Yarbrough, "Synthesis and Properties of a New Fluorescent Analog of ATP: Adenosine-5'-Triphosphoro-y-1-(5-SUlfonic Acid) Napthylamidate", *Biochemical and Biophysical Research Communications*, vol. 81, No. 1, Mar. 15, 1978, 35-41.
Yeo et al., "The patterned hydrophilic surfaces of glass slides to be applicable for the construction of protein chips", *Current Applied Physics*, vol. 6. 2006, 267-270.
Zarling et al., "Mapping of Lymphocyte Surface Polypeptide Antigens by Chemical Cross-Linking with BSOCOES", *Journal of Immunology*, vol. 124, No. 2, 1980, 913-920.
Zhang et al., "Artificial Polypeptide Scaffold for Protein Immobilization", *J. Am. Chem. Soc.*, vol. 127, No. 29, 2005, 10136-10137.
Zhu et al., "Analysis of Yeast Protein Kinases Using Protein Chips", *Nature Genetics*, vol. 26, 2000, 283-289.
Zhu et al,. "Protein Chip Technology", *Curr. Opin. Chem. Biol.*, vol. 7, No. 1, 2003, 55-63.

$$Y = b + \frac{a-b}{1+10^{(\log EC50-X)*c}}$$

Y: mP
X: log[phi29 mutant(nM)]
logEC50: 2.058
a (top): 400.3
b (bottom): 138
c (slope): 1.975

| oligo221 conc 150nM, 1x extension buffer pH7.5 C8-UDG-ugi-HP1 phi29 mutant Conc. (nM) | 10 | 20 | 30 | 40 |
|---|---|---|---|---|
| FP(mP) | 170.39 | 201.01 | 231.15 | 238.69 |
| log(HP1 phi29 mutant) conc.,nM)= | 1.6 | 1.8 | 1.9 | 2.0 |
| HP1 phi29 mutant conc.(nM)= | 42.4 | 63.8 | 84.5 | 89.9 |
| Number of active HP1 phi29 mutant per conjugate= | 4.2 | 3.2 | 2.8 | 2.2 |
| average= | 3.1 | | | |

FIG. 9C $$Y = b + \frac{a-b}{1+10^{(\log EC50-X)*c}}$$

Y: mP
X: log[HP1 B103(nM)]
logEC50: 1.96
a (top): 423
b (bottom): 153.3
c (slope): 2.762

| oligo221 conc 150nM, 1x extension buffer pH7.5 C8-HP1 B103-UDG-ugi Conc. (nM) | 10 | 20 | 30 | 40 |
|---|---|---|---|---|
| FP(mP) | 183.41 | 259.52 | 302.27 | 349.72 |
| log(HP1-B103conc, nM) = | 1.6 | 1.9 | 2.0 | 2.1 |
| HP1-B103 conc. (nM) = | 43.0 | 78.0 | 98.4 | 130.3 |
| Number of active HP1-B103 per conjugate = | 4.3 | 3.9 | 3.3 | 3.3 |
| average= | 3.7 | | | |

FIG. 10C

SEQUENCE LISTING

<160> NUMBER OF SEQ ID NOS: 67

<210> SEQ ID NO 1
<211> LENGTH: 572
<212> TYPE: PRT
<213> ORGANISM: Bacillus phage B103

<400> SEQUENCE: 1

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
            115                 120                 125

Lys Ile Ala Lys Asp Phe Gln Leu Pro Leu Leu Lys Gly Asp Ile Asp
130                 135                 140

Tyr His Ala Glu Arg Pro Val Gly His Glu Ile Thr Pro Glu Glu Tyr
145                 150                 155                 160

Glu Tyr Ile Lys Asn Ala Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Arg Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr

```
                260                 265                 270
Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
        290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
        355                 360                 365

Thr His Glu Lys Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Arg
    530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 2
<211> LENGTH: 572
<212> TYPE: PRT
<213> ORGANISM: Bacillus phage B103

<400> SEQUENCE: 2

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60
```

```
Ala Phe Ile Val Asn Trp Leu Glu His His Gly Phe Lys Trp Ser Asn
 65                  70                  75                  80

Glu Gly Leu Pro Asn Thr Tyr Asn Thr Ile Ile Ser Lys Met Gly Gln
                 85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
130                 135                 140

Tyr His Ala Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Arg Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
        355                 360                 365

Thr His Glu Lys Gly Ala Lys Lys Gln Leu Ala Lys Leu Met Leu Asn
370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
```

```
                      485                 490                 495
Tyr Ile Gln Asp Ile Tyr Ala Lys Glu Val Asp Gly Lys Leu Ile Glu
                500                 505                 510

Cys Ser Pro Asp Glu Ala Thr Thr Lys Phe Ser Val Lys Cys Ala
            515                 520                 525

Gly Met Thr Asp Thr Ile Lys Lys Val Thr Phe Asp Asn Phe Arg
        530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 3
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ser His His His His His His Ser Met Ser Gly Leu Asn Asp Ile
1               5                   10                  15

Phe Glu Ala Gln Lys Ile Glu Trp His Glu Gly Ala Pro Gly Ala Arg
            20                  25                  30

Gly Ser Lys His Met Pro Arg Lys Met Phe Ser Cys Asp Phe Glu Thr
        35                  40                  45

Thr Thr Lys Leu Asp Asp Cys Arg Val Trp Ala Tyr Gly Tyr Met Glu
    50                  55                  60

Ile Gly Asn Leu Asp Asn Tyr Lys Ile Gly Asn Ser Leu Asp Glu Phe
65                  70                  75                  80

Met Gln Trp Val Met Glu Ile Gln Ala Asp Leu Tyr Phe His Asn Leu
                85                  90                  95

Lys Phe Asp Gly Ala Phe Ile Val Asn Trp Leu Glu His His Gly Phe
            100                 105                 110

Lys Trp Ser Asn Glu Gly Leu Pro Asn Thr Tyr Asn Thr Ile Ile Ser
        115                 120                 125

Lys Met Gly Gln Trp Tyr Met Ile Asp Ile Cys Phe Gly Tyr Lys Gly
    130                 135                 140

Lys Arg Lys Leu His Thr Val Ile Tyr Asp Ser Leu Lys Lys Leu Pro
145                 150                 155                 160

Phe Pro Val Lys Lys Ile Ala Lys Asp Phe Gln Leu Pro Leu Leu Lys
                165                 170                 175

Gly Asp Ile Asp Tyr His Ala Glu Arg Pro Val Gly His Glu Ile Thr
            180                 185                 190

Pro Glu Glu Tyr Glu Tyr Ile Lys Asn Ala Ile Glu Ile Ala Arg
        195                 200                 205

Ala Leu Asp Ile Gln Phe Lys Gln Gly Leu Asp Arg Met Thr Ala Gly
    210                 215                 220

Ser Asp Ser Leu Lys Gly Phe Lys Asp Ile Leu Ser Thr Lys Lys Phe
225                 230                 235                 240

Asn Lys Val Phe Pro Lys Leu Ser Leu Pro Met Asp Lys Glu Ile Arg
                245                 250                 255

Arg Ala Tyr Arg Gly Gly Phe Thr Trp Leu Asn Asp Lys Tyr Lys Glu
            260                 265                 270
```

```
Lys Glu Ile Gly Glu Gly Met Val Phe Asp Val Asn Ser Leu Tyr Pro
            275                 280                 285

Ser Gln Met Tyr Ser Arg Pro Leu Pro Tyr Gly Ala Pro Ile Val Phe
    290                 295                 300

Gln Gly Lys Tyr Glu Lys Asp Glu Gln Tyr Pro Leu Tyr Ile Gln Arg
305                 310                 315                 320

Ile Arg Phe Glu Phe Glu Leu Lys Glu Gly Tyr Ile Pro Thr Ile Gln
                325                 330                 335

Ile Lys Lys Asn Pro Phe Phe Lys Gly Asn Glu Tyr Leu Lys Asn Ser
            340                 345                 350

Gly Ala Glu Pro Val Glu Leu Tyr Leu Thr Asn Val Asp Leu Glu Leu
        355                 360                 365

Ile Gln Glu His Tyr Glu Met Tyr Asn Val Glu Tyr Ile Asp Gly Phe
    370                 375                 380

Lys Phe Arg Glu Lys Thr Gly Leu Phe Lys Glu Phe Ile Asp Lys Trp
385                 390                 395                 400

Thr Tyr Val Lys Thr Arg Glu Lys Gly Ala Lys Lys Gln Leu Ala Lys
                405                 410                 415

Leu Met Leu Asn Ser Leu Tyr Gly Lys Phe Ala Ser Asn Pro Asp Val
            420                 425                 430

Thr Gly Lys Val Pro Tyr Leu Lys Glu Asp Gly Ser Leu Gly Phe Arg
        435                 440                 445

Val Gly Asp Glu Glu Tyr Lys Asp Pro Val Tyr Thr Pro Met Gly Val
    450                 455                 460

Phe Ile Thr Ala Trp Ala Arg Phe Thr Thr Ile Thr Ala Ala Gln Ala
465                 470                 475                 480

Cys Tyr Asp Arg Ile Ile Tyr Cys Asp Thr Asp Ser Ile His Leu Thr
                485                 490                 495

Gly Thr Glu Val Pro Glu Ile Ile Lys Asp Ile Val Asp Pro Lys Lys
            500                 505                 510

Leu Gly Tyr Trp Ala His Glu Ser Thr Phe Lys Arg Ala Lys Tyr Leu
        515                 520                 525

Arg Gln Lys Thr Tyr Ile Gln Asp Ile Tyr Ala Lys Glu Val Asp Gly
    530                 535                 540

Lys Leu Ile Glu Cys Ser Pro Asp Glu Ala Thr Thr Thr Lys Phe Ser
545                 550                 555                 560

Val Lys Cys Ala Gly Met Thr Asp Thr Ile Lys Lys Val Thr Phe
                565                 570                 575

Asp Asn Phe Arg Val Gly Phe Ser Ser Thr Gly Lys Pro Lys Pro Val
            580                 585                 590

Gln Val Asn Gly Gly Val Val Leu Val Asp Ser Val Phe Thr Ile Lys
        595                 600                 605

<210> SEQ ID NO 4
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asn His Leu Val His His His His His Ile Glu Gly Arg His
1               5                   10                  15

Met Glu Leu Gly Thr Leu Glu Gly Ser Met Lys His Met Pro Arg Lys
            20                  25                  30
```

```
Met Phe Ser Cys Asp Phe Glu Thr Thr Thr Lys Leu Asp Asp Cys Arg
         35                  40                  45

Val Trp Ala Tyr Gly Tyr Met Glu Ile Gly Asn Leu Asp Asn Tyr Lys
     50                  55                  60

Ile Gly Asn Ser Leu Asp Glu Phe Met Gln Trp Val Met Glu Ile Gln
 65                  70                  75                  80

Ala Asp Leu Tyr Phe His Asn Leu Lys Phe Asp Gly Ala Phe Ile Val
                 85                  90                  95

Asn Trp Leu Glu His His Gly Phe Lys Trp Ser Asn Glu Gly Leu Pro
                100                 105                 110

Asn Thr Tyr Asn Thr Ile Ile Ser Lys Met Gly Gln Trp Tyr Met Ile
            115                 120                 125

Asp Ile Cys Phe Gly Tyr Lys Gly Lys Arg Lys Leu His Thr Val Ile
        130                 135                 140

Tyr Asp Ser Leu Lys Lys Leu Pro Phe Pro Val Lys Lys Ile Ala Lys
145                 150                 155                 160

Asp Phe Gln Leu Pro Leu Leu Lys Gly Asp Ile Asp Tyr His Ala Glu
                165                 170                 175

Arg Pro Val Gly His Glu Ile Thr Pro Glu Glu Tyr Glu Tyr Ile Lys
            180                 185                 190

Asn Asp Ile Glu Ile Ile Ala Arg Ala Leu Asp Ile Gln Phe Lys Gln
        195                 200                 205

Gly Leu Asp Arg Met Thr Ala Gly Ser Asp Ser Leu Lys Gly Phe Lys
    210                 215                 220

Asp Ile Leu Ser Thr Lys Lys Phe Asn Lys Val Phe Pro Lys Leu Ser
225                 230                 235                 240

Leu Pro Met Asp Lys Glu Ile Arg Arg Ala Tyr Arg Gly Gly Phe Thr
                245                 250                 255

Trp Leu Asn Asp Lys Tyr Lys Glu Lys Glu Ile Gly Glu Gly Met Val
            260                 265                 270

Phe Asp Val Asn Ser Leu Tyr Pro Ser Gln Met Tyr Ser Arg Pro Leu
        275                 280                 285

Pro Tyr Gly Ala Pro Ile Val Phe Gln Gly Lys Tyr Glu Lys Asp Glu
    290                 295                 300

Gln Tyr Pro Leu Tyr Ile Gln Arg Ile Arg Phe Glu Phe Glu Leu Lys
305                 310                 315                 320

Glu Gly Tyr Ile Pro Thr Ile Gln Ile Lys Lys Asn Pro Phe Phe Lys
                325                 330                 335

Gly Asn Glu Tyr Leu Lys Asn Ser Gly Ala Glu Pro Val Glu Leu Tyr
            340                 345                 350

Leu Thr Asn Val Asp Leu Glu Leu Ile Gln Glu His Tyr Glu Met Tyr
        355                 360                 365

Asn Val Glu Tyr Ile Asp Gly Phe Lys Phe Arg Glu Lys Thr Gly Leu
    370                 375                 380

Phe Lys Glu Phe Ile Asp Lys Trp Thr Tyr Val Lys Thr His Glu Lys
385                 390                 395                 400

Gly Ala Lys Lys Gln Leu Ala Lys Leu Met Leu Asn Ser Leu Tyr Gly
                405                 410                 415

Lys Phe Ala Ser Asn Pro Asp Val Thr Gly Lys Val Pro Tyr Leu Lys
            420                 425                 430

Glu Asp Gly Ser Leu Gly Phe Arg Val Gly Asp Glu Glu Tyr Lys Asp
        435                 440                 445
```

-continued

Pro Val Tyr Thr Pro Met Gly Val Phe Ile Thr Ala Trp Ala Arg Phe
            450                 455                 460

Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Val Pro Glu Ile Ile
                485                 490                 495

Lys Asp Ile Val Asp Pro Lys Lys Leu Gly Tyr Trp Ala His Glu Ser
            500                 505                 510

Thr Phe Lys Arg Ala Lys Tyr Leu Arg Gln Lys Thr Tyr Ile Gln Asp
            515                 520                 525

Ile Tyr Ala Lys Glu Val Asp Gly Lys Leu Ile Glu Cys Ser Pro Asp
530                 535                 540

Glu Ala Thr Thr Thr Lys Phe Ser Val Lys Cys Ala Gly Met Thr Asp
545                 550                 555                 560

Thr Ile Lys Lys Lys Val Thr Phe Asp Asn Phe Arg Val Gly Phe Ser
            565                 570                 575

Ser Thr Gly Lys Pro Lys Pro Val Gln Val Asn Gly Gly Val Val Leu
            580                 585                 590

Val Asp Ser Val Phe Thr Ile Lys
            595                 600

<210> SEQ ID NO 5
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ser His His His His His His Ser Met Ser Gly Leu Asn Asp Ile
1               5                   10                  15

Phe Glu Ala Gln Lys Ile Glu Trp His Glu Gly Ala Pro Gly Ala Arg
                20                  25                  30

Gly Ser Lys His Met Pro Arg Lys Met Phe Ser Cys Asp Phe Glu Thr
            35                  40                  45

Thr Thr Lys Leu Asp Asp Cys Arg Val Trp Ala Tyr Gly Tyr Met Glu
50                  55                  60

Ile Gly Asn Leu Asp Asn Tyr Lys Ile Gly Asn Ser Leu Asp Glu Phe
65                  70                  75                  80

Met Gln Trp Val Met Glu Ile Gln Ala Asp Leu Tyr Phe His Asn Leu
                85                  90                  95

Lys Phe Asp Gly Ala Phe Ile Val Asn Trp Leu Glu His His Gly Phe
            100                 105                 110

Lys Trp Ser Asn Glu Gly Leu Pro Asn Thr Tyr Asn Thr Ile Ile Ser
            115                 120                 125

Lys Met Gly Gln Trp Tyr Met Ile Asp Ile Cys Phe Gly Tyr Lys Gly
            130                 135                 140

Lys Arg Lys Leu His Thr Val Ile Tyr Asp Ser Leu Lys Lys Leu Pro
145                 150                 155                 160

Phe Pro Val Lys Lys Ile Ala Lys Asp Phe Gln Leu Pro Leu Leu Lys
                165                 170                 175

Gly Asp Ile Asp Tyr His Ala Glu Arg Pro Val Gly His Glu Ile Thr
            180                 185                 190

Pro Glu Glu Tyr Glu Tyr Ile Lys Asn Ala Ile Glu Ile Ile Ala Arg
            195                 200                 205

-continued

```
Ala Leu Asp Ile Gln Phe Lys Gln Gly Leu Asp Arg Met Thr Ala Gly
        210                 215                 220
Ser Asp Ser Leu Lys Gly Phe Lys Asp Ile Leu Ser Thr Lys Lys Phe
225                 230                 235                 240
Asn Lys Val Phe Pro Lys Leu Ser Leu Pro Met Asp Lys Glu Ile Arg
                245                 250                 255
Arg Ala Tyr Arg Gly Phe Thr Trp Leu Asn Asp Lys Tyr Lys Glu
                260                 265                 270
Lys Glu Ile Gly Glu Gly Met Val Phe Asp Val Asn Ser Leu Tyr Pro
            275                 280                 285
Ser Gln Met Tyr Ser Arg Pro Leu Pro Tyr Gly Ala Pro Ile Val Phe
290                 295                 300
Gln Gly Lys Tyr Glu Lys Asp Glu Gln Tyr Pro Leu Tyr Ile Gln Arg
305                 310                 315                 320
Ile Arg Phe Glu Phe Glu Leu Lys Glu Gly Tyr Ile Pro Thr Ile Gln
                325                 330                 335
Ile Lys Lys Asn Pro Phe Phe Lys Gly Asn Glu Tyr Leu Lys Asn Ser
                340                 345                 350
Gly Ala Glu Pro Val Glu Leu Tyr Leu Thr Asn Val Asp Leu Glu Leu
            355                 360                 365
Ile Gln Glu His Tyr Glu Met Tyr Asn Val Glu Tyr Ile Asp Gly Phe
        370                 375                 380
Lys Phe Arg Glu Lys Thr Gly Leu Phe Lys Glu Phe Ile Asp Lys Trp
385                 390                 395                 400
Thr Tyr Val Lys Thr His Glu Lys Gly Ala Lys Lys Gln Leu Ala Lys
                405                 410                 415
Leu Met Leu Asn Ser Leu Tyr Gly Lys Phe Ala Ser Asn Pro Asp Val
                420                 425                 430
Thr Gly Lys Val Pro Tyr Leu Lys Glu Asp Gly Ser Leu Gly Phe Arg
            435                 440                 445
Val Gly Asp Glu Glu Tyr Lys Asp Pro Val Tyr Thr Pro Met Gly Val
        450                 455                 460
Phe Ile Thr Ala Trp Ala Arg Phe Thr Thr Ile Thr Ala Ala Gln Ala
465                 470                 475                 480
Cys Tyr Asp Arg Ile Ile Tyr Cys Asp Thr Asp Ser Ile His Leu Thr
                485                 490                 495
Gly Thr Glu Val Pro Glu Ile Ile Lys Asp Ile Val Asp Pro Lys Lys
            500                 505                 510
Leu Gly Tyr Trp Ala His Glu Ser Thr Phe Lys Arg Ala Lys Tyr Leu
        515                 520                 525
Arg Gln Lys Thr Tyr Ile Gln Asp Ile Tyr Ala Lys Glu Val Asp Gly
530                 535                 540
Lys Leu Ile Glu Cys Ser Pro Asp Glu Ala Thr Thr Lys Phe Ser
545                 550                 555                 560
Val Lys Cys Ala Gly Met Thr Asp Thr Ile Lys Lys Val Thr Phe
                565                 570                 575
Asp Asn Phe Arg Val Gly Phe Ser Ser Thr Gly Lys Pro Lys Pro Val
                580                 585                 590
Gln Val Asn Gly Gly Val Val Leu Val Asp Ser Val Phe Thr Ile Lys
            595                 600                 605
```

<210> SEQ ID NO 6
<211> LENGTH: 575

<212> TYPE: PRT
<213> ORGANISM: Bacillus phage phi29

<400> SEQUENCE: 6

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400
```

```
Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 7
<211> LENGTH: 599
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Leu Arg Arg Ala Ser Leu His His Leu Leu Gly Gly Gly Gly
1               5                   10                  15

Ser Gly Gly Gly Ser Ala Ala Ala Gly Ser Ala Ala Arg Lys Met
            20                  25                  30

Tyr Ser Cys Asp Phe Glu Thr Thr Thr Lys Val Glu Asp Cys Arg Val
        35                  40                  45

Trp Ala Tyr Gly Tyr Met Asn Ile Glu Asp His Ser Glu Tyr Lys Ile
    50                  55                  60

Gly Asn Ser Leu Asp Glu Phe Met Ala Trp Val Leu Lys Val Gln Ala
65                  70                  75                  80

Asp Leu Tyr Phe His Asn Leu Lys Phe Asp Gly Ala Phe Ile Ile Asn
                85                  90                  95

Trp Leu Glu Arg Asn Gly Phe Lys Trp Ser Ala Asp Gly Leu Pro Asn
            100                 105                 110

Thr Tyr Asn Thr Ile Ile Ser Arg Met Gly Gln Trp Tyr Met Ile Asp
        115                 120                 125

Ile Cys Leu Gly Tyr Lys Gly Lys Arg Lys Ile His Thr Val Ile Tyr
    130                 135                 140

Asp Ser Leu Lys Lys Leu Pro Phe Pro Val Lys Lys Ile Ala Lys Asp
145                 150                 155                 160

Phe Lys Leu Thr Val Leu Lys Gly Asp Ile Asp Tyr His Lys Glu Arg
                165                 170                 175

Pro Val Gly Tyr Lys Ile Thr Pro Glu Glu Tyr Ala Tyr Ile Lys Asn
```

```
            180                 185                 190
Asp Ile Gln Ile Ile Ala Glu Ala Leu Leu Ile Gln Phe Lys Gln Gly
            195                 200                 205
Leu Asp Arg Met Thr Ala Gly Ser Asp Ser Leu Lys Gly Phe Lys Asp
            210                 215                 220
Ile Ile Thr Thr Lys Lys Phe Lys Lys Val Phe Pro Thr Leu Ser Leu
225                 230                 235                 240
Gly Leu Asp Lys Glu Val Arg Tyr Ala Tyr Arg Gly Gly Phe Thr Trp
                245                 250                 255
Leu Asn Asp Arg Phe Lys Glu Lys Glu Ile Gly Glu Gly Met Val Phe
                260                 265                 270
Asp Val Asn Ser Leu Tyr Pro Ala Gln Met Tyr Ser Arg Leu Leu Pro
                275                 280                 285
Tyr Gly Glu Pro Ile Val Phe Glu Gly Lys Tyr Val Trp Asp Glu Asp
    290                 295                 300
Tyr Pro Leu His Ile Gln His Ile Arg Cys Glu Phe Glu Leu Lys Glu
305                 310                 315                 320
Gly Tyr Ile Pro Thr Ile Gln Ile Lys Arg Ser Arg Phe Tyr Lys Gly
                325                 330                 335
Asn Glu Tyr Leu Lys Ser Ser Gly Gly Glu Ile Ala Asp Leu Trp Leu
                340                 345                 350
Ser Asn Val Asp Leu Glu Leu Met Lys Glu His Tyr Asp Leu Tyr Asn
                355                 360                 365
Val Glu Tyr Ile Ser Gly Leu Lys Phe Lys Ala Thr Thr Gly Leu Phe
    370                 375                 380
Lys Asp Phe Ile Asp Lys Trp Thr Tyr Ile Lys Thr Thr Ser Glu Gly
385                 390                 395                 400
Ala Ile Lys Gln Leu Ala Lys Leu Met Leu Asn Ser Leu Tyr Gly Lys
                405                 410                 415
Phe Ala Ser Asn Pro Asp Val Thr Gly Lys Val Pro Tyr Leu Lys Glu
                420                 425                 430
Asn Gly Ala Leu Gly Phe Arg Leu Gly Glu Glu Thr Lys Asp Pro
                435                 440                 445
Val Tyr Thr Pro Met Gly Val Phe Ile Thr Ala Trp Ala Arg Tyr Thr
    450                 455                 460
Thr Ile Thr Ala Ala Gln Ala Cys Tyr Asp Arg Ile Ile Tyr Cys Asp
465                 470                 475                 480
Thr Asp Ser Ile His Leu Thr Gly Thr Glu Ile Pro Asp Val Ile Lys
                485                 490                 495
Asp Ile Val Asp Pro Lys Lys Leu Gly Tyr Trp Ala His Glu Ser Thr
                500                 505                 510
Phe Lys Arg Ala Lys Tyr Leu Arg Gln Lys Thr Tyr Ile Gln Asp Ile
                515                 520                 525
Tyr Met Lys Glu Val Asp Gly Lys Leu Val Glu Gly Ser Pro Asp Asp
    530                 535                 540
Tyr Thr Asp Ile Lys Phe Ser Val Lys Cys Ala Gly Met Thr Asp Lys
545                 550                 555                 560
Ile Lys Lys Glu Val Thr Phe Glu Asn Phe Lys Val Gly Phe Ser Arg
                565                 570                 575
Lys Met Lys Pro Lys Pro Val Gln Val Pro Gly Gly Val Val Leu Val
                580                 585                 590
Asp Asp Thr Phe Thr Ile Lys
                595
```

<210> SEQ ID NO 8
<211> LENGTH: 596
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met His His His His His Leu Leu Gly Gly Gly Ser Gly Gly
1               5                   10                  15

Gly Gly Ser Ala Ala Ala Gly Ser Ala Ala Arg Lys Met Tyr Ser Cys
            20                  25                  30

Asp Phe Glu Thr Thr Thr Lys Val Glu Asp Cys Arg Val Trp Ala Tyr
        35                  40                  45

Gly Tyr Met Asn Ile Glu Asp His Ser Glu Tyr Lys Ile Gly Asn Ser
    50                  55                  60

Leu Asp Glu Phe Met Ala Trp Val Leu Lys Val Gln Ala Asp Leu Tyr
65                  70                  75                  80

Phe His Asn Leu Lys Phe Asp Gly Ala Phe Ile Ile Asn Trp Leu Glu
                85                  90                  95

Arg Asn Gly Phe Lys Trp Ser Ala Asp Gly Leu Pro Asn Thr Tyr Asn
            100                 105                 110

Thr Ile Ile Ser Arg Met Gly Gln Trp Tyr Met Ile Asp Ile Cys Leu
        115                 120                 125

Gly Tyr Lys Gly Lys Arg Lys Ile His Thr Val Ile Tyr Asp Ser Leu
    130                 135                 140

Lys Lys Leu Pro Phe Pro Val Lys Lys Ile Ala Lys Asp Phe Lys Leu
145                 150                 155                 160

Thr Val Leu Lys Gly Asp Ile Asp Tyr His Lys Glu Arg Pro Val Gly
                165                 170                 175

Tyr Lys Ile Thr Pro Glu Glu Tyr Ala Tyr Ile Lys Asn Ala Ile Gln
            180                 185                 190

Ile Ile Ala Glu Ala Leu Leu Ile Gln Phe Lys Gln Gly Leu Asp Arg
        195                 200                 205

Met Thr Ala Gly Ser Asp Ser Leu Lys Gly Phe Lys Asp Ile Ile Thr
    210                 215                 220

Thr Lys Lys Phe Lys Lys Val Phe Pro Thr Leu Ser Leu Gly Leu Asp
225                 230                 235                 240

Lys Glu Val Arg Tyr Ala Tyr Arg Gly Gly Phe Thr Trp Leu Asn Asp
                245                 250                 255

Arg Phe Lys Glu Lys Glu Ile Gly Glu Gly Met Val Phe Asp Val Asn
            260                 265                 270

Ser Leu Tyr Pro Ala Gln Met Tyr Ser Arg Leu Leu Pro Tyr Gly Glu
        275                 280                 285

Pro Ile Val Phe Glu Gly Lys Tyr Val Trp Asp Glu Asp Tyr Pro Leu
    290                 295                 300

His Ile Gln His Ile Arg Cys Glu Phe Glu Leu Lys Glu Gly Tyr Ile
305                 310                 315                 320

Pro Thr Ile Gln Ile Lys Arg Ser Arg Phe Tyr Lys Gly Asn Glu Tyr
                325                 330                 335

Leu Lys Ser Ser Gly Gly Glu Ile Ala Asp Leu Trp Leu Ser Asn Val
            340                 345                 350

Asp Leu Glu Leu Met Lys Glu His Tyr Asp Leu Tyr Asn Val Glu Tyr

```
                355                 360                 365
Ile Ser Gly Leu Lys Phe Lys Ala Thr Thr Gly Leu Phe Lys Asp Phe
370                 375                 380

Ile Asp Lys Trp Thr Tyr Ile Lys Thr Thr Ser Glu Gly Ala Ile Lys
385                 390                 395                 400

Gln Leu Ala Lys Leu Met Leu Asn Ser Leu Tyr Gly Lys Phe Ala Ser
                405                 410                 415

Asn Pro Asp Val Thr Gly Lys Val Pro Tyr Leu Lys Glu Asn Gly Ala
                420                 425                 430

Leu Gly Phe Arg Leu Gly Glu Glu Thr Lys Asp Pro Val Tyr Thr
            435                 440                 445

Pro Met Gly Val Phe Ile Thr Ala Trp Ala Arg Tyr Thr Thr Ile Thr
        450                 455                 460

Ala Ala Gln Ala Cys Tyr Asp Arg Ile Ile Tyr Cys Asp Thr Asp Ser
465                 470                 475                 480

Ile His Leu Thr Gly Thr Glu Ile Pro Asp Val Ile Lys Asp Ile Val
                485                 490                 495

Asp Pro Lys Lys Leu Gly Tyr Trp Ala His Glu Ser Thr Phe Lys Arg
            500                 505                 510

Ala Lys Tyr Leu Arg Gln Lys Thr Tyr Ile Gln Asp Ile Tyr Met Lys
        515                 520                 525

Glu Val Asp Gly Lys Leu Val Glu Gly Ser Pro Asp Asp Tyr Thr Asp
    530                 535                 540

Ile Lys Phe Ser Val Lys Cys Ala Gly Met Thr Asp Lys Ile Lys Lys
545                 550                 555                 560

Glu Val Thr Phe Glu Asn Phe Lys Val Gly Phe Ser Arg Lys Met Lys
                565                 570                 575

Pro Lys Pro Val Gln Val Pro Gly Gly Val Val Leu Val Asp Asp Thr
            580                 585                 590

Phe Thr Ile Lys
        595

<210> SEQ ID NO 9
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asn His Leu Val His His His His Ile Glu Gly Arg His
1               5                   10                  15

Met Glu Leu Gly Thr Leu Glu Gly Ser Met Lys His Met Pro Arg Lys
                20                  25                  30

Met Tyr Ser Cys Ala Phe Glu Thr Thr Thr Lys Val Glu Asp Cys Arg
            35                  40                  45

Val Trp Ala Tyr Gly Tyr Met Asn Ile Glu Asp His Ser Glu Tyr Lys
        50                  55                  60

Ile Gly Asn Ser Leu Asp Glu Phe Met Ala Trp Val Leu Lys Val Gln
65                  70                  75                  80

Ala Asp Leu Tyr Phe His Asn Leu Lys Phe Ala Gly Ala Phe Ile Ile
                85                  90                  95

Asn Trp Leu Glu Arg Asn Gly Phe Lys Trp Ser Ala Asp Gly Leu Pro
            100                 105                 110
```

-continued

Asn Thr Tyr Asn Thr Ile Ile Ser Arg Met Gly Gln Trp Tyr Met Ile
            115                 120                 125

Asp Ile Cys Leu Gly Tyr Lys Gly Lys Arg Lys Ile His Thr Val Ile
130                 135                 140

Tyr Asp Ser Leu Lys Lys Leu Pro Phe Pro Val Lys Lys Ile Ala Lys
145                 150                 155                 160

Asp Phe Lys Leu Thr Val Leu Lys Gly Asp Ile Asp Tyr His Lys Glu
                165                 170                 175

Arg Pro Val Gly Tyr Lys Ile Thr Pro Glu Tyr Ala Tyr Ile Lys
            180                 185                 190

Asn Asp Ile Gln Ile Ile Ala Glu Ala Leu Leu Ile Gln Phe Lys Gln
            195                 200                 205

Gly Leu Asp Arg Met Thr Ala Gly Ser Asp Ser Leu Lys Gly Phe Lys
210                 215                 220

Asp Ile Ile Thr Thr Lys Lys Phe Lys Lys Val Phe Pro Thr Leu Ser
225                 230                 235                 240

Leu Gly Leu Asp Lys Glu Val Arg Tyr Ala Tyr Arg Gly Gly Phe Thr
                245                 250                 255

Trp Leu Asn Asp Arg Phe Lys Glu Lys Glu Ile Gly Glu Gly Met Val
            260                 265                 270

Phe Asp Val Asn Ser Leu Tyr Pro Ala Gln Met Tyr Ser Arg Leu Leu
            275                 280                 285

Pro Tyr Gly Glu Pro Ile Val Phe Glu Gly Lys Tyr Val Trp Asp Glu
            290                 295                 300

Asp Tyr Pro Leu His Ile Gln His Ile Arg Cys Glu Phe Glu Leu Lys
305                 310                 315                 320

Glu Gly Tyr Ile Pro Thr Ile Gln Ile Lys Arg Ser Arg Phe Tyr Lys
                325                 330                 335

Gly Asn Glu Tyr Leu Lys Ser Ser Gly Gly Glu Ile Ala Asp Leu Trp
            340                 345                 350

Leu Ser Asn Val Asp Leu Glu Leu Met Lys Glu His Tyr Asp Leu Tyr
            355                 360                 365

Asn Val Glu Tyr Ile Ser Gly Leu Lys Phe Lys Ala Thr Thr Gly Leu
370                 375                 380

Phe Lys Asp Phe Ile Asp Lys Trp Thr Tyr Ile Lys Thr Thr Ser Glu
385                 390                 395                 400

Gly Ala Ile Lys Gln Leu Ala Lys Leu Met Leu Asn Ser Leu Tyr Gly
                405                 410                 415

Lys Phe Ala Ser Asn Pro Asp Val Thr Gly Lys Val Pro Tyr Leu Lys
            420                 425                 430

Glu Asn Gly Ala Leu Gly Phe Arg Leu Gly Glu Glu Thr Lys Asp
            435                 440                 445

Pro Val Tyr Thr Pro Met Gly Val Phe Ile Thr Ala Trp Ala Arg Tyr
450                 455                 460

Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Ile Pro Asp Val Ile
                485                 490                 495

Lys Asp Ile Val Asp Pro Lys Lys Leu Gly Tyr Trp Ala His Glu Ser
            500                 505                 510

Thr Phe Lys Arg Ala Lys Tyr Leu Arg Gln Lys Thr Tyr Ile Gln Asp
            515                 520                 525

Ile Tyr Met Lys Glu Val Asp Gly Lys Leu Val Glu Gly Ser Pro Asp

```
                    530                 535                 540
Asp Tyr Thr Asp Ile Lys Phe Ser Val Lys Cys Ala Gly Met Thr Asp
545                 550                 555                 560

Lys Ile Lys Lys Glu Val Thr Phe Glu Asn Phe Lys Val Gly Phe Ser
                565                 570                 575

Arg Lys Met Lys Pro Lys Pro Val Gln Val Pro Gly Gly Val Val Leu
                580                 585                 590

Val Asp Asp Thr Phe Thr Ile Lys
                595                 600

<210> SEQ ID NO 10
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asn His Leu Val His His His His His Ile Glu Gly Arg His
1               5                   10                  15

Met Glu Leu Gly Thr Leu Glu Gly Ser Met Lys His Met Pro Arg Lys
                20                  25                  30

Met Tyr Ser Cys Ala Phe Glu Thr Thr Thr Lys Val Glu Asp Cys Arg
            35                  40                  45

Val Trp Ala Tyr Gly Tyr Met Asn Ile Glu Asp His Ser Glu Tyr Lys
        50                  55                  60

Ile Gly Asn Ser Leu Asp Glu Phe Met Ala Trp Val Leu Lys Val Gln
65                  70                  75                  80

Ala Asp Leu Tyr Phe His Asn Leu Lys Phe Ala Gly Ala Phe Ile Ile
                85                  90                  95

Asn Trp Leu Glu Arg Asn Gly Phe Lys Trp Ser Ala Asp Gly Leu Pro
            100                 105                 110

Asn Thr Tyr Asn Thr Ile Ile Ser Arg Met Gly Gln Trp Tyr Met Ile
        115                 120                 125

Asp Ile Cys Leu Gly Tyr Lys Gly Lys Arg Lys Ile His Thr Val Ile
    130                 135                 140

Tyr Asp Ser Leu Lys Lys Leu Pro Phe Pro Val Lys Lys Ile Ala Lys
145                 150                 155                 160

Asp Phe Lys Leu Thr Val Leu Lys Gly Asp Ile Asp Tyr His Lys Glu
                165                 170                 175

Arg Pro Val Gly Tyr Lys Ile Thr Pro Glu Glu Tyr Ala Tyr Ile Lys
            180                 185                 190

Asn Asp Ile Gln Ile Ile Ala Glu Ala Leu Leu Ile Gln Phe Lys Gln
        195                 200                 205

Gly Leu Asp Arg Met Thr Ala Gly Ser Asp Ser Leu Lys Gly Phe Lys
    210                 215                 220

Asp Ile Ile Thr Thr Lys Lys Phe Lys Lys Val Phe Pro Thr Leu Ser
225                 230                 235                 240

Leu Gly Leu Asp Lys Glu Val Arg Tyr Ala Tyr Arg Gly Gly Phe Thr
                245                 250                 255

Trp Leu Asn Asp Arg Phe Lys Glu Lys Glu Ile Gly Glu Gly Met Val
            260                 265                 270

Phe Asp Val Asn Ser Leu Tyr Pro Ala Gln Met Tyr Ser Arg Leu Leu
        275                 280                 285
```

Pro Tyr Gly Glu Pro Ile Val Phe Glu Gly Lys Tyr Val Trp Asp Glu
            290                 295                 300

Asp Tyr Pro Leu His Ile Gln His Ile Arg Cys Glu Phe Glu Leu Lys
305                 310                 315                 320

Glu Gly Tyr Ile Pro Thr Ile Gln Ile Lys Arg Ser Arg Phe Tyr Lys
            325                 330                 335

Gly Asn Glu Tyr Leu Lys Ser Ser Gly Gly Glu Ile Ala Asp Leu Trp
            340                 345                 350

Leu Ser Asn Val Asp Leu Glu Leu Met Lys Glu His Tyr Asp Leu Tyr
        355                 360                 365

Asn Val Glu Tyr Ile Ser Gly Leu Lys Phe Lys Ala Thr Thr Gly Leu
    370                 375                 380

Phe Lys Asp Phe Ile Asp Lys Trp Thr Tyr Ile Lys Thr Thr Ser Glu
385                 390                 395                 400

Gly Ala Ile Lys Ala Leu Ala Lys Leu Met Leu Asn Ser Leu Tyr Gly
            405                 410                 415

Lys Phe Ala Ser Asn Pro Asp Val Thr Gly Lys Val Pro Tyr Leu Lys
            420                 425                 430

Glu Asn Gly Ala Leu Gly Phe Arg Leu Gly Glu Glu Thr Lys Asp
        435                 440                 445

Pro Val Tyr Thr Pro Met Gly Val Phe Ile Thr Ala Trp Ala Arg Tyr
    450                 455                 460

Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Ile Pro Asp Val Ile
            485                 490                 495

Lys Asp Ile Val Asp Pro Lys Lys Leu Gly Tyr Trp Ala His Glu Ser
            500                 505                 510

Thr Phe Lys Arg Ala Lys Tyr Leu Arg Gln Lys Thr Tyr Ile Gln Asp
        515                 520                 525

Ile Tyr Met Lys Glu Val Asp Gly Lys Leu Val Glu Gly Ser Pro Asp
    530                 535                 540

Asp Tyr Thr Asp Ile Lys Phe Ser Val Lys Cys Ala Gly Met Thr Asp
545                 550                 555                 560

Lys Ile Lys Lys Glu Val Thr Phe Glu Asn Phe Lys Val Gly Phe Ser
            565                 570                 575

Arg Lys Met Lys Pro Lys Pro Val Gln Val Pro Gly Gly Val Val Leu
            580                 585                 590

Val Asp Asp Thr Phe Thr Ile Lys
            595                 600

<210> SEQ ID NO 11
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asn His Leu Val His His His His Ile Glu Gly Arg His
1               5                   10                  15

Met Glu Leu Gly Thr Leu Glu Gly Ser Met Lys His Met Pro Arg Lys
            20                  25                  30

Met Tyr Ser Cys Ala Phe Glu Thr Thr Lys Val Glu Asp Cys Arg
        35                  40                  45

```
Val Trp Ala Tyr Gly Tyr Met Asn Ile Glu Asp His Ser Glu Tyr Lys
    50                  55                  60

Ile Gly Asn Ser Leu Asp Glu Phe Met Ala Trp Val Leu Lys Val Gln
65                  70                  75                  80

Ala Asp Leu Tyr Phe His Asn Leu Lys Phe Ala Gly Ala Phe Ile Ile
                    85                  90                  95

Asn Trp Leu Glu Arg Asn Gly Phe Lys Trp Ser Ala Asp Gly Leu Pro
                100                 105                 110

Asn Thr Tyr Asn Thr Ile Ile Ser Arg Met Gly Gln Trp Tyr Met Ile
            115                 120                 125

Asp Ile Cys Leu Gly Tyr Lys Gly Lys Arg Lys Ile His Thr Val Ile
    130                 135                 140

Tyr Asp Ser Leu Lys Lys Leu Pro Phe Pro Val Lys Lys Ile Ala Lys
145                 150                 155                 160

Asp Phe Lys Leu Thr Val Leu Lys Gly Asp Ile Asp Tyr His Lys Glu
                165                 170                 175

Arg Pro Val Gly Tyr Lys Ile Thr Pro Glu Glu Tyr Ala Tyr Ile Lys
                180                 185                 190

Asn Asp Ile Gln Ile Ile Ala Glu Ala Leu Leu Ile Gln Phe Lys Gln
            195                 200                 205

Gly Leu Asp Arg Met Thr Ala Gly Ser Asp Ser Leu Lys Gly Phe Lys
    210                 215                 220

Asp Ile Ile Thr Thr Lys Lys Phe Lys Lys Val Phe Pro Thr Leu Ser
225                 230                 235                 240

Leu Gly Leu Asp Lys Glu Val Arg Tyr Ala Tyr Arg Gly Gly Phe Thr
                245                 250                 255

Trp Leu Asn Asp Arg Phe Lys Glu Lys Glu Ile Gly Glu Gly Met Val
                260                 265                 270

Phe Asp Val Asn Ser Leu Tyr Pro Ala Gln Met Tyr Ser Arg Leu Leu
            275                 280                 285

Pro Tyr Gly Glu Pro Ile Val Phe Glu Gly Lys Tyr Val Trp Asp Glu
    290                 295                 300

Asp Tyr Pro Leu His Ile Gln His Ile Arg Cys Glu Phe Glu Leu Lys
305                 310                 315                 320

Glu Gly Tyr Ile Pro Thr Ile Gln Ile Lys Arg Ser Arg Phe Tyr Lys
                325                 330                 335

Gly Asn Glu Tyr Leu Lys Ser Ser Gly Gly Glu Ile Ala Asp Leu Trp
            340                 345                 350

Leu Ser Asn Val Asp Leu Glu Leu Met Lys Glu His Tyr Asp Leu Tyr
    355                 360                 365

Asn Val Glu Tyr Ile Ser Gly Leu Lys Phe Lys Ala Thr Thr Gly Leu
370                 375                 380

Phe Lys Asp Phe Ile Asp Lys Trp Thr Tyr Ile Lys Thr Thr Ser Glu
385                 390                 395                 400

Gly Ala Ile Lys Gln Leu Ala Lys Leu Met Leu Asn Gly Leu Tyr Gly
                405                 410                 415

Lys Phe Ala Ser Asn Pro Asp Val Thr Gly Lys Val Pro Tyr Leu Lys
            420                 425                 430

Glu Asn Gly Ala Leu Gly Phe Arg Leu Gly Glu Glu Thr Lys Asp
    435                 440                 445

Pro Val Tyr Thr Pro Met Gly Val Phe Ile Thr Ala Trp Ala Arg Tyr
    450                 455                 460
```

```
Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Ile Pro Asp Val Ile
                485                 490                 495

Lys Asp Ile Val Asp Pro Lys Lys Leu Gly Tyr Trp Ala His Glu Ser
            500                 505                 510

Thr Phe Lys Arg Ala Lys Tyr Leu Arg Gln Lys Thr Tyr Ile Gln Asp
        515                 520                 525

Ile Tyr Met Lys Glu Val Asp Gly Lys Leu Val Gly Ser Pro Asp
    530                 535                 540

Asp Tyr Thr Asp Ile Lys Phe Ser Val Lys Cys Ala Gly Met Thr Asp
545                 550                 555                 560

Lys Ile Lys Lys Glu Val Thr Phe Glu Asn Phe Lys Val Gly Phe Ser
                565                 570                 575

Arg Lys Met Lys Pro Lys Pro Val Gln Val Pro Gly Gly Val Val Leu
            580                 585                 590

Val Asp Asp Thr Phe Thr Ile Lys
595                 600
```

<210> SEQ ID NO 12
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Ser His His His His His Ser Met Ser Gly Leu Asn Asp Ile
1               5                   10                  15

Phe Glu Ala Gln Lys Ile Glu Trp His Glu Gly Ala Pro Gly Ala Arg
                20                  25                  30

Gly Ser Lys His Met Pro Arg Lys Met Tyr Ser Cys Ala Phe Glu Thr
            35                  40                  45

Thr Thr Lys Val Glu Asp Cys Arg Val Trp Ala Tyr Gly Tyr Met Asn
50                  55                  60

Ile Glu Asp His Ser Glu Tyr Lys Ile Gly Asn Ser Leu Asp Glu Phe
65                  70                  75                  80

Met Ala Trp Val Leu Lys Val Gln Ala Asp Leu Tyr Phe His Asn Leu
                85                  90                  95

Lys Phe Ala Gly Ala Phe Ile Ile Asn Trp Leu Glu Arg Asn Gly Phe
            100                 105                 110

Lys Trp Ser Ala Asp Gly Leu Pro Asn Thr Tyr Asn Thr Ile Ile Ser
        115                 120                 125

Arg Met Gly Gln Trp Tyr Met Ile Asp Ile Cys Leu Gly Tyr Lys Gly
    130                 135                 140

Lys Arg Lys Ile His Thr Val Ile Tyr Asp Ser Leu Lys Lys Leu Pro
145                 150                 155                 160

Phe Pro Val Lys Lys Ile Ala Lys Asp Phe Lys Leu Thr Val Leu Lys
                165                 170                 175

Gly Asp Ile Asp Tyr His Lys Glu Arg Pro Val Gly Tyr Lys Ile Thr
            180                 185                 190

Pro Glu Glu Tyr Ala Tyr Ile Lys Asn Asp Ile Gln Ile Ile Ala Glu
        195                 200                 205

Ala Leu Leu Ile Gln Phe Lys Gln Gly Leu Asp Arg Met Thr Ala Gly
    210                 215                 220
```

Ser Asp Ser Leu Lys Gly Phe Lys Asp Ile Ile Thr Lys Lys Phe
225                 230                 235                 240

Lys Lys Val Phe Pro Thr Leu Ser Leu Gly Leu Asp Lys Glu Val Arg
            245                 250                 255

Tyr Ala Tyr Arg Gly Gly Phe Thr Trp Leu Asn Asp Arg Phe Lys Glu
                260                 265                 270

Lys Glu Ile Gly Glu Gly Met Val Phe Asp Val Asn Ser Leu Tyr Pro
        275                 280                 285

Ala Gln Met Tyr Ser Arg Leu Leu Pro Tyr Gly Glu Pro Ile Val Phe
        290                 295                 300

Glu Gly Lys Tyr Val Trp Asp Glu Asp Tyr Pro Leu His Ile Gln His
305                 310                 315                 320

Ile Arg Cys Glu Phe Glu Leu Lys Glu Gly Tyr Ile Pro Thr Ile Gln
                325                 330                 335

Ile Lys Arg Ser Arg Phe Tyr Lys Gly Asn Glu Tyr Leu Lys Ser Ser
                340                 345                 350

Gly Gly Glu Ile Ala Asp Leu Trp Leu Ser Asn Val Asp Leu Glu Leu
        355                 360                 365

Met Lys Glu His Tyr Asp Leu Tyr Asn Val Glu Tyr Ile Ser Gly Leu
370                 375                 380

Lys Phe Lys Ala Thr Thr Gly Leu Phe Lys Asp Phe Ile Asp Lys Trp
385                 390                 395                 400

Thr Tyr Ile Lys Thr Thr Ser Glu Gly Ala Ile Lys Gln Leu Ala Lys
                405                 410                 415

Leu Met Leu Asn Ser Leu Tyr Gly Lys Phe Ala Ser Asn Pro Asp Val
            420                 425                 430

Thr Gly Lys Val Pro Tyr Leu Lys Glu Asn Gly Ala Leu Gly Phe Arg
        435                 440                 445

Leu Gly Glu Glu Glu Thr Lys Asp Pro Val Tyr Thr Pro Met Gly Val
450                 455                 460

Phe Ile Thr Ala Trp Ala Arg Tyr Thr Thr Ile Thr Ala Ala Gln Ala
465                 470                 475                 480

Cys Tyr Asp Arg Ile Ile Tyr Cys Asp Thr Asp Ser Ile His Leu Thr
                485                 490                 495

Gly Thr Glu Ile Pro Asp Val Ile Lys Asp Ile Val Asp Pro Lys Lys
            500                 505                 510

Leu Gly Tyr Trp Ala His Glu Ser Thr Phe Lys Arg Ala Lys Tyr Leu
        515                 520                 525

Arg Gln Lys Thr Tyr Ile Gln Asp Ile Tyr Met Lys Glu Val Asp Gly
530                 535                 540

Lys Leu Val Glu Gly Ser Pro Asp Asp Tyr Thr Asp Ile Lys Phe Ser
545                 550                 555                 560

Val Lys Cys Ala Gly Met Thr Asp Lys Ile Lys Lys Glu Val Thr Phe
                565                 570                 575

Glu Asn Phe Lys Val Gly Phe Ser Arg Lys Met Lys Pro Lys Pro Val
            580                 585                 590

Gln Val Pro Gly Gly Val Val Leu Val Asp Asp Thr Phe Thr Ile Lys
        595                 600                 605

<210> SEQ ID NO 13
<211> LENGTH: 903
<212> TYPE: PRT
<213> ORGANISM: Enterobacteria phage RB69

<400> SEQUENCE: 13

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Asp Ile Pro
210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300

Tyr Asp Gly Pro Ile Ser Lys Leu Arg Glu Ser Asn His Gln Arg Tyr
305                 310                 315                 320

Ile Ser Tyr Asn Ile Ile Asp Val Tyr Arg Val Leu Gln Ile Asp Ala
                325                 330                 335

Lys Arg Gln Phe Ile Asn Leu Ser Leu Asp Met Gly Tyr Tyr Ala Lys
            340                 345                 350

Ile Gln Ile Gln Ser Val Phe Ser Pro Ile Lys Thr Trp Asp Ala Ile
        355                 360                 365

Ile Phe Asn Ser Leu Lys Glu Gln Asn Lys Val Ile Pro Gln Gly Arg
370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
                405                 410                 415

```
Pro Ser Ile Ile Arg Gln Val Asn Ile Ser Pro Glu Thr Ile Ala Gly
            420                 425                 430

Thr Phe Lys Val Ala Pro Leu His Asp Tyr Ile Asn Ala Val Ala Glu
            435                 440                 445

Arg Pro Ser Asp Val Tyr Ser Cys Ser Pro Asn Gly Met Met Tyr Tyr
            450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
            500                 505                 510

Pro Leu Asp Val Asp Tyr Arg Phe Asp Phe Ser Asp Glu Ile Lys Glu
            515                 520                 525

Lys Ile Lys Lys Leu Ser Ala Lys Ser Leu Asn Glu Met Leu Phe Arg
530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
            565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
            595                 600                 605

Cys Gly Thr Glu Gly Glu Ala Phe Val Leu Tyr Gly Asp Thr Asp Ser
            610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
            675                 680                 685

Ala Gly Pro Pro Leu Gly Ser Lys Gly Ile Gly Gly Phe Trp Thr Gly
            690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735

Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
            755                 760                 765

Lys Glu Phe Arg Gln Leu Asn Tyr Ile Ser Ile Ala Ser Val Ser Ser
            770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Glu Lys Val Tyr Val
            820                 825                 830
```

-continued

```
Leu Pro Leu Arg Glu Gly Asn Pro Phe Gly Asp Lys Cys Ile Ala Trp
            835                 840                 845

Pro Ser Gly Thr Glu Ile Thr Asp Leu Ile Lys Asp Asp Val Leu His
850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
                900
```

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Met Asn His Leu Val His His His His His Ile Glu Gly Arg His
1               5                   10                  15

Met Glu Leu Gly Thr Leu Glu Gly Ser
            20                  25
```

<210> SEQ ID NO 15
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Met Ser His His His His His His Ser Met Ser Gly Leu Asn Asp Ile
1               5                   10                  15

Phe Glu Ala Gln Lys Ile Glu Trp His Glu Gly Ala Pro Gly Ala Arg
            20                  25                  30

Gly Ser
```

<210> SEQ ID NO 16
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Met His His His His His His Leu Leu Gly Gly Gly Gly Ser Gly Gly
1               5                   10                  15

Gly Gly Ser Ala Ala Ala Gly Ser Ala Ala Arg
            20                  25
```

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Ala Thr Ser Asn Val Phe Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Lys Ala Ser Gly Pro Pro Val
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Arg Arg Ala Ser Leu Gly
1               5

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly Ser Gly Gly Gly Ser Ala Ala Ala Gly Ser Ala
1               5                   10                  15

Ala

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ala Ala Ala Lys Gly Ala Ala Ala Lys Gly Ser Ala Ala
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Lys Pro Gln Gln Phe
1               5

<210> SEQ ID NO 23
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 23

Pro Lys Pro Gln Gln Phe Met
1               5

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tttttttgca ggtgacaggt ttttcctgtc acctgc                              36

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttatctttgt gggtgacagg ttttcctgt caccc                                35

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tttttttgcc cccagggtga caggttttc ctgtcaccc                            39

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tttttgcggg tgacaggttt ttcctgtcac cc                                  32

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tttttttgca ggtgacaggt ttttcctgtc acctgc                              36

<210> SEQ ID NO 29
<211> LENGTH: 19
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 29
ggtactaagc ggccgcatg                                              19

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
taaagccccc ccatgcggcc gcttagtacc                                  30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
taaagttttt tcatgcggcc gcttagtacc                                  30

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggtactaagc ggccgcatga aaaaaa                                      26

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tgatagaacc tccgtgt                                                17

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggaacacgga ggttctatca tcgtcatcgt catcgtcatc g                     41

<210> SEQ ID NO 35
<211> LENGTH: 19
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 35
ggtactaagc ggccgcatg                                                     19

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttttacccat gcggccgctt agtacc                                             26

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggtactaagc ggccgc                                                        16

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttttacccat gcggccgctt agtacc                                             26

<210> SEQ ID NO 39
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gggggggggg gggggaaaaa aaaaaaaaaa gggggggggg gggggaaaaa aaaaaaaaaa        60

<210> SEQ ID NO 40
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttgaacggat gaggaccaga caccacttga acggatgagg aaaaaaaaaa tca               53

<210> SEQ ID NO 41
<211> LENGTH: 59
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 41
ttttgattcc cccttccccc gacacggagg ttctatcatc gtcatcgtca tcgtcatcg    59

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgatgacgat gacgatgacg atgatagaac ctccgtgtc                          39

<210> SEQ ID NO 43
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tgattttttt tttcctcatc cgttcaagtg gtgtctggtc ctcatccgtt caagacacgg    60
aggttctatc atcgtcatcg tcat                                          84

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tgatagaacc tccgtgt                                                  17

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 tttttttttac ccccgggtga caggtt                                       26

<210> SEQ ID NO 46
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tttttccccg acgatgcctc cccgacacgg aggttctatc atcgtcatcg tcatcgtcat    60
cg                                                                  62

<210> SEQ ID NO 47
<211> LENGTH: 18

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgatagaacc tccgtgtc                                                  18

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggggaggcat cgtcgggaaa a                                              21

<210> SEQ ID NO 49
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tttttccccg cgtaactctt taccccgaca cggaggttct atca                     44

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgatagaacc tccgtgtc                                                  18

<210> SEQ ID NO 51
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ttttgatttt ttttttttcc cccccccccc tttttttttt ttcccccccc ccccgacacg    60
gaggttctat catcgtcatc gtcatcgtca tcg                                 93

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tgatagaacc tccgtgtc                                                  18

<210> SEQ ID NO 53
```

```
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tgatagaacc tc                                                           12

<210> SEQ ID NO 54
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tttttccccg acgatgcctc ccctttttttt taccccgggg tgacaggtt                  49

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gggggaaggg ggaa                                                         14

<210> SEQ ID NO 56
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gggggtaaaa aaaaggggag gcatcgtcgg ggaaaaa                                37

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cgttaaccgc ccgctccttt gcaac                                             25

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gttgcaaagg agcgggcg                                                     18

<210> SEQ ID NO 59
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cagtaacgga gttggttgga cggctgcgag gc                                    32

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcctcgcagc cgtccaacca actcc                                            25

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Leu Asn Asp Ile Phe Glu Ala Gln Lys Ile Glu Trp His Glu
1               5                   10                  15

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Arg Arg Ala Ser Leu
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 63

His His His His His His
1               5

<210> SEQ ID NO 64
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ttatctttgt gggtgacagg ttttccctgt cacc                                  34
```

```
<210> SEQ ID NO 65
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ttcctgtcac cc                                                          12

<210> SEQ ID NO 66
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gggggtaaaa aaaa                                                        14

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Asp Asp Asp
1
```

METHODS AND APPARATUS FOR SINGLE MOLECULE SEQUENCING USING ENERGY TRANSFER DETECTION

This application is a divisional of U.S. application Ser. No. 14/584,829, filed on Dec. 29, 2014, which is a divisional of U.S. application Ser. No. 13/562,159, filed on Jul. 30, 2012, now U.S. Pat. No. 8,999,674, which is a continuation of U.S. application Ser. No. 12/748,168, filed on Mar. 26, 2010, now abandoned, which claims the filing date benefit of U.S. Provisional Application Nos. 61/307,356, filed on Feb. 23, 2010; 61/299,917, filed on Jan. 29, 2010; 61/299,919, filed on Jan. 29, 2010; 61/293,616, filed on Jan. 8, 2010; 61/293,618, filed on Jan. 8, 2010; 61/289,388; filed on Dec. 22, 2009; 61/263,974, filed on Nov. 24, 2009; 61/245,457, filed on Sep. 24, 2009; 61/242,771, filed on Sep. 15, 2009; 61/184,770, filed on Jun. 5, 2009; and 61/164,324, filed on Mar. 27, 2009. The contents of each foregoing patent applications are incorporated by reference in their entirety.

Throughout this application various publications are referenced. The disclosures of these publications in their entireties are hereby incorporated by reference into this application in order to more fully describe the state of the art to which this invention pertains.

SEQUENCE LISTING

The instant application contains a Sequence Listing which has been submitted via EFS-Web and is hereby incorporated by reference in its entirety. Said ASCII copy, created on Jun. 14, 2010, is named LT00019.txt and is 84,083 bytes in size.

FIELD

The disclosed embodiments are related generally to single molecule sequencing. More specifically, the disclosed embodiments relate to an energy transfer system which permits detection and monitoring of nucleotide polymerization.

BACKGROUND

Obtaining nucleic acid sequence information is an important starting point for medical and academic research endeavors. The sequence information facilitates medical studies of active disease, genetic disease predispositions, and assists in rational design of drugs targeting specific diseases. Sequence information is also the basis for genomic and evolutionary studies, and many genetic engineering applications. Reliable sequence information is critical for paternity tests, criminal investigations, and forensic studies.

Nucleic acid sequence information is typically obtained using chain termination and size separation procedures, such as those described by Sanger, et al., (1977 Proc. Nat. Acad. Sci. USA 74:5463-5467). Prior to gel separation, the nucleic acid target molecules of interest are cloned, amplified, and isolated. Then the sequencing reactions are conducted in four separate reaction vessels, one for each nucleotide: A, G, C and T. These sequencing methods are adequate for read lengths of 500-10000 nucleotides. However, they are time-consuming and require relatively large amounts of target molecules. Additionally, these methods can be expensive, as they require reagents for four reaction vessels. And the amplification steps are error-prone which can jeopardize acquiring reliable sequence information. Furthermore, these methods suffer from sequence-dependent artifacts including band compression during size separation.

The technological advances in automated sequencing machines, fluorescently-labeled nucleotides, and detector systems, have improved the read lengths, and permit massively parallel sequencing runs for high throughput methods. But these procedures are still inadequate for large projects, like sequencing the human genome. The human genome contains approximately three billion bases of DNA sequence. Procedures that can sequence and analyze the human genome (or the genome of any organism) in a relatively short time span and at a reduced cost will make it feasible to deliver genomic information as part of a healthcare program which can prevent, diagnose, and treat disease.

The energy transfer system provided herein overcomes many problems associated with current nucleotide incorporation procedures. The energy transfer system requires minute amounts of target molecule with no amplification steps, there is no need to perform four separate nucleotide incorporation reactions, and the reactions are not size separated or loaded on a gel. The energy transfer system is a single molecule sequencing system which facilitates rapid, accurate, and real-time sequencing of long nucleic acid fragments.

SUMMARY

In one embodiment, the disclosed relates to methods for generating an energy transfer signal, comprising: contacting (i) a polymerase having altered nucleotide incorporation kinetics and linked to an energy transfer donor moiety with (ii) a nucleic acid molecule and with (iii) at least one type of a nucleotide having an energy transfer acceptor moiety, so as to incorporate the nucleotide into the nucleic acid molecule thereby locating the polymerase and nucleotide in close proximity with each other to generate the energy transfer signal.

In another embodiment, the disclosed relates to methods for generating an energy transfer signal comprising the steps of: contacting (i) a polymerase having altered nucleotide incorporation kinetics and linked to an energy transfer donor moiety with (ii) a nucleic acid molecule and with (iii) at least one type of a hexaphosphate nucleotide having an energy transfer acceptor moiety, so as to incorporate the nucleotide into the nucleic acid molecule thereby locating the polymerase and nucleotide in close proximity with each other to generate the energy transfer signal.

In another embodiment, the disclosed relates to methods for generating an energy transfer signal comprising the steps of: contacting (i) a polymerase having altered nucleotide incorporation kinetics and linked to an energy transfer donor moiety with (ii) a target nucleic acid molecule which is base-paired with a polymerization initiation site having a terminal 3' OH group and with (iii) at least one type of a nucleotide having an energy transfer acceptor moiety, so as to incorporate the nucleotide onto the terminal 3' OH group thereby locating the polymerase and nucleotide in close proximity with each other to generate the energy transfer signal.

In another embodiment, the disclosed relates to methods for generating an energy transfer signal comprising the steps of: contacting (i) a polymerase having altered nucleotide incorporation kinetics and linked to an energy transfer donor moiety with (ii) a target nucleic acid molecule which is base-paired with a polymerization initiation site having a terminal 3' OH group and with (iii) at least one type of a hexaphosphate nucleotide having an energy transfer acceptor moiety, so as to incorporate the nucleotide onto the terminal 3' OH group thereby locating the polymerase and nucleotide in close proximity with each other to generate the energy transfer signal.

DESCRIPTION OF THE DRAWINGS

FIG. 9C is a table that lists the number of active phi29 polymerases per polymerase-nanoparticle conjugate, obtained by applying the equation shown in FIG. 9B.

FIG. 10C is a table that lists the number of active B103 polymerases per polymerase-nanoparticle conjugate, obtained by applying the equation shown in FIG. 10B.

DETAILED DESCRIPTION

Figure 1:
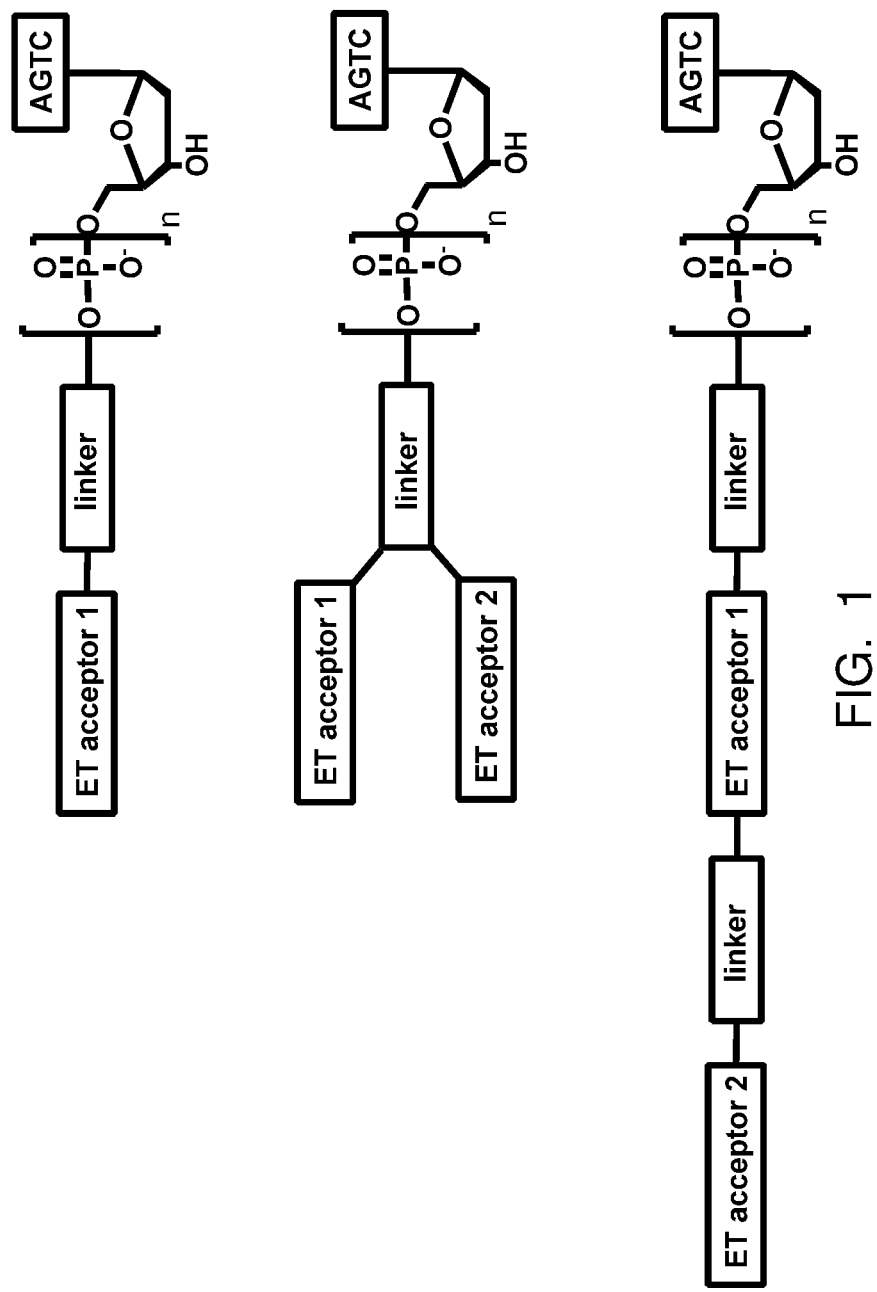
FIG. 1 illustrates non-limiting examples of the general structures of nucleotides linked with at least one energy transfer acceptor moiety.

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is explicitly or implicitly set forth herein that is contrary to or otherwise inconsistent with any definition set forth in the patents, patent applications, published applications, and other publications that are herein incorporated by reference, the definition and/or description set forth herein prevails over the definition that is incorporated by reference.

The practice of the present disclosure will employ, unless otherwise indicated, conventional techniques of molecular biology, microbiology and recombinant DNA techniques, which are within the skill of the art. Such techniques are explained fully in the literature. See, for example, Sambrook, J., and Russell, D. W., 2001, Molecular Cloning: A Laboratory Manual, Third Edition; Ausubel, F. M., et al., eds., 2002, Short Protocols In Molecular Biology, Fifth Edition.

As used herein, the terms "comprising" (and any form or variant of comprising, such as "comprise" and "comprises"), "having" (and any form or variant of having, such as "have" and "has"), "including" (and any form or variant of including, such as "includes" and "include"), or "containing" (and any form or variant of containing, such as "contains" and "contain"), are inclusive or open-ended and do not exclude additional, unrecited additives, components, integers, elements or method steps.

As used herein, the terms "a," "an," and "the" and similar referents used herein are to be construed to cover both the singular and the plural unless their usage in context indicates otherwise. Accordingly, the use of the word "a" or "an" when used in the claims or specification, including when used in conjunction with the term "comprising", may mean "one," but it is also consistent with the meaning of "one or more," "at least one," and "one or more than one."

As used herein, the terms "link", "linked", "linkage" and variants thereof comprise any type of fusion, bond, adherence or association that is of sufficient stability to withstand use in the particular biological application of interest. Such linkage can comprise, for example, covalent, ionic, hydrogen, dipole-dipole, hydrophilic, hydrophobic, or affinity bonding, bonds or associations involving van der Waals forces, mechanical bonding, and the like. Optionally, such linkage can occur between a combination of different molecules, including but not limited to: between a nanoparticle and a protein; between a protein and a label; between a linker and a functionalized nanoparticle; between a linker and a protein; between a nucleotide and a label; and the like. Some examples of linkages can be found, for example, in Hermanson, G., *Bioconjugate Techniques*, Second Edition (2008); Aslam, M., Dent, A., *Bioconjugation: Protein Cou-*

*pling Techniques for the Biomedical Sciences*, London: Macmillan (1998); Aslam, M., Dent, A., *Bioconjugation: Protein Coupling Techniques for the Biomedical Sciences*, London: Macmillan (1998).

As used herein, the term "linker" and its variants comprises any composition, including any molecular complex or molecular assembly that serves to link two or more compounds or molecules.

As used herein, the term "polymerase" and its variants comprise any enzyme that can catalyze the polymerization of nucleotides (including analogs thereof) into a nucleic acid strand. Typically but not necessarily such nucleotide polymerization can occur in a template-dependent fashion. Such polymerases can include without limitation naturally-occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids, or the linkage of parts of two or more polymerases. Typically, the polymerase comprises one or more active sites at which nucleotide binding and/or catalysis of nucleotide polymerization can occur. Some exemplary polymerases include without limitation DNA polymerases (such as for example Phi-29 DNA polymerase, reverse transcriptases and *E. coli* DNA polymerase) and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. One exemplary embodiment of such a polymerase is Phusion® DNA polymerase (New England Biolabs), which comprises a *Pyrococcus*-like polymerase fused to a processivity-enhancing domain as described, for example, in U.S. Pat. No. 6,627,424.

As used herein, the term "polymerase activity" and its variants, when used in reference to a given polymerase, comprises any in vivo or in vitro enzymatic activity characteristic of a given polymerase that relates to catalyzing the polymerization of nucleotides into a nucleic acid strand, e.g., primer extension activity, and the like. Typically, but not necessarily such nucleotide polymerization occurs in a template-dependent fashion. In addition to such polymerase activity, the polymerase can typically possess other enzymatic activities, for example, 3' to 5' or 5' to 3' exonuclease activity.

As used herein, the term "nucleotide" and its variants comprises any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally-occurring nucleotides but also any analogs, regardless of their structure, that can bind selectively to, or can be polymerized by, a polymerase. While naturally-occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. Some examples of nucleotide analogs are described in Xu, U.S. Pat. No. 7,405,281. In some embodiments, the nucleotide comprises a label (e.g., reporter moiety) and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group or substitute phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

As used herein, the term "nucleotide incorporation" and its variants comprises polymerization of one or more nucleotides into a nucleic acid strand.

As used herein, the term "biomolecule" and its variants comprises any compound isolated from a living organism, as well as analogs (including engineered and/or synthetic analogs), derivatives, mutants or variants and/or biologically active fragments of the same. For example, the biomolecule can be a protein (e.g., enzyme), nucleic acid, nucleotide, carbohydrate or lipid. In some embodiments, the biomolecule can be an engineered or synthetic analog of a compound isolated from a living cell that is structurally different from the compound but retains a biological activity characteristic of that compound.

As used herein, the term "target" and its variants comprises any compound that is capable of binding specifically to a particular biomolecule. In one exemplary embodiment, the target of an enzyme can be, for example, a substrate of the enzyme.

As used herein, the term "biological activity" and its variants, when used in reference to a biomolecule (such as, for example, an enzyme) refers to any in vivo or in vitro activity that is characteristic of the biomolecule itself, including the interaction of the biomolecule with one or more targets. For example, biological activity can optionally include the selective binding of an antibody to an antigen, the enzymatic activity of an enzyme, and the like. Such activity can also include, without limitation, binding, fusion, bond formation, association, approach, catalysis or chemical reaction, optionally with another biomolecule or with a target molecule.

As used herein, the term "biologically active fragment" and its variants refers to any fragment, derivative or analog of a biomolecule that possesses an in vivo or in vitro activity that is characteristic of the biomolecule itself. For example, the biomolecule can be an antibody that is characterized by antigen-binding activity, or an enzyme characterized by the ability to catalyze a particular biochemical reaction, etc. Biologically active fragments can optionally exist in vivo, such as, for example, fragments which arise from post transcriptional processing or which arise from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, insect or mammalian cells. Because biomolecules often exhibit a range of physiological properties and because such properties can be attributable to different portions of the biomolecule, a useful biologically active fragment can be a fragment of a biomolecule that exhibits a biological activity in any biological assay. In some embodiments, the fragment or analog possesses 10%, 40%, 60%, 70%, 80% or 90% or greater of the activity of the biomolecule in any in vivo or in vitro assay of interest.

The term "modification" or "modified" and their variants, as used herein with reference to a protein, comprise any change in the structural, biological and/or chemical properties of the protein, particularly a change in the amino acid sequence of the protein. In some embodiments, the modification can comprise one or more amino acid mutations, including without limitation amino acid additions, deletions and substitutions (including both conservative and non-conservative substitutions).

The terms "resonance energy transfer" and "RET" and their variants, as used herein, refer to a radiationless transmission of excitation energy from a first moiety, termed a donor moiety, to a second moiety termed an acceptor moiety. One type of RET includes Forster Resonance Energy Transfer (FRET), in which a fluorophore (the donor) in an excited state transfers its energy to a proximal molecule (the acceptor) by nonradiative dipole-dipole interaction. See, e.g., Forster, T. "Intermolecular Energy Migration and Fluorescence", *Ann. Phys.*, 2:55-75, 1948; Lakowicz, J. R., Principles of Fluorescence Spectroscopy, 2nd ed. Plenum, New York. 367-394, 1999. RET also comprises luminescence resonance energy transfer, bioluminescence resonance energy transfer, chemiluminescence resonance energy transfer, and similar types of energy transfer not strictly following the Forster's theory, such as nonoverlapping energy transfer occurring when nonoverlapping acceptors are utilized. See, for example, Anal. Chem. 2005, 77: 1483-1487.

The term "conservative" and its variants, as used herein with reference to any change in amino acid sequence, refers to an amino acid mutation wherein one or more amino acids is substituted by another amino acid having highly similar properties. For example, one or more amino acids comprising nonpolar or aliphatic side chains (for example, glycine, alanine, valine, leucine, isoleucine or proline) can be substituted for each other. Similarly, one or more amino acids comprising polar, uncharged side chains (for example, serine, threonine, cysteine, methionine, asparagine or glutamine) can be substituted for each other. Similarly, one or more amino acids comprising aromatic side chains (for example, phenylalanine, tyrosine or tryptophan) can be substituted for each other. Similarly, one or more amino acids comprising positively charged side chains (for example, lysine, arginine or histidine) can be substituted for each other. Similarly, one or more amino acids comprising negatively charged side chains (for example, aspartic acid or glutamic acid) can be substituted for each other. In some embodiments, the modified polymerase is a variant that comprises one or more of these conservative amino acid substitutions, or any combination thereof. In some embodiments, conservative substitutions for leucine include: alanine, isoleucine, valine, phenylalanine, tryptophan, methionine, and cysteine. In other embodiments, conservative substitutions for asparagine include: arginine, lysine, aspartate, glutamate, and glutamine.

The term "primer extension activity" and its variants, as used herein, when used in reference to a given polymerase, comprises any in vivo or in vitro enzymatic activity characteristic of a given polymerase that relates to catalyzing nucleotide incorporation onto the terminal 3'OH end of an extending nucleic acid molecule. Typically but not necessarily such nucleotide incorporation occurs in a template-dependent fashion. The primer extension activity is typically quantified as the total number of nucleotides incorporated (as measured by, e.g., radiometric or other suitable assay) by a unit amount of polymerase (in moles) per unit time (seconds) under a particular set of reaction conditions.

The terms "His tag" or "His-tag" and their variants as used herein refers to a stretch of amino acids comprising multiple histidine residues. Typically, the His tag can bind to metal ions, for example, $Zn^{2+}$, $Ni^{2+}$, $Co^{2+}$, or $Cu^{2+}$ ions. Optionally, the His tag comprises 2, 3, 4, 5, 6, 7, 8 or more histidine residues. In some embodiments, the His tag is fused to the N- or C-terminus of a protein; alternatively, it can be fused at any suitable location within the protein.

As used herein, the term "binding pair" or "binding partner" and its variants refers to two molecules, or portions thereof, which have a specific binding affinity for one another and typically will bind to each other in preference to binding to other molecules. Typically but not necessarily some or all of the structure of one member of a specific binding pair is complementary to some or all of the structure possessed by the other member, with the two members being able to bind together specifically by way of a bond between the complementary structures, optionally by virtue of multiple noncovalent attractions. The two members of a binding pair are referred to herein as the "first member" and the "second member" respectively. The following may be mentioned as non-limiting examples of molecules that can function as a member of a specific binding pair, without this being understood as any restriction: thyroxin-binding globulin, steroid-binding proteins, antibodies, antigens, haptens, enzymes, lectins, nucleic acids, repressors, oligonucleotides, polynucleotides, protein A, protein G, avidin, streptavidin, biotin, complement component C1q, nucleic acid-binding proteins, receptors, carbohydrates, complementary nucleic acid sequences, and the like. Examples of specific binding pairs include without limitation: an avidin moiety and a biotin moiety; an antigenic epitope and an antibody or immunogically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; and an oligonucleotide or polynucleotide and its corresponding complement.

As used herein, the term "biotin" and its variants comprises biotin (cis-hexahydro-2-oxo-1H-thieno[3,4]imidazole-4-pentanoic acid) and any derivatives and analogs thereof, including biotin-like compounds. Such compounds include, for example, biotin-e-N-lysine, biocytin hydrazide, amino or sulfhydryl derivatives of 2-iminobiotin and biotinyl-ε-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin, and the like. "Biotin moiety" also comprises biotin variants that can specifically bind to an avidin moiety.

The term "biotinylated" and its variants, as used herein, refer to any covalent or non-covalent adduct of biotin with other moieties such as biomolecules, e.g., proteins, nucleic acids (including DNA, RNA, DNA/RNA chimeric molecules, nucleic acid analogs and peptide nucleic acids), proteins (including enzymes, peptides and antibodies), carbohydrates, lipids, etc.

The terms "avidin" and "avidin moiety" and their variants, as used herein, comprises the native egg-white glycoprotein avidin, as well as any derivatives, analogs and other non-native forms of avidin, that can specifically bind to biotin moieties. In some embodiments, the avidin moiety can comprise deglycosylated forms of avidin, bacterial streptavidins produced by selected strains of *Streptomyces*, e.g., *Streptomyces avidinii*, to truncated streptavidins, and to recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin®, Captavidin®, Neutravidin® and Neutralite Avidin®. All forms of avidin-type molecules, including both native and recombinant avidin and streptavidin as well as derivatized molecules, e.g. nonglycosylated avidins, N-acyl avidins and truncated streptavidins, are encompassed within the terms "avidin" and "avidin moiety". Typically, but not necessarily, avidin exists as a tetrameric protein, wherein each of the four tetramers is capable of binding at least one biotin moiety.

As used herein, the term "biotin-avidin bond" and its variants refers to a specific linkage formed between a biotin moiety and an avidin moiety. Typically, a biotin moiety can bind with high affinity to an avidin moiety, with a dissociation constant $K_d$ typically in the order of $10^{-14}$ to $10^{-15}$ mol/L. Typically, such binding occurs via non-covalent interactions.

As used herein, the term "accessory compound" and its variants refer to any non-polymerase compound capable of attaching to a nanoparticle through one or more attachment sites. Optionally, the accessory compound can comprise a His tag.

As used herein, the term "modification enzyme recognition site" refers to an amino acid recognition sequence that is chemically modified in an enzyme-catalyzed reaction, wherein the enzyme catalyzing the reaction exhibits specificity for the amino acid recognition sequence. The amino acid recognition sequence may be inserted into a protein of interest, for example by conventional recombinant DNA techniques. Examples of modification enzyme recognition sites include, but are not limited to a biotin ligase modification site, for example a site comprising the amino acid sequence GLNDIFEAQKIEWHE (SEQ ID NO: 61), for introducing a biotin moiety; a protein kinase modification site, for example a site comprising the amino acid sequence LRRASLG (SEQ ID NO: 19), for introducing a phosphorothioate moiety; and a transglutaminase modification site, for example a site comprising the amino acid sequence PKPQQF (SEQ ID NO: 22), for introducing an amine moiety.

The terms "reporter" and "reporter moiety" and their variants, as used herein, refer to any moiety that generates, or causes to be generated, a detectable signal. Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. The reporter moiety generates, or causes to be generated, a detectable signal resulting from a chemical or physical change (e.g., heat, light, electrical, pH, salt concentration, enzymatic activity, or proximity events). A proximity event includes two reporter moieties approaching each other, or associating with each other, or binding each other. The appropriate procedures for detecting a signal, or change in the signal, generated by the reporter moiety are well known in the art. The reporter moieties can be linked to a solid surface, polymerase, nucleotide (or analog thereof), target nucleic acid molecule, or primer. In one embodiment, a nucleotide can be linked to a reporter moiety. The reporter moiety can generate a signal, or a change in a signal, upon excitation from an appropriated energy source (e.g., electromagnetic source). Some energy transfer reporter moieties can be optically or spectrally detectable.

The term "label" and its variants, as used herein, comprises any optically detectable moiety and includes any moiety that can be detected using, for example, fluorescence, luminescence and/or phosphoresecence spectroscopy, Raman scattering, or diffraction. Exemplary labels according to the present disclosure include fluorescent and luminescent moieties as well as quenchers thereof. Some typical labels include without limitation energy transfer moieties, nanoparticles and organic dyes.

Other objects, features and advantages of the disclosed compositions, methods, systems and kits will become apparent from the following detailed description. It should be understood, however, that the detailed description and the specific examples, while indicating specific embodiments, are given by way of illustration only, since various changes and modifications within the spirit and scope of the inventions provided herein will become apparent to those skilled in the art from this detailed description.

Provided herein are methods, compositions, systems and kits for nucleotide polymerization using energy transfer signals, or changes in energy transfer signals, from an energy transfer system which permits generating, detecting, measuring, and characterizing the energy transfer signals, which are associated with nucleotide polymerization, and permits identification of nucleotide binding and nucleotide incorporation events. The compositions and methods can permit accurate base identification for single molecule sequencing reactions.

The methods, compositions, systems and kits provided herein can be used for sequence-by-synthesis procedures for deducing the sequence of a target nucleic acid molecule. The methods permit detection and monitoring of nucleotide binding and nucleotide polymerization events. The systems comprise polymerases attached with an energy transfer donor moiety (or acceptor moiety), and nucleotides attached with at least one energy transfer acceptor moiety (or donor moiety). The donor and acceptor moieties undergo energy transfer when the polymerase and nucleotide are proximal to each other during nucleotide binding and/or nucleotide polymerization. As the donor and acceptor moieties undergo energy transfer, they generate an energy transfer signal (or a change in an energy transfer signal) which may correlate with nucleotide binding or polymerization. Detecting a time sequence of the generated energy transfer signals, or the change in the generated energy transfer signals, can be used to determine the order of the incorporated nucleotides, and can therefore be used to deduce the sequence of the target molecule.

Nucleotide Polymerization

Provided herein are methods, compositions, systems and kits for: nucleotide binding; nucleotide incorporation; nucleotide polymerization; generating an energy transfer signal which is associated with the proximity of the polymerase and nucleotide; generating an energy transfer signal which is associated with nucleotide incorporation; detecting an energy transfer signal which is associated with nucleotide incorporation; and identifying the energy transfer signal which is associated with nucleotide incorporation.

The methods include polymerase-dependent nucleotide polymerization in a continuous (i.e., asynchronous) manner. The compositions, systems, methods and kits comprise polymerases attached with at least one energy transfer donor moiety, and nucleotides attached with at least one energy transfer acceptor moiety. The donor and acceptor moieties undergo energy transfer when the polymerase and nucleotide are proximal to each other during nucleotide binding and/or nucleotide incorporation. As the donor and acceptor moieties undergo energy transfer, they generate an energy transfer signal (or a change in an energy transfer signal) which may correlate with nucleotide binding to the polymerase or with nucleotide incorporation during polymerization. Detecting the energy transfer signal, or change in the energy transfer signal, can be used to identify the incorporating nucleotide. Detecting a time sequence of the generated energy transfer signals, or the change in the generated energy transfer signals, from successive nucleotide incorporation events can be used to determine the order of the incorporated nucleotides, and can therefore be used to deduce the sequence of the target molecule. Nucleotide incorporation includes DNA polymerization and RNA polymerization.

By way of a non-limiting example of nucleotide polymerization, the steps or events of DNA polymerization are well known and comprise: (1) complementary base-pairing a target DNA molecule (e.g., a template molecule) with a DNA primer molecule having a terminal 3' OH (the terminal 3' OH provides the polymerization initiation site for DNA polymerase); (2) binding the base-paired target DNA/primer duplex with a DNA-dependent polymerase to form a complex (e.g., open complex); (3) a candidate nucleotide binds with the DNA polymerase which interrogates the candidate nucleotide for complementarity with the template nucleotide on the target DNA molecule; (4) the DNA polymerase may undergo a conformational change (e.g., to a closed complex if the candidate nucleotide is complementary); (5) the polymerase catalyzes nucleotide polymerization.

In one embodiment, the polymerase catalyzes nucleotide incorporation. For example, the polymerase catalyzes bond formation between the candidate nucleotide and the nucleotide at the terminal end of the polymerization initiation site. The polymerase can catalyze the terminal 3' OH of the primer exerting a nucleophilic attack on the bond between the $\alpha$ and $\beta$ phosphates of the candidate nucleotide to mediate a nucleotidyl transferase reaction resulting in phosphodiester bond formation between the terminal 3' end of the primer and the candidate nucleotide (i.e., nucleotide incorporation in a template-dependent manner), and concomitant cleavage to form a cleavage product. The polymerase can liberate the cleavage product. In some embodiments, where the polymerase incorporates a nucleotide having phosphate groups, the cleavage product includes one or more phosphate groups. In other embodiments, where the polymerase incorporates a nucleotide having substituted phosphate groups, the cleavage product may include one or more substituted phosphate groups.

The candidate nucleotide may or may not be complementary to the template nucleotide on the target molecule. The candidate nucleotide can dissociate from the polymerase. If the candidate nucleotide dissociates from the polymerase, it can be liberated and typically carries intact polyphosphate groups. When the candidate nucleotide dissociates from the DNA polymerase, the event is known as a "non-productive binding" event. The dissociating nucleotide may or may not be complementary to the template nucleotide on the target molecule.

The incorporated nucleotide may or may not be complementary to the template nucleotide on the target. When the candidate nucleotide binds the DNA polymerase and is incorporated, the event is a "productive binding" event. The incorporated nucleotide may or may not be complementary to the template nucleotide on the target molecule.

The length of time, frequency, or duration of the binding of the complementary candidate nucleotide to the polymerase can differ from that of the non-complementary candidate nucleotide. This time difference can be used to distinguish between the complementary and non-complementary nucleotides, and/or can be used to identify the incorporated nucleotide, and/or can be used to deduce the sequence of the target molecule.

The energy transfer signal (or change in energy transfer signal) generated by the energy transfer donor and/or acceptor can be detected before, during, and/or after any nucleotide incorporation event.

Nucleotide incorporation also includes RNA polymerization which may not require a primer to initiate nucleotide polymerization. Nucleotide incorporation events involving RNA polymerization are well known in the art.

Productive and Non-Productive Binding

The methods, compositions, systems and kits disclosed herein can be used for distinguishing between the productive and non-productive binding events. The compositions and methods can also provide base identity information during nucleotide incorporation. The compositions include nucleotides and polymerases each attached to at least one energy transfer moiety.

In a productive binding event, the nucleotide can bind/associate with the polymerase for a time period which is distinguishable (e.g., longer or shorter time period), compared to a non-productive binding event. In a non-productive binding event, the nucleotide can bind/associate with the polymerase and then dissociate. The donor and acceptor energy transfer moieties produce detectable energy transfer signals when they are in proximity to each other and can be associated with productive and non-productive binding events. Thus, the time-length difference between signals from the productive and non-productive binding events can provide distinction between the two types of events. Typically, the length of time for a productive binding event is longer compared the length of time for a non-productive event.

The detectable signals can be classified into true positive and false positive signals. For example, the true positive signals can arise from productive binding in which the nucleotide binds the polymerase and is incorporated. The incorporated nucleotide can be complementary to the template nucleotide. In another example, the false positive signals can arise from different binding events, including: non-specific binding, non-productive binding, and any event which brings the energy transfer donor and acceptor into sufficient proximity to induce a detectable signal, but the nucleotide is not incorporated.

Nucleotide Polymerization Reactions and Methods

The methods, compositions, systems and kits disclosed herein can be used for single molecule nucleic acid sequencing, by generating an energy transfer signal which is associated with nucleotide incorporation, detecting the generated energy transfer signal, measuring the generated energy transfer signal, characterizing the generated energy transfer signal, and identifying the incorporated nucleotide based on the characterized energy transfer signal.

Certain embodiments of the methods, composition, systems, and kits offer one or more advantages over other single molecule sequencing methods (see e.g., Korlach U.S. Pat. Nos. 7,033,764; 7,052,847; 7,056,661; 7,056,676; 7,361,466; and Hardin U.S. Pat. No. 7,329,492), although no individual embodiment necessarily displays all advantages. The advantages of the energy transfer system and methods include: (1) energy transfer methods, which require very small distances (about 5-10 nm) between the polymerase and nucleotide, to generate the energy transfer signals which are associated with the close proximity of the polymerase and nucleotide or are associated with nucleotide polymerization, rather than signals which are associated with non-productive binding events; (2) conjugates having a polymerase linked to an energy transfer moiety (e.g., donor moiety) in which the polymerase is enzymatically active; (3) polymerases having altered kinetics for nucleotide binding and/or nucleotide incorporation (e.g., U.S. Ser. Nos. 61/242,771 and 61/293,618) to improve distinction between productive and non-productive nucleotide binding events compared to polymerases traditionally used for nucleotide polymerization reactions; (4) polymerases having altered kinetics for nucleotide binding and/or nucleotide incorporation (e.g., U.S. Ser. Nos. 61/242,771 and 61/293,618) used in combination with labeled nucleotides having six or more phosphate groups (or substituted phosphate groups), which improve distinction between productive and non-productive binding events compared to polymerases and triphosphate nucleotides, which are traditionally used for nucleotide polymerization reactions; and (5) polymerases having improved photo-stability when exposed to electromagnetic energy (e.g., exposed to light during the nucleotide incorporation reactions) compared to polymerases traditionally used for nucleotide polymerization reactions.

The methods can be practiced using suitable conditions which mediate binding a nucleotide to the polymerase and/or which mediate nucleotide incorporation. The suitable conditions can include: any conjugate having a polymerase linked to at least one energy transfer moiety (e.g., donor moiety) in which the polymerase is enzymatically active; polymerases and/or nucleotides which improve distinction between productive and non-productive nucleotide binding events; and/or polymerases having improved photo-stability when exposed to electromagnetic energy (e.g., light).

The methods provided herein are performed under any conditions which are suitable for: forming the complex (target/polymerase or target/initiation site/polymerase); binding the nucleotide to the polymerase; permitting the energy transfer and reporter moieties to generate detectable energy transfer signals when the nucleotide binds the polymerase; incorporating the nucleotide; permitting the energy transfer and reporter moieties to generate an energy transfer signal upon close proximity and/or upon nucleotide binding or nucleotide incorporation; detecting the energy transfer signal, or change in the energy transfer signal, from the energy transfer or reporter moieties; measuring the energy transfer signal; and/or translocation of the polymerase to the next position on the target molecule.

The suitable conditions include parameters for time, temperature, pH, reagents, buffers, reagents, salts, co-factors, nucleotides, target DNA, primer DNA, enzymes such as nucleic acid-dependent polymerase, amounts and/or ratios of the components in the reactions, and the like. The reagents or buffers can include a source of monovalent cations, such as KCl, K-acetate, $NH_4$-acetate, K-glutamate, $NH_4Cl$, or ammonium sulfate. The reagents or buffers can include a source of divalent cations, such as $Mg^{2+}$ and/or $Mn^{2+}$, $MgCl_2$, or Mg-acetate. The buffer can include Tris, Tricine, HEPES, MOPS, ACES, or MES, which can provide a pH range of about 5.0 to about 9.5. The buffer can include chelating agents such as EDTA and EGTA, and the like. The suitable conditions can also include compounds which reduce photo-damage.

Divalent Cations

The methods, compositions, systems and kits disclosed herein can include any combination of divalent cations. The divalent cations can include any cation which permits nucleotide binding and/or nucleotide incorporation, including for example: manganese, magnesium, cobalt, strontium, or barium. The divalent cations can include any cation which promotes the formation and/or stability of the closed complex (polymerase/target/nucleotide), including magnesium, manganese, and chromium. The divalent cations can include any cation which permits nucleotide binding to the polymerase but inhibits nucleotide incorporation (e.g., calcium). The divalent cations can include chloride or acetate forms, including $MnCl_2$, Mn-acetate, $MgCl_2$, Mg-acetate, and the like.

In practicing the nucleotide incorporation methods, some polymerases exhibit improved nucleotide binding and/or nucleotide incorporation kinetics when used with (i) manganese and/or magnesium, and/or with (ii) tri-, tetra-, penta-, hexa-, or hepta-phosphate nucleotides. In one embodiment, the disclosed nucleotide incorporation methods can be practiced using manganese or magnesium, or a combination of manganese and magnesium. For example, the methods can include manganese at about 0.1-5 mM, or about 0.2-4 mM, or about 0.3-3 mM, or about 0.4-2 mM, or about 0.5-2 mM, or about 1-2 mM.

In another example, the methods can include magnesium at about 0.01-0.3 mM, or about 0.025-0.2 mM, or about 0.05-0.1 mM, or about 0.075-0.1 mM, or about 0.1 mM.

In yet another example, the methods can include a combination of manganese and magnesium at about 0.25-1 mM of manganese and 0.025-0.2 mM of magnesium, or about 0.5-0.75 mM of manganese and 0.05-0.075 mM of magnesium, or about 0.5 mM manganese and 0.1 mM magnesium.

In another example, the nucleotide incorporation reaction include B103 polymerase (SEQ ID NOS:1, 2 or 3) and labeled hexa-phosphate nucleotides, with about 0.5-2 mM $MnCl_2$, or with a combination of about 0.5 mM $MnCl_2$ and about 0.1 mM $MgCl_2$.

Polymerization Initiation Sites

The methods, compositions, systems and kits disclosed herein can include a polymerization initiation site. The polymerization initiation site can be used by the polymerase (e.g., DNA or RNA polymerase) to initiate nucleotide polymerization. In some embodiments, the polymerization initiation site can be a terminal 3' OH group. The 3' OH group can serve as a substrate for the polymerase for nucleotide polymerization. The 3' OH group can serve as a substrate for the polymerase to form a phosphodiester bond between the terminal 3' OH group and an incorporated nucleotide. The 3' OH group can be provided by: the terminal end of a primer molecule; a nick or gap within a nucleic acid molecule (e.g., oligonucleotide) which is base-paired with the target molecule; the terminal end of a secondary structure (e.g., the end of a hairpin-like structure); or an origin of replication. The polymerization initiation site can be provided by an accessory protein (e.g., RNA polymerase or helicase/primase). The polymerization initiation site can be provided by a terminal protein which can be bound (covalently or non-covalently) to the end of the target nucleic acid, including terminal protein (e.g., TP) found in phage (e.g., TP from phi29 phage). Thus, the polymerization initiation site may be at a terminal end or within a base-paired nucleic acid molecule. In other embodiments, the polymerization initiation site used by some polymerases (e.g., RNA polymerase) may not include a 3'OH group.

The portion of the target molecule which is base paired with the primer or with the oligonucleotide, or the self-primed portion of the target molecule, can form hydrogen bonding by Watson-Crick or Hoogstein binding to form a duplex nucleic acid structure. The primer, oligonucleotide, and self-priming sequence may be complementary, or partially complementary, to the nucleotide sequence of the target molecule. The complementary base pairing can be the standard A-T or C-G base pairing, or can be other forms of base-pairing interactions.

The polymerization initiation site can be in a position on the target nucleic acid molecule to permit nucleotide incorporation events in a direction away from, or towards, the solid surface.

Some polymerases exhibit a preference for binding single-stranded nucleic acid molecules. For example, multiple polymerases may preferentially bind the single-stranded portion of a target nucleic acid molecule which is base-paired with a primer. In cases where one target molecule is bound by multiple polymerases, the efficiency of polymerization initiation can be poor. Initiating nucleotide polymerization using a gap can improve the number of target nucleic acid molecules which can undergo polymerization. In one embodiment, an unexpected procedure for improving a nucleotide polymerization can include initiating the polymerization reaction with the terminal 3'OH within a gap, rather than from a primer (which is base-paired with the target molecule). In one embodiment, the polymerases which can initiate nucleotide polymerization from a gap include strand-displacing polymerases. For example, the strand-displacing polymerase can be a phi29-like polymerases including: phi29, B103 (SEQ ID NO:1, 2 or 3), and GA-1. In one embodiment, the gap can be the length of a polynucleotide molecule which is about 2-15 nucleotides in length, or about 3-14 in length, or about 4-13 in length, or about 5-12 in length, or about 6-11 in length, or about 7-10 in length. The gap can be formed by annealing a target nucleic acid molecule to two primer nucleic acid molecules. Forming a gap is well known in the art.

Primer Molecules

The methods, compositions, systems and kits disclosed herein can include a primer molecule which can hybridize with the target nucleic acid molecule. The sequence of the primer molecule can be complementary or non-complementary with the sequence of the sequence of the target molecule. The terminal 3' OH of the primer molecule can provide the polymerization initiation site.

The primers can be modified with a chemical moiety to protect the primer from serving as a polymerization initiation site or as a restriction enzyme recognition site. The chemical moiety can be a natural or synthetic amino acid linked through an amide bond to the primer.

The primer, oligonucleotide, or self-priming portion, may be naturally-occurring, or may be produced using enzymatic or chemical synthesis methods. The primer, oligonucleotide, or self-priming portion may be any suitable length including 5, 10, 15, 20, 25, 30, 40, 50, 75, or 100 nucleotides or longer in length. The primer, oligonucleotide, or self-priming portion may be linked to an energy transfer moiety (e.g., donor or acceptor) or to a reporter moiety (e.g., a dye) using methods well known in the art.

The primer molecule, oligonucleotide, and self-priming portion of the target molecule, may comprise ribonucleotides, deoxyribonucleotides, ribonucleotides, deoxyribonucleotides, peptide nucleotides, modified phosphate-sugar backbone nucleotides including phosphorothioate and phosphoramidate, metallonucleosides, phosphonate nucleosides, and any variants thereof, or combinations thereof.

In one embodiment, the primer molecule can be a recombinant DNA molecule. The primer can be linked at the 5' or 3' end, or internally, with at least one binding partner, such as biotin. The biotin can be used to immobilize the primer molecule to the surface (via an avidin-like molecule), or for attaching the primer to a reporter moiety. The primer can be linked to at least one energy transfer moiety, such as a fluorescent dye or a nanoparticle, or to a reporter moiety. The primer molecule can hybridize to the target nucleic acid molecule. The primer molecule can be used as a capture probe to immobilize the target molecule.

Reducing Photo-Damage

The methods, compositions, systems and kits disclosed herein can include compounds which reduce oxygen-damage or photo-damage. Illuminating the nucleotide binding and/or nucleotide incorporation reactions with electromagnetic radiation can induce formation of reactive oxygen species from the fluorophore or other components in the reaction. The reactive oxygen species can cause photo-damage to the fluorophores, polymerases, or any other component of the binding or incorporation reactions. The nucleotide binding or nucleotide incorporation reactions can include compounds which are capable of reducing photo-damage, including: protocatechuate-3,4-dioxygenase, protocatechuic acid; 6-Hydroxy-2,5,7,8-tetramethylchroman-2-carboxylic Acid (TROLOX); or cyclooctatetraene (COT).

Other compounds for reducing photo-damage include: ascorbic acid, astazanthin, bilirubin, biliverdin, bixin, captopril, canthazanthin, carotene (alpha, beta, and gamma), cysteine, beta-dimethyl cysteine, N-acetyl cysteine, diazobicyclooctane (DABCO), dithiothreitol (DTT), ergothioneine, glucose oxidase/catalase (GO/Cat), glutathione, glutathione peroxidase, hydrazine ($N_2H_4$), hydroxylamine, lycopene, lutein, polyene dialdehydes, melatonin, methionine, mercaptopropionylglycine, 2-mercaptoethane sulfonate (MESNA), pyridoxinel and its derivatives, mercaptoethylamine (MEA), β-mercaptoethanol (BME), n-propyl gallate, p-phenylenediamene (PPD), hydroquinone, sodium azide (NaN$_3$), sodium sulfite (Na$_2$SO$_3$), superoxide dismutase, tocopherols, α-tocopheryl succinate and its analogs, and zeaxanthin.

Methods for Generating an Energy Transfer Signal: Proximity

The methods, compositions, systems and kits disclosed herein can be used for generating a signal which is associated with close proximity of the polymerase and nucleotide.

Provided herein are methods for generating an energy transfer signal comprising the steps of: contacting (i) a polymerase having altered nucleotide incorporation kinetics and linked to an energy transfer donor moiety with (ii) a nucleic acid molecule and with (iii) at least one type of a nucleotide having an energy transfer acceptor moiety, so as to incorporate the nucleotide into the nucleic acid molecule thereby locating the polymerase and nucleotide in close proximity with each other to generate the energy transfer signal.

Provided herein are methods for generating an energy transfer signal comprising the steps of: contacting (i) a polymerase having altered nucleotide incorporation kinetics and linked to an energy transfer donor moiety with (ii) a nucleic acid molecule and with (iii) at least one type of a hexaphosphate nucleotide having an energy transfer acceptor moiety, so as to incorporate the hexaphosphate nucleotide into the nucleic acid molecule thereby locating the polymerase and nucleotide in close proximity with each other to generate the energy transfer signal.

Provided herein are methods for generating an energy transfer signal comprising the steps of: contacting (i) a polymerase having altered nucleotide incorporation kinetics and linked to an energy transfer donor moiety with (ii) a target nucleic acid molecule which is base-paired with a polymerization initiation site having a 3' OH group and with (iii) at least one type of a nucleotide having an energy transfer acceptor moiety, so as to incorporate the nucleotide onto the 3' OH group thereby locating the polymerase and nucleotide in close proximity with each other to generate the energy transfer signal.

Provided herein are methods for generating an energy transfer signal comprising the steps of: contacting (i) a polymerase having altered nucleotide incorporation kinetics and linked to an energy transfer donor moiety with (ii) a target nucleic acid molecule which is base-paired with a polymerization initiation site having a 3' OH group and with (iii) at least one type of a hexaphosphate nucleotide having an energy transfer acceptor moiety, so as to incorporate the hexaphosphate nucleotide onto the 3' OH group thereby locating the polymerase and nucleotide in close proximity with each other to generate the energy transfer signal.

Provided herein are methods for generating an energy transfer signal comprising the steps of: contacting (i) a polymerase having an energy transfer donor nanoparticle with (ii) a nucleic acid molecule and with (iii) at least one type of a nucleotide having an energy transfer acceptor moiety, so as to incorporate the nucleotide into the nucleic acid molecule thereby locating the polymerase and nucleotide in close proximity with each other to generate the energy transfer signal.

Provided herein are methods for generating an energy transfer signal comprising the steps of: contacting (i) a polymerase having an energy transfer donor nanoparticle with (ii) a nucleic acid molecule and with (iii) at least one type of a hexaphosphate nucleotide having an energy transfer acceptor moiety, so as to incorporate the hexaphosphate nucleotide into the nucleic acid molecule thereby locating the polymerase and nucleotide in close proximity with each other to generate the energy transfer signal.

Provided herein are methods for generating an energy transfer signal comprising the steps of: contacting (i) a polymerase having an energy transfer donor nanoparticle with (ii) a target nucleic acid molecule which is base-paired with a polymerization initiation site having a 3' OH group and with (iii) at least one type of a nucleotide having an energy transfer acceptor moiety, so as to incorporate the nucleotide onto the 3' OH group thereby locating the polymerase and nucleotide in close proximity with each other to generate the energy transfer signal.

Provided herein are methods for generating an energy transfer signal comprising the steps of: contacting (i) a polymerase having an energy transfer donor nanoparticle with (ii) a target nucleic acid molecule which is base-paired with a polymerization initiation site having a 3' OH group and with (iii) at least one type of a hexaphosphate nucleotide having an energy transfer acceptor moiety, so as to incorporate the hexaphosphate nucleotide onto the 3' OH group thereby locating the polymerase and nucleotide in close proximity with each other to generate the energy transfer signal.

Provided herein are methods for generating an energy transfer signal comprising the steps of: contacting (i) a polymerase according to any one of SEQ ID NO:1-3 and linked to an energy transfer donor moiety with (ii) a nucleic acid molecule and with (iii) at least one type of a hexaphosphate nucleotide linked to an energy transfer acceptor moiety, so as to incorporate the hexaphosphate nucleotide into the nucleic acid molecule thereby locating the polymerase and nucleotide in close proximity with each other to generate the energy transfer signal.

Detecting the Energy Transfer Signal

In one embodiment, additional steps can be conducted to detect the energy transfer signal or the change in the energy transfer signal. The additional steps comprise: (a) exciting the energy transfer donor moiety with an excitation source; and (b) detecting the energy transfer signal or a change in the energy transfer signal from the energy transfer donor moiety and the energy transfer acceptor moiety that are in close proximity to each other.

In one embodiment, the excitation source can be electromagnetic energy. In another embodiment, the excitation source can be a laser. In another embodiment, the energy transfer signal or the change in the energy transfer signal is a FRET signal. In yet another embodiment, the energy transfer signal or the change in the energy transfer signal can be optically detectable.

Identifying the Incorporated Nucleotide

In another embodiment, additional steps can be conducted to identify the energy transfer signal, which can also identify the incorporated nucleotide. The additional steps comprise: (a) exciting the energy transfer donor moiety with an excitation source; (b) detecting the energy transfer signal or a change in the energy transfer signal from the energy transfer donor moiety and the energy transfer acceptor moiety that are in close proximity to each other; and (c) identifying the energy transfer signal or the change in the energy transfer signal from the energy transfer accepter moiety.

In one embodiment, the excitation source can be electromagnetic energy. In another embodiment, the excitation source can be a laser. In another embodiment, the energy transfer signal or the change in the energy transfer signal is a FRET signal. In yet another embodiment, the energy transfer signal or the change in the energy transfer signal can be optically detectable.

Embodiments of Methods for Generating an Energy Transfer Signal: Proximity

In methods for generating an energy transfer signal, in one embodiment, the energy transfer donor and acceptor moieties can fluoresce in response to exposure to an excitation source, such as electromagnetic radiation. These fluorescence responses can be an energy transfer signal. In another embodiment, the energy transfer acceptor moiety can fluoresce in response to energy transferred from a proximal excited energy transfer donor moiety. These fluorescence responses can be an energy transfer signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the energy transfer signals from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the energy transfer signal can include a change in the ratio of the change of the energy transfer donor signal relative to change of the energy transfer acceptor signals. In another embodiment, the energy transfer signal from the donor can increase or decrease. In another embodiment, the energy transfer signal from the acceptor can increase or decrease. In another embodiment, the energy transfer signal associated with nucleotide incorporation includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

In one embodiment, the detecting the energy transfer signal can be performed using confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

In practicing the nucleotide binding and/or nucleotide incorporation methods, non-desirable fluorescent signals can come from sources including background and/or noise. In one embodiment, the energy transfer signals can be distinguished from the non-desirable fluorescent signals by measuring, analyzing and characterizing attributes of all fluorescent signals generated by the nucleotide incorporation reaction. In one embodiment, attributes of the energy transfer signal that can permit distinction from the non-desirable fluorescent signals can include: duration; wavelength; amplitude; photon count; and/or the rate of change of the duration, wavelength, amplitude; and/or photon count. In one embodiment, the identifying the energy transfer signal, includes measuring, analyzing and characterizing attributes of: duration; wavelength; amplitude; photon count and/or the rate of change of the duration, wavelength, amplitude; and/or photon count. In one embodiment, identifying the energy transfer signal can be used to identify the incorporated nucleotide.

In one embodiment, the nucleic acid molecule can be DNA, RNA or DNA/RNA.

In one embodiment, the polymerase has an active site. The nucleotide can bind the active site. In another embodiment, the polymerase can be a DNA-dependent or RNA-dependent polymerase, or a reverse transcriptase. In another embodiment, the polymerase having altered nucleotide binding and/or nucleotide incorporation kinetics can improve distinction between productive and non-productive binding events. In another embodiment, the altered nucleotide binding kinetics and/or altered nucleotide incorporation kinetics can include altered kinetics for: polymerase binding to the target molecule; polymerase binding to the nucleotide; polymerase catalyzing nucleotide incorporation; the polymerase cleaving the nucleotide and forming a cleavage product; and/or the polymerase releasing the cleavage product. In another embodiment, the polymerase can be linked to an energy transfer donor moiety to form a conjugate. In another embodiment, the polymerase component of the conjugate can be enzymatically active. In another embodiment, the polymerase has altered kinetics for nucleotide binding and/or nucleotide incorporation used in combination with labeled nucleotides having six or more phosphate groups (or substituted phosphate groups), which improve distinction between productive and non-productive binding events. In another embodiment, the polymerase can have improved photo-stability. The polymerase can be a Phi29-like polymerase, including Phi29 or B103 polymerase. The polymerase can be a mutant polymerase. The polymerase can be a B103 polymerase according to any one of SEQ ID NOS: 1-5.

In one embodiment, the energy transfer donor moiety can be a nanoparticle or a fluorescent dye. The nanoparticle can be about 1-20 nm in its largest dimensions. The nanoparticle can be a core/shell nanoparticle. The nanoparticle can include a core comprising semiconductor material(s). The core can include materials (including binary, ternary and quaternary mixtures thereof), from: Groups II-VI of the periodic table, including ZnS, ZnSe, ZnTe, CdS, CdSe, CdTe, HgS, HgSe, HgTe, MgTe; Groups III-V, including GaN, GaP, GaAs, GaSb, InN, InP, InAs, InSb, AlAs, AlP, AlSb, AlS; and/or Group IV, including Ge, Si, Pb. The nanoparticle can include at least one shell surrounding the core. The shell can include semiconductor material(s). The nanoparticle can include an inner shell and an outer shell. The shell can include materials (including binary, ternary and quaternary mixtures thereof) comprising: ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, or AlSb. In one embodiment, the nanoparticle comprises a core having CdSe. In another embodiment, the nanoparticle comprises an inner shell having CdS. In another embodiment, the nanoparticle comprises an outer shell having ZnS. The outermost surface of the core or shell can be coated with tightly associated ligands which are not removed by ordinary solvation. In some embodiments, the nanoparticle can have a layer of ligands on its surface which can further be cross-linked to each other. In some embodiments, the nanoparticle can have other or additional surface coatings which can modify the properties of the particle, for example, increasing or decreasing solubility in water or other solvents. The nanoparticle can be water dispersible. The nanoparticle can be a non-blinking nanoparticle. The nanoparticle can be photo-stable. The nanoparticle may not interfere with polymerase activity, including polymerase binding to the target molecule, polymerase binding to the nucleotide, polymerase catalyzing nucleotide incorporation, or the polymerase cleaving the nucleotide and/or releasing the cleavage product.

In one embodiment, the target nucleic acid molecule can be DNA or RNA or DNA/RNA molecule. In another embodiment, the target nucleic acid molecule is a single nucleic acid molecule. In another embodiment, the target nucleic acid molecule (e.g., target molecule) is base-paired with a polymerization initiation site. In another embodiment, the polymerization initiation site is a terminal 3'OH of a primer molecule or of a self-primed target molecule. In another embodiment, the polymerization initiation site is a 3'OH within a gap or nick. In another embodiment, the target nucleic acid molecule and/or the polymerization initiation site is immobilized to a solid surface. In another embodiment, the target nucleic acid molecule is a linear or circular nucleic acid molecule.

In one embodiment, the at least one type of nucleotide can include 3-10 phosphate groups or substituted phosphate groups, or a combination of phosphate groups and substituted phosphate groups. The nucleotide can include a terminal phosphate group or terminal substituted phosphate group which can be linked to the energy transfer acceptor moiety. The nucleotide can include the energy transfer acceptor moiety which is linked the base, sugar, or any phosphate group or substituted phosphate group. The nucleotide can be adenosine, guanosine, cytosine, thymidine, uridine, or any other type of nucleotide.

In one embodiment, the energy transfer acceptor moiety can be a fluorescent dye. The energy transfer acceptor moiety and the energy transfer donor moiety can be capable of energy transfer.

In one embodiment, more than one type of nucleotide can be contacted with the polymerase. Each of the different types of nucleotides can be linked to the same or to different types of energy transfer acceptor moieties, or any combination of the same or different types of acceptor moieties.

Methods for Generating an Energy Transfer Signal: Nucleotide Incorporation

Provided herein are methods for generating an energy transfer signal comprising the steps of: contacting (i) a polymerase having altered nucleotide incorporation kinetics and linked to an energy transfer donor moiety with (ii) a nucleic acid molecule and with (iii) at least one type of a nucleotide having an energy transfer acceptor moiety, so as to incorporate the nucleotide into the nucleic acid molecule thereby generating the energy transfer signal.

Provided herein are methods for generating an energy transfer signal comprising the steps of: contacting (i) a polymerase having altered nucleotide incorporation kinetics and linked to an energy transfer donor moiety with (ii) a nucleic acid molecule and with (iii) at least one type of a hexaphosphate nucleotide having an energy transfer acceptor moiety, so as to incorporate the hexaphosphate nucleotide into the nucleic acid molecule thereby generating the energy transfer signal.

Provided herein are methods for generating an energy transfer signal comprising the steps of: contacting (i) a polymerase having altered nucleotide incorporation kinetics and linked to an energy transfer donor moiety with (ii) a target nucleic acid molecule which is base-paired with a polymerization initiation site having a 3' OH group and with (iii) at least one type of a nucleotide having an energy transfer acceptor moiety, so as to incorporate the nucleotide onto the 3' OH group thereby generating the energy transfer signal.

Provided herein are methods for generating an energy transfer signal comprising the steps of: contacting (i) a polymerase having altered nucleotide incorporation kinetics and linked to an energy transfer donor moiety with (ii) a target nucleic acid molecule which is base-paired with a polymerization initiation site having a 3' OH group and with (iii) at least one type of a hexaphosphate nucleotide having an energy transfer acceptor moiety, so as to incorporate the hexaphosphate nucleotide onto the 3' OH group thereby generating the energy transfer signal.

Provided herein are methods for generating an energy transfer signal comprising the steps of: contacting (i) a polymerase having an energy transfer donor nanoparticle with (ii) a nucleic acid molecule and with (iii) at least one type of a nucleotide having an energy transfer acceptor moiety, so as to incorporate the nucleotide into the nucleic acid molecule thereby generating the energy transfer signal.

Provided herein are methods for generating an energy transfer signal comprising the steps of: contacting (i) a polymerase having an energy transfer donor nanoparticle with (ii) a nucleic acid molecule and with (iii) at least one type of a hexaphosphate nucleotide having an energy transfer acceptor moiety, so as to incorporate the hexaphosphate nucleotide into the nucleic acid molecule thereby generating the energy transfer signal.

Provided herein are methods for generating an energy transfer signal comprising the steps of: contacting (i) a polymerase having an energy transfer donor nanoparticle with (ii) a target nucleic acid molecule which is base-paired with a polymerization initiation site having a 3' OH group and with (iii) at least one type of a nucleotide having an energy transfer acceptor moiety, so as to incorporate the nucleotide onto the 3' OH group thereby generating the energy transfer signal.

Provided herein are methods for generating an energy transfer signal comprising the steps of: contacting (i) a polymerase having an energy transfer donor nanoparticle with (ii) a target nucleic acid molecule which is base-paired with a polymerization initiation site having a 3' OH group and with (iii) at least one type of a hexaphosphate nucleotide having an energy transfer acceptor moiety, so as to incorporate the hexaphosphate nucleotide onto the 3' OH group thereby generating the energy transfer signal.

Provided herein are methods for generating an energy transfer signal comprising the steps of: contacting (i) a polymerase according to any one of SEQ ID NOS:1-3 and linked to an energy transfer donor moiety with (ii) a nucleic acid molecule and with (iii) at least one type of a hexaphosphate nucleotide linked to an energy transfer acceptor moiety, so as to incorporate the hexaphosphate nucleotide into the nucleic acid molecule thereby generating the energy transfer signal.

Detecting the Energy Transfer Signal

In one embodiment, additional steps can be conducted to detect the energy transfer signal or the change in the energy transfer signal. The additional steps comprise: (a) exciting the energy transfer donor moiety with an excitation source; and (b) detecting the energy transfer signal or a change in the energy transfer signal from the energy transfer donor moiety and the energy transfer acceptor moiety that are in close proximity to each other.

In one embodiment, the excitation source can be electromagnetic energy. In another embodiment, the excitation source can be a laser. In another embodiment, the energy transfer signal or the change in the energy transfer signal is a FRET signal. In yet another embodiment, the energy transfer signal or the change in the energy transfer signal can be optically detectable.

Identifying the Incorporated Nucleotide

In another embodiment, additional steps can be conducted to identify the incorporated nucleotide. The additional steps comprise: (a) exciting the energy transfer donor moiety with an excitation source; (b) detecting the energy transfer signal or a change in the energy transfer signal from the energy transfer donor moiety and the energy transfer acceptor moiety that are in close proximity to each other; and (c) identifying the energy transfer signal or the change in the energy transfer signal from the energy transfer accepter moiety.

In one embodiment, the excitation source can be electromagnetic energy. In another embodiment, the excitation source can be a laser. In another embodiment, the energy transfer signal or the change in the energy transfer signal is a FRET signal. In yet another embodiment, the energy transfer signal or the change in the energy transfer signal can be optically detectable.

Embodiments of Methods for Generating an Energy Transfer Signal:

Nucleotide Incorporation:

In methods for generating an energy transfer signal, in one embodiment, the energy transfer donor and acceptor moieties can fluoresce in response to exposure to an excitation source, such as electromagnetic radiation. These fluorescence responses can be an energy transfer signal. In another embodiment, the energy transfer acceptor moiety can fluoresce in response to energy transferred from a proximal excited energy transfer donor moiety. These fluorescence responses can be an energy transfer signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the energy transfer signals from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the energy transfer signal can include a change in the ratio of the change of the energy transfer donor signal relative to change of the energy transfer acceptor signals. In another embodiment, the energy transfer signal from the donor can increase or decrease. In another embodiment, the energy transfer signal from the acceptor can increase or decrease. In another embodiment, the energy transfer signal associated with nucleotide incorporation includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

In one embodiment, the detecting the energy transfer signal can be performed using confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

In practicing the nucleotide binding and/or nucleotide incorporation methods, non-desirable fluorescent signals can come from sources including background and/or noise. In one embodiment, the energy transfer signals can be distinguished from the non-desirable fluorescent signals by measuring, analyzing and characterizing attributes of all fluorescent signals generated by the nucleotide incorporation reaction. In one embodiment, attributes of the energy transfer signal that can permit distinction from the non-desirable fluorescent signals can include: duration; wavelength; amplitude; photon count; and/or the rate of change of the duration, wavelength, amplitude; and/or photon count. In one embodiment, the identifying the energy transfer signal, includes measuring, analyzing and characterizing attributes of: duration; wavelength; amplitude; photon count and/or the rate of change of the duration, wavelength, amplitude; and/or photon count. In one embodiment, identifying the energy transfer signal can be used to identify the incorporated nucleotide.

In one embodiment, the nucleic acid molecule can be DNA, RNA or DNA/RNA.

In one embodiment, the polymerase has an active site. The nucleotide can bind the active site. In another embodiment, the polymerase can be a DNA-dependent or RNA-dependent polymerase, or a reverse transcriptase. In another embodiment, the polymerase having altered nucleotide binding and/or nucleotide incorporation kinetics can improve distinction between productive and non-productive binding events. In another embodiment, the altered nucleotide binding kinetics and/or altered nucleotide incorporation kinetics can include altered kinetics for: polymerase binding to the target molecule; polymerase binding to the nucleotide; polymerase catalyzing nucleotide incorporation; the polymerase cleaving the nucleotide and forming a cleavage product; and/or the polymerase releasing the cleavage product. In another embodiment, the polymerase can be linked to an energy transfer donor moiety to form a conjugate. In another embodiment, the polymerase component of the conjugate can be enzymatically active. In another embodiment, the polymerase has altered kinetics for nucleotide binding and/or nucleotide incorporation used in combination with labeled nucleotides having six or more phosphate groups (or substituted phosphate groups), which improve distinction between productive and non-productive binding events. In another embodiment, the polymerase can have improved photo-stability. The polymerase can be a Phi29-like polymerase, including Phi29 or B103 polymerase. The polymerase can be a mutant polymerase. The polymerase can be a B103 polymerase according to any one of SEQ ID NOS: 1-5.

In one embodiment, the energy transfer donor moiety can be a nanoparticle or a fluorescent dye. The nanoparticle can be about 1-20 nm in its largest dimensions. The nanoparticle can be a core/shell nanoparticle. The nanoparticle can include a core comprising semiconductor material(s). The core can include materials (including binary, ternary and quaternary mixtures thereof), from: Groups II-VI of the periodic table, including ZnS, ZnSe, ZnTe, CdS, CdSe, CdTe, HgS, HgSe, HgTe, MgTe; Groups III-V, including GaN, GaP, GaAs, GaSb, InN, InP, InAs, InSb, AlAs, AlP, AlSb, AlS; and/or Group IV, including Ge, Si, Pb. The nanoparticle can include at least one shell surrounding the core. The shell can include semiconductor material(s). The nanoparticle can include an inner shell and an outer shell. The shell can include materials (including binary, ternary and quaternary mixtures thereof) comprising: ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, or AlSb. In one embodiment, the nanoparticle comprises a core having CdSe. In another embodiment, the nanoparticle comprises an inner shell having CdS. In another embodiment, the nanoparticle comprises an outer shell having ZnS. The outermost surface of the core or shell can be coated with tightly associated ligands which are not removed by ordinary solvation. In some embodiments, the nanoparticle can have a layer of ligands on its surface which can further be cross-linked to each other. In some embodiments, the nanoparticle can have other or additional surface coatings which can modify the properties of the particle, for example, increasing or decreasing solubility in water or other solvents. The nanoparticle can be water dispersible. The nanoparticle can be a non-blinking nanoparticle. The nanoparticle can be photo-stable. The nanoparticle may not interfere with polymerase activity, including polymerase binding to the target molecule, polymerase binding to the nucleotide, polymerase catalyzing nucleotide incorporation, or the polymerase cleaving the nucleotide and/or releasing the cleavage product.

In one embodiment, the target nucleic acid molecule can be DNA or RNA or DNA/RNA molecule. In another embodiment, the target nucleic acid molecule is a single nucleic acid molecule. In another embodiment, the target nucleic acid molecule (e.g., target molecule) is base-paired with a polymerization initiation site. In another embodiment, the polymerization initiation site is a terminal 3'OH of a primer molecule or of a self-primed target molecule. In another embodiment, the polymerization initiation site is a 3'OH within a gap or nick. In another embodiment, the target nucleic acid molecule and/or the polymerization initiation site is immobilized to a solid surface. In another embodiment, the target nucleic acid molecule is a linear or circular nucleic acid molecule.

In one embodiment, the at least one type of nucleotide can include 3-10 phosphate groups or substituted phosphate groups, or a combination of phosphate groups and substituted phosphate groups. The nucleotide can include a terminal phosphate group or terminal substituted phosphate group which can be linked to the energy transfer acceptor moiety. The nucleotide can include the energy transfer acceptor moiety which is linked the base, sugar, or any phosphate group or substituted phosphate group. The nucleotide can be adenosine, guanosine, cytosine, thymidine, uridine, or any other type of nucleotide.

In one embodiment, the energy transfer acceptor moiety can be a fluorescent dye. The energy transfer acceptor moiety and the energy transfer donor moiety can be capable of energy transfer.

In one embodiment, more than one type of nucleotide can be contacted with the polymerase. Each of the different types of nucleotides can be linked to the same or to different types of energy transfer acceptor moieties, or any combination of the same or different types of acceptor moieties.

Methods for Incorporating Nucleotides

The methods, compositions, systems and kits disclosed herein can be used for incorporating nucleotides. Provided herein are methods for incorporating a nucleotide, comprising: contacting (i) a polymerase having altered nucleotide incorporation kinetics and linked to an energy transfer donor moiety with (ii) a nucleic acid molecule and with (iii) at least one type of a nucleotide having an energy transfer acceptor moiety, so as to incorporate the nucleotide into the nucleic acid molecule. In one embodiment, the nucleic acid molecule includes a polymerization initiation site having a 3' OH group.

Provided herein are methods for incorporating a nucleotide comprising the steps of: contacting (i) a polymerase having altered nucleotide incorporation kinetics and linked to an energy transfer donor moiety with (ii) a nucleic acid molecule and with (iii) at least one type of a nucleotide having an energy transfer acceptor moiety, so as to incorporate the nucleotide into the nucleic acid molecule.

Provided herein are methods for incorporating a nucleotide comprising the steps of: contacting (i) a polymerase having altered nucleotide incorporation kinetics and linked to an energy transfer donor moiety with (ii) a nucleic acid molecule and with (iii) at least one type of a hexaphosphate nucleotide having an energy transfer acceptor moiety, so as to incorporate the hexaphosphate nucleotide into the nucleic acid molecule.

Provided herein are methods for incorporating a nucleotide comprising the steps of: contacting (i) a polymerase having altered nucleotide incorporation kinetics and linked to an energy transfer donor moiety with (ii) a target nucleic acid molecule which is base-paired with a polymerization initiation site having a 3' OH group and with (iii) at least one type of a nucleotide having an energy transfer acceptor moiety, so as to incorporate the nucleotide onto the 3'OH group.

Provided herein are methods for incorporating a nucleotide comprising the steps of: contacting (i) a polymerase having altered nucleotide incorporation kinetics and linked to an energy transfer donor moiety with (ii) a target nucleic acid molecule which is base-paired with a polymerization initiation site having a 3' OH group and with (iii) at least one type of a hexaphosphate nucleotide having an energy transfer acceptor moiety, so as to incorporate the hexaphosphate nucleotide onto the 3'OH group.

Provided herein are methods for incorporating a nucleotide, comprising the steps of: contacting (i) a polymerase including an energy transfer donor nanoparticle with (ii) a nucleic acid molecule and with (iii) at least one type of a nucleotide having an energy transfer acceptor moiety, so as to incorporate the nucleotide into the nucleic acid molecule.

Provided herein are methods for incorporating a nucleotide comprising the steps of: contacting (i) a polymerase including an energy transfer donor nanoparticle with (ii) a nucleic acid molecule and with (iii) at least one type of a hexaphosphate phosphate nucleotide having an energy transfer acceptor moiety, so as to incorporate the hexaphosphate nucleotide into the nucleic acid molecule.

Provided herein are methods for incorporating a nucleotide comprising the steps of: contacting (i) a polymerase including an energy transfer donor nanoparticle with (ii) a target nucleic acid molecule which is base-paired with a polymerization initiation site having a 3' OH group and with (iii) at least one type of a nucleotide having an energy transfer acceptor moiety, so as to incorporate the nucleotide onto the 3'OH group.

Provided herein are methods for incorporating a nucleotide comprising the steps of: contacting (i) a polymerase including an energy transfer donor nanoparticle with (ii) a target nucleic acid molecule which is base-paired with a polymerization initiation site having a 3' OH group and with (iii) at least one type of a hexaphosphate nucleotide having an energy transfer acceptor moiety, so as to incorporate the hexaphosphate nucleotide onto the 3'OH group.

Provided herein are methods for conducting a plurality of nucleotide incorporation reactions (e.g., arrays), each nucleotide incorporation reaction comprises the steps of: contacting (i) a polymerase having altered nucleotide incorporation kinetics and linked to an energy transfer donor moiety with (ii) a nucleic acid molecule and with (iii) at least one type of a nucleotide having an energy transfer acceptor moiety, so as to incorporate the nucleotide into the nucleic acid molecule.

Provided herein are methods for conducting a plurality of nucleotide incorporation reactions (e.g., arrays), each nucleotide incorporation reaction comprises the steps of: contacting (i) a polymerase including an energy transfer donor nanoparticle with (ii) a nucleic acid molecule and with (iii) at least one type of a nucleotide having an energy transfer acceptor moiety, so as to incorporate the nucleotide into the nucleic acid molecule.

Provided herein are methods for successively incorporating nucleotides comprising the steps of: contacting (i) a polymerase having altered nucleotide incorporation kinetics and linked to an energy transfer donor moiety with (ii) a nucleic acid molecule and with (iii) a plurality of more than one type of a nucleotide each type of nucleotide having a different type of energy transfer acceptor moiety, so as to successively incorporate the nucleotides into the nucleic acid molecule.

Provided herein are methods for successively incorporating nucleotides comprising the steps of: contacting (i) a polymerase including an energy transfer donor nanoparticle with (ii) a nucleic acid molecule and with (iii) a plurality of more than one type of a nucleotide each type of nucleotide having a different type of energy transfer acceptor moiety, so as to successively incorporate the nucleotides into the nucleic acid molecule.

Provided herein are methods for successively incorporating nucleotides, comprising the steps of: contacting (i) a mutant polymerase having altered nucleotide incorporation kinetics and linked to an energy transfer donor moiety with (ii) a target DNA molecule which is base-paired with a polymerization initiation site having a 3' OH group and with (iii) a plurality of more than one type of a hexaphosphate nucleotide each type of hexaphosphate nucleotide having a different type of fluorescent dye acceptor, so as to successively incorporate the hexaphosphate nucleotides onto the 3' OH group.

Provided herein are methods for incorporating a nucleotide comprising the steps of: contacting (i) a polymerase according to any one of SEQ ID NO:1-3 and linked to an energy transfer donor moiety with (ii) a nucleic acid molecule (iii) at least one type of a hexaphosphate nucleotide linked to an energy transfer acceptor moiety, so as to incorporate the hexaphosphate nucleotide into the nucleic acid molecule.

Provided herein are methods for incorporating a nucleotide comprising the steps of: contacting (i) a polymerase according to any one of SEQ ID NO:1-3 and linked to an energy transfer donor moiety with (ii) a nucleic acid molecule which is base-paired with a polymerization initiation site having a terminal 3' OH group and with (iii) at least one type of a hexaphosphate nucleotide linked to an energy transfer acceptor moiety, so as to incorporate the hexaphosphate nucleotide onto the 3'OH group.

Provided herein are methods for successively incorporating nucleotides comprising the steps of: contacting (i) a polymerase according to any one of SEQ ID NO:1-3 and linked to an energy transfer donor moiety with (ii) a nucleic acid molecule and with (iii) a plurality of more than one type of a hexaphosphate nucleotide each type of hexaphosphate nucleotide linked to a different type of energy transfer acceptor moiety, so as to successively incorporate the hexaphosphate nucleotides into the nucleic acid molecule.

Provided herein are methods for conducting a plurality of nucleotide incorporation reactions, each nucleotide incorporation reaction comprises the steps of: contacting (i) a polymerase according to any one of SEQ ID NO:1-3 and linked to an energy transfer donor moiety with (ii) a nucleic acid molecule and with (iii) at least one type of a hexaphosphate nucleotide linked to an energy transfer acceptor moiety, so as to incorporate the hexaphosphate nucleotide into the nucleic acid molecule.

Provided herein are methods for successively incorporating nucleotides comprising the steps of: contacting (i) a polymerase according to any one of SEQ ID NO:1-3 and linked to an energy transfer donor nanoparticle with (ii) a nucleic acid molecule and with (iii) a plurality of more than one type of a hexaphosphate nucleotide each type of hexaphosphate nucleotide linked to a different type of energy transfer acceptor moiety, so as to successively incorporate the hexaphosphate nucleotides into the nucleic acid molecule.

Provided herein are methods for conducting a plurality of nucleotide incorporation reactions, each nucleotide incorporation reaction comprises the steps of: contacting (i) a polymerase according to any one of SEQ ID NO:1-3 and linked to an energy transfer donor nanoparticle with (ii) a nucleic acid molecule and with (iii) at least one type of a hexaphosphate nucleotide linked to an energy transfer acceptor moiety, so as to incorporate the hexaphosphate nucleotide into the nucleic acid molecule.

Detecting Nucleotide Incorporation

In one embodiment, additional steps can be conducted to detect nucleotide incorporation. The additional steps comprise: (a) exciting the energy transfer donor moiety with an excitation source; and (b) detecting the energy transfer signal or a change in the energy transfer signal from the incorporated nucleotide whereby the energy transfer donor moiety and the energy transfer acceptor moiety are located in close proximity to each other.

In one embodiment, the excitation source can be electromagnetic energy. In another embodiment, the excitation source can be light. In another embodiment, the energy transfer signal or the change in the energy transfer signal can be a FRET signal. In yet another embodiment, the energy transfer signal or the change in the energy transfer signal can be spectrally or optically detectable.

Identifying the Incorporated Nucleotide

In another embodiment, additional steps can be conducted to identify the incorporated nucleotide. The additional steps comprise: (a) exciting the energy transfer donor moiety with an excitation source; (b) detecting the energy transfer signal or a change in the energy transfer signal from the incorporated nucleotide whereby the energy transfer donor moiety and the energy transfer acceptor moiety are located in close proximity to each other; and (c) identifying the energy transfer signal or the change in the energy transfer signal from the incorporated nucleotide.

In one embodiment, the excitation source can be electromagnetic energy. In another embodiment, the excitation source can be light. In another embodiment, the energy transfer signal or the change in the energy transfer signal can be a FRET signal. In yet another embodiment, the energy transfer signal or the change in the energy transfer signal can be spectrally or optically detectable.

Embodiments of Methods for Incorporating Nucleotides

In methods for generating an energy transfer signal, in one embodiment, the energy transfer donor and acceptor moieties can fluoresce in response to exposure to an excitation source, such as electromagnetic radiation. These fluorescence responses can be an energy transfer signal. In another embodiment, the energy transfer acceptor moiety can fluoresce in response to energy transferred from a proximal excited energy transfer donor moiety. These fluorescence responses can be an energy transfer signal. The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the energy transfer signals from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the energy transfer signal can include a change in the ratio of the change of the energy transfer donor signal relative to change of the energy transfer acceptor signals. In another embodiment, the energy transfer signal from the donor can increase or decrease. In another embodiment, the energy transfer signal from the acceptor can increase or decrease. In another embodiment, the energy transfer signal associated with nucleotide incorporation includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

In one embodiment, the detecting the energy transfer signal can be performed using confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

In practicing the nucleotide binding and/or nucleotide incorporation methods, non-desirable fluorescent signals can come from sources including background and/or noise. In one embodiment, the energy transfer signals can be distinguished from the non-desirable fluorescent signals by measuring, analyzing and characterizing attributes of all fluorescent signals generated by the nucleotide incorporation reaction. In one embodiment, attributes of the energy transfer signal that can permit distinction from the non-desirable fluorescent signals can include: duration; wavelength; amplitude; photon count; and/or the rate of change of the duration, wavelength, amplitude; and/or photon count. In one embodiment, the identifying the energy transfer signal, includes measuring, analyzing and characterizing attributes of: duration; wavelength; amplitude; photon count and/or the rate of change of the duration, wavelength, amplitude; and/or photon count. In one embodiment, identifying the energy transfer signal can be used to identify the incorporated nucleotide.

In one embodiment, the nucleic acid molecule can be DNA, RNA or DNA/RNA.

In one embodiment, the polymerase has an active site. The nucleotide can bind the active site. In another embodiment, the polymerase can be a DNA-dependent or RNA-dependent polymerase, or a reverse transcriptase. In another embodiment, the polymerase having altered nucleotide binding and/or nucleotide incorporation kinetics can improve distinction between productive and non-productive binding events. In another embodiment, the altered nucleotide binding kinetics and/or altered nucleotide incorporation kinetics can include altered kinetics for: polymerase binding to the target molecule; polymerase binding to the nucleotide; polymerase catalyzing nucleotide incorporation; the polymerase cleaving the nucleotide and forming a cleavage product; and/or the polymerase releasing the cleavage product. In another embodiment, the polymerase can be linked to an energy transfer donor moiety to form a conjugate. In another embodiment, the polymerase component of the conjugate can be enzymatically active. In another embodiment, the polymerase has altered kinetics for nucleotide binding and/or nucleotide incorporation used in combination with labeled nucleotides having six or more phosphate groups (or substituted phosphate groups), which improve distinction between productive and non-productive binding events. In another embodiment, the polymerase can have improved photo-stability. The polymerase can be a Phi29-like polymerase, including Phi29 or B103 polymerase. The polymerase can be a mutant polymerase. The polymerase can be a B103 polymerase according to any one of SEQ ID NOS: 1-5.

In one embodiment, the energy transfer donor moiety can be a nanoparticle or a fluorescent dye. The nanoparticle can be about 1-20 nm in its largest dimensions. The nanoparticle can be a core/shell nanoparticle. The nanoparticle can include a core comprising semiconductor material(s). The core can include materials (including binary, ternary and quaternary mixtures thereof), from: Groups II-VI of the periodic table, including ZnS, ZnSe, ZnTe, CdS, CdSe, CdTe, HgS, HgSe, HgTe, MgTe; Groups III-V, including GaN, GaP, GaAs, GaSb, InN, InP, InAs, InSb, AlAs, AlP, AlSb, AlS; and/or Group IV, including Ge, Si, Pb. The nanoparticle can include at least one shell surrounding the core. The shell can include semiconductor material(s). The nanoparticle can include an inner shell and an outer shell. The shell can include materials (including binary, ternary and quaternary mixtures thereof) comprising: ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, or AlSb. In one embodiment, the nanoparticle comprises a core having CdSe. In another embodiment, the nanoparticle comprises an inner shell having CdS. In another embodiment, the nanoparticle comprises an outer shell having ZnS. The outermost surface of the core or shell can be coated with tightly associated ligands which are not removed by ordinary solvation. In some embodiments, the nanoparticle can have a layer of ligands on its surface which can further be cross-linked to each other. In some embodiments, the nanoparticle can have other or additional surface coatings which can modify the properties of the particle, for example, increasing or decreasing solubility in water or other solvents. The nanoparticle can be water dispersible. The nanoparticle can be a non-blinking nanoparticle. The nanoparticle can be photo-stable. The nanoparticle may not interfere with polymerase activity, including polymerase binding to the target molecule, polymerase binding to the nucleotide, polymerase catalyzing nucleotide incorporation, or the polymerase cleaving the nucleotide and/or releasing the cleavage product.

In one embodiment, the target nucleic acid molecule can be DNA or RNA or DNA/RNA molecule. In another embodiment, the target nucleic acid molecule is a single nucleic acid molecule. In another embodiment, the target nucleic acid molecule (e.g., target molecule) is base-paired with a polymerization initiation site. In another embodiment, the polymerization initiation site is a terminal 3'OH of a primer molecule or of a self-primed target molecule. In another embodiment, the polymerization initiation site is a 3'OH within a gap or nick. In another embodiment, the target nucleic acid molecule and/or the polymerization initiation site is immobilized to a solid surface. In another embodiment, the target nucleic acid molecule is a linear or circular nucleic acid molecule.

In one embodiment, the at least one type of nucleotide can include 3-10 phosphate groups or substituted phosphate groups, or a combination of phosphate groups and substituted phosphate groups. The nucleotide can include a terminal phosphate group or terminal substituted phosphate group which can be linked to the energy transfer acceptor moiety. The nucleotide can include the energy transfer acceptor moiety which is linked the base, sugar, or any phosphate group or substituted phosphate group. The nucleotide can be adenosine, guanosine, cytosine, thymidine, uridine, or any other type of nucleotide.

In one embodiment, the energy transfer acceptor moiety can be a fluorescent dye. The energy transfer acceptor moiety and the energy transfer donor moiety can be capable of energy transfer.

In one embodiment, more than one type of nucleotide can be contacted with the polymerase. Each of the different types of nucleotides can be linked to the same or to different types of energy transfer acceptor moieties, or any combination of the same or different types of acceptor moieties.

In another embodiment, a plurality of one or more different types of nucleotides can be included in the nucleotide incorporation reaction to permit successive nucleotide incorporation.

Compositions and Systems

Provided herein are compositions and systems, comprising a DNA-dependent polymerase having properties which offer advantages over other DNA-dependent polymerase which are traditionally used for nucleotide polymerization reactions.

For example, the compositions and systems comprise a DNA-dependent polymerase having altered kinetics for nucleotide binding and/or nucleotide incorporation for improved distinction between productive and non-productive nucleotide binding events. In another example, the compositions and systems comprise a DNA-dependent polymerase which can polymerize nucleotides having 4, 5, 6, or more phosphate groups. In another example, the compositions and systems comprise a DNA-dependent polymerase having improved photo-stability when exposed to electromagnetic energy (e.g., exposed to light during the nucleotide incorporation reactions). In another example, the compositions and systems comprise a DNA-dependent polymerase which is enzymatically stable and retains enzymatic activity when linked to an energy transfer moiety. In yet another example, the compositions and systems comprise a DNA-dependent polymerase according to SEQ ID NOS:1, 2 or 3.

The compositions comprise an energy transfer moiety linked to a DNA-dependent polymerase having altered kinetics for nucleotide binding and/or nucleotide incorporation for improved distinction between productive and non-productive nucleotide binding events. For example, the compositions comprise a nanoparticle or fluorescent dye linked to DNA-dependent polymerase having altered kinetics for nucleotide binding and/or nucleotide incorporation. In yet another example, the compositions comprise an energy transfer donor (e.g., nanoparticle or fluorescent dye) linked to DNA-dependent polymerase according to SEQ ID NOS:1, 2 or 3.

The compositions comprise an energy transfer moiety linked to a DNA-dependent polymerase having altered kinetics for nucleotide binding and/or nucleotide incorporation and the polymerase is bound to a target nucleic acid molecule. In one embodiment, the compositions comprises an energy transfer moiety linked to a DNA-dependent polymerase having altered kinetics for nucleotide binding and/or nucleotide incorporation and the polymerase is bound to a target nucleic acid molecule which is base-paired with a polymerization initiation site having a 3'OH group. In another embodiment, the compositions comprises an energy transfer moiety linked to a DNA-dependent polymerase according to SEQ ID NOS:1, 2 or 3, and the polymerase is bound to a target nucleic acid molecule. In another embodiment, the compositions comprises an energy transfer moiety linked to a DNA-dependent polymerase according to SEQ ID NOS:1, 2 or 3, and the polymerase is bound to a target nucleic acid molecule which is base-paired with a polymerization initiation site having a 3'OH group.

Embodiments of the compositions include: the target molecule can be base-paired with a polymerization initiation site having a 3' OH group; the target molecule can be base-paired with a nucleic acid primer; the target molecule can be immobilized; the nucleic acid primer molecule can be immobilized; and/or the target and primer molecules can be immobilized.

Provided herein are systems, comprising a DNA-dependent polymerase having properties which offer advantages over other DNA-dependent polymerase which are traditionally used for nucleotide polymerization reactions.

For example, the systems comprise an energy transfer moiety linked to a DNA-dependent polymerase having altered kinetics for nucleotide binding and/or nucleotide incorporation.

In another example, the systems comprise a nanoparticle or fluorescent dye linked to a DNA-dependent polymerase having altered kinetics for nucleotide binding and/or nucleotide incorporation.

In another example, the systems comprise an energy transfer moiety (e.g., nanoparticle or fluorescent dye) linked to a DNA-dependent polymerase having altered kinetics for nucleotide binding and/or nucleotide incorporation and the polymerase is bound to a target nucleic acid molecule.

In another example, the systems comprise an energy transfer moiety (e.g., nanoparticle or fluorescent dye) linked to a DNA-dependent polymerase having altered kinetics for nucleotide binding and/or nucleotide incorporation and the polymerase is bound to a target nucleic acid molecule which is base-paired with a polymerization initiation site having a 3'OH group.

In another example, the systems comprise an energy transfer moiety (e.g., nanoparticle or fluorescent dye) linked to a DNA-dependent polymerase having altered kinetics for nucleotide binding and/or nucleotide incorporation and the polymerase is bound to a target nucleic acid molecule which is base-paired with a nucleic acid primer molecule.

In another example, the systems comprise (i) an energy transfer moiety (e.g., nanoparticle or fluorescent dye) linked to a DNA-dependent polymerase having altered kinetics for nucleotide binding and/or nucleotide incorporation and the polymerase is bound to a target nucleic acid molecule and (ii) a nucleotide linked to an energy transfer moiety.

In another example, the systems comprise (i) an energy transfer moiety (e.g., nanoparticle or fluorescent dye) linked to a DNA-dependent polymerase having altered kinetics for nucleotide binding and/or nucleotide incorporation and the polymerase is bound to a target nucleic acid molecule which is base-paired with a polymerization initiation site having a 3'OH group and (ii) a nucleotide linked to an energy transfer moiety.

In another example, the systems comprise (i) an energy transfer moiety (e.g., nanoparticle or fluorescent dye) linked to a DNA-dependent polymerase having altered kinetics for nucleotide binding and/or nucleotide incorporation and the polymerase is bound to a target nucleic acid molecule which is base-paired with a nucleic acid primer and (ii) a nucleotide linked to an energy transfer moiety.

Embodiments of the systems include: the DNA-dependent polymerase having altered kinetics for nucleotide binding and/or nucleotide incorporation can be any of SEQ ID NOS:1, 2, or 3; the target molecule can be base-paired with a polymerization initiation site having a 3' OH group; the target molecule can be base-paired with a nucleic acid primer; the target molecule can be immobilized; the nucleic acid primer molecule can be immobilized; the target and primer molecules can be immobilized; the energy transfer moiety which is linked to the nucleotide can be an energy transfer acceptor moiety (e.g., fluorescent dye).

Reagent Exchange Methods

Provided herein are compositions, systems, methods, and kits, for exchanging (e.g., replacing) the reagents for nucleotide binding or nucleotide incorporation reactions with fresh reagents on the same target nucleic acid molecule.

The methods for exchanging the reagents can be used for: re-sequencing at least a portion of the same nucleic acid molecule; or replacing any reagent used to practice nucleotide binding and/or nucleotide incorporation with functional reagents to permit continuing the nucleotide incorporation reaction on the same nucleic acid molecule; or performing nucleotide binding or nucleotide incorporation reactions and switching to reactions having different nucleotide binding and/or nucleotide incorporation reaction properties on the same nucleic acid molecule.

The reagents which can be exchanged include any reagent which is used in a nucleotide binding or nucleotide incorporation reaction, including but not limited to any type of: target molecule; primer; polymerization initiation site; polymerase; nucleotides (e.g., hydrolyzable, non-hydrolyzable, chain-terminating, or labeled or non-labeled nucleotides); the synthesized strand; compounds which reduce photodamage; buffers; salts; co-factors; divalent cations; and chelating agents. The fresh reagents can be the same or different types of reagents compared to the old reagents.

For example, one round of a reagent exchange reaction can be conducted using three types of nucleotides (e.g., A, G, and C) labeled with a different type of energy transfer acceptor dye, and another different type of nucleotide (e.g., T) can be unlabeled. In one embodiment, the A nucleotides can be labeled with dye type 1, G nucleotides can be labeled with dye type 2, and C nucleotides can be labeled with dye type 3. In a second round, the reagent exchange reaction can be conducted using three types of nucleotides (e.g., G, C, and T) labeled with a different type of energy transfer acceptor dye, and another different type of nucleotide (e.g., A) can be unlabeled. In a third round, the reagent exchange reaction can be conducted using three types of nucleotides (e.g., C, T, and A) labeled with a different type of energy transfer acceptor dye, and another different type of nucleotide (e.g., G) can be unlabeled. In a fourth round, the reagent exchange reaction can be conducted using three types of nucleotides (e.g., T, A, and G) labeled with a different type of energy transfer acceptor dye, and another different type of nucleotide (e.g., C) can be unlabeled. The first, second, third, and fourth rounds of reagent exchange reactions can be conducted in any order, and in any combination. In any of the rounds of reagent exchange reactions, the different types of nucleotides can be linked to the same or different type of energy transfer dye.

In another example, multiple rounds of reagent exchange reactions can be conducted using four types of nucleotides (e.g., A, G, C, and T) each labeled with a different type of energy transfer acceptor dye in each round. In one embodiment, in round one, the A nucleotides can be labeled with dye type 1, G labeled with dye type 2, C labeled with dye type 3, and T labeled with dye type 4. In a subsequent round, the reagent exchange reaction can be conducted using A labeled with dye type 2, G labeled with dye type 3, C labeled with dye type 4, and T labeled with dye type 1. One skilled in the art will readily recognize that many combinations are possible.

In one aspect, the reagent exchange methods can be used to sequence the same target nucleic acid molecule 1, 2, 3, 4, or 5 times, or up to 10 times, or up to 25 times, or up to 50 times, or more than 50 times. For example, errors in detecting and/or identifying the incorporated nucleotides may necessitate re-sequencing the same target molecule. The errors can arise when a non-reporting nucleotide (e.g., which is linked to a non-reporting energy transfer acceptor dye) is incorporated but does not emit a detectable signal. The same target molecule can be sequenced one or more times to provide redundant nucleotide sequence information. The reagent exchange methods can be used to sequence the strand which is synthesized during a nucleotide incorporation reaction. The synthesized strand can be sequenced 1, 2, 3, 4, or 5 times, or up to 10 times, or up to 25 times, or up to 50 times, or more than 50 times, to provide redundant nucleotide sequence information. The same target molecule, or synthesized strand, can be re-sequenced using exchanged primers having sequences which are the same or a different from the sequence of the old primers. Sequencing the same target molecule multiple times, and/or sequencing the same synthesized strand multiple times, can provide multiple data sets of sequence information which can be aligned and compared. In one embodiment, the alignment can be used to deduce a consensus sequence of the target molecule or the synthesized strand. The alignment can be used to provide multi-fold coverage of the nucleotides which are contained within the target molecule or synthesized strand.

The reagent exchange methods can be used to replace inactive polymerases and/or non-functional nucleotides or energy transfer moieties, with fresh polymerase, nucleotides, and/or other reagents, in order to continue the nucleotide incorporation reaction on the same target molecule or synthesized strand. For example, fresh polymerase, nucleotides, and/or reagents can be added to the immobilized target/primer molecules to permit continuation of the nucleotide incorporation reaction on the same target or synthesized molecule.

The reagent exchange methods can be used to replace the reagents in an on-going nucleotide binding or incorporation reaction, in order to switch to a different type of nucleotide binding or nucleotide incorporation reaction on the same target or synthesized molecule. For example, the first nucleotide incorporation reaction can be conducted using a polymerase, nucleotides, and other reagents, which exhibit certain properties, such as: nucleotide fidelity; rate of nucleotide incorporation; processivity; strand displacement; kinetics of nucleotide binding, catalysis, release of the cleavage product, and/or polymerase translocation; exonuclease activity; and/or activity at certain temperatures. The reagents (e.g., polymerases and/or nucleotides) can be exchanged with different reagents to conduct a nucleotide incorporation reaction which exhibits different nucleotide incorporation properties (on the same target molecule or on the same synthesized strand).

The reagent exchange methods can be practiced using any type of nucleotide binding or nucleotide incorporation reactions, including but not limited to: the energy transfer methods disclosed herein; any type of discontinuous reactions (e.g., synchronous nucleotide incorporation methods described in: (U.S. Ser. No. 61/184,774, filed on Jun. 5, 2009; U.S. Ser. No. 61/242,762, filed on Sep. 15, 2009; and U.S. Ser. No. 61/180,811, filed on May 22, 2009; U.S. Ser. No. 61/295,533, filed on Jan. 15, 2010); and any type of continuous reactions (e.g., asynchronous nucleotide incorporation methods as described in: (U.S. Ser. No. 61/077,090, filed on Jun. 30, 2008; U.S. Ser. No. 61/089,497, filed on Aug. 15, 2008; U.S. Ser. No. 61/090,346, filed on Aug. 20, 2008; PCT application No. PCT/US09/049324, filed on Jun. 30, 2009; U.S. Ser. No. 61/164,324, filed on Mar. 27, 2009; and U.S. Ser. No. 61/263,974, filed on Nov. 24, 2009; U.S. Ser. Nos. 61/289,388; 61/293,616; 61/299,917; 61/307,356).

The reagent exchange methods can be practiced using any type of format using an immobilized: primer; target molecule; synthesized strand; and/or polymerase. The reagent exchange methods can be practiced on a single target nucleic acid molecule, or on random or organized arrays of single nucleic acid molecules, and using any type of solid surface (U.S. Ser. No. 61/220,174, filed on Jun. 24, 2009; and U.S. Ser. No. 61/245,248, filed on Sep. 23, 2009; U.S. Ser. No. 61/302,475). The target molecules and synthesized strands can be genomic, recombinant, DNA, RNA, double-stranded, or single-stranded nucleic acid molecules. The target nucleic acid molecules can be linear or circular. The target nucleic acid molecules can be self-priming molecules or can be associated with primer molecules. The target nucleic acid molecules can be immobilized using any method, including the methods depicted in any of FIGS. 2-8.

Provided herein are reagent exchange methods, where the existing target molecule, synthesized strand, primer, polymerase, nucleotides, and/or other reagents, can be removed in a manner which does not remove the immobilized target molecule, primer, or synthesized strand. In some embodiments, the primer, target molecule, or synthesized strand can be removed. Methods for removing the components include physical, chemical, and/or enzymatic methods.

The polymerase can be inactivated and/or removed using physical, chemical, and/or enzymatic method, in any combination and in any order. For example, the polymerase can be deactivated using elevated temperatures, such as 45-80° C., for about 30 seconds to 10 minutes. In another example, the polymerase can be removed from the target molecule or synthesized strand using a protein-degrading enzyme, such as proteinase-K. In another example, the polymerase can be removed from the target molecule or synthesized strand using compounds known to disrupt protein complexes, where the compounds include detergents (e.g., N-lauroyl sarcosine, SDS), chaotropic salt (e.g., guanidinium hydrochloride), lithium sulfate, and EDTA.

Any combination of capture molecule, primer, target molecule, and/or synthesized strand, can be dissociated (e.g., denatured) from each other using physical, chemical, and/or enzymatic methods, in any combination and in any order. For example, the target molecule/synthesized strand duplex can be denatured using elevated temperatures, such as about 75-100° C. (e.g., without formamide) or about 45-90° C. (e.g., with formamide). In another example, the target molecule or synthesized strand can be degraded using a nucleic acid degrading enzyme, such as a 5'→3' or 3'→5' exonuclease (e.g., exonuclease III, T7 gene 6 exonuclease, exonuclease I). In yet another example, the target molecule or synthesized strand can be denatured using any compound known to dissociate double-stranded nucleic acid molecules, such as any combination of: formamide, urea, DMSO, alkali conditions (e.g., NaOH at about 0.01-0.3 M, or about 0.05-0.1 M; e.g., elevated pH of about 7-12), or low salt or very-low salt conditions (e.g., about less than 0.001-0.3 mM cationic conditions), or water.

In practicing the reagent exchange methods, the target molecule, synthesized strand, polymerase, primer, capture molecule, or any reagent, can be removed using fluid flow, washing, and/or aspiration. The target molecule, primer molecule, synthesized strand, or capture molecule can be operably linked to the solid surface in a manner which withstands flowing, washing, aspirating, and changes in salt, temperature, chemical, enzymatic, and/or pH conditions. A fresh supply of polymerase, nucleotides, reagents, primer molecules, splinter molecules, and/or adaptor molecules, can be added to the immobilized nucleic acid molecules. The polymerase (e.g., donor-labeled) and nucleotides (e.g., and acceptor-labeled) can be added to the immobilized nucleic acid molecules under conditions which are suitable for nucleotide binding and/or nucleotide incorporation to occur. The fresh polymerase, nucleotides, and reagents, can be the same or different from the old polymerase, nucleotides, and/or reagents.

In the following embodiments (e.g., FIGS. 2-8), the "N" can be any nucleotide base, and the "I" can be a universal base such as inosine.

Figure 2:
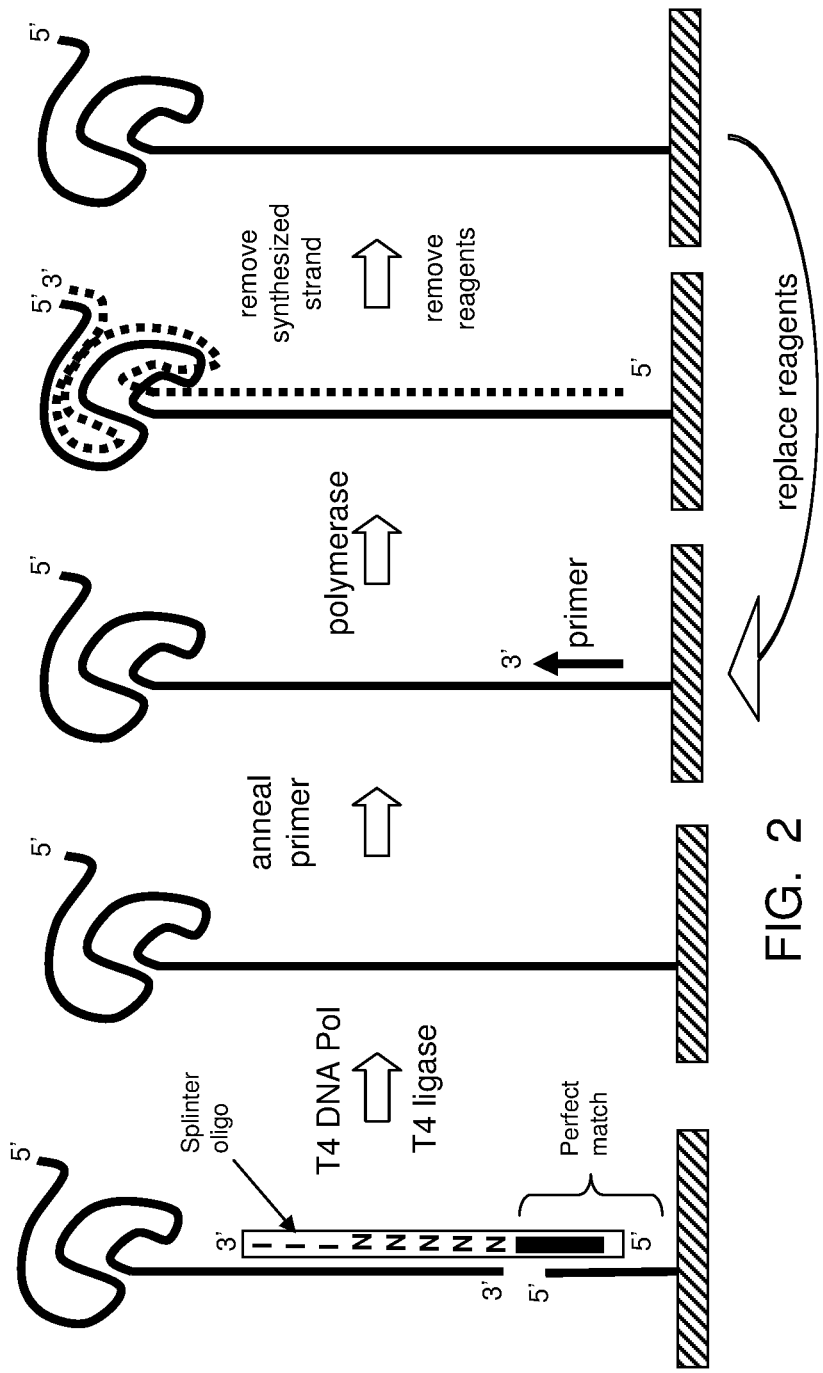
FIG. 2 depicts one embodiment showing an immobilized target molecule/primer duplex to re-sequence the same target molecule, in a direction away from the solid surface, using the reagent exchange methods.

In one embodiment, a target molecule can be ligated to an immobilized capture molecule using a splinter oligonucleotide (which can hybridize to the target molecule and capture oligonucleotide) and enzymes for ligation and/or nucleotide polymerization (e.g., T4 ligase and T4 DNA polymerase, respectively) (see FIG. 2). A primer can be annealed to the immobilized target molecule, and a synthesized strand can be produced using a polymerase and nucleotides. Physical, chemical, and/or enzymatic conditions can be used to remove the synthesized strand, polymerase, and nucleotides. The remaining target molecule can be contacted with fresh reagents to permit re-sequencing the same target molecule. FIG. 2 depicts re-sequencing the same target molecule, in a direction away from the solid surface. A "two-pass" method for re-sequencing the same nucleic acid molecule has been described (Harris, et al., 2008 Science 320:106-109, and supporting online material).

Figure 3:
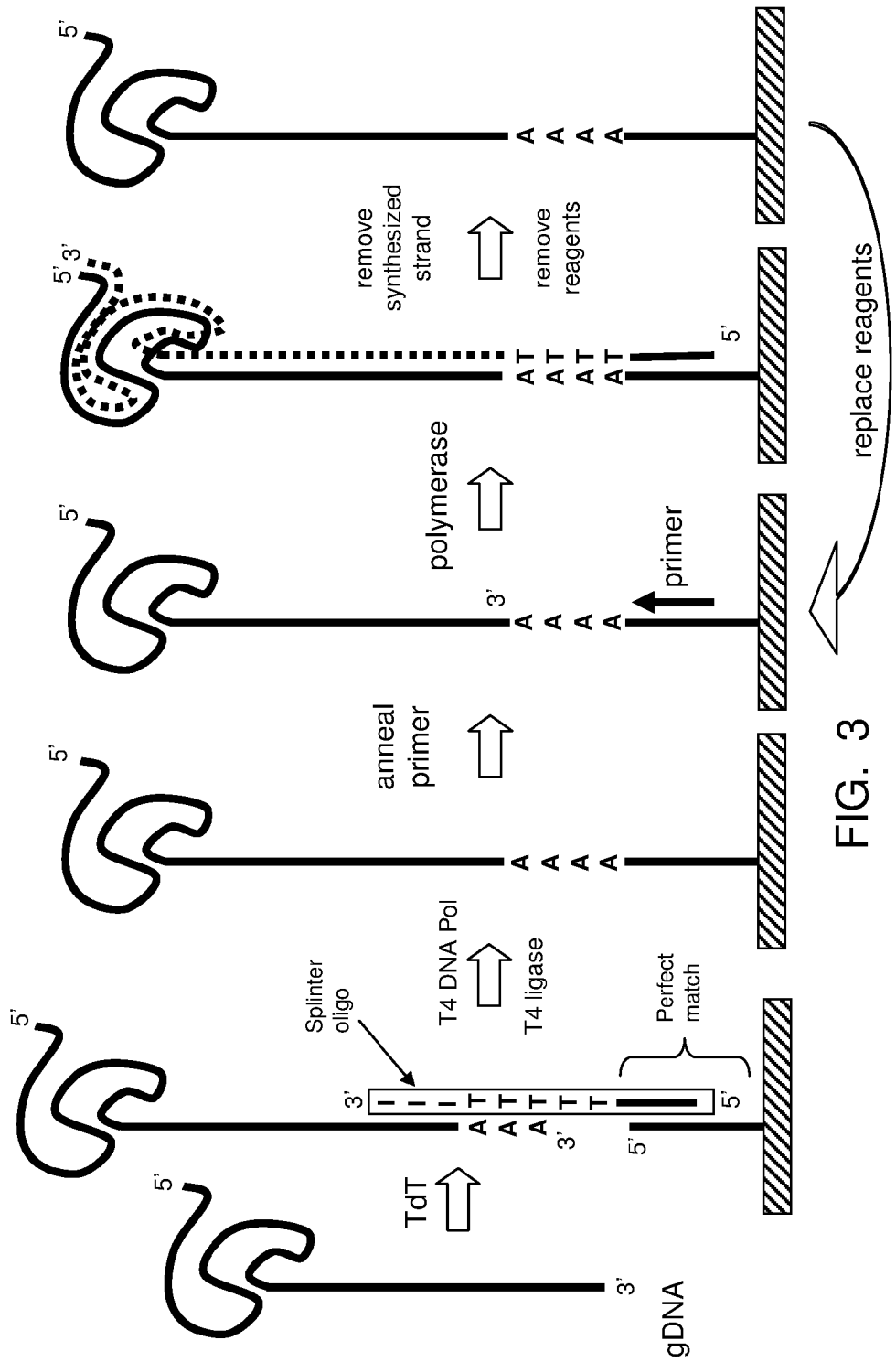
FIG. 3 depicts another embodiment showing an immobilized target molecule/primer duplex to re-sequence the same target molecule, in a direction away from solid surface, using the reagent exchange methods.

In another embodiment, a polynucleotide tail (e.g., poly-A, -G, -C, or -T) can be added to a target molecule, for example using a terminal transferase enzyme (TdT in FIG. 3). The tailed target molecule can be ligated to an immobilized capture molecule using a splinter oligonucleotide (which can hybridize to the target molecule and capture oligonucleotide) and enzymes for ligation and/or nucleotide polymerization (e.g., T4 ligase and T4 DNA polymerase, respectively). A primer can be annealed to the immobilized target molecule, and a synthesized strand can be produced using a polymerase and nucleotides. Physical, chemical, and/or enzymatic conditions can be used to remove the synthesized strand, polymerase, and nucleotides. The remaining target molecule can be contacted with fresh reagents to permit re-sequencing the same target molecule. FIG. 3 depicts re-sequencing the same target molecule, in a direction away from the solid surface.

Figure 4:
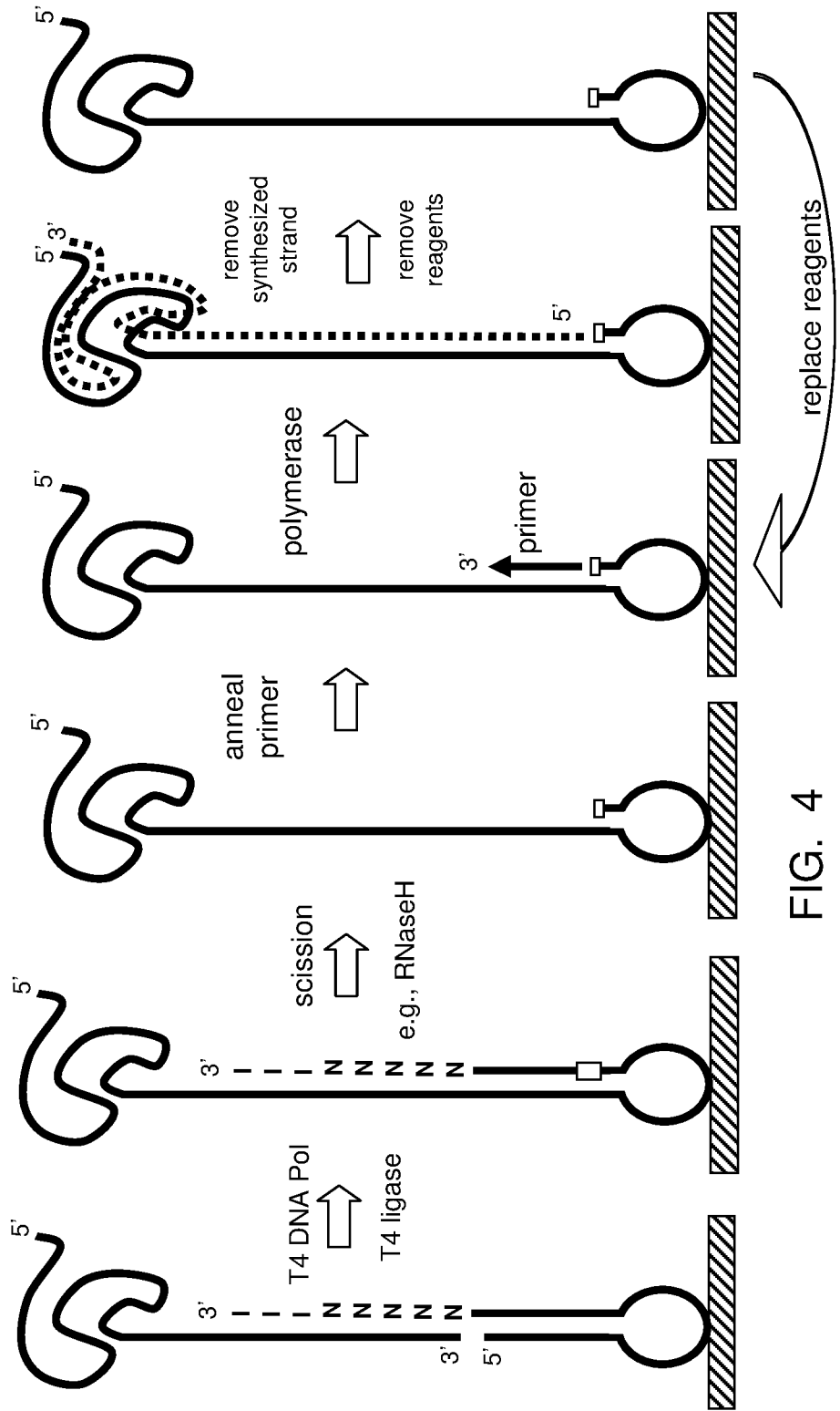
FIG. 4 depicts another embodiment showing an immobilized, self-primed target molecule to re-sequence the same target molecule, in a direction away from the solid surface, using the reagent exchange methods.

In yet another embodiment, a target molecule can be ligated to an immobilized hairpin capture molecule, where a portion of the capture molecule can hybridize to the target molecule (see FIG. 4). The target molecule can be ligated to the hairpin capture molecule using enzymes for ligation and/or nucleotide polymerization (e.g., T4 ligase and T4 DNA polymerase, respectively). The hairpin adaptor molecule can include a recognition sequence for cleavage (scission) by an endonuclease enzyme. For example, the recognition sequence can be an RNA portion which can be 3-6 nt in length, to form a DNA/RNA hybrid. The RNA portion can be 4 nt in length. The RNA portion can include purines (A and G) in any order. The RNA portion of the RNA/DNA duplex can be a substrate for cleavage by an endoribonuclease (e.g., RNase H). In another example, the recognition sequence can be an AP site (apurinic/apyrimidinic) having a THF substrate (tetrahydrofuran) which can be cleaved by an AP endonuclease. In another example, the recognition sequence can include nucleotide analogs (e.g., 8-oxo-7,8-dihydroguanine, 8-oxoguanine, or 8-hydroxyguanine) which can be cleaved by DNA glycosylase OGG1. In yet another example, the recognition sequence can include any sequence which can be cleaved by a nicking enzyme. After scission, a primer can be annealed to the target molecule, and a synthesized strand can be produced using a polymerase and nucleotides. Physical, chemical, and/or enzymatic conditions can be used to remove the synthesized strand, polymerase, and nucleotides. The remaining target molecule can be contacted with fresh reagents to permit re-sequencing the same target molecule. FIG. 4 depicts re-sequencing the same target molecule, in a direction away from the solid surface.

Figure 5A:
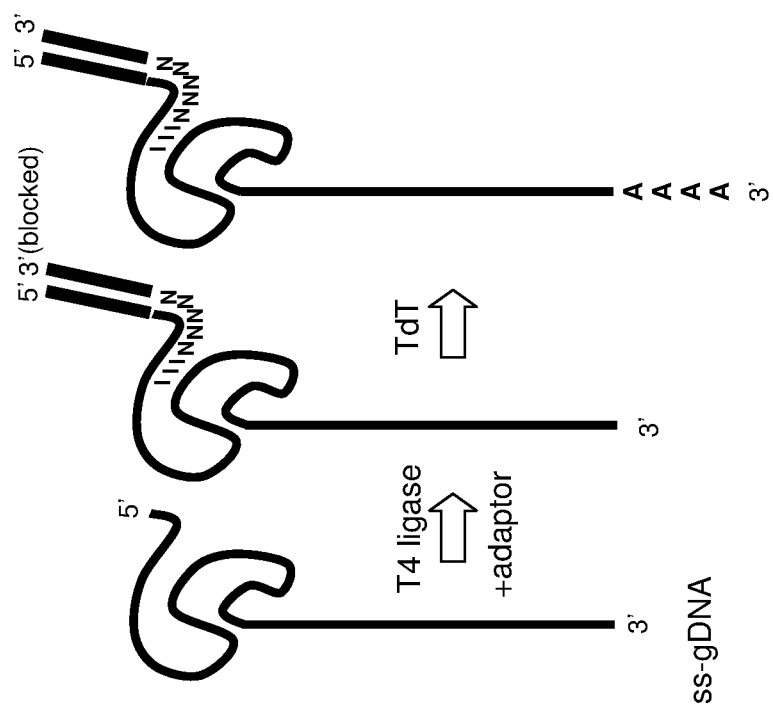
FIG. 5A depicts one embodiment showing an immobilized target molecule/primer duplex to synthesize an extension product, where the same extension product is re-sequenced in a direction towards the solid surface, using the reagent exchange methods.
Figure 5B:
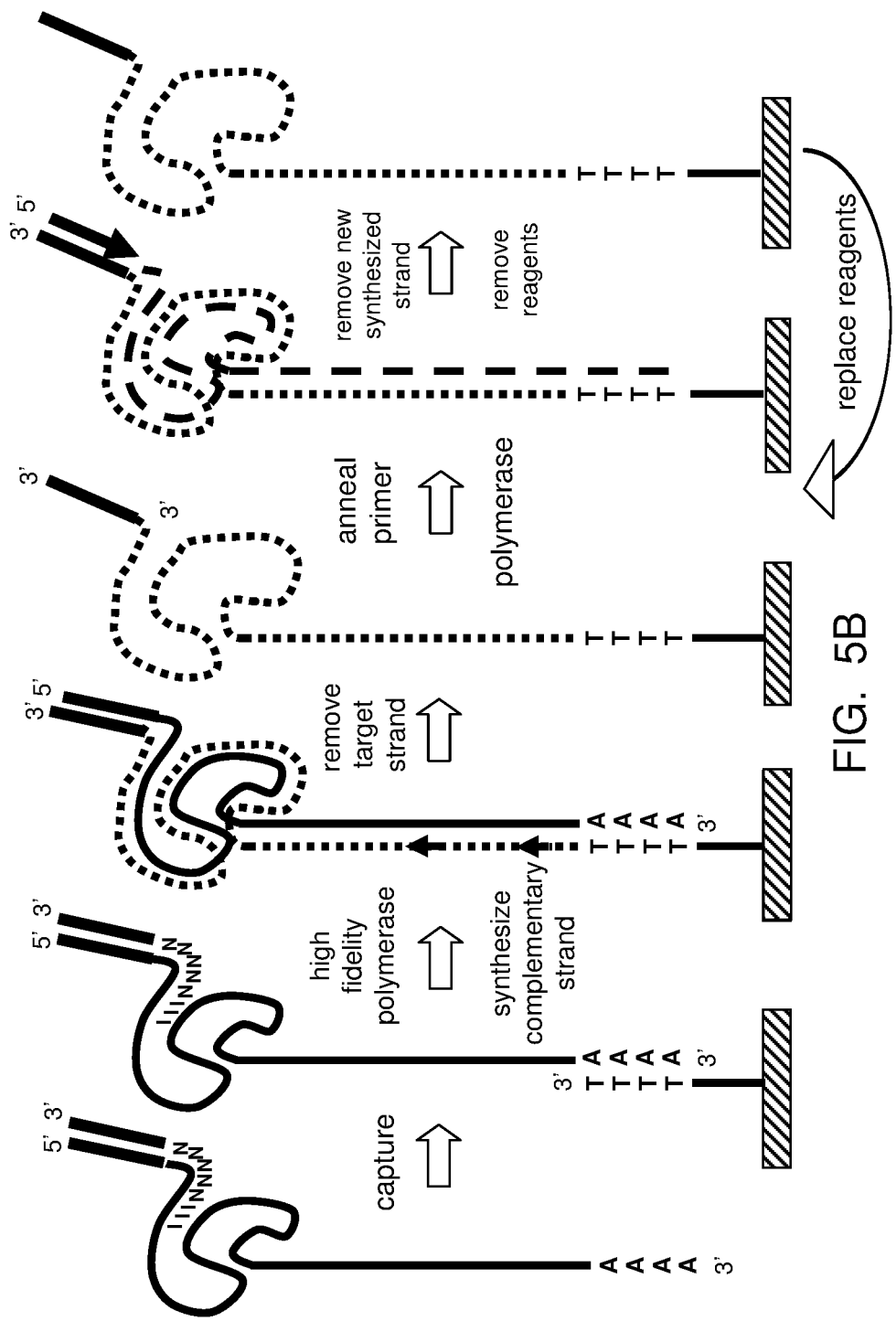
FIG. 5B depicts one embodiment showing an immobilized target molecule/primer duplex to synthesize an extension product, where the same extension product is re-sequenced in a direction towards the solid surface, using the reagent exchange methods.

In yet another embodiment, the 5' end of a target molecule can be ligated to an adaptor molecule using T4 ligase (FIG. 5A). The adaptor molecule can be annealed with a primer having a blocked 3' end (FIG. 5A). The target molecule can be reacted with terminal transferase to add a poly-nucleotide tail (e.g., poly-A, -G, -C, or -T) (TdT in FIG. 5A). The tailed target molecule can be captured by an immobilized oligonucleotide (FIG. 5B). The immobilized oligonucleotide can be used to produce a synthesized strand, using a polymerase and nucleotides (FIG. 5B). Physical, chemical, and/or enzymatic conditions can be used to remove the target strand, polymerase, and nucleotides. A primer can be annealed to the remaining synthesized strand. A newly synthesized strand can be produced using a polymerase and nucleotides. Physical, chemical, and/or enzymatic conditions can be used to remove the newly synthesized strand, polymerase, and nucleotides. The remaining synthesized strand can be contacted with fresh reagents to permit re-sequencing the same synthesized strand. FIGS. 5A and B depict re-sequencing the same synthesized strand, in a direction towards the solid surface.

Figure 6A:
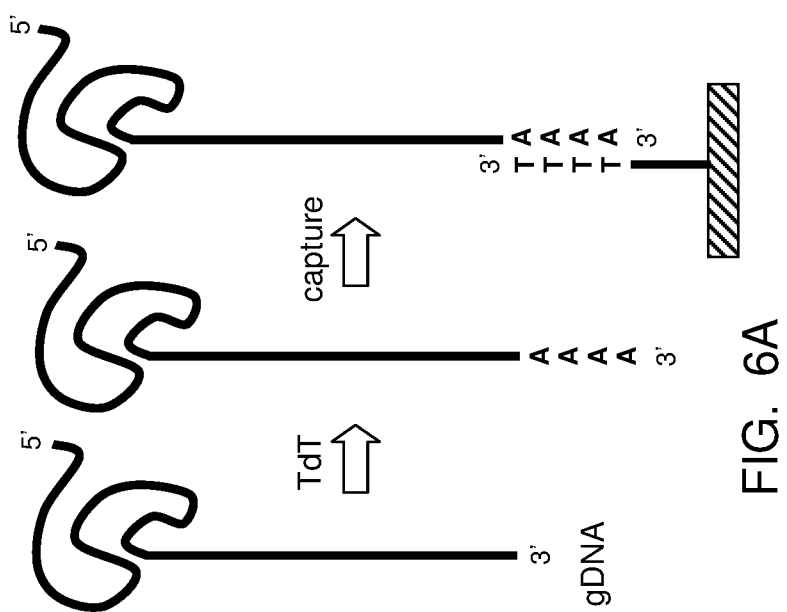
FIG. 6A depicts another embodiment showing an immobilized target molecule/primer duplex to synthesize an extension product, where the same extension product is re-sequenced in a direction towards the solid surface, using the reagent exchange methods.
Figure 6B:
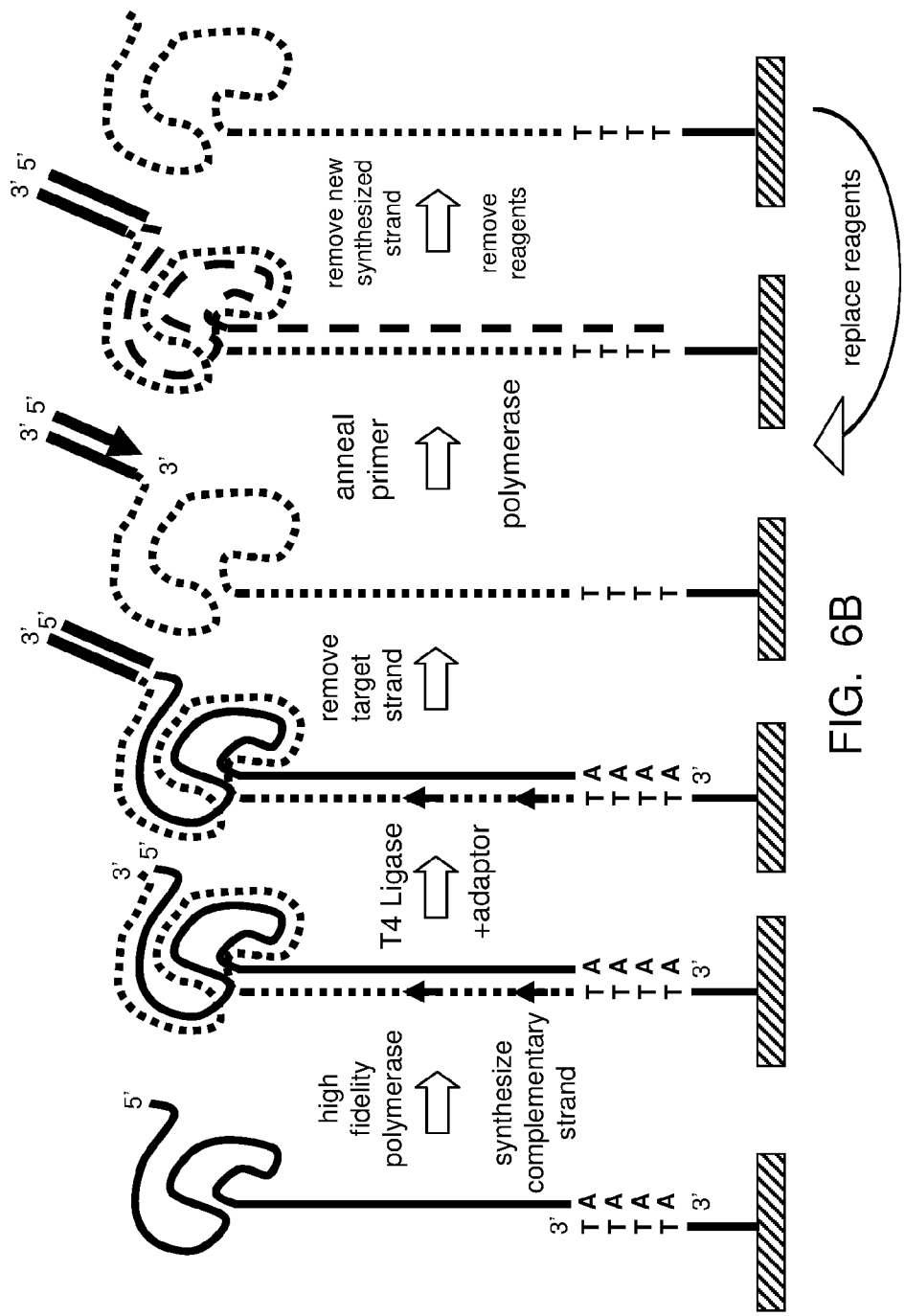
FIG. 6B depicts another embodiment showing an immobilized target molecule/primer duplex to synthesize an extension product, where the same extension product is re-sequenced in a direction towards the solid surface, using the reagent exchange methods.

In yet another embodiment, the target molecule can be reacted with terminal transferase to add a poly-nucleotide tail (e.g., poly-A, -G, -C, or -T) (TdT in FIG. 6A). The tailed target molecule can be captured by an immobilized capture oligonucleotide (FIG. 6A). The immobilized capture oligonucleotide can be used to generate a synthesized strand, using a polymerase and nucleotides (FIG. 6B). The 3' end of the synthesized strand can be ligated to an adaptor molecule. Physical, chemical, and/or enzymatic conditions can be used to remove the target molecule, polymerase, and nucleotides. The 3' end of the remaining synthesized strand can be annealed to a primer. A newly synthesized strand can be generated with a polymerase and nucleotides. Physical, chemical, and/or enzymatic conditions can be used to remove the newly synthesized strand, polymerase, and nucleotides. The remaining synthesized strand can be contacted with fresh reagents to permit re-sequencing the same synthesized strand. FIGS. 6A and B depict re-sequencing the same synthesized strand, in a direction towards the solid surface.

Figure 7:
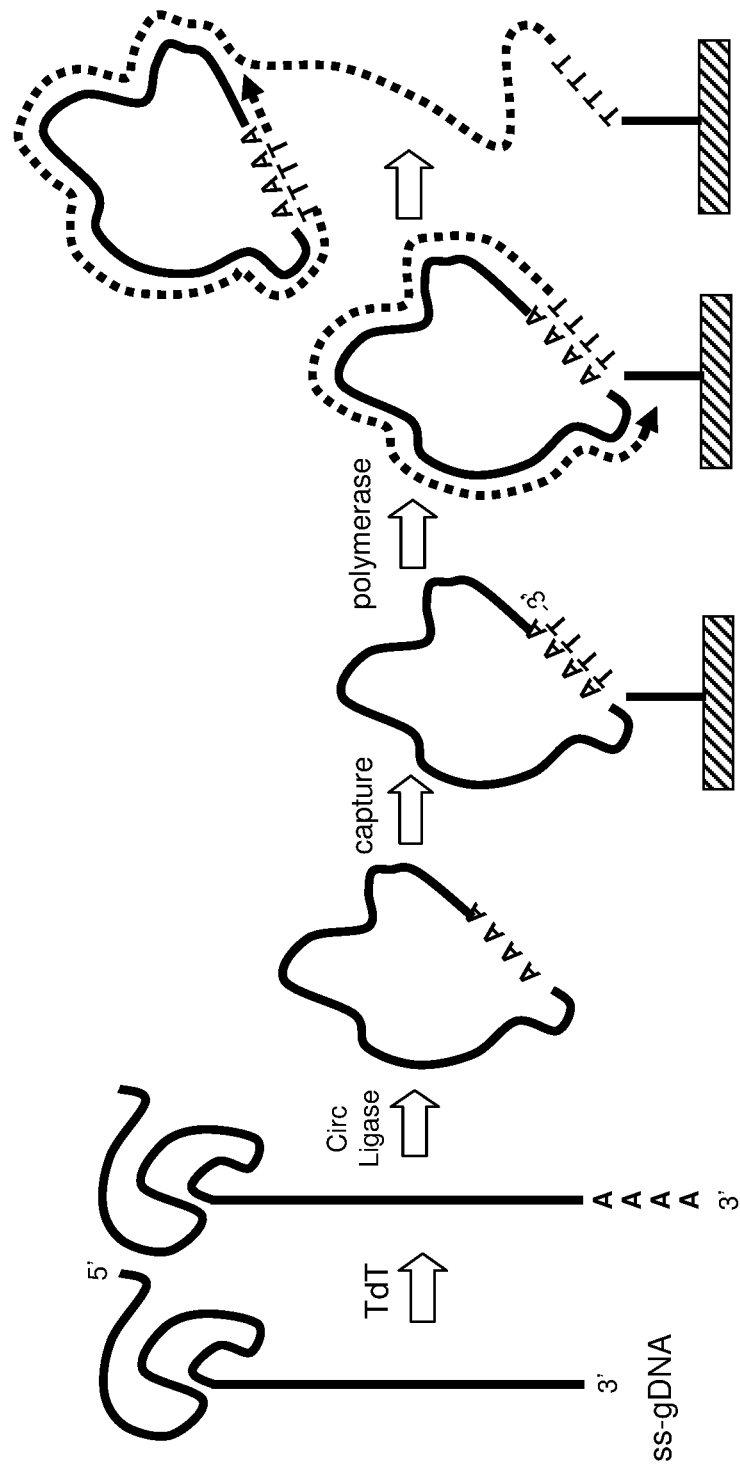
FIG. 7 depicts one embodiment showing an immobilized circular target nucleic acid molecule and a primer for rolling circle replication to re-sequence the same target molecule multiple times.
Figure 8:
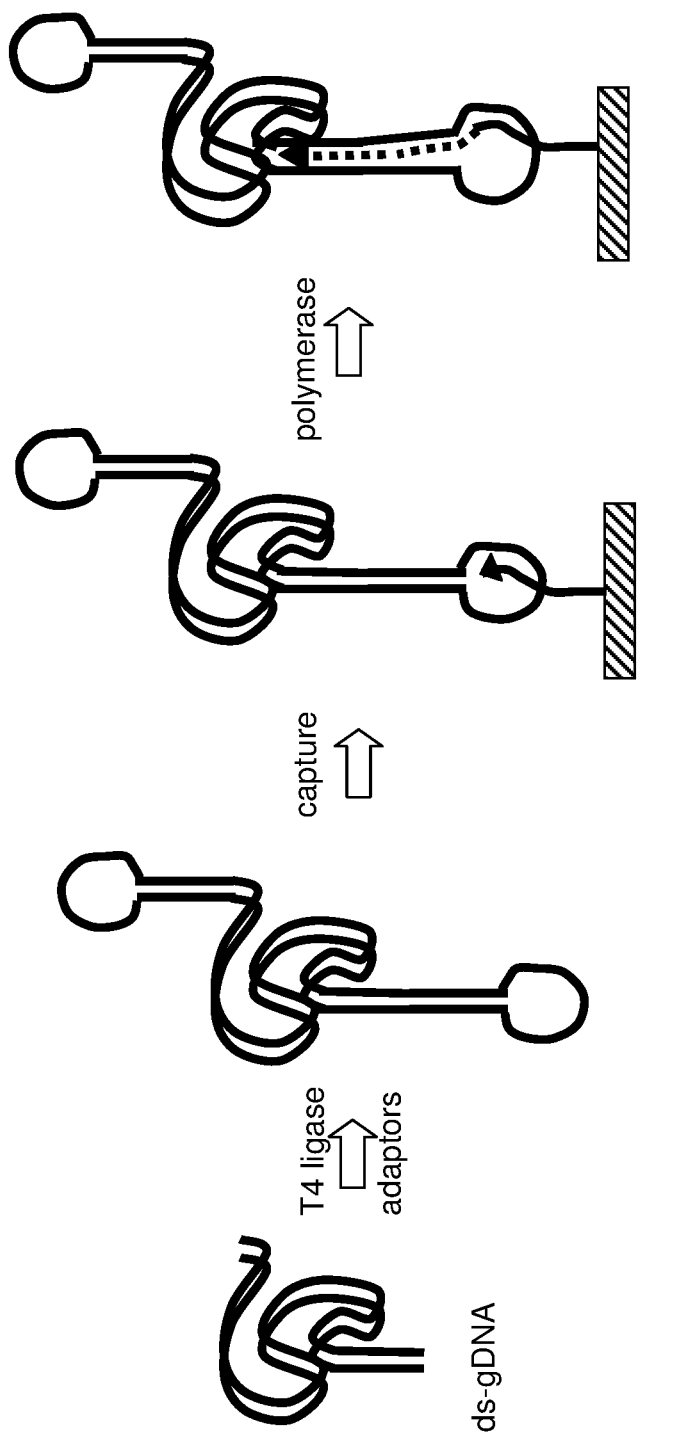
FIG. 8 depicts one embodiment showing an immobilized double-stranded target nucleic acid molecule, which is ligated at both ends with adaptors, for rolling circle replication to re-sequence the same target molecule multiple times.

In yet another embodiment, the target molecule can be reacted with terminal transferase to add a poly-nucleotide tail (e.g., poly-A, -G, -C, or -T) (TdT in FIG. 7). The tailed target molecule can be circularized. The circularized target molecule can be captured by an immobilized oligonucleotide. The 3' end of the capture oligonucleotide can be used to generate a synthesized strand using a polymerase and nucleotides, in a rolling circle replication mode. A strand-displacement DNA polymerase can be used for the rolling circle replication.

In another embodiment, stem-loop adaptor molecules can be ligated to both ends of a double-stranded target molecule using T4 ligase (FIG. 8) to produce a closed-ended molecule. The resulting molecule can be captured by an immobilized oligonucleotide via complementary sequences in one of the stem-loop adaptor molecules. The immobilized capture oligonucleotide can be used as a primer to generate the synthesized strand, using a polymerase and nucleotides.

Nucleotides

The methods, compositions, systems and kits disclosed herein can include nucleotides. The nucleotides can be linked with at least one energy transfer moiety (FIG. 1). The energy transfer moiety can be an energy transfer acceptor or donor moiety. The different types of nucleotides (e.g., adenosine, thymidine, cytidine, guanosine, and uridine) can be labeled with a different type energy transfer acceptor or donor moiety so that the detectable signals (e.g., energy transfer signals) from each of the different types nucleotides can be distinguishable to permit base identity. In one embodiment, the different types of nucleotides (e.g., adenosine, thymidine, cytidine, guanosine, and uridine) can be labeled with a different type of energy transfer acceptor moiety so that the detectable signals (e.g., energy transfer signals) from each of the different types nucleotides can be distinguishable to permit base identity. The nucleotides can be labeled in a way that does not interfere with the events of nucleotide polymerization. For example the attached energy transfer acceptor moiety does not interfere with: nucleotide binding; nucleotide incorporation; cleavage of the nucleotide; or release of the cleavage product. See for example, U.S. Ser. No. 61/164,091, Ronald Graham, concurrently filed Mar. 27, 2009. See for example U.S. Pat. Nos. 7,041, 812, 7,052,839, 7,125,671, and 7,223,541; U.S. Pub. Nos. 2007/0072196 and 2008/0091005; Sood et al., 2005, J. Am. Chem. Soc. 127:2394-2395; Arzumanov et al., 1996, J. Biol. Chem. 271:24389-24394; and Kumar et al., 2005, Nucleosides, Nucleotides & Nucleic Acids, 24(5):401-408.

In one aspect, the energy transfer acceptor moiety may be linked to any position of the nucleotide. For example, the energy transfer acceptor moiety can be linked to any phosphate group (or substituted phosphate group), the sugar or the base. In another example, the energy transfer moiety can be linked to any phosphate group (or substituted phosphate group) which is released as part of a phosphate cleavage product upon incorporation. In yet another example, the energy transfer acceptor moiety can be linked to the terminal phosphate group (or substituted phosphate group). In another aspect, the nucleotide may be linked with an additional energy transfer acceptor moiety, so that the nucleotide is attached with two or more energy transfer acceptor moieties. The additional energy transfer acceptor moiety can be the same or different as the first energy transfer acceptor moiety. In one embodiment, the energy transfer acceptor moiety can be a FRET acceptor moiety.

In one aspect, the nucleotide may be linked with a reporter moiety which is not an energy transfer moiety. For example, the reporter moiety can be a fluorophore.

In one aspect, the energy transfer acceptor moieties and/or the reporter moiety can be attached to the nucleotide via a linear or branched linker moiety. An intervening linker moiety can connect the energy transfer acceptor moieties with each other and/or to the reporter moiety, in any combination of linking arrangements.

In another aspect, the nucleotides comprise a sugar moiety, base moiety, and at least three, four, five, six, seven, eight, nine, ten, or more phosphate groups (or substituted phosphate groups) linked to the sugar moiety by an ester or phosphoramide linkage. The phosphates can be linked to the 3' or 5' C of the sugar moiety.

In one aspect, different linkers can be used to operably link the different nucleotides (e.g., A, G, C, T or U) to the energy transfer moieties or reporter moieties. For example, adenosine nucleotide can be attached to one type of energy transfer moiety using one type of linker, and guanosine nucleotide can be linked to a different type of energy transfer moiety using a different type of linker. In another example, adenosine nucleotide can be attached to one type of energy transfer moiety using one type of linker, and the other types of nucleotides can be attached to different types of energy transfer moieties using the same type of linker. One skilled in the art will appreciate that many different combinations of nucleotides, energy transfer moieties, and linkers are possible.

In one aspect, the distance between the nucleotide and the energy transfer moiety can be altered. For example, the linker length and/or number of phosphate groups (or substitute phosphate groups) can lengthen or shorten the distance from the sugar moiety to the energy transfer moiety. In another example, the distance between the nucleotide and the energy transfer moiety can differ for each type of nucleotide (e.g., A, G, C, T or U).

In another aspect, the number of energy transfer moieties which are linked to the different types of nucleotides (e.g., A, G, C, T or U) can be the same or different. For example: A can have one dye, and G, C, and T have two; A can have one dye, C has two, G has three, and T has four; A can have one dye, C and G have two, and T has four. One skilled in the art will recognize that many different combinations are possible.

In another aspect, the concentration of the labeled nucleotides used to conduct the nucleotide binding or nucleotide incorporation reactions, or the concentration included in the systems or kits, can be about 0.0001 nM-1 µM, or about 0.0001 nM-0.001 nM, or about 0.001 nM-0.01 nM, or about 0.01 nM-0.1 nM, or about 0.1 nM-1.0 nM, or about 1 nM-25 nM, or about 25 nM-50 nM, or about 50 nM-75 nM, or about 75 nM-100 nM, or about 100 nM-200 nM, or about 200 nM-500 nM, or about 500 nM-750 nM, or about 750 nM-1000 nM, or about 0.1 µM-20 µM, or about 20 µM-50 µM, or about 50 µM-75 µM, or about 75 µM-100 µM, or about 100 µM-200 µM, or about 200 µM-500 µM, or about 500 µM-750 µM, or about 750 µM-1000 µM.

In another aspect, the concentration of the different types of labeled nucleotides, which are used to conduct the nucleotide binding or incorporation reaction, can be the same or different from each other.

Sugar Moieties

The nucleotides typically comprise suitable sugar moieties, such as carbocyclic moieties (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other suitable sugar moieties (Joeng, et al., 1993 J. Med. Chem. 36: 2627-2638; Kim, et al., 1993 J. Med. Chem. 36: 30-7; Eschenmosser 1999 Science 284: 2118-2124; and U.S. Pat. No. 5,558,991). The sugar moiety may be selected from the following: ribosyl, 2'-deoxyribosyl, 3'-deoxyribosyl, 2',3'-dideoxyribosyl, 2',3'-didehydrodideoxyribosyl, 2'-alkoxyribosyl, 2'-azidoribosyl, 2'-aminoribosyl, 2'-fluororibosyl, 2'-mercaptoriboxyl, 2'-alkylthioribosyl, 3'-alkoxyribosyl, 3'-azidoribosyl, 3'-aminoribosyl, 3'-fluororibosyl, 3'-mercaptoriboxyl, 3'-alkylthioribosyl carbocyclic, acyclic and other modified sugars. In one aspect, the 3'-position has a hydroxyl group, for strand/chain elongation.

Base Moieties

The nucleotides typically comprise a hetero cyclic base which includes substituted or unsubstituted nitrogen-containing parent heteroaromatic ring which is commonly found in nucleic acids, including naturally-occurring, substituted, modified, or engineered variants. The base is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethylcytosines; 5-methycytosines; base (Y); as well as methylated, glycosylated, and acylated base moieties; and the like. Additional exemplary bases can be found in Fasman, 1989, in: *Practical Handbook of Biochemistry and Molecular Biology*, pp. 385-394, CRC Press, Boca Raton, Fla., and the references cited therein.

Phosphate Groups

The nucleotides typically comprise phosphate groups which can be linked to the 2', 3' and/or 5' position of the sugar moiety. The phosphate groups include analogs, such as phosphoramidate, phosphorothioate, phosphorodithioate, and O-methylphosphoroamidite groups. In one embodiment, at least one of the phosphate groups can be substituted with a fluoro and/or chloro group. The phosphate groups can be linked to the sugar moiety by an ester or phosphoramide linkage. Typically, the nucleotide comprises three, four, five, six, seven, eight, nine, ten, or more phosphate groups linked to the 5' position of the sugar moiety.

Non-Hydrolyzable Nucleotides

The methods, compositions, systems and kits disclosed herein can include non-hydrolyzable nucleotides. The nucleotide binding and nucleotide incorporation methods can be practiced using incorporatable nucleotides and non-hydrolyzable nucleotides. In the presence of the incorporatable nucleotides (e.g., labeled), the non-hydrolyzable nucleotides (e.g., non-labeled) can compete for the polymerase binding site to permit distinction between the complementary and non-complementary nucleotides, or for distinguishing between productive and non-productive binding events. In the nucleotide incorporation reaction, the presence of the non-hydrolyzable nucleotides can alter the length of time, frequency, and/or duration of the binding of the labeled incorporatable nucleotides to the polymerase.

The non-hydrolyzable nucleotides can be non-labeled or can be linked to a reporter moiety (e.g., energy transfer moiety). The labeled non-hydrolyzable nucleotides can be linked to a reporter moiety at any position, such as the sugar, base, or any phosphate (or substituted phosphate group). For example, the non-hydrolyzable nucleotides can have the general structure:

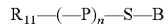

Where B can be a base moiety, such as a hetero cyclic base which includes substituted or unsubstituted nitrogen-containing heteroaromatic ring. Where S can be a sugar moiety, such as a ribosyl, riboxyl, or glucosyl group. Where n can be 1-10, or more. Where P can be one or more substituted or unsubstituted phosphate or phosphonate groups. Where $R_{11}$, if included, can be a reporter moiety (e.g., a fluorescent dye). In one embodiment, the non-hydrolyzable nucleotide having multiple phosphate or phosphonate groups, the linkage between the phosphate or phosphonate groups can be non-hydrolyzable by the polymerase. The non-hydrolyzable linkages include, but are not limited to, amino, alkyl, methyl, and thio groups. The phosphate or phosphonate portion of the non-hydrolyzable nucleotide can have the general structure:

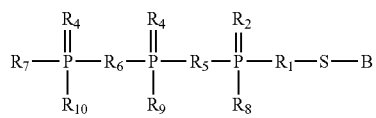

Where B can be a base moiety and S can be a sugar moiety. Where any one of the $R_1$-$R_7$ groups can render the nucleotide non-hydrolyzable by a polymerase. Where the sugar C5 position can be $CH_2$, $CH_2O$, $CH=$, CHR, or $CH_2CH_2$. Where the $R_1$ group can be O, S, $CH=$, CH(CN), or NH. Where the $R_2$, $R_3$, and $R_4$ groups can independently be O, $BH_3$, or SH. Where the $R_5$ and $R_6$ groups can independently be an amino, alkyl, methyl, thio group, or CHF, $CF_2$, CHBr, $CCl_2$, O—O, or —C≡C—. Where the $R_7$ group can be oxygen, or one or more additional phosphate or phosphonate groups, or can be a reporter moiety. Where $R_8$ can be SH, $BH_3$, $CH_3$, $NH_2$, or a phenyl group or phenyl ring. Where $R_9$ can be SH. Where $R_{10}$ can be $CH_3$, $N_3CH_2CH_2$, $NH_2$, ANS, $N_3$, MeO, SH, Ph, F, PhNH, PhO, or RS (where Ph can be a phenyl group or phenyl ring, and F can be a fluorine atom or group). The substituted groups can be in the S or R configuration.

The non-hydrolyzable nucleotides can be alpha-phosphate modified nucleotides, alpha-beta nucleotides, beta-phosphate modified nucleotides, beta-gamma nucleotides, gamma-phosphate modified nucleotides, caged nucleotides, or di-nucleotides.

Many examples of non-hydrolyzable nucleotides are known (Rienitz 1985 Nucleic Acids Research 13:5685-5695), including commercially-available ones from Jena Bioscience (Jena, Germany).

Polymerases

The compositions, methods, systems and kits disclosed herein involve the use of one or more polymerases. In some embodiments, the polymerase incorporates one or more nucleotides into a nucleic acid molecule.

In some embodiments, the polymerase provided herein can offer unexpected advantages over polymerases that are traditionally used for nucleotide polymerization reactions. In some embodiments, the polymerases can be enzymatically active when conjugated to an energy transfer moiety (e.g., donor moiety). In some embodiments, the polymerases have altered kinetics for nucleotide binding and/or nucleotide incorporation which improve distinction between productive and non-productive nucleotide binding events. In some embodiments, the polymerases having altered kinetics for nucleotide binding and/or nucleotide incorporation can be used in combination with labeled nucleotides having six or more phosphate groups (or substituted phosphate groups), which improves distinction between productive and non-productive binding events. In some embodiments, the polymerases have improved photo-stability compared to polymerases traditionally used for nucleotide polymerization. Examples of polymerases having altered kinetics for nucleotide binding and/or nucleotide incorporation include B103 polymerases disclosed in U.S. Ser. Nos. 61/242,771, 61/293,618, and any one of SEQ ID NOS:1-5.

In some embodiments, the polymerase can be unlabeled. Alternatively, the polymerase can be linked to one or more reporter moiety. In some embodiments, the reporter moiety comprises at least one energy transfer moiety.

The polymerase may be linked with at least one energy transfer donor or acceptor moiety. One or more energy transfer donor or acceptor moiety can be linked to the polymerase at the amino end or carboxyl end or may be inserted at any site therebetween. Optionally, the energy transfer donor or acceptor moiety can be attached to the polymerase in a manner which does not significantly interfere with the nucleotide binding activity, or with the nucleotide incorporation activity of the polymerase. In such embodiments, the energy transfer donor or acceptor moiety is attached to the polymerase in a manner that does not significantly interfere with polymerase activity.

In one aspect, a single energy transfer donor or acceptor moiety can be linked to more than one polymerase and the attachment can be at the amino end or carboxyl end or may be inserted within the polymerase.

In another aspect, a single energy transfer donor or acceptor moiety can be linked to one polymerase.

In one aspect, the energy transfer donor moiety can be a nanoparticle (e.g., a fluorescent nanoparticle) or a fluorescent dye. The polymerase, which can be linked to the nanoparticle or fluorescent dye, typically retains one or more activities that are characteristic of the polymerase, e.g., polymerase activity, exonuclease activity, nucleotide binding, and the like.

In one aspect, the polymerases can be replicases, DNA-dependent polymerases, primases, RNA-dependent polymerases (including RNA-dependent DNA polymerases such as, for example, reverse transcriptases), strand-displacement polymerases, or thermo-stable polymerases. In another aspect, the polymerase can be any Family A or B type polymerase. Many types of Family A (e.g., *E. coli* Pol I), B (e.g., *E. coli* Pol II), C (e.g., *E. coli* Pol III), D (e.g., Euryarchaeotic Pol II), X (e.g., human Pol beta), and Y (e.g., *E. coli* UmuC/DinB and eukaryotic RAD30/xeroderma pigmentosum variants) polymerases are described in Rothwell and Watsman 2005 Advances in Protein Chemistry 71:401-440.

In yet another aspect, the polymerases can be isolated from a cell, or generated using recombinant DNA technology or chemical synthesis methods. In another aspect, the polymerases can be expressed in prokaryote, eukaryote, viral, or phage organisms. In another aspect, the polymerases can be post-translationally modified proteins or fragments thereof.

In one aspect, the polymerase can be a recombinant protein which is produced by a suitable expression vector/host cell system. The polymerases can be encoded by suitable recombinant expression vectors carrying inserted nucleotide sequences of the polymerases. The polymerase sequence can be linked to a suitable expression vector. The polymerase sequence can be inserted in-frame into the suitable expression vector. The suitable expression vector can replicate in a phage host, or a prokaryotic or eukaryotic host cell. The suitable expression vector can replicate autonomously in the host cell, or can be inserted into the host cell's genome and be replicated as part of the host genome. The suitable expression vector can carry a selectable marker which confers resistance to drugs (e.g., kanamycin, ampicillin, tetracycline, chloramphenicol, or the like), or confers a nutrient requirement. The suitable expression vector can have one or more restriction sites for inserting the nucleic acid molecule of interest. The suitable expression vector can include expression control sequences for regulating transcription and/or translation of the encoded sequence. The expression control sequences can include: promoters (e.g., inducible or constitutive), enhancers, transcription terminators, and secretion signals. The expression vector can be a plasmid, cosmid, or phage vector. The expression vector can enter a host cell which can replicate the vector, produce an RNA transcript of the inserted sequence, and/or produce protein encoded by the inserted sequence. The recombinant polymerase can include an affinity tag for enrichment or purification, including a poly-amino acid tag (e.g., poly His tag), GST, and/or HA sequence tag. Methods for preparing suitable recombinant expression vectors and expressing the RNA and/or protein encoded by the inserted sequences are well known (Sambrook et al, *Molecular Cloning* (1989)).

The polymerases may be DNA polymerases and include without limitation bacterial DNA polymerases, prokaryotic DNA polymerase, eukaryotic DNA polymerases, archaeal DNA polymerases, viral DNA polymerases and phage DNA polymerases. The polymerase can be a commercially available polymerase.

In some embodiments, the polymerase can be a DNA polymerase and include without limitation bacterial DNA polymerases, eukaryotic DNA polymerases, archaeal DNA polymerases, viral DNA polymerases and phage DNA polymerases.

Suitable bacterial DNA polymerase include without limitation *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase.

Suitable eukaryotic DNA polymerases include without limitation the DNA polymerases α, δ, ε, η, ζ, γ, β, σ, λ, μ, ι, and κ, as well as the Rev1 polymerase (terminal deoxycytidyl transferase) and terminal deoxynucleotidyl transferase (TdT).

Suitable viral and/or phage DNA polymerases include without limitation T4 DNA polymerase, T5 DNA polymerase, T7 DNA polymerase, Phi-15 DNA polymerase, Phi-29 DNA polymerase (see, e.g., U.S. Pat. No. 5,198,543; also referred to variously as Φ29 polymerase, phi29 polymerase, phi 29 polymerase, Phi 29 polymerase, and Phi29 polymerase); Φ15 polymerase (also referred to herein as Phi-15 polymerase); Φ21 polymerase (Phi-21 polymerase); PZA polymerase; PZE polymerase; PRD1 polymerase; Nf polymerase; M2Y polymerase; SF5 polymerase; fl DNA polymerase, Cp-1 polymerase; Cp-5 polymerase; Cp-7 polymerase; PR4 polymerase; PR5 polymerase; PR722 polymerase; L17 polymerase; M13 DNA polymerase, RB69 DNA polymerase, G1 polymerase; GA-1 polymerase, BS32 polymerase; B103 polymerase; BA103 polymerase, a polymerase obtained from any phi-29 like phage or derivatives thereof, etc. See, e.g., U.S. Pat. No. 5,576,204, filed Feb. 11, 1993; U.S. Pat. Appl. No. 2007/0196846, published Aug. 23, 2007.

Suitable archaeal DNA polymerases include without limitation the thermostable and/or thermophilic DNA polymerases such as, for example, DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase as well as Turbo Pfu DNA polymerase, *Thermococcus litoralis* (Tli) DNA polymerase or Vent DNA polymerase, *Pyrococcus* sp. GB-D polymerase, "Deep Vent" DNA polymerase, New England Biolabs), *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. 9° N-7 DNA polymerase; *Thermococcus* sp. NA1; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; the heterodimeric DNA polymerase DP1/DP2, etc.

Suitable RNA polymerases include, without limitation, T3, T5, T7, and SP6 RNA polymerases.

Suitable reverse transcriptases include without limitation reverse transcriptases from HIV, HTLV-I, HTLV-II, FeLV, FIV, SIV, AMV, MMTV and MoMuLV, as well as the commercially available "Superscript" reverse transcriptases, (Life Technologies Corp., Carlsbad, Calif.) and telomerases.

In some embodiments, the polymerase is selected from the group consisting of: Phi-29 DNA polymerase, a variant of Phi-29 DNA polymerase, B103 DNA polymerase and a variant of B103 DNA polymerase.

In another aspect, the polymerases can include one or more mutations that improve the performance of the polymerase in the particular biological assay of interest. The mutations can include amino acid substitutions, insertions, or deletions.

Selecting a Polymerase

The selection of the polymerase for use in the disclosed methods can be based on the desired polymerase behavior in the particular biological assay of interest. For example, the polymerase can be selected to exhibit enhanced or reduced activity in a particular assay, or enhanced or reduced interaction with one or more particular substrates.

For example, in some embodiments the polymerase is selected based on the polymerization kinetics of the polymerase either in unconjugated form or when linked to a reporter moiety (labeled polymerase conjugate). For example, the polymerase can be a polymerase having altered nucleotide binding and/or altered nucleotide incorporation kinetics which are selected on the basis of kinetic behavior relating to nucleotide binding (e.g., association), nucleotide dissociation (intact nucleotide), nucleotide fidelity, nucleotide incorporation (e.g., catalysis), and/or release of the cleavage product. The selected polymerase can be wild-type or mutant.

In one embodiment, polymerases may be selected that retain the ability to selectively bind complementary nucleotides. In another embodiment, the polymerases may be selected which exhibit a modulated rate (faster or slower) of nucleotide association or dissociation. In another embodiment, the polymerases may be selected which exhibit a reduced rate of nucleotide incorporation activity (e.g., catalysis) and/or a reduced rate of dissociation of the cleavage product and/or a reduced rate of polymerase translocation (after nucleotide incorporation). Some modified polymerases which exhibit nucleotide binding and a reduced rate of nucleotide incorporation have been described (Rank, U.S. published patent application No. 2008/0108082; Hanzel, U.S. published patent application No. 2007/0196846).

In polymerases from different classes (including DNA-dependent polymerases), an active-site lysine can interact with the phosphate groups of a nucleoside triphosphate molecule bound to the active site. The lysine residue has been shown to protonate the pyrophosphate leaving-group upon nucleotidyl transfer. Mutant polymerases having this lysine substituted with leucine, arginine, histidine or other amino acids, exhibit greatly reduced nucleotide incorporation rates (Castro, et al., 2009 Nature Structural and Molecular Biology 16:212-218). One skilled in the art can use amino acid alignment and/or comparison of crystal structures of polymerases as a guide to determine which lysine residue to replace with alternative amino acids. The sequences of Phi29 (SEQ ID NOS:6-12), RB69 (SEQ ID NO:13), B103 (SEQ ID NOS:1-5), and Klenow fragment can be used as the basis for selecting the amino acid residues to be modified (for B103 polymerase, see Hendricks, et al., U.S. Ser. No. 61/242,771, filed on Sep. 15, 2009, or U.S. Ser. No. 61/293,618, filed on Jan. 8, 2010). In one embodiment, a modified phi29 polymerase can include lysine at position 379 and/or 383 substituted with leucine, arginine or histidine.

In other embodiments, the polymerase can be selected based on the combination of the polymerase and nucleotides, and the reaction conditions, to be used for the nucleotide binding and/or nucleotide incorporation reactions. For example, certain polymerases in combination with nucleotides which comprise 3, 4, 5, 6, 7, 8, 9, 10 or more phosphate groups can be selected for performing the disclosed methods. In another example, certain polymerases in combination with nucleotides which are linked to an energy transfer moiety can be selected for performing the nucleotide incorporation methods.

The polymerases, nucleotides, and reaction conditions, can be screened for their suitability for use in the nucleotide binding and/or nucleotide incorporation methods, using well known screening techniques. For example, the suitable polymerase may be capable of binding nucleotides and/or incorporating nucleotides. For example, the reaction kinetics for nucleotide binding, association, incorporation, and/or dissociation rates, can be determined using rapid kinetics techniques (e.g., stopped-flow or quench flow techniques). Using stopped-flow or quench flow techniques, the binding kinetics of a nucleotide can be estimated by calculating the $1/k_d$ value. Stopped-flow techniques which analyze absorption and/or fluorescence spectroscopy properties of the nucleotide binding, incorporation, or dissociation rates to a polymerase are well known in the art (Kumar and Patel 1997 Biochemistry 36:13954-13962; Tsai and Johnson 2006 Biochemistry 45:9675-9687; Hanzel, U.S. published patent application No. 2007/0196846). Other methods include quench flow (Johnson 1986 Methods Enzymology 134:677-705), time-gated fluorescence decay time measurements (Korlach, U.S. Pat. No. 7,485,424), plate-based assays (Clark, U.S. published patent application No. 2009/0176233), and X-ray crystal structure analysis (Berman 2007 EMBO Journal 26:3494). Nucleotide incorporation by a polymerase can also be analyzed by gel separation of the primer extension products. In one embodiment, stopped-flow techniques can be used to screen and select combinations of nucleotides with polymerases having a $t_{pol}$ value (e.g., $1/k_{pol}$) which is less than a $t_{-1}$ (e.g., $1/k_{-1}$) value. Stopped-flow techniques for measuring $t_{pol}$ (M P Roettger 2008 Biochemistry 47:9718-9727; M Bakhtina 2009 Biochemistry 48:3197-320) and $t_{-1}$ (M Bakhtina 2009 Biochemistry 48:3197-3208) are known in the art.

For example, some phi29 or B103 (SEQ ID NOS:1, 2, or 3) polymerases (wild-type or mutant) exhibit $t_{pol}$ values which are less than $t_{-1}$ values, when reacted with tetraphosphate, pentaphosphate or hexaphosphate nucleotides. These polymerases can offer improvements in distinguishing between productive and non-productive nucleotide binding events compared to other polymerases. In another embodiment, polymerases can be modified by binding it to a chemical compound or an antibody, in order to inhibit nucleotide incorporation.

In some embodiments, the selection of the polymerase may be determined by the level of processivity desired for conducting nucleotide incorporation or polymerization reactions. The polymerase processivity can be gauged by the number of nucleotides incorporated for a single binding event between the polymerase and the target molecule base-paired with the polymerization initiation site. For example, the processivity level of the polymerase may be about 1, 5, 10, 20, 25, 50, 100, 250, 500, 750, 1000, 2000, 5000, or 10,000 or more nucleotides incorporated with a single binding event. Processivity levels typically correlate with read lengths of a polymerase. Optionally, the polymerase can be selected to retain the desired level of processivity when conjugated to a reporter moiety.

The selection of the polymerase may be determined by the level of fidelity desired, such as the error rate per nucleotide incorporation. The fidelity of a polymerase may be partly determined by the 3'→5' exonuclease activity associated with a DNA polymerase. The fidelity of a DNA polymerase may be measured using assays well known in the art (Lundburg et al., 1991 Gene, 108:1-6). The error rate of the polymerase can be one error per about 100, or about 250, or about 500, or about 1000, or about 1500 incorporated nucleotides. In some embodiments, the polymerase is selected to exhibit high fidelity. Such high-fidelity polymerases include those exhibiting error rates typically of about $5 \times 10^{-6}$ per base pair or lower.

In some embodiments, the selection of the polymerase may be determined by the rate of nucleotide incorporation such as about one nucleotide per 2-5 seconds, or about one nucleotide per second, or about 5 nucleotides per second, or about 10 nucleotides per second, or about 20 nucleotides per second, or about 30 nucleotides per second, or more than 40 nucleotides per second, or more than 50-100 per second, or more than 100 per second. In one embodiment, polymerases exhibiting reduced nucleotide incorporation rates include mutant phi29 polymerase having lysine substituted with leucine, arginine, histidine or other amino acids (Castro 2009 Nature Structural and Molecular Biology 16:212-218).

In some embodiments, the polymerase can be selected to exhibit either reduced or enhanced rates of nucleotide incorporation when reacted with nucleotides linked at the terminal phosphate group with an energy transfer acceptor.

In some embodiments, the polymerase can be selected to exhibit either reduced or enhanced nucleotide binding times for a particular nucleotide of interest. In some embodiments, the nucleotide binding time of the selected polymerase for the particular labeled nucleotide of interest can be between about 20 msec and about 300 msec, typically between about 55 msec and about 100 msec. In some embodiments, the nucleotide binding time of the selected polymerase for the particular labeled nucleotide of interest can be between about 1.5 and about 4 times the nucleotide binding time of the corresponding wild-type polymerase for the labeled nucleotide. These polymerases can offer improvements in distinguishing between productive and non-productive nucleotide binding events compared to other polymerases.

In some embodiments, the polymerase can be selected, mutated, modified, evolved or otherwise engineered to exhibit either reduced or enhanced entry of nucleotides, particularly labeled nucleotides, into the polymerase active site. These polymerases can offer improvements in distinguishing between productive and non-productive nucleotide binding events compared to other polymerases.

In some embodiments, the polymerase can be selected to exhibit a reduced $K_{sub}$ for a substrate, particularly a labeled nucleotide. In some embodiments, the polymerase can comprise one or more mutations resulting in altered $K_{cat}/K_{sub}$ and/or $V_{max}/K_{sub}$ for a particular labeled nucleotide. In some embodiments, the $K_{cat}/K_{sub}$, the $V_{max}/K_{sub}$, or both, are increased compared to the wild type polymerase.

In one embodiment, mutant polymerases having altered nucleotide binding kinetics and/or altered nucleotide incorporation kinetics can be selected for use in the nucleotide incorporation methods. The altered kinetics for nucleotide binding and/or for nucleotide incorporation include: polymerase binding to the target molecule; polymerase binding to the nucleotide; polymerase catalyzing nucleotide incorporation; the polymerase cleaving the phosphate group or substituted phosphate group; and/or the polymerase releasing the cleavage product. These polymerases can offer improvements in distinguishing between productive and non-productive nucleotide binding events compared to other polymerases.

In one embodiment, the selected polymerases can have improved photo-stability compared to polymerases traditionally used in nucleotide polymerization reactions. The desirable polymerases can remain enzymatically active during and/or after exposure to electromagnetic energy (e.g., light). For example, the desirable polymerase can retain a level of enzymatic activity, and/or be enzymatically active for a greater length of time, compared to polymerases traditionally used in nucleotide polymerization reactions after exposure to electromagnetic energy. Methods for measuring enzymatic activity are well known in the art.

In one embodiment, the selected polymerase can be enzymatically active when conjugated to an energy transfer moiety (e.g., nanoparticle or fluorescent dye). The selected polymerase, as part of a polymerase-energy transfer moiety conjugate, can polymerize nucleotides. For example, various forms of B103 polymerase (SEQ ID NOS: 1, 2, and 3) retain enzymatic activity when linked to a nanoparticle or fluorescent dye. Conjugates having these types of selected polymerases offer advantages over other polymerases which may lose most or all enzymatic activity when linked to an energy transfer moiety.

In some embodiments, the polymerase can be a deletion mutant which retains nucleotide polymerization activity but lacks the 3'→5' or 5'→3' exonuclease activity (SEQ ID NOS:1-12). For example, mutant phi29 polymerases having exonuclease-minus activity, or reduced exonuclease activity, can optionally comprise the amino acid sequence of SEQ ID NOS:7-12 and further comprise one or more amino acid substitutions at positions selected from the group consisting of: 12, 14, 15, 62, 66, 165 and 169 (wherein the numbering is relative to the amino acid sequence of wild type phi29 according to SEQ ID NO:6). In some embodiments, the polymerase is a phi29 polymerase comprising the amino acid sequence of SEQ ID NO:6 and one or more of the following amino acid substitutions: D12A, E14I, E14A, T15I, N62D, D66A, Y165F, Y165C, and D169A, wherein the numbering is relative to SEQ ID NO:6.

In one embodiment, the mutant phi29 polymerases include one or more amino acid mutations at positions selected from the group consisting of: 132, 135, 250, 266, 332, 342, 368, 371, 375, 379, 380, 383, 387, 390, 458, 478, 480, 484, 486 and 512, wherein the numbering is relative to the amino acid sequence of SEQ ID NO:6. In some embodiments, the phi29 polymerase can comprise an amino acid deletion, wherein the deletion includes some of all of the amino acids spanning positions 306 to 311 (relative to the numbering in SEQ ID NO:6).

In one embodiment, the mutant phi29 polymerase includes one or more amino acid mutations selected from the group consisting of: K132A, K135A, K135D, K135E, V250A, V250C, Y266F, D332Y, L342G, T368D, T368E, T368F, K370A, K371E, T372D, T372E, T372R, T372K, E375A, E375F, E375H, E375K, E375Q, E375R, E375S, E375W, E375Y, K379A, Q380A, K383E, K383H, K383L, K383R, N387Y, Y390F, D458N, K478D, K478E, K478R, L480K, L480R, A484E, E486A, E486D, K512A K512D, K512E, K512R, K512Y, K371E/K383E/N387Y/D458N, Y266F/Y390F, Y266F/Y390F/K379A/Q380A, K379A/Q380A, E375Y/Q380A/K383R, E375Y/Q380A/K383H, E375Y/Q380A/K383L, E375Y/Q380A/V250A, E375Y/ Q380A/V250C, E375Y/K512Y/T368F, E375Y/K512Y/ T368F/A484E, K379A/E375Y, K379A/K383R, K379A/ K383H, K379A/K383L, K379A/Q380A, V250A/K379A, V250A/K379A/Q380A, V250C/K379A/Q380A, K132A/ K379A and deletion of some or all of the amino acid residues spanning R306 to K311, wherein the numbering is relative to the amino acid sequence of SEQ ID NO:6.

Without being bound to any particular theory, it is thought that the domain comprising amino acid residues 304-314 of the amino acid sequence of SEQ ID NO: 6 (Phi-29 polymerase), or homologs thereof, can reduce or otherwise interfere with DNA initiation and/or elongation by inhibiting access to the Phi-29 polymerase active site, and that this region must be displaced in order to allow access to the active site. See, e.g., Kamtekar et al., "The Φ29 DNA polymerase:protein primer structure suggests a model for the initiation to elongation transition", EMBO J., 25:1335-1343 (2005).

In another embodiment, the polymerase can be a B103 polymerase comprising the amino acid sequence of SEQ ID NOS:1-5. The B103 polymerase can optionally include one or more mutations that reduce the exonuclease activity of the polymerase. Optionally, such mutations can include any one or a combination of mutations at the following amino acid positions: 2, 9, 11, 12, 14, 15, 58, 59, 63, 162, 166, 377 and 385, wherein the numbering is relative to SEQ ID NOS:1 or 2. In some embodiments, the B103 polymerase can optionally comprise the amino acid sequence of SEQ ID NOS:1 or 2, and further comprise one or more amino acid substitutions selected from the group consisting of: D9A, E11A, E11I, T121, H58R, N59D, D63A, Y162F, Y162C, D166A, Q377A and 5385G, wherein the numbering is relative to SEQ ID NOS:1 or 2.

In some embodiments, the B103 polymerase can optionally the amino acid sequence of SEQ ID NOS:1 or 2, and further comprise one or more amino acid substitutions selected from the group consisting of (in single letter amino acid code): H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D5075, D507R, D507A, D507R, D507Q, D507W, D507Y, D507F, K509H, K509G, K509D, K509R, K509E, K509T, K5095, K509R, K509A, K509Q, K509W, K509Y and K509F, wherein the numbering is relative to the sequence shown in SEQ ID NOS:1 or 2. The B103 polymerase can optionally further comprise the amino acid sequence of any of the polymerases disclosed by Hendricks, in U.S. Ser. No. 61/242,771, filed on Sep. 15, 2009, or U.S. Ser. No. 61/293,618, filed on Jan. 8, 2010.

Polymerases having desirable properties, including those having altered nucleotide binding and/or nucleotide incorporation kinetics, having improved photo-stability, and/or having improved enzymatic activity when conjugated to an energy transfer moiety, include polymerases according to SEQ ID NOS:1-5.

SEQ ID NO: 1
MPRKMFSCDFETTTKLDDCRVWAYGYMEIGNLDNYKIGNSLDEFMQWVME

IQADLYFHNLKFDGAFIVNWLEHHGFKWSNEGLPNTYNTIISKMGQWYMI

DICFGYKGKRKLHTVIYDSLKKLPFPVKKIAKDFQLPLLKGDIDYHAERP

VGHEITPEEYEYIKNAIEIIARALDIQFKQGLDRMTAGSDSLKGFKDILS

TKKFNKVFPKLSLPMDKEIRRAYRGGFTWLNDKYKEKEIGEGMVFDVNSL

YPSQMYSRPLPYGAPIVFQGKYEKDEQYPLYIQRIRFEFELKEGYIPTIQ

IKKNPFFKGNEYLKNSGAEPVELYLTNVDLELIQEHYEMYNVEYIDGFKF

REKTGLFKEFIDKWTYVKTHEKGAKKQLAKLMLNSLYGKFASNPDVTGKV

PYLKEDGSLGFRVGDEEYKDPVYTPMGVFITAWARFTTITAAQACYDRII

YCDTDSIHLTGTEVPEIIKDIVDPKKLGYWAHESTFKRAKYLRQKTYIQD

IYAKEVDGKLIECSPDEATTTKFSVKCAGMTDTIKKKVTFDNFRVGFSST

GKPKPVQVNGGVVLVDSVFTIK

SEQ ID NO: 2
MPRKMFSCDFETTTKLDDCRVWAYGYMEIGNLDNYKIGNSLDEFMQWVME

IQADLYFHNLKFDGAFIVNWLEHHGFKWSNEGLPNTYNTIISKMGQWYMI

DICFGYKGKRKLHTVIYDSLKKLPFPVKKIAKDFQLPLLKGDIDYHAERP

VGHEITPEEYEYIKNDIEIIARALDIQFKQGLDRMTAGSDSLKGFKDILS

TKKFNKVFPKLSLPMDKEIRRAYRGGFTWLNDKYKEKEIGEGMVFDVNSL

YPSQMYSRPLPYGAPIVFQGKYEKDEQYPLYIQRIRFEFELKEGYIPTIQ

IKKNPFFKGNEYLKNSGAEPVELYLTNVDLELIQEHYEMYNVEYIDGFKF

REKTGLFKEFIDKWTYVKTHEKGAKKQLAKLMLNSLYGKFASNPDVTGKV

PYLKEDGSLGFRVGDEEYKDPVYTPMGVFITAWARFTTITAAQACYDRII

YCDTDSIHLTGTEVPEIIKDIVDPKKLGYWAHESTFKRAKYLRQKTYIQD

IYAKEVDGKLIECSPDEATTTKFSVKCAGMTDTIKKKVTFDNFRVGFSST

GKPKPVQVNGGVVLVDSVFTIK

SEQ ID NO: 3
MSHHHHHHSMSGLNDIFEAQKIEWHEGAPGARGSKHMPRKMFSCDFETTT

KLDDCRVWAYGYMEIGNLDNYKIGNSLDEFMQWVMEIQADLYFHNLKFDG

AFIVNWLEHHGFKWSNEGLPNTYNTIISKMGQWYMIDICFGYKGKRKLHT

VIYDSLKKLPFPVKKIAKDFQLPLLKGDIDYHAERPVGHEITPEEYEYIK

NAIEIIARALDIQFKQGLDRMTAGSDSLKGFKDILSTKKFNKVFPKLSLP

MDKEIRRAYRGGFTWLNDKYKEKEIGEGMVFDVNSLYPSQMYSRPLPYGA

PIVFQGKYEKDEQYPLYIQRIRFEFELKEGYIPTIQIKKNPFFKGNEYLK

NSGAEPVELYLTNVDLELIQEHYEMYNVEYIDGFKFREKTGLFKEFIDKW

TYVKTREKGAKKQLAKLMLNSLYGKFASNPDVTGKVPYLKEDGSLGFRVG

DEEYKDPVYTPMGVFITAWARFTTITAAQACYDRIIYCDTDSIHLTGTEV

PEIIKDIVDPKKLGYWAHESTFKRAKYLRQKTYIQDIYAKEVDGKLIECS

PDEATTTKFSVKCAGMTDTIKKKVTFDNFRVGFSSTGKPKPVQVNGGVVL

VDSVFTIK

SEQ ID NO: 4
MNHLVHHHHHHIEGRHMELGTLEGSMKHMPRKMFSCDFETTTKLDDCRVW

AYGYMEIGNLDNYKIGNSLDEFMQWVMEIQADLYFHNLKFDGAFIVNWLE

HHGFKWSNEGLPNTYNTIISKMGQWYMIDICFGYKGKRKLHTVIYDSLKK

LPFPVKKIAKDFQLPLLKGDIDYHAERPVGHEITPEEYEYIKNDIEIIAR

ALDIQFKQGLDRMTAGSDSLKGFKDILSTKKFNKVFPKLSLPMDKEIRRA

-continued

YRGGFTWLNDKYKEKEIGEGMVFDVNSLYPSQMYSRPLPYGAPIVFQGKY
EKDEQYPLYIQRIRFEFELKEGYIPTIQIKKNPFFKGNEYLKNSGAEPVE
LYLTNVDLELIQEHYEMYNVEYIDGFKFREKTGLFKEFIDKWTYVKTHEK
GAKKQLAKLMLNSLYGKFASNPDVTGKVPYLKEDGSLGFRVGDEEYKDPV
YTPMGVFITAWARFTTITAAQACYDRIIYCDTDSIHLTGTEVPEIIKDIV
DPKKLGYWAHESTFKRAKYLRQKTYIQDIYAKEVDGKLIECSPDEATTTK
FSVKCAGMTDTIKKKVTFDNFRVGFSSTGKPKPVQVNGGVVLVDSVFTIK

SEQ ID NO: 5
MSHHHHHHSMSGLNDIFEAQKIEWHEGAPGARGSKHMPRKMFSCDFETTT
KLDDCRVWAYGYMEIGNLDNYKIGNSLDEFMQWVMEIQADLYFHNLKFDG
AFIVNWLEHHGFKWSNEGLPNTYNTIISKMGQWYMIDICFGYKGKRKLHT
VIYDSLKKLPFPVKKIAKDFQLPLLKGDIDYHAERPVGHEITPEEYEYIK
NAIEIIARALDIQFKQGLDRMTAGSDSLKGFKDILSTKKFNKVFPKLSLP
MDKEIRRAYRGGFTWLNDKYKEKEIGEGMVFDVNSLYPSQMYSRPLPYGA
PIVFQGKYEKDEQYPLYIQRIRFEFELKEGYIPTIQIKKNPFFKGNEYLK
NSGAEPVELYLTNVDLELIQEHYEMYNVEYIDGFKFREKTGLFKEFIDKW
TYVKTHEKGAKKQLAKLMLNSLYGKFASNPDVTGKVPYLKEDGSLGFRVG
DEEYKDPVYTPMGVFITAWARFTTITAAQACYDRIIYCDTDSIHLTGTEV
PEIIKDIVDPKKLGYWAHESTFKRAKYLRQKTYIQDIYAKEVDGKLIECS
PDEATTTKFSVKCAGMTDTIKKKVTFDNFRVGFSSTGKPKPVQVNGGVVL
VDSVFTIK

SEQ ID NO: 6
MKHMPRKMYSCDFETTTKVEDCRVWAYGYMNIEDHSEYKIGNSLDEFMAW
VLKVQADLYFHNLKFDGAFIINWLERNGFKWSADGLPNTYNTIISRMGQW
YMIDICLGYKGKRKIHTVIYDSLKKLPFPVKKIAKDFKLTVLKGDIDYHK
ERPVGYKITPEEYAYIKNDIQIIAEALLIQFKQGLDRMTAGSDSLKGFKD
IITTKKFKKVFPTLSLGLDKEVRYAYRGGFTWLNDRFKEKEIGEGMVFDV
NSLYPAQMYSRLLPYGEPIVFEGKYVWDEDYPLHIQHIRCEFELKEGYIP
TIQIKRSRFYKGNEYLKSSGGEIADLWLSNVDLELMKEHYDLYNVEYISG
LKFKATTGLFKDFIDKWTYIKTTSEGAIKQLAKLMLNSLYGKFASNPDVT
GKVPYLKENGALGFRLGEEETKDPVYTPMGVFITAWARYTTITAAQACYD
RIIYCDTDSIHLTGTEIPDVIKDIVDPKKLGYWAHESTFKRAKYLRQKTY
IQDIYMKEVDGKLVEGSPDDYTDIKFSVKCAGMTDKIKKEVTFENFKVGF
SRKMKPKPVQVPGGVVLVDDTFTIK

SEQ ID NO: 7
MGLRRASLHHLLGGGGSGGGGSAAAGSAARKMYSCDFETTTKVEDCRVWA
YGYMNIEDHSEYKIGNSLDEFMAWVLKVQADLYFHNLKFDGAFIINWLER
NGFKWSADGLPNTYNTIISRMGQWYMIDICLGYKGKRKIHTVIYDSLKKL
PFPVKKIAKDFKLTVLKGDIDYHKERPVGYKITPEEYAYIKNDIQIIAEA
LLIQFKQGLDRMTAGSDSLKGFKDIITTKKFKKVFPTLSLGLDKEVRYAY
RGGFTWLNDRFKEKEIGEGMVFDVNSLYPAQMYSRLLPYGEPIVFEGKYV
WDEDYPLHIQHIRCEFELKEGYIPTIQIKRSRFYKGNEYLKSSGGEIADL
WLSNVDLELMKEHYDLYNVEYISGLKFKATTGLFKDFIDKWTYIKTTSEG
AIKQLAKLMLNSLYGKFASNPDVTGKVPYLKENGALGFRLGEEETKDPVY
TPMGVFITAWARYTTITAAQACYDRIIYCDTDSIHLTGTEIPDVIKDIVD
PKKLGYWAHESTFKRAKYLRQKTYIQDIYMKEVDGKLVEGSPDDYTDIKF
SVKCAGMTDKIKKEVTFENFKVGFSRKMKPKPVQVPGGVVLVDDTFTIK

SEQ ID NO: 8
MHHHHHHLLGGGGSGGGGSAAAGSAARKMYSCDFETTTKVEDCRVWAYGY
MNIEDHSEYKIGNSLDEFMAWVLKVQADLYFHNLKFDGAFIINWLERNGF
KWSADGLPNTYNTIISRMGQWYMIDICLGYKGKRKIHTVIYDSLKKLPFP
VKKIAKDFKLTVLKGDIDYHKERPVGYKITPEEYAYIKNAIQIIAEALLI
QFKQGLDRMTAGSDSLKGFKDIITTKKFKKVFPTLSLGLDKEVRYAYRGG
FTWLNDRFKEKEIGEGMVFDVNSLYPAQMYSRLLPYGEPIVFEGKYVWDE
DYPLHIQHIRCEFELKEGYIPTIQIKRSRFYKGNEYLKSSGGEIADLWLS
NVDLELMKEHYDLYNVEYISGLKFKATTGLFKDFIDKWTYIKTTSEGAIK
QLAKLMLNSLYGKFASNPDVTGKVPYLKENGALGFRLGEEETKDPVYTPM
GVFITAWARYTTITAAQACYDRIIYCDTDSIHLTGTEIPDVIKDIVDPKK
LGYWAHESTFKRAKYLRQKTYIQDIYMKEVDGKLVEGSPDDYTDIKFSVK
CAGMTDKIKKEVTFENFKVGFSRKMKPKPVQVPGGVVLVDDTFTIK

SEQ ID NO: 9
MNHLVHHHHHHIEGRHMELGTLEGSMKHMPRKMYSCAFETTTKVEDCRVW
AYGYMNIEDHSEYKIGNSLDEFMAWVLKVQADLYFHNLKFAGAFIINWLE
RNGFKWSADGLPNTYNTIISRMGQWYMIDICLGYKGKRKIHTVIYDSLKK
LPFPVKKIAKDFKLTVLKGDIDYHKERPVGYKITPEEYAYIKNDIQIIAE
ALLIQFKQGLDRMTAGSDSLKGFKDIITIKKFKKVFPILSLGLDKEVRYA
YRGGFTWLNDRFKEKEIGEGMVFDVNSLYPAQMYSRLLPYGEPIVFEGKY
VWDEDYPLHIQHIRCEFELKEGYIPTIQIKRSRFYKGNEYLKSSGGEIAD
LWLSNVDLELMKEHYDLYNVEYISGLKFKATTGLFKDFIDKWTYIKTTSE
GAIKQLAKLMLNSLYGKFASNPDVTGKVPYLKENGALGFRLGEEETKDPV
YTPMGVFITAWARYTTITAAQACYDRIIYCDTDSIHLTGTEIPDVIKDIV
DPKKLGYWAHESTFKRAKYLRQKTYIQDIYMKEVDGKLVEGSPDDYTDIK
FSVKCAGMTDKIKKEVTFENFKVGFSRKMKPKPVQVPGGVVLVDDTFTIK

SEQ ID NO: 10
MNHLVHHHHHHIEGRHMELGTLEGSMKHMPRKMYSCAFETTTKVEDCRVW
AYGYMNIEDHSEYKIGNSLDEFMAWVLKVQADLYFHNLKFAGAFIINWLE
RNGFKWSADGLPNTYNTIISRMGQWYMIDICLGYKGKRKIHTVIYDSLKK
LPFPVKKIAKDFKLTVLKGDIDYHKERPVGYKITPEEYAYIKNDIQIIAE
ALLIQFKQGLDRMTAGSDSLKGFKDIITIKKFKKVFPILSLGLDKEVRYA
YRGGFTWLNDRFKEKEIGEGMVFDVNSLYPAQMYSRLLPYGEPIVFEGKY
VWDEDYPLHIQHIRCEFELKEGYIPTIQIKRSRFYKGNEYLKSSGGEIAD
LWLSNVDLELMKEHYDLYNVEYISGLKFKATTGLFKDFIDKWTYIKTTSE
GAIKALAKLMLNSLYGKFASNPDVTGKVPYLKENGALGFRLGEEETKDPV
YTPMGVFITAWARYTTITAAQACYDRIIYCDTDSIHLTGTEIPDVIKDIV

DPKKLGYWAHESTFKRAKYLRQKTYIQDIYMKEVDGKLVEGSPDDYTDIK

FSVKCAGMTDKIKKEVTFENFKVGFSRKMKPKPVQVPGGVVLVDDTFTIK

SEQ ID NO: 11
MNHLVHHHHHHIEGRHMELGTLEGSMKHMPRKMYSCAFETTTKVEDCRVW

AYGYMNIEDHSEYKIGNSLDEFMAWVLKVQADLYFHNLKFAGAFIINWLE

RNGFKWSADGLPNTYNTIISRMGQWYMIDICLGYKGKRKIHTVIYDSLKK

LPFPVKKIAKDFKLTVLKGDIDYHKERPVGYKITPEEYAYIKNDIQIIAE

ALLIQFKQGLDRMTAGSDSLKGFKDIITIKKFKKVFPILSLGLDKEVRYA

YRGGFTWLNDRFKEKEIGEGMVFDVNSLYPAQMYSRLLPYGEPIVFEGKY

VWDEDYPLHIQHIRCEFELKEGYIPTIQIKRSRFYKGNEYLKSSGGEIAD

LWLSNVDLELMKEHYDLYNVEYISGLKFKATTGLFKDFIDKWTYIKTTSE

GAIKQLAKLMLNGLYGKFASNPDVTGKVPYLKENGALGFRLGEEETKDPV

YTPMGVFITAWARYTTITAAQACYDRIIYCDTDSIHLTGTEIPDVIKDIV

DPKKLGYWAHESTFKRAKYLRQKTYIQDIYMKEVDGKLVEGSPDDYTDIK

FSVKCAGMTDKIKKEVTFENFKVGFSRKMKPKPVQVPGGVVLVDDTFTIK

SEQ ID NO: 12
MSHHHHHHSMSGLNDIFEAQKIEWHEGAPGARGSKHMPRKMYSCAFETTT

KVEDCRVWAYGYMNIEDHSEYKIGNSLDEFMAWVLKVQADLYFHNLKFAG

AFIINWLERNGFKWSADGLPNTYNTIISRMGQWYMIDICLGYKGKRKIHT

VIYDSLKKLPFPVKKIAKDFKLTVLKGDIDYHKERPVGYKITPEEYAYIK

NDIQIIAEALLIQFKQGLDRMTAGSDSLKGFKDIITTKKFKKVFPTLSLG

LDKEVRYAYRGGFTWLNDRFKEKEIGEGMVFDVNSLYPAQMYSRLLPYGE

PIVFEGKYVWDEDYPLHIQHIRCEFELKEGYIPTIQIKRSRFYKGNEYLK

SSGGEIADLWLSNVDLELMKEHYDLYNVEYISGLKFKATTGLFKDFIDKW

TYIKTTSEGAIKQLAKLMLNSLYGKFASNPDVTGKVPYLKENGALGFRLG

EEETKDPVYTPMGVFITAWARYTTITAAQACYDRIIYCDTDSIHLTGTEI

PDVIKDIVDPKKLGYWAHESTFKRAKYLRQKTYIQDIYMKEVDGKLVEGS

PDDYTDIKFSVKCAGMTDKIKKEVTFENFKVGFSRKMKPKPVQVPGGVVL

VDDTFTIK

SEQ ID NO: 13
MKEFYLTVEQIGDSIFERYIDSNGRERTREVEYKPSLFAHCPESQATKYF

DIYGKPCTRKLFANMRDASQWIKRMEDIGLEALGMDDFKLAYLSDTYNYE

IKYDHTKIRVANFDIEVTSPDGFPEPSQAKHPIDAITHYDSIDDRFYVFD

LLNSPYGNVEEWSIEIAAKLQEQGGDEVPSEIIDKIIYMPFDNEKELLME

YLNFWQQKTPVILTGWNVESFDIPYVYNRIKNIFGESTAKRLSPHRKTRV

KVIENMYGSREIITLFGISVLDYIDLYKKFSFTNQPSYSLDYISEFELNV

GKLKYDGPISKLRESNHQRYISYNIIDVYRVLQIDAKRQFINLSLDMGYY

AKIQIQSVFSPIKTWDAIIFNSLKEQNKVIPQGRSHPVQPYPGAFVKEPI

PNRYKYVMSFDLTSLYPSIIRQVNISPETIAGTFKVAPLHDYINAVAERP

SDVYSCSPNGMMYYKDRDGVVPTEITKVFNQRKEHKGYMLAAQRNGEIIK

EALHNPNLSVDEPLDVDYRFDFSDEIKEKIKKLSAKSLNEMLFRAQRTEV

AGMTAQINRKLLINSLYGALGNVWFRYYDLRNATAITTFGQMALQWIERK

VNEYLNEVCGTEGEAFVLYGDTDSIYVSADKIIDKVGESKFRDTNHWVDF

LDKFARERMEPAIDRGFREMCEYMNNKQHLMFMDREAIAGPPLGSKGIGG

FWTGKKRYALNVWDMEGTRYAEPKLKIMGLETQKSSTPKAVQKALKECIR

RMLQEGEESLQEYFKEFEKEFRQLNYISIASVSSANKIAKYDVGGFPGPK

CPFHIRGILTYNRAIKGNIDAPQVVEGEKVYVLPLREGNPFGDKCIAWPS

GTEITDLIKDDVLHWMDYTVLLEKTFIKPLEGFTSAAKLDYEKKASLFDM

FDF

Fusion Proteins

In one aspect, the polymerase can be a fusion protein comprising the amino acid sequence of a nucleic acid-dependent polymerase (the polymerase portion) linked to the amino acid sequence of a second enzyme or a biologically active fragment thereof (the second enzyme portion). The second enzyme portion of the fusion protein may be linked to the amino or carboxyl end of the polymerase portion, or may be inserted within the polymerase portion. The polymerase portion of the fusion protein may be linked to the amino or carboxyl end of the second enzyme portion, or may be inserted within the second enzyme portion. In some embodiments, the polymerase and second enzyme portions can be linked to each other in a manner which does not significantly interfere with polymerase activity of the fusion or with the ability of the fusion to bind nucleotides, or does not significantly interfere with the activity of the second enzyme portion. In the fusion protein, the polymerase portion or the second enzyme portions can be linked with at least one energy transfer donor moiety. The fusion protein can be a recombinant protein having a polymerase portion and a second enzyme portion. In some embodiments, the fusion protein can include a polymerase portion chemically linked to the second enzyme portion.

Evolved Polymerases

The polymerase can be a modified polymerase having certain desired characteristics, such as an evolved polymerase selected from a directed or non-directed molecular evolution procedure. The evolved polymerase can exhibit modulated characteristics or functions, such as changes in: affinity, specificity, or binding rates for substrates (e.g., target molecules, polymerization initiation sites, or nucleotides); binding stability to the substrates (e.g., target molecules, polymerization initiation sites, or nucleotides); nucleotide incorporation rate; nucleotide permissiveness; exonuclease activity (e.g., 3'→5' or 5'→3'); rate of extension; processivity; fidelity; stability; or sensitivity and/or requirement for temperature, chemicals (e.g., DTT), salts, metals, pH, or electromagnetic energy (e.g., excitation or emitted energy). Many examples of evolved polymerases having altered functions or activities can be found in U.S. provisional patent application No. 61/020,995, filed Jan. 14, 2008.

Methods for creating and selecting proteins and enzymes having the desired characteristics are known in the art, and include: oligonucleotide-directed mutagenesis in which a short sequence is replaced with a mutagenized oligonucleotide; error-prone polymerase chain reaction in which low-fidelity polymerization conditions are used to introduce point mutations randomly across a sequence up to about 1 kb in length (R. C. Caldwell, et al., 1992 PCR Methods and Applications 2:28-33; H. Gramm, et al., 1992 Proc. Natl. Acad. Sci. USA 89:3576-3580); and cassette mutagenesis in which a portion of a sequence is replaced with a partially randomized sequence (A. R. Oliphant, et al., 1986 Gene 44:177-183; J. D. Hermes, et al., 1990 Proc. Natl. Acad. Sci. USA 87:696-700; A. Arkin and D. C. Youvan 1992 Proc. Natl. Acad. Sci. USA 89:7811-7815; E. R. Goldman and D. C. Youvan 1992 Bio/Technology 10:1557-1561; Delagrave et al., 1993 Protein Engineering 6: 327-331; Delagrave et al., 1993 Bio/Technology 11: 1548-155); and domain shuffling.

Methods for creating evolved antibody and antibody-like polypeptides can be adapted for creating evolved polymerases, and include applied molecular evolution formats in which an evolutionary design algorithm is applied to achieve specific mutant characteristics. Many library formats can be used for evolving polymerases including: phage libraries (J. K. Scott and G. P. Smith 1990 Science 249:386-390; S. E. Cwirla, et al. 1990 Proc. Natl. Acad. Sci. USA 87:6378-6382; J. McCafferty, et al. 1990 Nature 348:552-554) and lad (M. G. Cull, et al., 1992 Proc. Natl. Acad. Sci. USA 89:1865-1869).

Another adaptable method for evolving polymerases employs recombination (crossing-over) to create the mutagenized polypeptides, such as recombination between two different plasmid libraries (Caren et al. 1994 Bio/Technology 12: 517-520), or homologous recombination to create a hybrid gene sequence (Calogero, et al., 1992 FEMS Microbiology Lett. 97: 41-44; Galizzi et al., WO91/01087). Another recombination method utilizes host cells with defective mismatch repair enzymes (Radman et al., WO90/07576). Other methods for evolving polymerases include random fragmentation, shuffling, and re-assembly to create mutagenized polypeptides (published application No. U.S. 2008/0261833, Stemmer). Adapting these mutagenesis procedures to generate evolved polymerases is well within the skill of the art.

In some embodiments, the polymerase can be fused with, or otherwise engineered to include, DNA-binding or other domains from other proteins that are capable of modulating DNA polymerase activity. For example, fusion of suitable portions of the Single-Stranded DNA Binding Protein (SSBP), thioredoxin and/or T7 DNA polymerase to bacterial or viral DNA polymerases has been shown to enhance both the processivity and fidelity of the DNA polymerase. Similarly, other groups have described efforts to engineer polymerases so as to broaden their substrate range. See, e.g., Ghadessy et al, Nat. Biotech., 22 (6):755-759 (2004). Similarly, the conjugates of the present disclosure can optionally comprise any polymerase engineered to provide suitable performance characteristics, including for example a polymerase fused to intact SSBP or fragments thereof, or to domains from other DNA-binding proteins (such as the herpes simplex virus UL42 protein.)

In some embodiments, a blend of different conjugates, each of which comprises a polymerase of unique sequence and characteristics, can be used according to the methods described herein. Use of such conjugate blends can additionally increase the fidelity and processivity of DNA synthesis. For example, use of a blend of processive and non-processive polymerases has been shown to result in increased overall read length during DNA synthesis, as described in U.S. Published App. No. 2004/0197800. Alternatively, conjugates comprising polymerases of different affinities for specific acceptor-labeled nucleotides can be used so as to achieve efficient incorporation of all four nucleotides.

In one embodiment, the polymerase can be a mutant which retains nucleotide polymerization activity but lacks the 3'→5' or 5'→3' exonuclease activity (SEQ ID NOS:1-12). In another embodiment, the polymerase can be an exonuclease minus mutant which is based on wild type phi29 polymerase (SEQ ID NO:6) (Blanco, U.S. Pat. Nos. 5,001,050, 5,198,543, and 5,576,204; and Hardin PCT/US2009/31027 with an International filing date of Jan. 14, 2009) and comprising one or more substitution mutations, including: D12A, D66A, D169A, H61R, N62D, Q380A, and/or S388G, and any combination thereof.

In some embodiments, the polymerase can comprise the amino acid sequence of any polymerase disclosed in U.S. Provisional Application No. 61/242,771, filed on Sep. 15, 2009; 61/263,974, filed on Nov. 24, 2009 and 61/299,919, filed on Jan. 29, 2010, or any variant thereof.

Polymerases Linked with Energy Transfer Moieties

The polymerase (or polymerase fusion protein) may be linked with at least one energy transfer donor moiety. In the polymerase fusion protein, the energy transfer donor moiety can be attached to the polymerase portion or to the second enzyme portion. One or more energy transfer donor moieties can be linked to the polymerase (or polymerase fusion protein) at the amino end or carboxyl end or may be inserted in the interior of the polymerase (or fusion protein sequence). The energy transfer donor moiety can be attached to the fusion protein in a manner which does not interfere with the nucleotide binding activity, or with the nucleotide incorporation activity, or with the activity of the second enzyme.

In one aspect, a single energy transfer donor moiety can be operably attached with more than one polymerase (or more than one polymerase fusion protein) and the attachment can be at the amino end or carboxyl end or may be inserted within the polymerase (or fusion protein sequence).

In another aspect, a single energy transfer donor moiety can be linked to one polymerase or polymerase fusion protein.

Target Nucleic Acid Molecules

The methods, compositions, systems and kits disclosed herein can involve the use of target nucleic acid molecules. The target nucleic acid molecule may be single or double-stranded molecules. The target nucleic acid molecules can be linear or circular. The target nucleic acid molecules may be DNA, RNA or hybrid DNA-RNA molecules, DNA hairpins, DNA/RNA hybrids, or RNA hairpins. The target nucleic acid molecules may be isolated in any form including chromosomal, genomic, organellar (e.g., mitochondrial, chloroplast or ribosomal), recombinant molecules, cloned, amplified, cDNA, RNA such as precursor mRNA or mRNA, oligonucleotide, or any type of nucleic acid library. The target nucleic acid molecules may be isolated from any source including from: organisms such as prokaryotes, eukaryotes (e.g., humans, plants and animals), fungus, and viruses; cells; tissues; body fluids including blood, urine, serum, lymph, tumor, saliva, anal and vaginal secretions, amniotic samples, perspiration, and semen; environmental samples; culture samples; or synthesized nucleic acid molecules prepared using recombinant molecular biology or chemical synthesis methods.

The target nucleic acid molecules comprise naturally-occurring nucleotides, nucleotide variants, or any combination thereof. For example, the target molecules comprise alternate backbones, including: phosphoramidate; phosphorothioate; phosphorodithioate; O-methylphosphoroamidite linkages; and peptide nucleic acid backbones and linkages. Other nucleic acids include those with bicyclic structures including locked nucleic acids; positive backbones; non-ionic backbones; and non-ribose backbones.

The target nucleic acid molecules can carry a tag (e.g., His-tag), a polynucleotide tail (e.g., polynucleotide tail of A, G, C, T, or U), or can be methylated. The target nucleic acid molecules may be nicked, sheared, or treated with an enzyme such as a restriction endonuclease or a nuclease. The target nucleic acid molecules can be about 10-50 nucleotides, about 50-100 nucleotides, about 100-250 nucleotides, about 250-500 nucleotides, or about 500-1000 nucleotides in length, or longer. The target nucleic acid molecules may be linked to an energy transfer moiety (e.g., donor or acceptor) or to a reporter moiety (e.g., dye) using methods well known in the art.

The target nucleic acid molecules can have a nucleotide sequence which has been previously determined or is unknown (e.g., de novo sequencing). The target molecule can be fragmented into shorter pieces and/or modified for immobilization. Selection of the fragmentation and modification technique may depend upon the desired fragment sizes and subsequent preparation steps. Any combination of fragmentation and/or modification techniques may be practiced in any order.

Single- or Double-Stranded Nucleic Acid Molecules

The target molecules can be single-stranded nucleic acid molecules which are isolated by denaturing double-stranded molecules, or by chemically synthesizing single-stranded molecules. The target molecules can be double-stranded nucleic acid molecules. The single-stranded molecules can be isolated away from double-stranded molecules by bead (e.g., magnetic, biotinylated, or probe capture) attachment and enrichment procedures, CsCl gradient centrifugation methods, gel electrophoresis (e.g., polyacrylamide), or by capillary gel electrophoresis. The nucleic acid molecules can be attached to the beads via covalent or non-covalent linkage.

Nucleic Acid Sample Preparation

The nucleic acid molecules, including the target molecules, primers, and oligonucleotides, may be isolated and modified at their ends and/or the interior of the molecules using well known procedures, including: fragmentation, ligation, hybridization, enzymatic, and/or chemical modification, conjugation with an energy transfer (donor or acceptor) or reporter moiety, or any combination of these procedures.

Nucleic Acid Molecules—Fragmentation

Techniques which fragment the nucleic acid molecules at random or specific sites, or a combination of these techniques can be used.

The nucleic acid molecules can be fragmented at random or specific sites using any fragmentation procedures. The nucleic acid molecules can be fragmented using mechanical force, including: shear forces (e.g., small orifice or a needle); nebulization (S. Surzycki 1990 In: "The International Conference on the Status and Future of Research on the Human Genome. Human Genome II", San Diego, Calif., pp. 51; and S. J. Surzycki, 2000 in: "Basic Methods in Molecular Biology", New York, N.Y.: Springer-Verlag); or sonication. For example, nucleic acid molecules can be fragmented by sonicating in a COVARIS (e.g., Models S2, E210, or AFA).

The nucleic acid molecules can be chemically fragmented using, for example: acid-catalyzed hydrolysis of the backbone and cleavage with piperidine; internucleosomal DNA fragmentation using a copper (II) complex of 1,10-phenanthroline (o-phenanthroline, OP), CuII(OP)$_2$ in the presence of ascorbic acid (Shui Ying Tsang 1996 Biochem. Journal 317:13-16).

The nucleic acid molecules can be enzymatically fragmented using type I, II or II restriction endonucleases (N. E. Murray 2000 Microbiol. Mol. Biol. Rev. 64: 412-34; A. Pingoud and A. Jeltsch 2001 Nucleic Acids Res. 29: 3705-27; D. T. Dryden, et al., 2001 Nucleic Acids Res. 29: 3728-41; and A. Meisel, et al., 1992 Nature 355: 467-9). Enzymatic cleavage of DNA may include digestion using various ribo- and deoxyribonucleases or glycosylases. The nucleic acid molecules can be digested with DNase I or II. The nucleic acid fragments can be generated by enzymatically copying an RNA template. Fragments can be generated using processive enzymatic degradation (e.g., Si nuclease). The enzymatic reactions can be conducted in the presence or absence of salts (e.g., $Mg^{2+}$, $Mn^{2+}$, and/or $Ca^{2+}$), and the pH and temperature conditions can be varied according to the desired rate of reaction and results, as is well known in the art.

Modified Nucleic Acid Molecules

The 5' or 3' overhang ends of a nucleic acid molecule can be converted to blunt-ends using a "fill-in" procedure (e.g., dNTPS and DNA polymerase, Klenow, or Pfu or T4 polymerase) or using exonuclease procedure to digest away the protruding end.

The nucleic acid molecule ends can be ligated to one or more oligonucleotides using DNA ligase or RNA ligase. The nucleic acid molecules can be hybridized to one or more oligonucleotides. The oligonucleotides can serve as linkers, adaptors, bridges, clamps, anchors, or capture oligonucleotides.

The oligonucleotides can be ligation-ready, having overhang ends which can be ligated to the ends of the target molecules. The ligation-ready oligonucleotides can be used to circularize the target molecules.

A pair of oligonucleotides can include complementary sequences for hybridization. These paired oligonucleotides can be used as end-ligated oligonucleotides to permit circularization of the target molecule. These paired oligonucleotides can be used to hybridize to capture probes immobilized on a surface.

The oligonucleotides can include sequences which are: enzyme recognition sequences (e.g., restriction endonuclease recognition sites, DNA or RNA polymerase recognition sites); hybridization sites; or can include a detachable portion.

The oligonucleotide can be linked to a protein-binding molecule such as biotin or streptavidin.

The oligonucleotides can be 4-20 nt/bp in length, or 20-40 nt/bp in length, or 40-60 nt/bp in length, or longer.

Enzymatic and Chemical Modifications

The nucleic acid molecules can be methylated, for example, to confer resistance to restriction enzyme digestion (e.g., EcoRI).

The nucleic acid molecule ends can be phosphorylated or dephosphorylated.

A nick can be introduced into the nucleic acid molecules using, for example DNase I. A pre-designed nick site can be introduced in dsDNA using a double stranded probe, type II restriction enzyme, ligase, and dephosphorylation (Fu Dong-Jing, 1997 Nucleic Acids Research 25:677-679).

A nick can be repaired using polymerase (e.g., DNA pol I or phi29), ligase (e.g., T4 ligase) and kinase (polynucleotide kinase).

A poly tail can be added to the 3' end of the fragment using terminal transferase (e.g., polyA, polyG, polyC, polyT, or polyU).

The target nucleic acid molecule can include pre-existing methylation sites. The target molecule can be modified using bisulfite treatment (e.g., disodium bisulfite) to convert unmethylated cytosines to uracils, which permits detection of methylated cytosines using, for example, methylation specific procedures (e.g., PCR or bisulfite genomic sequencing).

Size Selection

The nucleic acid molecules can be size selected, or the desired nucleic acid molecules can separated from undesirable molecules, using any art known methods, including gel electrophoresis, size exclusion chromatography (e.g., spin columns), sucrose sedimentation, or gradient centrifugation. Very large nucleic acid molecules, including whole chromosomes, can be size separated using pulsed-field gel electrophoresis (Schwartz and Cantor 1984 Cell, 37: 67-75).

Amplification

The nucleic acid molecules can be amplified using methods, including: polymerase chain reaction (PCR); ligation chain reaction, which is sometimes referred to as oligonucleotide ligase amplification (OLA); cycling probe technology (CPT); strand displacement assay (SDA); transcription mediated amplification (TMA); nucleic acid sequence based amplification (NASBA); rolling circle amplification (RCA); and invasive cleavage technology.

Enrichment

Undesired compounds, or undesired fragments, can be removed or separated from the desired target nucleic acid molecules to facilitate enrichment of the desired target molecules. Enrichment methods can be achieved using well known methods, including gel electrophoresis, chromatography, or solid phase immobilization (reversible or non-reversible). For example, AMPURE beads (Agencourt) can bind DNA fragments but not bind unincorporated nucleotides, free primers, DNA polymerases, and salts, thereby facilitating enrichment of the desired DNA fragments.

Embodiments of the Target Molecule

In one embodiment, the target molecule can be a recombinant DNA molecule which is a self-priming hairpin oligonucleotide. The hairpin oligonucleotide can be linked at the 5' or 3'end, or internally, to at least one molecule of a binding partner (e.g., biotin). The biotin molecule can be used to immobilize the hairpin oligonucleotide to the surface (via avidin-like molecule), or for attachment to a reporter moiety. The hairpin oligonucleotide can be linked to at least one energy transfer moiety, such as a fluorescent dye or a nanoparticle.

In another embodiment, a plurality of target nucleic acid molecules can be linked to a solid surface (via the 5' or 3' end, or via an internal site) to form a DNA curtain (see Greene, U.S. published patent application No. 2008/0274905, published on Nov. 6, 2008; and Fazio, et al., 2008 Langmuir 24:10524-10531). The nucleotide incorporation methods can be practiced on the DNA curtain in an aqueous flowing condition.

Reporter Moieties

The methods, systems, compositions and kits disclosed herein can involve the use of one or more reporter moieties which are linked to the solid surfaces, nanoparticles, polymerases, nucleotides, target nucleic acid molecules, primers, and/or oligonucleotides.

The reporter moieties may be selected so that each absorbs excitation radiation and/or emits fluorescence at a wavelength distinguishable from the other reporter moieties to permit monitoring the presence of different reporter moieties in the same reaction. Two or more different reporter moieties can be selected having spectrally distinct emission profiles, or having minimal overlapping spectral emission profiles.

In one aspect, the signals (e.g., energy transfer signals) from the different reporter moieties do not significantly overlap or interfere, by quenching, colorimetric interference, or spectral interference.

The chromophore moiety may be 5-bromo-4-chloro-3-indolyl phosphate, 3-indoxyl phosphate, p-nitrophenyl phosphate, β-lactamase, peroxidase-based chemistry, and derivatives thereof.

The chemiluminescent moiety may be a phosphatase-activated 1,2-dioxetane compound. The 1,2-dioxetane compound includes disodium 2-chloro-5-(4-methoxyspiro[1,2-dioxetane-3,2'-(5-chloro-)tricyclo[3,3,1-1$^{3,7}$]-decan]-1-yl)-1-phenyl phosphate (e.g., CDP-STAR), chloroadamant-2'-ylidenemethoxyphenoxy phosphorylated dioxetane (e.g., CSPD), and 3-(2'-spiroadamantane)-4-methoxy-4-(3"-phosphoryloxy)phenyl-1,2-dioxetane (e.g., AMPPD).

In some embodiments, the fluorescent moiety can optionally include: rhodols; resorufins; coumarins; xanthenes; acridines; fluoresceins; rhodamines; erythrins; cyanins; phthalaldehydes; naphthylamines; fluorescamines; benzoxadiazoles; stilbenes; pyrenes; indoles; borapolyazaindacenes; quinazolinones; eosin; erythrosin; Malachite green; CY dyes (GE Biosciences), including Cy3 (and its derivatives) and Cy5 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (boron-dipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610 (N-succinimidyl ester), ATTO 635 (NHS ester); ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1,3-dichloro-9,9-dimethylacridin-2-one or any derivatives thereof) (Molecular Probes); QUASAR dyes (Biosearch); IRDYES dyes (LiCor) including IRDYE 700DX (NHS ester), IRDYE 800RS (NHS ester) and IRDYE 800CW (NHS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED (phosphoramidate), EPOCH YAKIMA YELLOW (phosphoramidate), EPOCH GIG HARBOR GREEN (phosphoramidate); Tokyo green (M Kamiya, et al., 2005 Angew. Chem. Int. Ed. 44:5439-5441); and CF dyes including CF 647 and CF555 (Biotium).

Quencher dyes may include: ATTO 540Q, ATTO 580Q, and ATTO 612Q (Atto-Tec); QSY dyes including QSY 7, QSY 9, QSY 21, and QSY 35 (Molecular Probes); and EPOCH ECLIPSE QUENCHER (phosphoramidate) (Glen Research). The fluorescent moiety can be a 7-hydroxycoumarin-hemicyanine hybrid molecule which is a far-red emitting dye (Richard 2008 Org. Lett. 10:4175-4178).

The fluorescent moiety may be a fluorescence-emitting metal such as a lanthanide complex, including those of Europium and Terbium.

A number of examples of fluorescent moieties are found in PCT publication WO/2008/030115, and in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999).

In one aspect, the reporter moieties can be energy transfer moieties.

FRET

In some embodiments, the methods, compositions, systems and kits disclosed herein can involve the use of one or more moieties capable of undergoing energy transfer. Such energy transfer moieties can include energy transfer donors and acceptors. The energy transfer moieties can be linked to the solid surfaces, nanoparticles, polymerases, nucleotides, target nucleic acid molecules, primers, and/or oligonucleotides.

In one aspect, the energy transfer moiety can be an energy transfer donor. For example, the energy transfer donor can be a nanoparticle or an energy transfer donor moiety (e.g., fluorescent dye). In another aspect, the energy transfer moiety can be an energy transfer acceptor. For example, the energy transfer acceptor can be an energy acceptor dye. In another aspect, the energy transfer moiety can be a quencher moiety.

In one aspect, the energy transfer pair can be linked to the same molecule. For example, the energy transfer donor and acceptor pair can be linked to a single polymerase, which can provide detection of conformational changes in the polymerase. In another aspect, the donor and acceptor can be linked to different molecules in any combination. For example, the donor can be linked to the polymerase, target molecule, or primer molecule, and/or the acceptor can be linked to the nucleotide, the target molecule, or the primer molecule.

The energy transfer donor is capable of absorbing electromagnetic energy (e.g., light) at a first wavelength and emitting excitation energy in response. The energy acceptor is capable of absorbing excitation energy emitted by the donor and fluorescing at a second wavelength in response.

The donor and acceptor moieties can interact with each other physically or optically in a manner which produces a detectable signal (e.g., energy transfer signal) when the two moieties are in proximity with each other. A proximity event includes two different moieties (e.g., energy transfer donor and acceptor) approaching each other, or associating with each other, or binding each other.

The donor and acceptor moieties can transfer energy in various modes, including: fluorescence resonance energy transfer (FRET) (L. Stryer 1978 Ann. Rev. Biochem. 47: 819-846; Schneider, U.S. Pat. No. 6,982,146; Hardin, U.S. Pat. No. 7,329,492; Hanzel U.S. published patent application No. 2007/0196846), scintillation proximity assays (SPA) (Hart and Greenwald 1979 Molecular Immunology 16:265-267; U.S. Pat. No. 4,658,649), luminescence resonance energy transfer (LRET) (G. Mathis 1995 Clin. Chem. 41:1391-1397), direct quenching (Tyagi et al, 1998 Nature Biotechnology 16:49-53), chemiluminescence energy transfer (CRET) (Campbell and Patel 1983 Biochem. Journal 216:185-194), bioluminescence resonance energy transfer (BRET) (Y. Xu, et al., 1999 Proc. Natl. Acad. Sci. 96:151-156), and excimer formation (J. R. Lakowicz 1999 "Principles of Fluorescence Spectroscopy", Kluwer Academic/Plenum Press, New York).

In one exemplary embodiment, the energy transfer moieties can be a FRET donor/acceptor pair. FRET is a distance-dependent radiationless transmission of excitation energy from a first moiety, referred to as a donor moiety, to a second moiety, referred to as an acceptor moiety. Typically, the efficiency of FRET energy transmission is dependent on the inverse sixth-power of the separation distance between the donor and acceptor, r. For a typical donor-acceptor pair, r can vary between approximately 10-100 Angstroms. FRET is useful for investigating changes in proximity between and/or within biological molecules. In some embodiments, FRET efficiency may depend on donor-acceptor distance r as $1/r^6$ or $1/r^4$. The efficiency of FRET energy transfer can sometimes be dependent on energy transfer from a point to a plane which varies by the fourth power of distance separation (E. Jares-Erijman, et al., 2003 Nat. Biotechnol. 21:1387). The distance where FRET efficiency is 50% is termed $R_0$, also know as the Forster distance. $R_0$ is unique for each donor-acceptor combination and may be about 1-20 nm, or about 1-10 nm, or about 1-5 nm, or about 5-10 nm. A change in fluorescence from a donor or acceptor during a FRET event (e.g., increase or decrease in the signal) can be an indication of proximity between the donor and acceptor.

In biological applications, FRET can provide an on-off type signal indicating when the donor and acceptor moieties are proximal (e.g., within $R_0$) of each other. Additional factors affecting FRET efficiency include the quantum yield of the donor, the extinction coefficient of the acceptor, and the degree of spectral overlap between the donor and acceptor. Procedures are well known for maximizing the FRET signal and detection by selecting high yielding donors and high absorbing acceptors with the greatest possible spectral overlap between the two (D. W. Piston and G. J. Kremers 2007 Trends Biochem. Sci. 32:407). Resonance energy transfer may be either an intermolecular or intramolecular event. Thus, the spectral properties of the energy transfer pair as a whole, change in some measurable way if the distance and/or orientation between the moieties are altered.

The production of signals from FRET donors and acceptors can be sensitive to the distance between donor and acceptor moieties, the orientation of the donor and acceptor moieties, and/or a change in the environment of one of the moieties (Deuschle et al. 2005 Protein Science 14: 2304-2314; Smith et al. 2005 Protein Science 14:64-73). For example, a nucleotide linked with a FRET moiety (e.g., acceptor) may produce a detectable signal when it approaches, associates with, or binds a polymerase linked to a FRET moiety (e.g., donor). In another example, a FRET donor and acceptor linked to one protein can emit a FRET signal upon conformational change of the protein. Some FRET donor/acceptor pairs exhibit changes in absorbance or emission in response to changes in their environment, such as changes in pH, ionic strength, ionic type ($NO_2$, $Ca^{+2}$, $Mg^{+2}$, $Zn^{+2}$, $Na^+$, $Cl^-$, $K^+$), oxygen saturation, and solvation polarity.

The FRET donor and/or acceptor may be a fluorophore, luminophore, chemiluminophore, bioluminophore, or quencher (P. Selvin 1995 Methods Enzymol 246:300-334; C. G. dos Remedios 1995 J. Struct. Biol. 115:175-185; P. Wu and L. Brand 1994 Anal Biochem 218:1-13).

In some embodiments, the energy transfer moieties may not undergo FRET, but may undergo other types of energy transfer with each other, including luminescence resonance energy transfer, bioluminescence resonance energy transfer, chemiluminescence resonance energy transfer, and similar types of energy transfer not strictly following the Forster's theory, such as the non-overlapping energy transfer when non-overlapping acceptors are utilized (Laitala and Hemmila 2005 Anal. Chem. 77: 1483-1487).

In one embodiment, the polymerase can be linked to an energy transfer donor moiety. In another embodiment, the nucleotide can be linked to an energy transfer acceptor moiety. For example, in one embodiment the nucleotide comprises a polyphosphate chain and an energy transfer moiety linked to the terminal phosphate group of the polyphosphate chain. A change in a fluorescent signal can occur when the labeled nucleotide is proximal to the labeled polymerase.

In one embodiment, when an acceptor-labeled nucleotide is proximal to a donor-labeled polymerase, the signal emitted by the donor moiety decreases. In another embodiment, when the acceptor-labeled nucleotide is proximal to the donor-labeled polymerase, the signal emitted by the acceptor moiety increases. In another embodiment, a decrease in donor signal and increase in acceptor signal correlates with nucleotide binding to the polymerase and/or correlates with polymerase-dependent nucleotide incorporation.

Quenchers

The energy transfer moiety can be a FRET quencher. Typically, quenchers have an absorption spectrum with large extinction coefficients, however the quantum yield for quenchers is reduced, such that the quencher emits little to no light upon excitation. Quenching can be used to reduce the background fluorescence, thereby enhancing the signal-to-noise ratio. In one aspect, energy transferred from the donor may be absorbed by the quencher which emits moderated (e.g., reduced) fluorescence. In another aspect, the acceptor can be a non-fluorescent chromophore which absorbs the energy transferred from the donor and emits heat (e.g., the energy acceptor is a dark quencher).

For an example, a quencher can be used as an energy acceptor with a nanoparticle donor in a FRET system, see I. L. Medintz, et al., 2003 Nature Materials 2:630. One exemplary method involves the use of quenchers in conjunction with reporters comprising fluorescent reporter moieties. In this strategy, certain nucleotides in the reaction mixture are labeled with a reporter comprising a fluorescent label, while the remaining nucleotides are labeled with one or more quenchers. Alternatively, each of the nucleotides in the reaction mixture is labeled with one or more quenchers. Discrimination of the nucleotide bases is based on the wavelength and/or intensity of light emitted from the FRET acceptor, as well as the intensity of light emitted from the FRET donor. If no signal is detected from the FRET acceptor, a corresponding reduction in light emission from the FRET donor indicates incorporation of a nucleotide labeled with a quencher. The degree of intensity reduction may be used to distinguish between different quenchers.

Examples of fluorescent donors and non-fluorescent acceptor (e.g., quencher) combinations have been developed for detection of proteolysis (Matayoshi 1990 Science 247: 954-958) and nucleic acid hybridization (L. Morrison, in: Nonisotopic DNA Probe Techniques, ed., L. Kricka, Academic Press, San Diego, (1992) pp. 31 1-352; S. Tyagi 1998 Nat. Biotechnol. 16:49-53; S. Tyagi 1996 Nat. Biotechnol. 14:947-8). FRET donors, acceptors and quenchers can be moieties which absorb electromagnetic energy (e.g., light) at about 300-900 nm, or about 350-800 nm, or about 390-800 nm.

Materials for Energy Transfer Moieties

Energy transfer donor and acceptor moieties can be made from materials which typically fall into four general categories (see the review in: K. E. Sapford, et al., 2006 Angew. Chem. Int. Ed. 45:4562-4588), including: (1) organic fluorescent dyes, dark quenchers and polymers (e.g., dendrimers); (2) inorganic material such as metals, metal chelates and semiconductors nanoparticles; (3) biomolecules such as proteins and amino acids (e.g., green fluorescent protein and derivatives thereof); and (4) enzymatically catalyzed bioluminescent molecules. The material for making the energy transfer donor and acceptor moieties can be selected from the same or different categories.

The FRET donor and acceptor moieties which are organic fluorescent dyes, quenchers or polymers can include traditional dyes which emit in the UV, visible, or near-infrared region. The UV emitting dyes include coumarin-, pyrene-, and naphthalene-related compounds. The visible and near-infrared dyes include xanthene-, fluorescein-, rhodol-, rhodamine-, and cyanine-related compounds. The fluorescent dyes also includes DDAO ((7-hydroxy-9H-(1,3-dichloro-9,9-dimethylacridin-2-one)), resorufin, ALEXA FLUOR and BODIPY dyes (both Molecular Probes), HILYTE Fluors (AnaSpec), ATTO dyes (Atto-Tec), DY dyes (Dyomics GmbH), TAMRA (Perkin Elmer), tetramethylrhodamine (TMR), TEXAS RED, DYLIGHT (Thermo Fisher Scientific), FAM (AnaSpec), JOE and ROX (both Applied Biosystems), and Tokyo Green.

Additional fluorescent dyes which can be used as quenchers includes: DNP, DABSYL, QSY (Molecular Probes), ATTO (Atto-Tec), BHQ (Biosearch Technologies), QXL (AnaSpec), BBQ (Berry and Associates) and CY5Q/7Q (Amersham Biosciences).

The FRET donor and acceptor moieties which comprise inorganic materials include gold (e.g., quencher), silver, copper, silicon, semiconductor nanoparticles, and fluorescence-emitting metal such as a lanthanide complex, including those of Europium and Terbium.

Suitable FRET donor/acceptor pairs include: FAM as the donor and JOE, TAMRA, and ROX as the acceptor dyes. Other suitable pairs include: CYA as the donor and R6G, TAMRA, and ROX as the donor dyes. Other suitable donor/acceptor pairs include: a nanoparticle as the donor, and ALEXA FLUORS dyes (e.g., 610, 647, 660, 680, 700). DYOMICS dyes, such as 634 and 734 can be used as energy transfer acceptor dyes.

Nanoparticles

The methods, compositions, systems and kits disclosed herein can involve the use of any suitable nanoparticles which can serve as donor fluorophores in energy transfer reactions such as FRET.

The nanoparticles can be attached to the solid surface or to any component of the nucleotide incorporation or nucleotide polymerization reactions in any combination (e.g., polymerases, nucleotides, target nucleic acid molecules, primers, and/or oligonucleotides).

"Nanoparticle" may refer to any particle with at least one major dimension in the nanosize range. In general, nanoparticles can be made from any suitable metal (e.g., noble metals, semiconductors, etc.) and/or non-metal atoms. Nanoparticles can have different shapes, each of which can have distinctive properties including spatial distribution of the surface charge; orientation dependence of polarization of the incident light wave; and spatial extent of the electric field. The shapes include, but are not limited to: spheres, rods, discs, triangles, nanorings, nanoshells, tetrapods, nanowires, etc.

In one embodiment, the nanoparticle can be a core/shell nanoparticle which typically comprises a core nanoparticle surrounded by at least one shell. For example, the core/shell nanoparticle can be surrounded by an inner and outer shell. In another embodiment, the nanoparticle is a core nanoparticle which has a core but no surrounding shell. The outmost surface of the core or shell can be coated with tightly associated ligands which are not removed by ordinary solvation.

Examples of a nanoparticle include a nanocrystal, such as a core/shell nanocrystal, plus any associated organic ligands (which are not removed by ordinary solvation) or other materials which may coat the surface of the nanocrystal. In one embodiment, a nanoparticle has at least one major dimension ranging from about 1 to about 1000 nm. In other embodiments, a nanoparticle has at least one major dimension ranging from about 1 to about 20 nm, about 1 to about 15 nm, about 1 to about 10 nm or about 1 to 5 nm.

In some embodiments, a nanoparticle can have a layer of ligands on its surface which can further be cross-linked to each other. In some embodiments, a nanoparticle can have other or additional surface coatings which can modify the properties of the particle, for example, increasing or decreasing solubility in water or other solvents. Such layers on the surface are included in the term 'nanoparticle.'

In one embodiment, nanoparticle can refer to a nanocrystal having a crystalline core, or to a core/shell nanocrystal, and may be about 1 nm to about 100 nm in its largest dimension, about 1 nm to about 20 nm, about 1 nm to about 15 nm, about 1 nm to about 10 nm or preferably about 5 nm to about 10 nm in its largest dimension. Small nanoparticles are typically less than about 20 nm in their largest dimension.

"Nanocrystal" as used herein can refer to a nanoparticle made out of an inorganic substance that typically has an ordered crystalline structure. It can refer to a nanocrystal having a crystalline core (core nanocrystal) or to a core/shell nanocrystal.

A core nanocrystal is a nanocrystal to which no shell has been applied. Typically, it is a semiconductor nanocrystal that includes a single semiconductor material. It can have a homogeneous composition or its composition can vary with depth inside the nanocrystal.

A core/shell nanocrystal is a nanocrystal that includes a core nanocrystal and a shell disposed over the core nanocrystal. Typically, the shell is a semiconductor shell that includes a single semiconductor material. In some embodiments, the core and the shell of a core/shell nanocrystal are composed of different semiconductor materials, meaning that at least one atom type of a binary semiconductor material of the core of a core/shell is different from the atom types in the shell of the core/shell nanocrystal.

The semiconductor nanocrystal core can be composed of a semiconductor material (including binary, ternary and quaternary mixtures thereof), from: Groups II-VI of the periodic table, including ZnS, ZnSe, ZnTe, CdS, CdSe, CdTe, HgS, HgSe, HgTe, MgTe; Groups III-V, including GaN, GaP, GaAs, GaSb, InN, InP, InAs, InSb, AlAs, AlP, AlSb, AlS; and/or Group IV, including Ge, Si, Pb.

The semiconductor nanocrystal shell can be composed of materials (including binary, ternary and quaternary mixtures thereof) comprising: ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, or AlSb.

Many types of nanocrystals are known, and any suitable method for making a nanocrystal core and applying a shell to the core may be employed. Nanocrystals can have a surface layer of ligands to protect the nanocrystal from degradation in use or during storage.

"Quantum dot" as used herein refers to a crystalline nanoparticle made from a material which in the bulk is a semiconductor or insulating material, which has a tunable photophysical property in the near ultraviolet (UV) to far infrared (IR) range.

"Water-soluble" or "water-dispersible" is used herein to mean the item can be soluble or suspendable in an aqueous-based solution, such as in water or water-based solutions or buffer solutions, including those used in biological or molecular detection systems as known by those skilled in the art. While water-soluble nanoparticles are not truly 'dissolved' in the sense that term is used to describe individually solvated small molecules, they are solvated (via hydrogen, electrostatic or other suitable physical/chemical bonding) and suspended in solvents which are compatible with their outer surface layer, thus a nanoparticle which is readily dispersed in water is considered water-soluble or water-dispersible. A water-soluble nanoparticle can also be considered hydrophilic, since its surface is compatible with water and with water solubility.

"Hydrophobic nanoparticle" as used herein refers to a nanoparticle which is readily dispersed in or dissolved in a water-immiscible solvent like hexanes, toluene, and the like. Such nanoparticles are generally not readily dispersed in water.

"Hydrophilic" as used herein refers to a surface property of a solid, or a bulk property of a liquid, where the solid or liquid exhibits greater miscibility or solubility in a high-dielectric medium than it does in a lower dielectric medium. By way of example, a material which is more soluble in methanol than in a hydrocarbon solvent such as decane would be considered hydrophilic.

"Coordinating solvents" as used herein refers to a solvent such as TDPA, OP, TOP, TOPO, carboxylic acids, and amines, which are effective to coordinate to the surface of a nanocrystal. 'Coordinating solvents' also include phosphines, phosphine oxides, phosphonic acids, phosphinic acids, amines, and carboxylic acids, which are often used in growth media for nanocrystals, and which form a coating or layer on the nanocrystal surface. Coordinating solvents can exclude hydrocarbon solvents such as hexanes, toluene, hexadecane, octadecene and the like, which do not have heteroatoms that provide bonding pairs of electrons to coordinate with the nanocrystal surface. Hydrocarbon solvents which do not contain heteroatoms such as O, S, N or P to coordinate to a nanocrystal surface are referred to herein as non-coordinating solvents. Note that the term 'solvent' is used in its ordinary way in these terms: it refers to a medium which supports, dissolves or disperses materials and reactions between them, but which does not ordinarily participate in or become modified by the reactions of the reactant materials. However, in certain instances, the solvent can be modified by the reaction conditions. For example, TOP may be oxidized to TOPO, or a carboxylic acid can be reduced to an alcohol.

As used herein, the term "population" refers to a plurality of nanoparticles having similar physical and/or optical properties. 'Population' can refer to a solution or structure with more than one nanoparticle at a concentration suitable for single molecule analysis. In some embodiments, the population can be monodisperse and can exhibit less than at least 15% rms deviation in diameter of the nanoparticles, and spectral emissions in a narrow range of no greater than about 75 nm full width at half max (FWHM). In the context of a solution, suspension, gel, plastic, or colloidal dispersion of nanoparticles, the nature of the population can be further characterized by the number of nanoparticles present, on average, within a particular volume of the liquid or solid, or the concentration. In a two-dimensional format such as an array of nanoparticles adhered to a solid substrate, the concept of concentration is less convenient than the related measure of particle density, or the number of individual particles per two-dimensional area. In this case, the maximum density would typically be that obtained by packing particles "shoulder-to-shoulder" in an array. The actual number of particles in this case would vary due to the size of the particles—a given array could contain a large number of small particles or a small number of larger particles.

As used herein, the terms "moderate to high excitation" refers to monochromatic illumination or excitation (e.g., laser illumination) having a high power intensity sufficiently high such that the absorbed photons per second for a given sample is between about 200,000 and about 1,600,000.

In one aspect, the nanoparticle is a semiconductor nanoparticle having size-dependent optical and electronic properties. For example, the nanoparticle can emit a fluorescent signal in response to excitation energy. The spectral emission of the nanoparticle can be tunable to a desired energy by selecting the particle size, size distribution, and/or composition of the semiconductor nanoparticle. For example, depending on the dimensions, the semiconductor nanoparticle can be a fluorescent nanoparticle which emits light in the UV-visible-IR spectrum. The shell material can have a bandgap greater than the bandgap of the core material.

In one aspect, the nanoparticle is an energy transfer donor. The nanoparticle can be excited by an electromagnetic source such as a laser beam, multi-photon excitation, or electrical excitation. The excitation wavelength can range between about 190 to about 800 nm including all values and ranges there in between. In some embodiments, the nanoparticle can be excited by an energy source having a wavelength of about 405 nm. In other embodiments, in response to excitation, the nanoparticle can emit a fluorescent signal at about 400-800 nm, or about 605 nm.

In one aspect, the nanoparticle can undergo Raman scattering when subjected to an electromagnetic source (incident photon source) such as a laser beam. The scattered photons have a frequency that is different from the frequency of the incident photons. As result, the wavelength of the scattered photons is different than the incident photon source. In one embodiment, the nanoparticle can be attached to a suitable tag or label to enhance the detectability of the nanoparticle via Raman spectroscopy. The associated tag can be fluorescent or nonfluorescent. Such approaches can be advantageous in avoiding problems that can arise in the context of fluorescent nanoparticles, such as photobleaching and blinking. See, e.g., Sun et al., "Surface-Enhanced Raman Scattering Based Nonfluorescent Probe for Multiplex DNA Detection", Anal. Chem. 79(11):3981-3988 (2007)

In one aspect, the nanoparticle is comprised of a multi-shell layered core which is achieved by a sequential shell material deposition process, where one shell material is added at a time, to provide a nanoparticle having a substantially uniform shell of desired thickness which is substantially free of defects. The nanoparticle can be prepared by sequential, controlled addition of materials to build and/or applying layers of shell material to the core. See e.g., U.S. PCT Application Serial No. PCT/US09/061951 which is incorporated herein by reference as if set forth in full.

In another aspect, a method is provided for making a nanoparticle comprising a core and a layered shell, where the shell comprises at least one inner shell layer and at least one outer shell layer. The method comprises the steps: (a) providing a mixture comprising a core, at least one coordinating solvent; (b) heating the mixture to a temperature suitable for formation of an inner shell layer; (c) adding a first inner shell precursor alternately with a second inner shell precursor in layer additions, to form an inner shell layer which is a desired number of layers thick; (d) heating the mixture to a temperature suitable for formation of an outer shell layer; and (e) adding a first outer shell precursor alternately with a second outer shell precursor in layer additions, to form an outer shell layer which is a desired number of layers thick. In one embodiment, if the coordinating solvent of (a) is not amine, the method further comprises an amine in (a).

In one aspect, at least one coordinating solvent comprises a trialkylphosphine, a trialkylphosphine oxide, phosphonic acid, or a mixture of these. In another aspect, at least one coordinating solvent comprises trioctylphosphine (TOP), trioctylphosphine oxide (TOPO), tetradecylphosphonic acid (TDPA), or a mixture of these. In yet another aspect, the coordinating solvent comprises a primary or secondary amine, for example, decylamine, hexadecylamine, or dioctylamine.

In one aspect, the nanoparticle comprises a core comprising CdSe. In another aspect, the nanoparticle shell can comprise YZ wherein Y is Cd or Zn, and Z is S, or Se. In one embodiment, at least one inner shell layer comprises CdS, and the at least one outer shell layer comprises ZnS.

In one aspect, the first inner shell precursor is $Cd(OAc)_2$ and the second inner shell precursor is bis(trimethylsilyl) sulfide ($TMS_2S$). In other aspects, the first and second inner shell precursors are added as a solution in trioctylphosphine (TOP). In other aspects, the first outer shell precursor is diethylzinc ($Et_2Zn$) and the second inner shell precursor is dimethyl zinc ($TMS_2S$). Sometimes, the first and second outer shell precursors are added as a solution in trioctylphosphine (TOP).

In one aspect, the nanoparticle can have ligands which coat the surface. The ligand coating can comprise any suitable compound(s) which provide surface functionality (e.g., changing physicochemical properties, permitting binding and/or other interaction with a biomolecule, etc.). In some embodiments, the disclosed nanoparticle has a surface ligand coating (in direct contact with the external shell layer) that adds various functionalities which facilitate it being water-dispersible or soluble in aqueous solutions. There are a number of suitable surface coatings which can be employed to permit aqueous dispersibility of the described nanoparticle. For example, the nanoparticle(s) disclosed herein can comprise a core/shell nanocrystal which is coated directly or indirectly with lipids, phospholipids, fatty acids, polynucleic acids, polyethylene glycol (PEG), primary antibodies, secondary antibodies, antibody fragments, protein or nucleic acid based aptamers, biotin, streptavidin, proteins, peptides, small organic molecules (e.g., ligands), organic or inorganic dyes, precious or noble metal clusters. Specific examples of ligand coatings can include, but are not limited to, amphiphilic polymer (AMP), bidentate thiols (i.e., DHLA), tridentate thiols, dipeptides, functionalized organophosphorous compounds (e.g., phosphonic acids, phosphinic acids), etc.

Non-Blinking Nanoparticles

Provided herein are nanoparticles which exhibit modulated, reduced, or no intermittent (e.g., continuous, non-blinking) fluorescence.

In one aspect, the nanoparticle or populations thereof exhibit modulated, reduced or non-detectable intermittent (e.g., continuous, etc.) fluorescence properties. The nanoparticles can have a stochastic blinking profile in a timescale which is shifted to very rapid blinking or very slow or infrequent blinking relative to a nanoparticle previously described in the art (conventional nanoparticles are described in the art as having on-time fractions of <0.2 in the best of conditions examined). For example, the nanoparticles may blink on and off on a timescale which is too rapid to be detected under the methods employed to study this behavior.

In one aspect the nanoparticle or populations thereof are photostable. The nanoparticles can exhibit a reduced or no photobleaching with long exposure to moderate to high intensity excitation source while maintaining a consistent spectral emission pattern.

In one aspect, the nanoparticle or populations thereof have a consistently high quantum yield. For example, the nanoparticles can have a quantum yield greater than: about 10%, or about 20%, or about 30%, or about 40%, or about 50%, or about 60%, or about 70% or about 80%.

As used herein, fluorescence (or Forster) resonance energy transfer (FRET) is a process by which a fluorophore (the donor) in an excited state transfers its energy to a proximal molecule (the acceptor) by nonradiative dipole-dipole interaction (Forster, T. "Intermolecular Energy Migration and Fluorescence", Ann. Phys., 2:55-75, 1948; Lakowicz, J. R., *Principles of Fluorescence Spectroscopy*, 2nd ed. Plenum, New York. 367-394, 1999).

FRET efficiency (E) can be defined as the quantum yield of the energy transfer transition, i.e. the fraction of energy transfer event occurring per donor excitation event. It is a direct measure of the fraction of photon energy absorbed by the donor which is transferred to an acceptor, as expressed in Equation 1: $E=k_{ET}/k_f+k_{ET}+\Sigma k_i$ where $k_{ET}$ is the rate of energy transfer, $k_f$ the radiative decay rate and the $k_i$ are the rate constants of any other de-excitation pathway.

FRET efficiency E generally depends on the inverse of the sixth power of the distance r (nm) between the two fluorophores (i.e., donor and acceptor pair), as expressed in Equation 2: $E=1/1+(r/R_0)^6$.

The distance where FRET efficiency is at 50% is termed $R_0$, also know as the Forster distance. $R_0$ can be unique for each donor-acceptor combination and can range from between about 5 nm to about 10 nm. Therefore, the FRET efficiency of a donor (i.e., nanoparticle) describes the maximum theoretical fraction of photon energy which is absorbed by the donor (i.e., nanoparticle) and which can then be transferred to a typical organic dye (e.g., fluoresceins, rhodamines, cyanines, etc.).

In some embodiments, the disclosed nanoparticles are relatively small (i.e., <15 nm) and thus may be particularly well suited to be used as a donor or an acceptor in a FRET reaction. That is, some embodiments of the disclosed nanoparticles exhibit higher FRET efficiency than conventional nanoparticles and thus are excellent partners (e.g., donors or acceptors) in a FRET reaction.

"Quantum yield" as used herein refers to the emission efficiency of a given fluorophore assessed by the number of times which a defined event, e.g., light emission, occurs per photon absorbed by the system. In other words, a higher quantum yield indicates greater efficiency and thus greater brightness of the described nanoparticle or populations thereof.

Any suitable method can be used to measure quantum yield. In one example, quantum yield can be obtained using standard methods such as those described in Casper et al (Casper, J. V.; Meyer, T. J. *J. Am. Chem. Soc.* 1983, 105, 5583) and can be analyzed relative to known fluorophores chosen as appropriate for maximal overlap between standard emission and sample emission (e.g., fluorescein, Rhodamine 6G, Rhodamine 101). Dilute solutions of the standard and sample can be matched or nearly matched in optical density prior to acquisition of absorbance and emission spectra for both. The emission quantum yield ($\phi_m$) then can be determined according to Equation 3:

$$\phi_{em} = \phi'_{em}\left(\frac{I}{I'}\right)\left(\frac{A'}{A}\right)$$

where A and A' are the absorbances at the excitation wavelength for the sample and the standard respectively and I and I' are the integrated emission intensities for the sample and standard respectively. In this case $\phi'_{em}$ can be the agreed upon quantum yield for the standard.

Disclosed herein are fluorescent nanoparticles with superior and robust properties which significantly expand the applications in which nanoparticles are useful. These nanoparticles are superior and surprisingly robust in that they are simultaneously stable, bright, and sensitive to environmental stimuli. Moreover, the disclosed nanoparticles have limited or no detectable blinking (i.e., where the nanoparticle emits light non-intermittently when subject to excitation), are highly photostable, have a consistently high quantum yield, are small (e.g., ≤20 nm) and can act as a donor which undergoes FRET with a suitable acceptor moiety (e.g., fluorescent dyes, etc.). The photostability of these nanoparticles is reflected in their exhibiting reduced or no photobleaching (i.e., fading) behavior when subjected to moderate to high intensity excitation for at least about 20 minutes. Additionally, the particles can remain substantially free from photo-induced color shifting.

Put another way, the nanoparticles can maintain a consistent spectral emission pattern (i.e., maintain the ability to fluoresce) even when exposed to a large quantity of photons (i.e., moderate to high intensity excitation) for a long period of time. This unique combination of characteristics makes these types of nanoparticles sensitive tools for single molecule analysis and other sensitive high throughput applications. Moreover, these properties make the nanoparticles particularly well suited for use as highly efficient donor fluorophores in energy transfer reactions such as FRET reactions (i.e., high FRET efficiency) or other reactions as well as applications which require or are enhanced by greater response to the environment.

Without being bound to a particular theory, blinking or fluorescence intermittency may arise during the nanoparticle charging process when an electron is temporarily lost to the surrounding matrix (Auger ejection or charge tunneling) or captured to surface-related trap states. The nanoparticle is "on" or fluorescing when all of the electrons are intact and the particle is "neutral" and the particle is "off" or dark when the electron is lost and the particle is temporarily (or in some cases permanently) charged. It is important to note that the complete suppression of blinking may not necessarily be required and in some instances may not be desirable. Blinking which occurs on a timescale much shorter or much longer than the interrogation period for a particular assay has relatively little impact on the performance of the system. Thus, nanoparticles and nanoparticle populations having modulated blinking properties, where blinking occurs on a very short or very fast timescale relative to the assay interrogation periods are also useful and fall within the scope of the present disclosure. Localization of timescale or simply pushing timescale to one side (e.g., to where the blinking is undetectable within the assay system) can provide substantial benefit in application development.

The blinking behavior of the nanoparticles described herein can be analyzed and characterized by any suitable number of parameters using suitable methodologies. The probability distribution function of the "on" and "off" blinking time durations (i.e., blinking behavior) can be determined using the form of an inverse power law. A value, alpha ($\alpha$) can be calculated, wherein $\alpha$ represents an exponent in the power law. As the percentage of the population which is non-blinking increases, the value of $\alpha_{on}$ theoretically approaches zero. In conventional nanoparticle populations previously described, $\alpha_{on}$ typically ranges from about 1.5 to about 2.5, under moderate to high excitation energy.

Most alpha calculations can use a predetermined threshold to determine the "on" and "off" values of alpha-on and alpha-off (i.e., $\alpha_{on}$ and $\alpha_{off}$). Typically, an alpha estimator which calculates the on/off threshold for each dot individually can be employed. The data can be represented by a plot of signal versus frequency, and typically appears as a series of Gaussian distributions around the "off state" and one or more "on states." A log-log plot of frequency versus time for each period of time that the dot is "on" provides a straight line having a slope of $\alpha_{on}$. The value of alpha-off ($\alpha_{off}$) can be similarly determined.

In a specific example (the "TIRF example"), the fluorescent intermittency measurements can be made using a Total Internal Reflection Fluorescence (TIRF) microscope fitted with a 60× oil immersion objective lens, using a dual view with a longpass filter on the acceptor side and a bandpass filter on the donor side. Using the TIRF setup, the nanoparticles were imaged at 30 Hz (33 ms), typically for 5 minutes, to produce a movie showing the time and intensity of the emitted light for each individual spot (corresponding to a single particle) within a binned frame which was 33 ms long; the intensity for each binned frame can be integrated. Each data set can be manually analyzed dot-by-dot, and aggregates and other artifacts were excluded. From the edited results, the following parameters can be calculated: alpha-on ("$\alpha_{off}$"); alpha-off ("$\alpha_{off}$"); the percent on; longest on/longest off; overlap scores; and the median values for each of these parameters.

In some aspects, provided herein is a nanoparticle or population thereof which has an $\alpha_{on}$ of less than about 1.5, $\alpha_{on}$ of less than about 1.4, $\alpha_{on}$ of less than about 1.3, $\alpha_{on}$ of less than about 1.2, or an $\alpha_{on}$ of less than about 1.1, under moderate to high excitation energy. In some embodiments, at least about 50%, at least about 60%, at least about 70%, at least about 80%, at least about 90%, at least about 95%, at least about 98%, at least about 99% or more of the population has an $\alpha_{on}$ of less than about 1.5, $\alpha_{on}$ of less than about 1.4, $\alpha_{on}$ of less than about 1.3, $\alpha_{on}$ of less than about 1.2, or $\alpha_{on}$ of less than about 1.1 for the time observed, under moderate to high excitation energy. The observation time can be at least about 5 minutes, at least about 10 minutes, at least about 15 minutes, at least about 30 minutes, at least about 45 minutes, at least about 60 minutes, at least about 90 minutes, at least about 120 minutes or more under moderate to high excitation energy. Compositions comprising such a nanoparticle and populations thereof also are contemplated.

In some aspects, provided herein is a nanoparticle or a population thereof having a stochastic blinking profile which is either undetectable or rare (e.g., no more than 1-2 events during the interrogation period) over an observed timescale. In this case, "undetectable" encompasses the situation in which evidence might exist for ultra-fast blinking on a timescale which is faster than the binning timescale (e.g., dimming and brightening from bin to bin) but there are no "off" events persisting for longer than the bin time. Therefore, in some embodiments, a nanoparticle or population thereof has a stochastic blinking profile which is undetectable for at least about 50%, at least about 60%, at least about 70%, at least about 80%, at least about 85%, at least about 90%, at least about 95%, at least about 98%, at least about 99% or more of the time observed, under moderate to high excitation energy. In other embodiments, at least about 50%, at least about 60%, at least about 70%, at least about 80%, at least about 90%, at least about 95%, at least about 98%, at least about 99% or more of the individual nanoparticles in a population have a stochastic blinking on a timescale which is undetectable for the time observed, under moderate to high excitation energy. The timescale can be at least about 5 minutes, at least about 10 minutes, at least about 15 minutes, at least about 30 minutes, at least about 45 minutes, at least about 60 minutes, at least about 90 minutes, at least about 120 minutes or more under moderate to high excitation energy.

In some aspects, the longest on and longest off values can relate to the longest period of time a nanoparticle is observed to be in either the "on" or the "off" state. In particular, the longest on value can be important to determining the length of time and amount of data which may be measured in a particular assay.

Thus, the blinking characteristics of the nanoparticles herein can also be characterized by their on-time fraction, which represents the (total on-time)/(total experiment time). Under the TIRF example disclosed herein, the total on time can be determined by the total number of frames "on" multiplied by 33 ms, and the total experiment time is 5 minutes. For example, the blinking properties of the disclosed nanoparticles or populations thereof can be determined under continuous irradiation conditions using a 405 nm laser with an intensity of about 1 watt per cm$^2$ during an experimental window of at least 5 minutes.

On-time fractions can be used to characterize the blinking behavior of a single nanoparticle or of a population of nanoparticles. It is important to note that the on-time fraction for a particular nanoparticle or population of nanoparticles is a function of the specific conditions under which the percent of blinking or "non-blinking" nanoparticles is determined.

In some aspects, provided herein is a nanoparticle or population thereof having an on-time fraction of at least about 0.50, at least about 0.60, at least about 0.70, at least about 0.75, at least about 0.80, at least about 0.85, at least about 0.90, at least about 0.95, at least about 0.96, at least about 0.97, at least about 0.98, or at least about 0.99 or more, under moderate to high excitation energy. In some embodiments, a nanoparticle or populations thereof having a percent on-time of about 98%, about 99% (i.e., on-time fraction of about 0.99) can be considered to be "non-blinking," under moderate to high excitation energy. In some embodiments, at least about 50%, at least about 60%, at least about 70%, at least about 80%, at least about 90%, at least about 95%, at least about 98%, at least about 99%, or more of the individual nanoparticles in a population of nanoparticles can have an on-time fraction of at least about 0.50, at least about 0.60, at least about 0.70, at least about 0.75, at least about 0.80, at least about 0.85, at least about 0.90, at least about 0.95, at least about 0.96, at least about 0.97, at least about 0.98, or at least about 0.99 or more, under moderate to high excitation energy. The on-times of the nanoparticles are typically for at least about 5 minutes, at least about 10 minutes, at least about 15 minutes, at least about 20 minutes, at least about 30 minutes, at least about 45 minutes, at least about 60 minutes, at least about 70 minutes, at least about 80 minutes, at least about 90 minutes, at least about 120 minutes under moderate to high intensity excitation of the nanoparticle or nanoparticle population. Under one set of conditions, continuous irradiation with 405 nm laser with an approximate intensity of 1 watt per cm$^2$ was used to determine the stochastic blinking profile.

In some embodiments, nanoparticles which have a stochastic (i.e., random) blinking profile in a timescale which shifts from very rapid blinking or very slow/infrequent blinking (relative to a nanoparticle previously described in the art) can be considered to have modulated blinking properties. In some embodiments, these nanoparticles may blink on and off on a timescale which is too rapid to be detected under the methods employed to study this behavior. Thus, certain nanoparticles can effectively appear to be "always on" or to have on-time fractions of about 0.99, when in fact they flicker on and off at a rate too fast or too slow to be detected. Such flickering has relatively little impact on the performance of a system, and for practical purposes such nanoparticles can be considered to be non-blinking.

In some instances, the disclosed nanoparticles and populations thereof are not observed to blink off under the analysis conditions, and such particles can be assessed as "always on" (e.g., non-blinking). The percent of usable dots which are "always on" can be a useful way to compare nanoparticles or populations of nanoparticles. However, a determination of "always on" may mean that the "off" time was insufficient to provide enough a signal gap for accurate determination and thus the value in the regime of particles is insufficient to calculate. Even these "non-blinking" nanoparticles may flicker on and off on a timescale which is not detected under the conditions used to assess blinking. For example, certain particles may blink on a timescale which is too fast to be detected, or they may blink very rarely, and, in some embodiments, such particles may also be considered to be "always-on" or non-blinking, as the terms are used herein.

In one aspect, provided herein is a nanoparticle or population thereof which demonstrate some fluctuation in fluorescence intensity. In some embodiments, the change in fluorescence intensity for the nanoparticle is less than about 5%, less than about 10%, less than about 20%, or less than about 25% of the nanoparticle or populations thereof at its greatest intensity, under moderate to high excitation energy. In some embodiments, such changes in fluorescence intensity of less than about 5%, less than about 10%, less than about 20%, or less than about 25% of the highest intensity can occur in at least about 50%, at least about 60%, at least about 70%, at least about 80%, at least about 85%, at least about 90%, at least about 95%, at least about 98%, at least about 99% of the nanoparticles in the population, under moderate to high excitation energy.

In some aspects, the nanoparticles with modulated, reduced or no intermittent (e.g., continuous, non-blinking) fluorescence provided herein can comprise of a core and a layered gradient shell. In some embodiments, the nanoparticle(s) disclosed herein can be comprised of a nanocrystal core (e.g., CdSe, etc.), at least one inner (intermediate) shell layer (e.g., CdS, etc.), and at least one outer (external) shell layer (e.g., ZnS, etc.). In some embodiments, the inner and/or outer shell layers are each comprised of two or more discrete monolayers of the same material. In some embodiments, the largest dimension of the disclosed nanoparticle(s) is less than about 15 nm. See for example, PCT Application Serial No. PCT US/09/61951. See also PCT/US09/061951 and PCT/US09/061953 both filed on Oct. 23, 2009.

As discussed previously, the disclosed nanoparticles may be particularly well suited for use as a donor or acceptor which undergoes FRET with a suitable complementary partner (donor or acceptor). A "FRET capable" nanoparticle refers to a nanoparticle which can undergo a measurable FRET energy transfer event with a donor or an acceptor moiety. In some embodiments, a FRET capable nanoparticle is one which has at least about 25% efficiency in a FRET reaction.

Thus, in one aspect, a FRET capable fluorescent nanoparticle or population thereof with modulated, reduced or non intermittent (e.g., continuous, etc.) fluorescence is provided. In some embodiments, the nanoparticle is the donor in a FRET reaction. In some embodiments, the nanoparticle is the acceptor in the FRET reaction.

In some embodiments, the FRET capable non-blinking fluorescent nanoparticle(s) disclosed herein can comprise a core and a layered gradient shell. In some embodiments, the FRET capable non-blinking nanoparticle(s) disclosed herein can be comprised of a nanocrystal core (e.g., CdSe, etc.), at least one inner (intermediate) shell layer (e.g., CdS, etc.), and at least one outer (external) shell layer (e.g., ZnS, etc.). In some embodiments, the inner and/or outer shell layers are each comprised of two or more discrete monolayers of the same material. In some embodiments, the largest dimension of the disclosed FRET capable nanoparticle(s) is less than about 15 nm.

In some embodiments, the nanoparticle or population thereof has a FRET efficiency of at least about 20%, at least about 40%, at least about 50%, at least about 60%, at least about 70%, at least about 80%, at least about 90%, at least about 95%, at least about 98%, at least about 99%, or greater.

In some embodiments, at least about 30%, at least about 40%, at least about 50%, at least about 60% at least about 70%, at least about 80%, at least about 90%, at least about 95%, at least about 98%, at least about 99% or more of the individual nanoparticles in the population have a FRET efficiency of at least about 20%, at least about 40%, at least about 50%, at least about 60%, at least about 70%, at least about 80%, at least about 90%, at least about 95%, at least about 98%, at least about 99% or more.

In some embodiments, the FRET efficiency of the disclosed nanoparticle or population thereof can be maintained for at least about the first 10%, at least about the first 20%, at least about the first 30%, at least about the first 40%, at least about the first 50%, at least about the first 60%, at least about the first 70%, at least about the first 80%, at least about the first 90% or more of the total emitted photons under conditions of moderate to high excitation.

As discussed above, the nanoparticle(s) provided herein can be considered to be surprisingly photostable. In particular, the nanoparticle and populations described herein can be photostable over an extended period of time while maintaining the ability to effectively participate in energy transfer (i.e., FRET) reactions. The disclosed nanoparticles can be stable under high intensity conditions involving prolonged or continuous irradiation over an extended period of time from a moderate to high excitation source.

Thus, in one aspect, provided herein is a non-blinking fluorescent nanoparticle and population thereof which is photostable.

In some embodiments, the disclosed photostable nanoparticle and population thereof can have an emitted light or energy intensity sustained for at least about 10 minutes and does not decrease by more than about 20% of maximal intensity achieved during that time. Further, these nanoparticles and populations thereof can have a wavelength spectrum of emitted light which does not change more than about 10% upon prolonged or continuous exposure to an appropriate energy source (e.g. irradiation).

In one embodiment, the photostable nanoparticles disclosed herein can remain photostable under moderate to high intensity excitation from at least about 10 minutes to about 2 hours. In another embodiment, the photostable nanoparticles disclosed herein can remain photostable under moderate to high intensity excitation from at least about 10 minutes to about 10 hours. In still another embodiment, the photostable nanoparticles disclosed herein can remain photostable under moderate to high from about 10 minutes to about 48 hours. However, it should be appreciated, that these are just example photostable times for the disclosed nanoparticles, in practice the nanoparticles can remain photostable for longer periods of time depending on the particular application.

It should be appreciated that nanoparticles which are photostable over longer timescales in combination with moderate to high excitation energy sources are well suited for more sensitive and broad-ranging applications such as the real-time monitoring of single molecules involving FRET. That is, the nanoparticle and population thereof described herein can be photostable over an extended period of time while maintaining the ability to effectively participate in energy transfer (i.e., FRET) reactions, which makes the subject nanoparticles particularly useful for many applications involving the real-time monitoring of single molecules. As such, in some embodiments the photostable nanoparticles disclosed herein have FRET efficiencies of at least about 20%.

In some embodiments, the disclosed nanoparticles are stable upon prolonged or continuous irradiation (under moderate to high excitation rate) in which they do not exhibit significant photo-bleaching on the timescales indicated. Photobleaching can result from the photochemical destruction of a fluorophore (and can be characterized by the nanoparticles losing the ability to produce a fluorescent signal) by the light exposure or excitation source used to stimulate the fluorescence. Photobleaching can complicate the observation of fluorescent molecules in microscopy and the interpretation of energy transfer reactions because the signals can be destroyed or diminished increasingly as timescales for the experiment increase or the energy intensity increases.

Photobleaching can be assessed by measuring the intensity of the emitted light or energy for a nanoparticle or nanoparticle population using any suitable method. In some embodiments, the intensity of emitted light or energy from the disclosed nanoparticle or population thereof does not decrease by more than about 20% (and in some embodiments, not more than about 10%) upon prolonged or continuous irradiation (under moderate to high excitation rate). In some embodiments, the intensity of emitted light from the disclosed nanoparticle or population thereof does not decrease by more than about 20%, about 15%, about 10%, about 5% or less upon irradiation from about 10 minutes, about 20 minutes, about 30 minutes, about 45 minutes, about 60 minutes, about 90 minutes, about 2 hours, about 3 hours to about 4 hours, under moderate to high excitation energy.

In some embodiments, the photostable nanoparticles provided herein further demonstrate enhanced stability in which they exhibit a reduction in or absence of spectral shifting during prolonged excitation. In the conventional nanoparticles previously described in the art, increased exposure to an excitation source—whether via increase time or power—results in a spectral shift of the wavelength emission wavelength profile of a nanoparticle and populations thereof from a longer wavelength to an increasingly shorter wavelength. Such spectral shifting of emission wavelength represents a significant limitation as precise resolution of emission spectra is required for applications which require rapid detection, multi-color analysis, and the like. Shifting of any significance then requires that the wavelength emissions used in an assay be sufficiently separated to permit resolution, thus reducing the number of colors available as well as increasing signal to noise ratio to an unacceptable level as the initial spectral profile cannot be relied upon once spectral shifting begins. Such shifting may require shortened observation times or use of fluorophores with widely separated emission spectra. The nanoparticles provided herein have little to no spectral shift, particularly over extended periods of excitation.

Wavelength emission spectra can be assessed by any suitable method. For example, spectral characteristics of nanoparticles can generally be monitored using any suitable light-measuring or light-accumulating instrumentation. Examples of such instrumentation are CCD (charge-coupled device) cameras, video devices, CIT imaging, digital cameras mounted on a fluorescent microscope, photomultipliers, fluorometers and luminometers, microscopes of various configurations, and even the human eye. The emission can be monitored continuously or at one or more discrete time points. The photostability and sensitivity of nanoparticles allow recording of changes in electrical potential over extended periods of time.

Thus, in some embodiments, the photostable nanoparticle and population thereof has a wavelength spectrum of emitted light which does not change more than about 10% upon prolonged or continuous exposure to an appropriate energy source (e.g. irradiation) over about 4 minutes to about 10 minutes, under moderate to high excitation energy. In some embodiments, the wavelength emission spectra does not change more than about 5%, more than about 10%, more than about 20% over 10 minutes, about 20 minutes, about 30 minutes, about 45 minutes, about 60 minutes, about 90 minutes, about 2 hours, about 3 hours to about 4 hours.

It should be appreciated that there can be various other objective indicia of nanoparticle photostability. For example, a nanoparticle can be classified as photostable when the nanoparticle, under moderate to high excitation, emits about 1,000,000 to about 100,000,000 photons or more preferably about 100,000,001 to about 100,000,000,000 photons or even more preferably more than about 100,000,000,000 photons before becoming non-emissive (i.e., bleached).

A nanoparticle with modulated, reduced or no fluorescent intermittency (e.g., continuous, non-blinking, etc.); reduced or absent spectral shifting; low to no photobleaching; high quantum yield; and sufficient FRET efficiency can be of any suitable size. Typically, it is sized to provide fluorescence in the UV-visible portion of the electromagnetic spectrum as this range is convenient for use in monitoring biological and biochemical events in relevant media. The disclosed nanoparticle and population thereof can have any combination of the properties described herein.

Thus, in some embodiments the nanoparticle or population thereof has modulated or no blinking, are photostable (e.g., limited or no photobleaching, limited or no spectral shift), has high quantum yield, have high FRET efficiency, has a diameter of less than about 15 nm, is spherical or substantially spherical shape, or any combination of all these properties as described herein.

Likewise, in some embodiments, at least about 50%, at least about 60%, at least about 70%, at least about 80%, at least about 90%, at least about 95%, at least about 98%, at least about 99%, or more of the individual nanoparticles in a population of nanoparticles have modulated or no blinking, are photostable (e.g., limited or no photobleaching, limited or no spectral shift), have high quantum yield, have high FRET efficiency, have diameters of less than about 15 nm, are spherical or substantially spherical shape, or any combination of or all of these properties as described herein.

In one aspect, the FRET capable, non-blinking and/or photostable nanoparticle or population thereof provided herein has a maximum diameter of less than about 20 nm. In some embodiments, the nanoparticle(s) can be less than about 15 nm, less than about 10 nm, less than about 8 nm, less than about 6 nm, less than about 5 nm, less than about 4 nm, less than about 3 nm or less in its largest diameter when measuring the core/shell structure. Any suitable method may be used to determine the diameter of the nanoparticle(s). The nanoparticle(s) provided herein can be grown to the desired size using any of the methods disclosed herein. In some embodiments, at least about 50%, at least about 60%, at least about 70%, at least about 80%, at least about 90%, at least about 95%, at least about 98%, at least about 99%, or more of the individual members of a population of nanoparticles have maximum diameters (when measuring the core, core/shell or core/shell/ligand structure) which are less than about 20 nm, less than about 15 nm, less than about 10 nm, less than about 8 nm, less than about 6 nm, less than about 5 nm, less than about 4 nm, less than about 3 nm or less.

The FRET capable, non-blinking and/or photostable nanoparticle(s) provided herein and populations thereof can be spherical or substantially spherical. In some embodiments, a substantially spherical nanoparticle can be one where any two radius measurements do not differ by more than about 10%, about 8%, about 5%, about 3% or less. In some embodiments, at least about 50%, at least about 60%, at least about 70%, at least about 80%, at least about 90%, at least about 95%, at least about 98%, at least about 99%, or more of the individual members of a population of nanoparticles are spherical or substantially spherical.

Nanoparticles can be synthesized in shapes of different complexity such as spheres, rods, discs, triangles, nanorings, nanoshells, tetrapods, nanowires and so on. Each of these geometries can have distinctive properties: spatial distribution of the surface charge, orientation dependence of polarization of the incident light wave, and spatial extent of the electric field. In some embodiments, the nanoparticles are substantially spherical or spheroidal.

For embodiments where the nanoparticle is not spherical or spheroidal, e.g. rod-shaped, it may be from about 1 to about 15 nm, from about 1 nm to about 10 nm, or 1 nm to about 5 nm in its smallest dimension. In some such embodiments, the nanoparticles may have a smallest dimension of about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 25 nm, about 30 nm, about 35 nm, about 40 nm, about 45 nm, about 50 nm and ranges between any two of these values.

The single-color preparation of the nanoparticles disclosed herein can have individual nanoparticles which are of substantially identical size and shape. Thus, in some embodiments, the size and shape between the individual nanoparticles in a population of nanoparticles vary by no more than about 20%, no more than about 15%, no more than about 10%, no more than about 8%, no more than about 6%, no more than about 5%, no more than about 4%, no more than about 3% or less in at least one measured dimension. In some embodiments, disclosed herein is a population of nanoparticles, where at least about 60%, at least about 70%, at least about 80%, at least about 90%, at least about 95%, and ideally about 100% of the particles are of the same size. Size deviation can be measured as root mean square ("rms") of the diameter, with the population having less than about 30% rms, preferably less than about 20% rms, more preferably less than about 10% rms. Size deviation can be less than about 10% rms, less than about 9% rms, less than about 8% rms, less than about 7% rms, less than about 6% rms, less than about 5% rms, less than about 3% rms, or ranges between any two of these values. Such a collection of particles is sometimes referred to as being a "monodisperse" population.

The color (emitted light) of a nanoparticle can be "tuned" by varying the size and composition of the particle. Nanoparticles as disclosed herein can absorb a wide spectrum of wavelengths, and emit a relatively narrow wavelength of light. The excitation and emission wavelengths are typically different, and non-overlapping. The nanoparticles of a monodisperse population may be characterized in that they produce a fluorescence emission having a relatively narrow wavelength band. Examples of emission widths include less than about 200 nm, less than about 175 nm, less than about 150 nm, less than about 125 nm, less than about 100 nm, less than about 75 nm, less than about 60 nm, less than about 50 nm, less than about 40 nm, less than about 30 nm, less than about 20 nm, and less than about 10 nm. In some embodiments, the width of emission is less than about 60 nm full width at half maximum (FWHM), or less than about 50 nm FWHM, and sometimes less than about 40 nm FWHM, less than about 30 nm FWHM or less than about 20 nm FWHM. In some embodiments, the emitted light preferably has a symmetrical emission of wavelengths.

The emission maxima of the disclosed nanoparticle and population thereof can generally be at any wavelength from about 200 nm to about 2,000 nm. Examples of emission maxima include about 200 nm, about 400 nm, about 600 nm, about 800 nm, about 1,000 nm, about 1,200 nm, about 1,400 nm, about 1,600 nm, about 1,800 nm, about 2,000 nm, and ranges between any two of these values.

As discussed previously, the disclosed nanoparticle or populations thereof can comprise a core and a layered shell, wherein the shell includes at least one inner (intermediate) shell layer comprising a first shell material and at least one outer (external) shell layer comprising a second shell material, and wherein the layered shell is substantially uniform in coverage around the core and is substantially free of defects.

Thus, in one aspect, the nanoparticle or population thereof comprises a core ($M^1Y$) and a layered shell, wherein the shell comprises m inner shell monolayers comprising a first shell material $(M^1X)_m$ and n outer shell monolayers comprising a second shell material $(M^2X)_n$, wherein M can be a metal atom and X can be a non-metal atom, each of m and n is independently an integer from 1 to 10, and the layered shell is substantially uniform in coverage around the core and is substantially free of defects. In specific embodiments, the sum of m+n is 3-20, or 5-14, or 6-12, or 7-10.

In certain embodiments, the disclosed nanoparticles can further comprise one or more additional shell layers between the at least one inner shell layer and the at least one outer shell layer.

In some embodiments, the nanoparticle core and population thereof can have a first bandgap energy and the first shell material can have a second bandgap energy, wherein the second bandgap energy can be greater than the first bandgap energy.

In a further aspect, provided herein is a nanoparticle or population thereof comprising a core and a layered shell, wherein the shell comprises sequential monolayers comprising an alloyed multi-component shell material of the form $M^1_xM^2_yX$, where $M^1$ and $M^2$ can be metal atoms and X can be a non metal atom, where the composition becomes successively enriched in $M^2$ as the monolayers of shell material are deposited, where x and y represent the ratio of $M^1$ and $M^2$ in the shell material, and wherein the monolayered shell is substantially uniform in coverage around the core and is substantially free of defects. In some embodiments, the layered shell sometimes has about 3-20 monolayers of shell material, sometimes about 5-14 monolayers of shell material, sometimes about 6-12 monolayers of shell material, or sometimes about 7-10 monolayers of shell material.

In one aspect, provided herein is a nanoparticle or population thereof comprising a core and a layered shell having a gradient potential, wherein the shell comprises at least one inner shell layer and at least one outer shell layer, and wherein the layered shell is substantially uniform in coverage around the core and is substantially free of defects.

The layered shell may be engineered such that the sequential monolayers are selected to provide a gradient potential from the nanoparticle core to the outer surface of the nanoparticle shell. The steepness of the potential gradient may vary depending on the nature of the shell materials selected for each monolayer or group of monolayers. For example, a nanoparticle comprising several sequential monolayers of the same shell material may reduce the potential through a series of steps, while a more continuous gradient may be achievable through the use of sequential monolayers of a multi-component alloyed shell material. In some embodiments, both single component and multi-component shell materials may be applied as different monolayers of a multi-layer shell on a nanoparticle.

The nanoparticles can be synthesized as disclosed to the desired size by sequential, controlled addition of materials to build and/or apply monolayers of shell material to the core. This is in contrast to conventional methods of adding shells where materials (e.g., diethylzinc and bis(trimethylsilyl) sulfide) are added together. Sequential addition permits the formation of thick (e.g., >2 nm) relatively uniform individual shells (e.g., uniform size and depth) on a core. The layer additions generally require the addition of an appropriate amount of the shell precursors to form a single monolayer, based on the starting size of the underlying core. This means that as each monolayer of shell material is added, a new "core" size must be determined by taking the previous "core" size and adding to it the thickness of just-added shell monolayer. This leads to a slightly larger volume of the following shell material needing to be added for each subsequent monolayer of shell material being added.

Each monolayer of shell material can be independently selected, and may be made up of a single component, or may comprise a multi-component (e.g., alloyed, etc.) shell material. In some embodiments, it is suitable to apply one or more sequential monolayers of a first shell material, followed by one or more sequential monolayers of a second shell material. This approach allows the deposition of at least one inner shell layer of a material having a bandgap and lattice size compatible with the core, followed by the deposition of at least one outer shell layer of a material having a bandgap and lattice size compatible with the inner shell layer. In some embodiments, multiple sequential monolayers of a single shell material can be applied to provide a uniform shell of a desired number of monolayers of a single shell material; in these embodiments, the first and second shell materials are the same. In other embodiments, sequential monolayers of an alloyed shell material are applied, where the ratio of the components varies such that the composition becomes successively enriched in one component of the multi-component mixture as the successive monolayers of shell material are deposited.

In some embodiments, the layered shell can be about 3-20 monolayers of shell material thick, sometimes about 5-14 monolayers of shell material thick, sometimes about 6-12 monolayers of shell material thick or sometimes about 7-10 monolayers of shell material thick. In some embodiments, at least one inner shell layer can be comprised of about 3-5 monolayers, sometimes about 3-7 monolayers, of the first shell material. In other embodiments, at least one outer shell layer can be comprised of about 3-5 monolayers, sometimes about 3-7 monolayers, of the second shell material. In some embodiments, the inner shell layer can be at least 3 monolayers thick; in other embodiments, the outer shell layer can be at least 3 monolayers thick. The individual monolayers can be formed by the controlled, sequential addition of the layer materials methods described herein. The monolayers may not always be completely distinct as they may, in some embodiments, be a latticing between the surfaces of contacting monolayers.

In certain embodiments, provided herein are nanoparticles having a thick, uniform, layered shell, as described herein, wherein the core comprises CdSe, the at least one inner shell layer comprises CdS, and the at least one outer shell layer comprises ZnS. In a particular embodiment, provided herein is a nanoparticle or population thereof having a CdSe core and a layered shell comprising 4CdS+3.5ZnS layers. In some embodiments, provided herein is a nanoparticle which consists essentially of CdSe/4CdS–3.5ZnS.

Also disclosed herein are methods of making a nanoparticle and population thereof with modulated, reduced or no fluorescence intermittency or "blinking". These nanoparticles can be small, photostable, bright, highly FRET efficient or some combination thereof. These nanoparticles can have a multi-shell layered core achieved by a sequential shell material deposition process, whereby one shell material is added at a time, to provide a nanoparticle having a substantially uniform shell of desired thickness which is substantially free of defects.

In one aspect, provided herein is a method for making a nanoparticle or population thereof with modulated, reduced or no fluorescence intermittency, comprising: providing a mixture comprising a core and at least one coordinating solvent; adding a first inner shell precursor alternately with a second inner shell precursor in layer additions, to form an inner shell layer which is a desired number of layers thick; and adding a first outer shell precursor alternately with a second outer shell precursor in layer additions, to form an outer shell layer which is a desired number of layers thick. If the coordinating solvent of is not amine, the method further comprises an amine in.

In some embodiments, the mixture can be heated to a temperature which is suitable for shell formation before and/or after every sequential addition of a shell precursor. In some embodiments, the shell is substantially uniform in coverage around the core and is substantially free of defects. In some embodiments, the resulting nanoparticles have a diameter of less than about 15 nm. In other embodiments, the nanoparticles have a diameter of between about 6 nm to about 10 nm. The nanoparticles made by this method can have quantum yields greater than about 80%. The nanoparticle made by this method can have on-time fractions (i.e., ratio of the time which nanoparticle emission is turned "on" when the nanoparticle is excited) of greater than about 0.80 (under moderate to high excitation energy).

In another aspect, provided herein is a method for making a FRET capable nanoparticle and populations thereof with modulated, reduced or no fluorescence intermittency, comprising: (a) providing a mixture comprising a plurality of nanocrystal cores and at least one coordinating solvent; (b) adding a first intermediate shell precursor alternately with a second intermediate shell precursor in layer additions to form an intermediate shell layer on each of the plurality of nanocrystal cores, wherein the intermediate shell layer is comprised of more than one monolayer; (c) adding a first external shell precursor alternately with a second external shell precursor in layer additions to form an external shell layer on each of the plurality of nanocrystal cores, wherein the external shell layer is disposed on top of the intermediate shell layer and is comprised of more than one monolayer; (d) adding an aqueous solution comprising a hydrophilic ligand; and (e) maintaining the mixture under conditions which cause the plurality of nanocrystals to migrate into an aqueous phase. If the coordinating solvent is not an amine, at least one amine can be included in step (a). In some embodiments, the resulting population of FRET capable non-blinking nanoparticles has a $\alpha_{on}$ value which is less than about 1.4. In other embodiments, the resulting population of FRET capable non-blinking nanoparticles has an on-time fraction of least about 0.8 (under moderate to high excitation energy). In some embodiments, the resulting population of FRET capable non-blinking nanoparticles has diameters which are less than about 15 nm. In some embodiments, the resulting population of FRET capable non-blinking nanoparticles has a FRET efficiency of at least 20%. In some embodiments, the resulting population of FRET capable non-blinking nanoparticles has a quantum yield of at least about 40%.

In some embodiments, the methods disclosed above utilize a one step or a two step ligand exchange process to replace the hydrophobic ligands on the nanoparticles with hydrophilic ligands to cause the plurality of nanocrystals to migrate into the aqueous phase. See PCT Application Serial No. PCT/US09/053018 and PCT/US09/059456 which are expressly incorporated herein by reference as if set forth in full.

In another aspect, provided herein is a method for making a FRET capable nanoparticle and populations thereof with modulated, reduced or no fluorescence intermittency, comprising: providing a mixture comprising a plurality of nanocrystal cores, functionalized organophosphorous-based hydrophilic ligands and at least one coordinating solvent; adding a first intermediate shell precursor alternately with a second intermediate shell precursor in layer additions to form an intermediate shell layer on each of the plurality of nanocrystal cores; and adding a first external shell precursor alternately with a second external shell precursor in layer additions to form an external shell layer on each of the plurality of nanocrystal cores. In some embodiments, the resulting population of FRET capable non-blinking nanoparticles has an $\alpha_{on}$ value which is less than about 1.4. In other embodiments, the resulting population of FRET capable non-blinking nanoparticles has an on-time fraction of least about 0.8. In some embodiments, the resulting population of FRET capable non-blinking nanoparticles has diameters which are less than about 15 nm. In some embodiments, the resulting population of FRET capable non-blinking nanoparticles has a FRET efficiency of at least 20%. In some embodiments, the resulting population of FRET capable non-blinking nanoparticles has a quantum yield of at least about 40%.

In some embodiments, the functionalized organophosphorous-based hydrophilic ligands are multi-functional surface ligands which include a phosphonate/phosphinate nanocrystal binding center, a linker, and a functional group, which imparts functionality on the nanocrystal. As used herein the term "functional group" may refer to a group which affects reactivity, solubility, or both reactivity and solubility when present on a multi-functional surface ligand. Embodiments can include a wide variety of functional groups which can impart various types of functionality on the nanocrystal including hydrophilicity, water-solubility, or dispersibility and/or reactivity, and the functionality may generally not include only hydrophobicity or only solubility in organic solvents without increasing reactivity. For example, a functional group which is generally hydrophobic but which increases reactivity such as an alkene or alkyne and certain esters and ethers can be encompassed by embodiments, whereas alkyl groups, which do not generally impart reactivity but increase hydrophobicity may be excluded.

In certain embodiments, the FRET capable and non-blinking nanoparticles produced by the disclosed methods may be coated with ligands which impart water solubility and/or reactivity on the nanoparticle obviating the need for ligand replacement. Without wishing to be bound by theory, eliminating ligand replacement may provide more consistent thermodynamic properties, which may lead to reduction in variability of coating and less loss of quantum yield, among other improvements in the properties of nanoparticles produced by the methods embodied herein. Eliminating ligand replacement may also allow for the production of nanoparticles having a wide variety of functional groups associated with the coating. In particular, while ligand replacement is generally limited to production of nanoparticles having amine and/or carboxylic acid functional groups, in various embodiments, the skilled artisan may choose among numerous functional groups when preparing the multi-functional ligands and may, therefore, generate nanoparticles which provide improved water-solubility or water-dispersity and/or support improved crosslinking and/or improved reactivity with cargo molecules. See PCT Application Serial No. PCT/US09/059117 which is expressly incorporated herein by reference as if set forth in full.

In another aspect, provided herein is a method of making a nanoparticle or population thereof comprising a core and a layered gradient shell, wherein the shell comprises an multi-component (e.g., alloy, etc.) shell material of the form $M^1{}_xM^2{}_yX$, where x and y represent the ratio of $M^1$ and $M^2$ in the shell material. The method comprising: (a) providing a mixture comprising a core, at least one coordinating solvent; (b) heating said mixture to a temperature suitable for formation of the shell layer; and (c) adding a first inner shell precursor comprising $M^1{}_x$ and $M^2{}_y$ alternately with a second inner shell precursor comprising X in layer additions, wherein the ratio of y to x gradually increases in sequential layer additions, such that the shell layers becomes successively enriched in $M^2$, to form a layered gradient shell which is a desired number of monolayers thick. If the coordinating solvent is not an amine, at least one amine can be included in step (a).

In one embodiment, the method described above provides a nanoparticle having a layered gradient shell, wherein the core comprises CdSe and the shell comprises sequential layers of $Cd_xZn_yS$, where the ratio of y to x increases gradually from the innermost shell layer to the outermost shell layer, to provide a layered gradient shell with a finely graded potential. In some such embodiments, the outermost shell layer is essentially pure ZnS. In some embodiments, the percent of Zn in the gradient shell varies from less than about 10% at the innermost shell layer to greater than about 80% at the outermost shell layer.

Typically, the heating steps in the disclosed methods are conducted at a temperature within the range of about 150-350° C., more preferably within the range of about 200-300° C. In some embodiments, the temperature suitable for formation of at least one inner shell layer is about 215° C. In some embodiments, the temperature suitable for formation of at least one outer shell layer is about 245° C. It is understood that the above ranges are merely exemplary and are not intended to be limiting in any manner as the actual temperature ranges may vary, dependent upon the relative stability of the precursors, ligands, and solvents. Higher or lower temperatures may be appropriate for a particular reaction. The determination of suitable time and temperature conditions for providing nanoparticles is within the level of skill in the art using routine experimentation.

It can be advantageous to conduct the nanoparticle-forming reactions described herein with the exclusion of oxygen and moisture. In some embodiments the reactions are conducted in an inert atmosphere, such as in a dry box. The solvents and reagents are also typically rigorously purified to remove moisture and oxygen and other impurities, and are generally handled and transferred using methods and apparatus designed to minimize exposure to moisture and/or oxygen. In addition, the mixing and heating steps can be conducted in a vessel which is evacuated and filled and/or flushed with an inert gas such as nitrogen. The filling can be periodic or the filling can occur, followed by continuous flushing for a set period of time.

In some embodiments, the at least one coordinating solvent comprises a trialkylphosphine, a trialkylphosphine oxide, a phosphonic acid, or a mixture of these. Sometimes, the at least one coordinating solvent comprises TOP, TOPO, TDPA, OPA or a mixture of these. The solvent for these reactions often comprises a primary or secondary amine, for example, decylamine, hexadecylamine, or dioctylamine. In some embodiments, the amine is decylamine. In some embodiments, the first inner shell precursor is $Cd(OAc)_2$ and the second inner shell precursor is bis(trimethylsilyl)sulfide ($TMS_2S$). Sometimes, the first and second inner shell precursors are added as a solution in TOP. In some embodiments, the first outer shell precursor is $Et_2Zn$ and the second inner shell precursor is $TMS_2S$. Sometimes, the first and second outer shell precursors are added as a solution in TOP.

In certain embodiments, the disclosed nanoparticles may be prepared using the method described herein to build a layered CdS—ZnS shell on a CdSe quantum size core. The shells for these materials can have varying numbers of layers of CdS and ZnS. Prototypical materials containing a CdSe core and approximately 4 monolayers CdS and 3.5 monolayers of ZnS (the final 0.5 monolayer is essentially pure Zn), or a CdSe core and 9 monolayers CdS and 3.5 monolayers of ZnS were prepared as described in the examples.

In some embodiments, for either the inner or outer layer, or both, less than a full layer of the appropriate first shell precursor can be added alternately with less than a full layer of the appropriate second shell precursor, so the total amount of the first and second shell precursor required is added in two or more portions. Sometimes, the portion is about 0.25 monolayers of shell material, so that the 4 portions of 0.25 monolayer of first shell precursor are added alternately with 4 portions of 0.25 monolayer of second shell precursor; sometimes the portion is about 0.5 monolayers of shell material, and sometimes about 0.75 monolayers of shell material.

Examples of compounds useful as the first precursor can include, but are not limited to: organometallic compounds such as alkyl metal species, salts such as metal halides, metal acetates, metal carboxylates, metal phosphonates, metal phosphinates, metal oxides, or other salts. In some embodiments, the first precursor provides a neutral species in solution. For example, alkyl metal species such as diethyl-zinc ($Et_2Zn$) or dimethyl cadmium are typically considered to be a source of neutral zinc atoms ($Zn^0$) in solution. In other embodiments, the first precursor provides an ionic species (i.e., a metal cation) in solution. For example, zinc chloride ($ZnCl_2$) and other zinc halides, zinc acetate ($Zn(OAc)_2$) and zinc carboxylates are typically considered to be sources of $Zn^{2+}$ cations in solution.

By way of example only, suitable first precursors providing neutral metal species include dialkyl metal sources, such as dimethyl cadmium ($Me_2Cd$), diethyl zinc ($Et_2Zn$), and the like. Suitable first precursors providing metal cations in solution include, e.g., cadmium salts, such as cadmium acetate ($Cd(OAc)_2$), cadmium nitrate ($Cd(NO_3)_2$), cadmium oxide (CdO), and other cadmium salts; and zinc salts such as zinc chloride ($ZnCl_2$), zinc acetate ($Zn(OAc)_2$), zinc oleate ($Zn(oleate)_2$), zinc chloro(oleate), zinc undecylenate, zinc salicylate, and other zinc salts. In some embodiments, the first precursor is salt of Cd or Zn. In some embodiments, it is a halide, acetate, carboxylate, or oxide salt of Cd or Zn. In other embodiments, the first precursor is a salt of the form $M(O_2CR)X$, wherein M is Cd or Zn; X is a halide or $O_2CR$; and R is a C4-C24 alkyl group which is optionally unsaturated. Other suitable forms of Groups 2, 12, 13 and 14 elements useful as first precursors are known in the art.

Precursors useful as the "second" precursor in the disclosed methods include compounds containing elements from Group 16 of the Periodic Table of the Elements (e.g., S, Se, Te, and the like), compounds containing elements from Group 15 of the Periodic Table of the Elements (N, P, As, Sb, and the like), and compounds containing elements from Group 14 of the Periodic Table of the Elements (Ge, Si, and the like). Many forms of the precursors can be used in the disclosed methods. It will be understood that in some embodiments, the second precursor will provide a neutral species in solution, while in other embodiments the second precursor will provide an ionic species in solution.

When the first precursor comprises a metal cation, the second precursor can provide an uncharged (i.e., neutral) non-metal atom in solution. In frequent embodiments, when the first precursor comprises a metal cation, the second precursor contributes a neutral chalcogen atom, most commonly $S^0$, $Se^0$ or $Te^0$.

Suitable second precursors for providing a neutral chalcogen atom include, for example, elemental sulfur (often as a solution in an amine, e.g., decylamine, oleylamine, or dioctylamine, or an alkene, such as octadecene), and trialkylphosphine adducts of S, Se and Te. Such trialkylphosphine adducts are sometimes described herein as $R3P=X$, wherein X is S, Se or Te, and each R is independently H, or a C1-C24 hydrocarbon group which can be straight-chain, branched, cyclic, or a combination of these, and which can be unsaturated. Exemplary second precursors of this type include tri-n (butylphosphine)selenide (TBP=Se), tri-n-(octylphosphine)selenide (TOP=Se), and the corresponding sulfur and tellurium reagents, TBP=S, TOP=S, TBP=Te and TOP=Te. These reagents are frequently formed by combining a desired element, such as Se, S, or Te with an appropriate coordinating solvent, e.g., TOP or TBP. Precursors which provide anionic species under the reaction conditions are typically used with a first precursor which provides a neutral metal atom, such as alkylmetal compounds and others described above or known in the art.

In some embodiments, the second precursor provides a negatively charged non-metal ion in solution (e.g., S-2, Se-2 or Te-2). Examples of suitable second precursors providing an ionic species include silyl compounds such as bis(trimethylsilyl)selenide ((TMS)$_2$Se), bis(trimethylsilyl)sulfide ((TMS)$_2$S) and bis(trimethylsilyl)telluride ((TMS)$_2$Te). Also included are hydrogenated compounds such as H2Se, H2S, H2Te; and metal salts such as NaHSe, NaSH or NaHTe. In this situation, an oxidant can be used to oxidize a neutral metal species to a cationic species which can react with the anionic precursor in a 'matched' reaction, or an oxidant can be used increase the oxidation state of the anionic precursor to provide a neutral species which can undergo a 'matched' reaction with a neutral metal species.

Other exemplary organic precursors are described in U.S. Pat. Nos. 6,207,229 and 6,322,901 to Bawendi et al., and synthesis methods using weak acids as precursor materials are disclosed by Qu et al., (2001), Nano Lett., 1(6):333-337, the disclosures of each of which are incorporated herein by reference in their entirety.

Both the first and the second precursors can be combined with an appropriate solvent to form a solution for use in the disclosed methods. The solvent or solvent mixture used to form a first precursor solution may be the same or different from that used to form a second precursor solution. Typical coordinating solvents include alkyl phosphines, alkyl phosphine oxides, alkyl phosphonic acids, alkyl phosphinic acids, or carboxylic acid containing solvents, or mixtures of these.

Suitable reaction solvents include, by way of illustration and not limitation, hydrocarbons, amines, alkyl phosphines, alkyl phosphine oxides, carboxylic acids, ethers, furans, phosphoacids, pyridines and mixtures thereof. The solvent may actually comprise a mixture of solvents, often referred to in the art as a "solvent system". In some embodiments, the solvent comprises at least one coordinating solvent. In some embodiments, the solvent system comprises a secondary amine and a trialkyl phosphine (e.g., TBP or TOP) or a trialkylphosphine oxide (e.g., TOPO). If the coordinating solvent is not an amine, an amine can be included.

A coordinating solvent might be a mixture of an essentially non-coordinating solvent such as an alkane and a ligand as defined below.

Suitable hydrocarbons include alkanes, alkenes and aromatic hydrocarbons from 10 to about 30 carbon atoms; examples include octadecene and squalane. The hydrocarbon may comprise a mixture of alkane, alkene and aromatic moieties, such as alkylbenzenes (e.g., mesitylene).

Suitable amines include, but are not limited to, monoalkylamines, dialkylamines, and trialkylamines, for example dioctylamine, oleylamine, decylamine, dodecylamine, hexyldecylamine, and so forth. Alkyl groups for these amines typically contain about 6-24 carbon atoms per alkyl, and can include an unsaturated carbon-carbon bond, and each amine typically has a total number of carbon atoms in all of its alkyl groups combined of about 10-30 carbon atoms.

Exemplary alkyl phosphines include, but are not limited to, the trialkyl phosphines, tri-n-butylphosphine (TBP), tri-n-octylphosphine (TOP), and so forth. Alkyl groups for these phosphines contain about 6-24 carbon atoms per alkyl, and can contain an unsaturated carbon-carbon bond, and each phosphine has a total number of carbon atoms in all of its alkyl groups combined of about 10-30 carbon atoms.

Suitable alkyl phosphine oxides include, but are not limited to, the trialkyl phosphine oxide, tri-n-octylphosphine oxide (TOPO), and so forth. Alkyl groups for these phosphine oxides contain about 6-24 carbon atoms per alkyl, and can contain an unsaturated carbon-carbon bond, and each phosphine oxide has a total number of carbon atoms in all of its alkyl groups combined of about 10-30 carbon atoms.

Exemplary fatty acids include, but are not limited to, stearic, oleic, palmitic, myristic and lauric acids, as well as other carboxylic acids of the formula R—COOH, wherein R is a C6-C24 hydrocarbon group and can contain an unsaturated carbon-carbon bond. It will be appreciated that the rate of nanocrystal growth generally increases as the length of the fatty acid chain decreases.

Exemplary ethers and furans include, but are not limited to, tetrahydrofuran and its methylated forms, glymes, and so forth.

Suitable phosphonic and phosphinic acids include, but are not limited to hexylphosphonic acid (HPA), tetradecylphosphonic acid (TDPA), and octylphosphinic acid (OPA), and are frequently used in combination with an alkyl phosphine oxide such as TOPO. Suitable phosphonic and phosphinic acids are of the formula RPO$_3$H$_2$ or R$_2$PO2H, wherein each R is independently a C6-C24 hydrocarbon group and can contain an unsaturated carbon-carbon bond.

Exemplary pyridines include, but are not limited to, pyridine, alkylated pyridines, nicotinic acid, and so forth.

Suitable alkenes include, e.g., octadecene and other C4-C24 hydrocarbons which are unsaturated.

Nanoparticle core or shell precursors can be represented as a M-source and an X-donor. The M-source can be an M-containing salt, such as a halide, carboxylate, phosphonate, carbonate, hydroxide, or diketonate, or a mixed salt thereof (e.g., a halo carboxylate salt, such as Cd(halo) (oleate)), of a metal, M, in which M can be, e.g., Cd, Zn, Mg, Hg, Al, Ga, In, or Tl. In the X-donor, X can be, e.g., O, S, Se, Te, N, P, As, or Sb. The mixture can include an amine, such as a primary amine (e.g., a C8-C20 alkyl amine). The X donor can include, for example, a phosphine chalcogenide, a bis(trialkylsilyl)chalcogenide, a dioxygen species, an ammonium salt, or a tris(trialkylsilyl)phosphine, or the like.

The M-source and the X donor can be combined by contacting a metal, M, or an M-containing salt, and a reducing agent to form an M-containing precursor. The reducing agent can include an alkyl phosphine, a 1,2-diol or an aldehyde, such as a C$_6$-C$_{20}$ alkyl diol or a C$_6$-C$_{20}$ aldehyde.

Suitable M-containing salts include, for example, cadmium acetylacetonate, cadmium iodide, cadmium bromide, cadmium chloride, cadmium hydroxide, cadmium carbonate, cadmium acetate, cadmium oxide, zinc acetylacetonate, zinc iodide, zinc bromide, zinc chloride, zinc hydroxide, zinc carbonate, zinc acetate, zinc oxide, magnesium acetylacetonate, magnesium iodide, magnesium bromide, magnesium chloride, magnesium hydroxide, magnesium carbonate, magnesium acetate, magnesium oxide, mercury acetylacetonate, mercury iodide, mercury bromide, mercury chloride, mercury hydroxide, mercury carbonate, mercury acetate, aluminum acetylacetonate, aluminum iodide, aluminum bromide, aluminum chloride, aluminum hydroxide, aluminum carbonate, aluminum acetate, gallium acetylacetonate, gallium iodide, gallium bromide, gallium chloride, gallium hydroxide, gallium carbonate, gallium acetate, indium acetylacetonate, indium iodide, indium bromide, indium chloride, indium hydroxide, indium carbonate, indium acetate, thallium acetylacetonate, thallium iodide, thallium bromide, thallium chloride, thallium hydroxide, thallium carbonate, or thallium acetate. Suitable M-containing salts also include, for example, carboxylate salts, such as oleate, stearate, myristate, and palmitate salts, mixed halo carboxylate salts, such as M(halo)(oleate) salts, as well as phosphonate salts.

Alkyl is a branched or unbranched saturated hydrocarbon group of 1 to 100 carbon atoms, preferably 1 to 30 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. Optionally, an alkyl can contain 1 to 6 linkages selected from the group consisting of —O—, —S—, -M- and —NR— where R is hydrogen, or C1-C8 alkyl or lower alkenyl.

The X donor is a compound capable of reacting with the M-containing salt to form a material with the general formula MX. The X donor is generally a chalcogenide donor or a phosphine donor, such as a phosphine chalcogenide, a bis(silyl) chalcogenide, dioxygen, an ammonium salt, or a tris(trialkylsilyl) phosphine. Suitable X donors include dioxygen, elemental sulfur, bis(trimethylsilyl) selenide ((TMS)$_2$Se), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTTe), bis(trimethylsilyl) telluride ((TMS)$_2$Te), sulfur, bis(trimethylsilyl)sulfide ((TMS)$_2$S), a trialkyl phosphine sulfide such as (tri-n-octylphosphine) sulfide (TOPS), tris(dimethylamino) arsine, an ammonium salt such as an ammonium halide (e.g., NH$_4$Cl), tris(trimethylsilyl) phosphide ((TMS)$_3$P), tris(trimethylsilyl) arsenide ((TMS)$_3$As), or tris(trimethylsilyl) antimonide ((TMS)$_3$Sb). In certain embodiments, the M donor and the X donor can be moieties within the same molecule.

Ligand Exchange Processes for Coating Nanoparticles

Provided herein are ligand exchange processes that permit efficient conversion of a conventional hydrophobic nanoparticle or population thereof into a water-dispersible and functionalized nanoparticle or population of nanoparticles. It also permits preparation of small nanoparticles which are highly stable and bright enough to be useful in biochemical and biological assays. The resulting nanoparticles can also be linked to a target molecule or cell or enzyme (e.g., polymerase) of interest.

Typically, the nanoparticle used for this process is a core/shell nanocrystal which is coated with a hydrophobic ligand such as tetradecylphosphonic acid (TDPA), trioctylphosphine oxide (TOPO), trioctyl phosphine (TOP), octylphosphonic acid (OPA), and the like, or a mixture of such ligands; these hydrophobic ligands typically have at least one long-chain alkyl group, i.e. an alkyl group having at least 8 carbons, or for the phosphine/phosphine oxide ligands, this hydrophobic character may be provided by two or three alkyl chains on a single ligand molecule having a total of at least 10 carbon atoms. Therefore, in some embodiments, the surface of the core/shell nanocrystal or population thereof can be coated with varying quantities of TDPA hydrophobic ligands prior to replacement with hydrophilic ligand(s). For example, TDPA can represent at least about 10%, at least about 20%, at least about 30%, at least about 40%, at least about 50%, at least about 80%, at least about 95%, at least about 98%, at least about 99% or more of the total surface ligands coating the core/shell nanoparticles. Moreover, certain hydrophobic ligands show an unexpected and apparent ease of replacement with the hydrophilic ligand. For example, nanoparticles with OPA on the surface have been observed to transfer into aqueous buffer more readily and more completely than the same type of core-shell with TDPA on the surface. Therefore, in some embodiments, the surface of the core/shell nanocrystal or populations thereof can be coated with varying quantities of OPA hydrophobic ligands prior to replacement with hydrophilic ligand(s). For example, OPA can represent at least about 10%, at least about 20%, at least about 30%, at least about 40%, at least about 50%, at least about 80%, at least about 95%, at least about 98%, at least about 99% or more of the total surface ligands coating the core/shell nanocrystal.

In one aspect, provided herein is a "one-step" ligand exchange process to apply various types of ligands to the surface of a nanoparticle, by substituting a desired hydrophilic ligand for a conventional hydrophobic ligand like TOPO, TOP, TDPA, OPA, and the like. The process steps, comprising: providing a nanocrystal coated with a surface layer comprising a hydrophobic ligand, and dissolved or dispersed in a non-aqueous solvent, contacting the nanocrystal dispersion with a phase transfer agent and an aqueous solution comprising a hydrophilic ligand, to form a biphasic mixture having an aqueous phase and a non-aqueous phase and maintaining the mixture under conditions that cause the nanocrystal to migrate from the non-aqueous solvent into the aqueous phase. See PCT Application Serial No. PCT/US09/053018 which is expressly incorporated herein by reference as if set forth in full.

The 'one-step' ligand exchange process described herein utilizes phase transfer catalysts which are particularly effective, and provide faster exchange reactions. Butanol has been utilized as a phase transfer catalyst for this type of exchange reaction; however, the reaction takes several days typically, and requires heating to about 70° C. The time for this reaction exposes the nanoparticles to these reaction conditions for a long period of time, which may contribute to some reduction in its ultimate stability. The embodiments disclosed herein provide more efficient conditions which achieve ligand exchange more rapidly, thus better protecting the nanoparticles. As a result of accelerating the exchange reaction and allowing use of milder conditions, these phase transfer catalysts produce higher quality nanoparticles.

The phase transfer agent for this process can be a crown ether, a PEG, a trialkylsulfonium, a tetralkylphosphonium, and an alkylammonium salt, or a mixture of these. In some embodiments, the phase transfer agent is 18-crown-6, 15-crown-5, or 12-crown-4. In some embodiments, the phase transfer agent is a PEG, which can have a molecular weight from about 500 to about 5000. In some embodiments, the phase transfer agent is a trialkylsulfonium, tetralkylphosphonium, or alkylammonium (including monoalkylammonium, dialkylammonium, trialkylammonium and tetralkylammonium) salt.

Tetralkylammonium salts are sometimes preferred as phase transfer agents. Examples of suitable tetralkylammonium salts include triethylbenzyl ammonium, tetrabutylammonium, tetraoctylammonium, and other such quaternary salts. Other tetralkylammonium salts, where each alkyl group is a C1-C12 alkyl or arylalkyl group, can also be used. Typically, counting all of the carbons on the alkyl groups of a trialkylsulfonium, tetralkylphosphonium, and alkylammonium salt, the phase transfer agent will contain a total of at least 2 carbons, at least 10 carbons and preferably at least 12 carbon atoms. Each of the trialkylsulfonium, tetralkylphosphonium, and alkylammonium salts has a counterion associated with it; suitable counterions include halides, preferably chloride or fluoride; sulfate, nitrate, perchlorate, and sulfonates such as mesylate, tosylate, or triflate; mixtures of such counterions can also be used. The counterion can also be a buffer or base, such as borate, hydroxide or carbonate; thus, for example, tetrabutylammonium hydroxide can be used to provide the phase transfer catalyst and a base. Specific phase transfer salts for use in these methods include tetrabutylammonium chloride (or bromide) and tetraoctylammonium bromide (or chloride).

Suitable hydrophilic ligands are organic molecules which provide at least one binding group to associate tightly with the surface of a nanocrystal. The hydrophilic ligand typically is an organic moiety having a molecular weight between about 100 and 1500, and contains enough polar functional groups to be water soluble. Some examples of suitable hydrophilic ligands include small peptide having 2-10 amino acid residues (preferably including at least one histidine or cysteine residue), mono- or polydentate thiol containing compounds.

Following ligand exchange, the surface layer can optionally be crosslinked.

In another aspect, provided herein is a "two-step" ligand exchange process to apply various types of ligands to the surface of a nanoparticle, by substituting a desired hydrophilic ligand for a conventional hydrophobic ligand like TOPO, TOP, TDPA, OPA, and the like. The process involves the removal of phosphonate or phosphinate ligands from the surface of a nanoparticle or nanocrystal by treatment with sulfonate reagents, particularly silylsulfonate derivatives of weak bases or other poorly coordinating groups.

The process steps, comprising: providing a nanocrystal whose surface comprises a phosphonate ligand, contacting the nanocrystal with a sulfonate reagent in an organic solvent, contacting the sulfonate ligand coated nanocrystal with a functionalized organic molecule (i.e., hydrophilic ligand) comprising at least one nanocrystal surface attachment group, contacting the nanocrystal dispersion with an aqueous solution to form a biphasic mixture having an aqueous phase and a non-aqueous phase, and maintaining the biphasic mixture under conditions which cause the nanocrystal to migrate from the non-aqueous phase into the aqueous phase. See PCT Application Serial No. PCT/US09/59456 which is expressly incorporated herein by reference as if set forth in full.

The result of this removal of phosphonate ligands is replacement of the phosphonates with the weakly coordinating groups. One example is the use of silyl sulfonates, such as trimethylsilyl triflate, to form a sulfonate-coated nanoparticle. Triflate is a conventional/common name for a trifluoromethanesulfonyloxy group, $CF_3SO_2O$—.

The same type of replacement process can also occur on nanoparticles having phosphinic acid ligands of the formula $R_2P(=O)$—OH or on nanoparticles having carboxylic acid ligands of the formula $RC(=O)$—OH, which could be incorporated on the surface of a nanocrystal by known methods; R can be a $C_1$-$C_{24}$ hydrocarbon group in these phosphinates, and the two R groups can be the same or different. Thus, it is understood that when phosphonate-containing nanocrystals are described herein, phosphinate-containing nanocrystals can be used instead, with similar results.

This process provides a mild and selective method for removing phosphonate, phosphinate, and carboxylate ligands from the surface of a nanocrystal. As a result, it provides a way for a user to remove these groups and replace them, without removing other ligands which are not displaced or affected by the silylsulfonate.

The sulfonate ligands can comprise an alkyl or aryl moiety linked to —$SO_3X$, where X can represent whatever the sulfonate group is attached to. For example, where the sulfonate ligand is a sulfonate anion (i.e., triflate), X would represent a nanocrystal, or the surface of a nanocrystal.

Some of the sulfonate embodiments disclosed herein can also be described with reference to feature 'A' of Formula I, as set forth below.

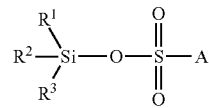

wherein $R^1$, $R^2$, $R^3$ and A are each, independently, C1-C10 alkyl or C5-C10 aryl; and each alkyl and aryl is optionally substituted.

The alkyl groups for Formula I compounds are independently selected, and can be straight chain, branched, cyclic, or combinations of these, and optionally can include a C1-C4 alkoxy group as a substituent. Typically, the alkyl groups are lower alkyls, e.g., C1-C4 alkyl groups which are linear or branched. Methyl is one suitable example.

The aryl group for the compounds of Formula I can be phenyl, naphthyl or a heteroaryl having up to 10 ring members, and can be monocyclic or bicyclic, and optionally contain up to two heteroatoms selected from N, O and S as ring members in each ring. (It will be understood by those skilled in the art that the 5-membered aryl is a heteroaryl ring.) Phenyl is a preferred aryl group; and an aryl group is typically only present if the other organic groups on the silicon other than the sulfonate are lower alkyls, and preferably they are each Me.

Examples of silylsulfonate ligands can include, but are not limited to: (trimethylsilyl)triflate, (triethylsilyl)triflate, (t-butyldimethylsilyl)triflate, (phenyldimethylsily)triflate, trimethylsilyl fluoromethanesulfonate, trimethylsilyl methanesulfonate, trimethylsilyl nitrophenylsulfonate, trimethylsilyl trifluoroethylsulfonate, trimethylsilyl phenylsulfonate, trimethylsilyl toluenesulfonate, diisopropylsilyl bis(trifluoromethanesulfonate), tertbutyldimethylsilyl trifluoromethanesulfonate, triisopropylsilyl trifluoromethanesulfonate and trimethylsilyl chlorosulfonate.

Examples of other sulfonate ligands can include, but are not limited to: trifluoromethanesulfonate (triflate), fluoromethanesulfonate, methanesulfonate (mesylate), nitrophenylsulfonate (nosylate), trifluorethylsulfonate, phenylsulfonate (besylate) and toluenesulfonate (tosylate).

Some suitable examples of the hydrophilic ligand are disclosed, for example, in Naasani, U.S. Pat. Nos. 6,955,855; 7,198,847; 7,205,048; 7,214,428; and 7,368,086. Suitable hydrophilic ligands also include imidazole containing compounds such as peptides, particularly dipeptides, having at least one histidine residue, and peptides, particularly dipeptides, having at least one cysteine residue. Specific ligands of interest for this purpose can include carnosine (which contains beta-alanine and histidine); His-Leu; Gly-His; His-Lys; His-Glu; His-Ala; His-His; His-Cys; Cys-His; His-Ile; His-Val; and other dipeptides where His or Cys is paired with any of the common alpha-amino acids; and tripeptides, such as Gly-His-Gly, His-Gly-His, and the like. The chiral centers in these amino acids can be the natural L-configuration, or they can be of the D-configuration or a mixture of L and D. Thus a dipeptide having two chiral centers such as His-Leu can be of the L,L-configuration, or it can be L,D- or D,L; or it can be a mixture of diastereomers.

Furthermore, suitable hydrophilic ligands can also include mono- or polydentate thiol containing compounds, for example: monodentate thiols such as mercaptoacetic acid, bidentate thiols such as dihydrolipoic acid (DHLA), tridentate thiols such as compounds of Formula II-VII as shown below, and the like.

II
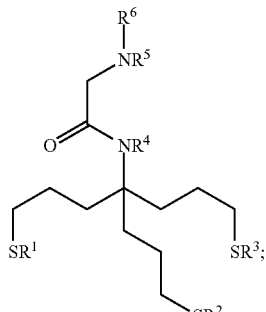

III
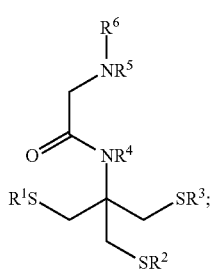

IV
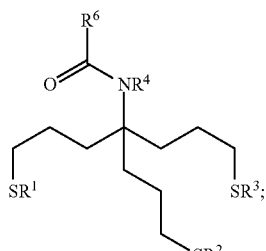

V
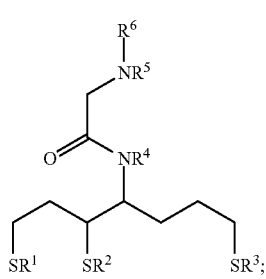

VI
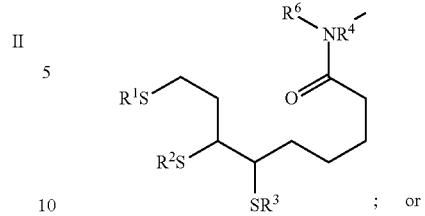

VII
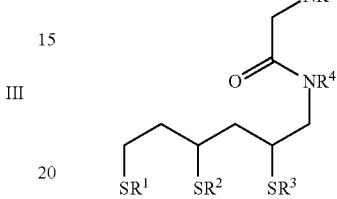

In compounds of Formula II-VII, $R^1$, $R^2$, $R^3$ can independently be H, halo, hydroxyl, (—(C=O)—$C_1$-$C_{22}$, —(C=O)$CF_3$,) alkanoyl, $C_1$-$C_{22}$ alkyl, $C_1$-$C_{22}$ heteroalkyl, ((CO)O$C_1$-$C_{22}$) alkylcarbonato, alkylthio ($C_1$-$C_{22}$) or (—(CO)NH($C_1$-$C_{20}$) or —(CO)N($C_1$-$C_{20}$)$_2$) alkylcarbamoyl. In some embodiments, $R^1$, $R^2$, and $R^3$ are different. In other embodiments, $R^1$, $R^2$, and $R^3$ are the same.

In compounds of Formula II-VII, $R^4$, and $R^5$ can independently be H, $C_1$-$C_{20}$ alkyl, $C_6$-$C_{18}$ aryl, $C_1$-$C_{22}$ heteroalkyl or $C_1$-$C_{22}$ heteroaryl. In some embodiments, $R^4$ and $R^5$ are different. In other embodiments, $R^4$ and $R^5$ are the same.

In compounds of Formula II-VII, $R^6$ can be H or a polyethylene glycol based moiety of Formula VIII:

VIII
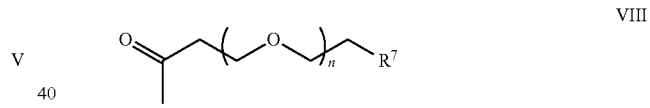

In certain embodiments of Formula VIII, $R^7$ can be —$NH_2$, —$N_3$, —NHBoc, —NHFmoc, —NHCbz, —COOH, —COOt-Bu, —COOMe, iodoaryl, hydroxyl, alkyne, boronic acid, allylic alcohol carbonate, —NHBiotin, —(CO)NHNHBoc, —(CO)NHNHFmoc or —OMe. In some embodiments, n can be an integer from 1 to 100.

In still further embodiments, the tridentate thiol ligands can be a compound of Formula IX, X, XI, XII, XIII, XIV, XV, XVI, XVII, XVIII, XIX, XX, XXI, XXII, XXIII or XXIV:

IX
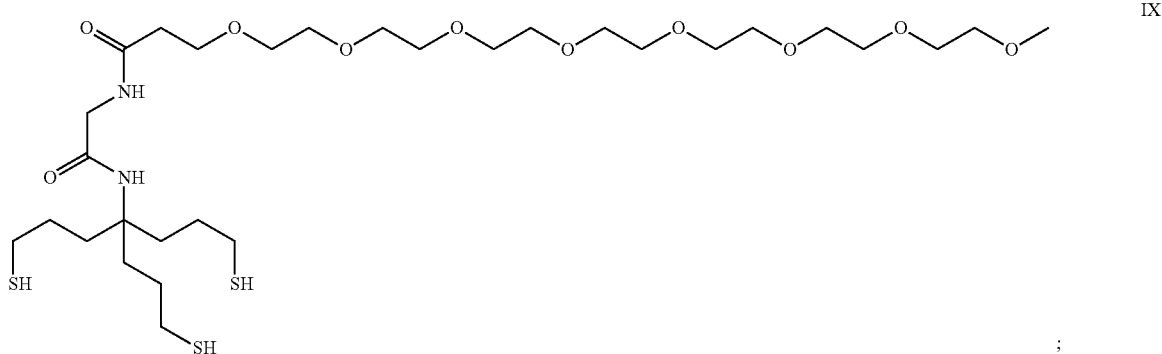

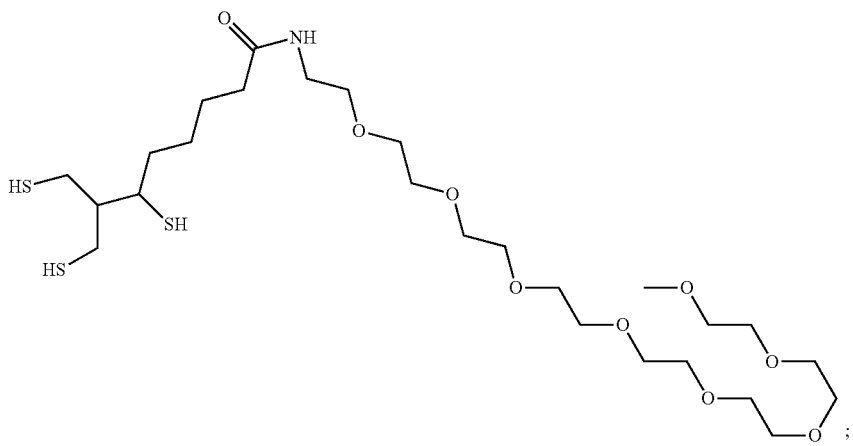
X
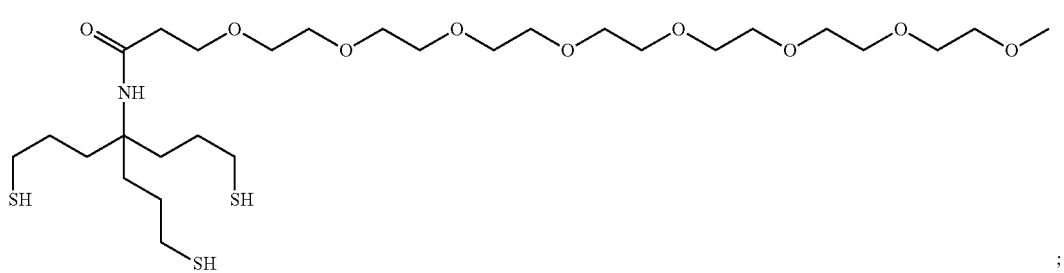
XI
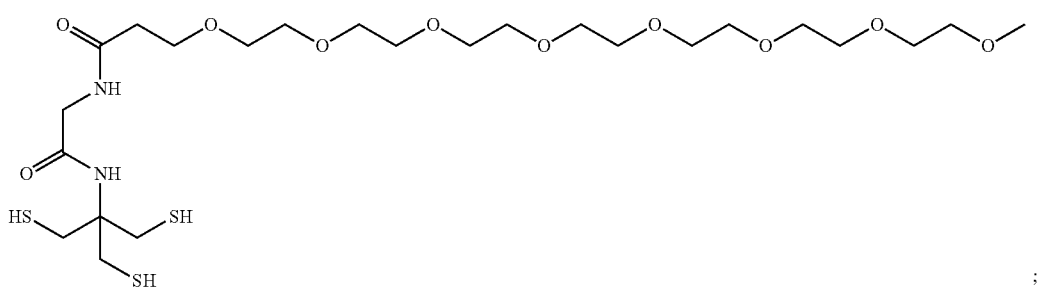
XII
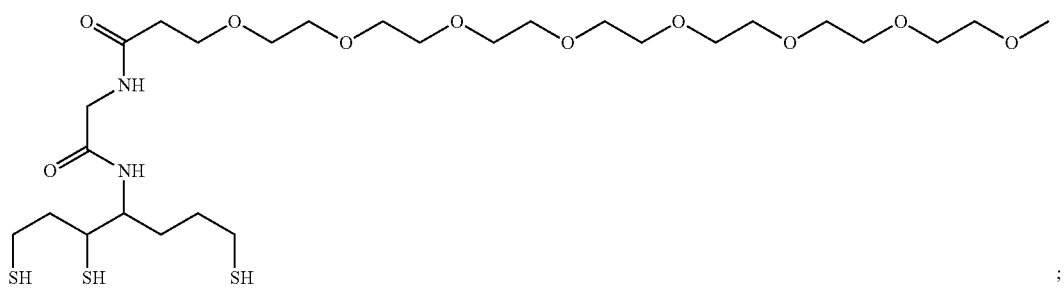
XIII
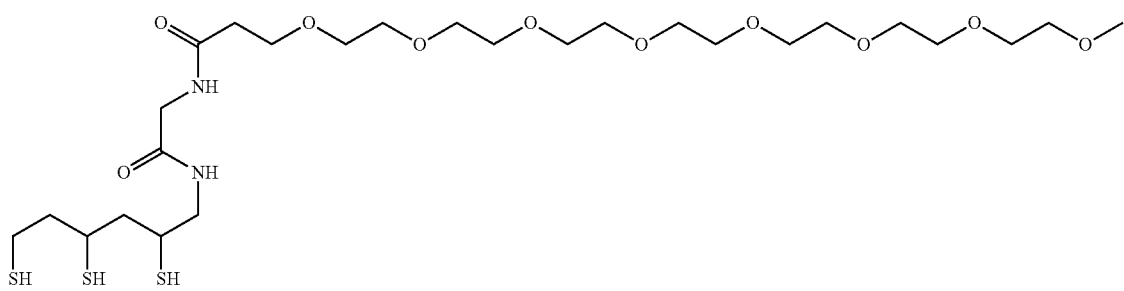
XIV

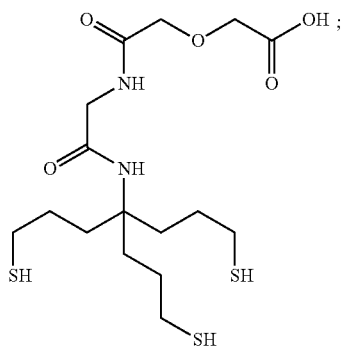 XV
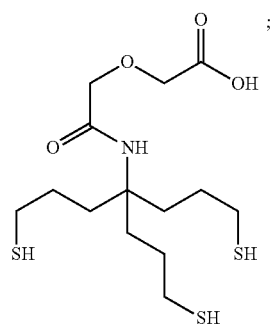 XVI
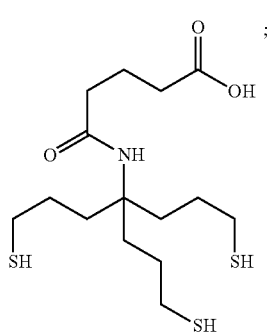 XVII
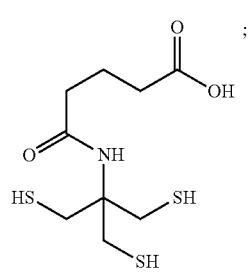 XVIII
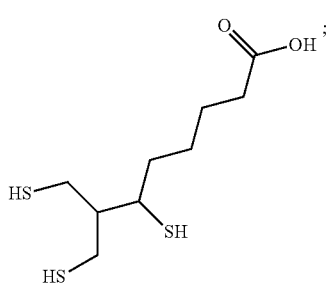 XIX
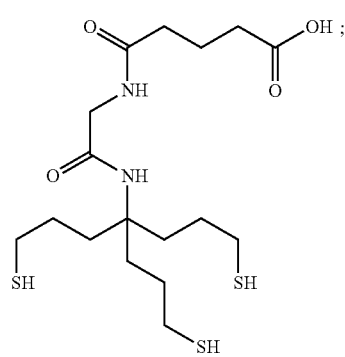 XX
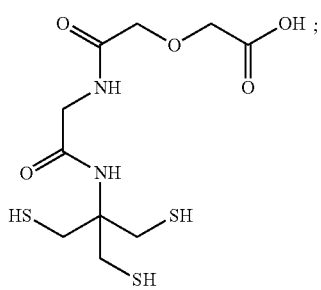 XXI
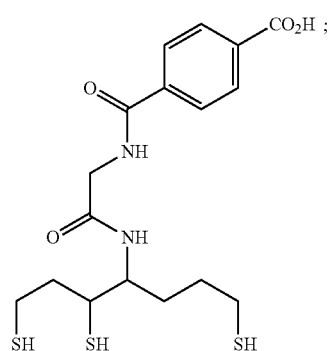 XXII

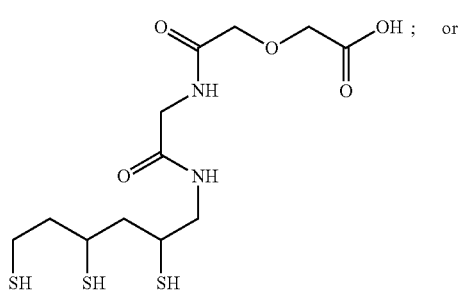

XXIII or

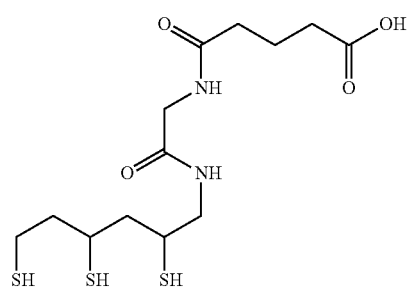

XXIV

Functionalized TDPA Ligands on Nanoparticles

Provided herein are methods for preparing water-soluble semi-conducting, insulating, or metallic nanoparticles including the steps of admixing one or more nanocrystal precursors and one or more multi-functional surface ligands with a solvent to form a solution and heating the solution to a suitable temperature, and in certain embodiments, methods may include the steps of admixing nanocrystal cores, one or more nanocrystal precursors, and one or more multi-functional surface ligands with a solvent to form a solution and heating the solution to a suitable temperature. In such embodiments, the one or more multi-functional surface ligands may at least include a nanocrystal binding center, a linker, and a functional group, which imparts functionality on the nanocrystal. As used herein the term "functional group" may refer to a group which affects reactivity, solubility, or both reactivity and solubility when present on a multi-functional surface ligand. Embodiments can include a wide variety of functional groups which can impart various types of functionality on the nanocrystal including hydrophilicity, water-solubility, or dispersibility and/or reactivity, and the functionality may generally not include only hydrophobicity or only solubility in organic solvents without increasing reactivity. For example, a functional group which is generally hydrophobic but which increases reactivity such as an alkene or alkyne and certain esters and ethers can be encompassed by embodiments, whereas alkyl groups, which do not generally impart reactivity but increase hydrophobicity may be excluded.

In certain embodiments, the nanoparticles produced by the methods of such embodiments may be coated with ligands which impart water solubility and/or reactivity on the nanoparticle obviating the need for ligand replacement. Without wishing to be bound by theory, eliminating ligand replacement may provide more consistent thermodynamic properties, which may lead to reduction in variability of coating and less loss of quantum yield, among other improvements in the properties of nanoparticles produced by the methods embodied herein. Eliminating ligand replacement may also allow for the production of nanoparticles having a wide variety of functional groups associated with the coating. In particular, while ligand replacement is generally limited to production of nanoparticles having amine and/or carboxylic acid functional groups, in various embodiments, the skilled artisan may choose among numerous functional groups when preparing the multi-functional ligands and may, therefore, generate nanoparticles which provide improved water-solubility or water-dispersity and/or support improved crosslinking and/or improved reactivity with cargo molecules. See for example PCT Application Serial No. PCT/US09/59117 filed Sep. 30, 2009 which are expressly incorporated herein by reference as if set forth in full.

Solid Surfaces

The methods, compositions, systems and kits disclosed herein can involve the use of surfaces (e.g., solid surfaces) which can be attached covalently or non-covalently with the nanoparticles and/or the biomolecules (polymerases, nucleotides, target nucleic acid molecules, primers, and/or oligonucleotides) described herein. The attachment can be reversible or irreversible. The immobilized biomolecules include the: polymerases, nucleotides, target nucleic acid molecules, primer molecules and/or oligonucleotides which are components in the nucleotide binding and/or nucleotide incorporation reactions. The immobilized nanoparticles and/or biomolecules may be attached to the surface in a manner that they are accessible to components of the nucleotide incorporation reaction and/or in a manner which does not interfere with nucleotide binding or nucleotide incorporation. The immobilized nanoparticles and/or biomolecules may be attached to the surface in a manner which renders them resistant to removal or degradation during the incorporation reactions, including procedures which involve washing, flowing, temperatures or pH changes, and reagent changes. In another aspect, the immobilized nanoparticles and/or biomolecules may be reversibly attached to the surface.

The surface may be a solid surface, and includes planar surfaces, as well as concave, convex, or any combination thereof. The surface may comprise texture (e.g., etched, cavitated or bumps). The surface includes the inner walls of a capillary, a channel, a well, groove, channel, reservoir, bead, particle, sphere, filter, gel or a nanoscale device. The surface can be optically transparent, minimally reflective, minimally absorptive, or exhibit low fluorescence. The surface may be non-porous. The surface may be made from materials such as glass, borosilicate glass, silica, quartz, fused quartz, mica, polyacrylamide, plastic polystyrene, polycarbonate, polymethacrylate (PMA), polymethyl methacrylate (PMMA), polydimethylsiloxane (PDMS), silicon, germanium, graphite, ceramics, silicon, semiconductor, high refractive index dielectrics, crystals, gels, polymers, or films (e.g., films of gold, silver, aluminum, or diamond). The surface can include a solid substrate having a metal film or metal coat.

The immobilized nanoparticles and/or biomolecules may be arranged in a random or ordered array on a surface. The ordered array includes rectilinear and hexagonal patterns. The distance and organization of the immobilized molecules may permit distinction of the signals generated by the different immobilized molecules. The surface can be coated with an adhesive and/or resist layer which can be applied to the surface to create the patterned array and can be applied to the surface in any order. The adhesive layer can bind/link the nanoparticle or biomolecules (e.g., polymerases, nucleotides, target nucleic acid molecules, primers, and/or oligonucleotides). The resist layer does not bind/link, or exhibits decreased binding/linking, to the nanoparticle or biomolecules (e.g., polymerases, nucleotides, target nucleic acid molecules, primers, and/or oligonucleotides).

The immobilized nucleic acid molecules (e.g., target and/or primer molecules) may be attached to the surface at their 5' ends or 3' ends, along their length, or along their length with a 5' or 3' portion exposed. The immobilized proteins (e.g., polymerases) can be attached to the surface in a manner which orients them to mediate their activities (nucleotide binding or nucleotide incorporation).

The surface can be coated to facilitate attachment of nucleic acid molecules (target and/or primers). For example, a glass surface can be coated with a polyelectrolyte multilayer (PEM) via light-directed attachment (U.S. Pat. Nos. 5,599,695, 5,831,070, and 5,959,837) or via chemical attachment. The PEM chemical attachment can occur by sequential addition of polycations and polyanions (Decher, et al., 1992 Thin Solid Films 210:831-835). In one embodiment, the glass surface can be coated with a polyelectrolyte multilayer which terminated with polyanions or polycations. The polyelectrolyte multilayer can be coated with biotin and an avidin-like compound. Biotinylated molecules (nucleic acid molecules or polymerases or nanoparticles) can be attached to the PEM/biotin/avidin coated surface (Quake, U.S. Pat. Nos. 6,818,395; 6,911,345; and 7,501,245).

Nanoscale Devices

The surface can be the surface of a nanoscale device. The components of the nucleotide binding or nucleotide incorporation reaction (e.g., nanoparticles, polymerase, nucleotides, target nucleic acid molecules, primers and/or oligonucleotides) can be associated with or immobilized onto the nanoscale device.

The nanoscale device can have microscopic features (e.g., at the micro meter, nano meter size level, or pico meter level) which permit manipulation or analysis of biological molecules at a nanoscale level.

The nanoscale device can include open or enclosed (i.e., sealed) structures (e.g., nanostructures) including: channels, slits, pores, wells, pillars, loops, arrays, pumps valves. The nanostructures can have length, width, and height dimensions. The nanostructures can be linear or branched, or can have inlet and/or outlet ports. The branched nanostructures (e.g., branched channels) can form a T or Y junction, or other shape and geometries.

The nanostructure dimensions can be between about 10-25 nm, or about 25-50 nm, or about 50-100 nm, or about 100-200 nm, or about 200-500 nm, or about 500-700 nm, or about 700-900 nm, or about 900-1000 nm. The nanostructures can have a trench width equal to or less than about 150 nanometers. The nanostructures can be wells which are 50-10,000 nm in diameter. The nanostructures can have a trench depth equal to or less than about 200 nanometers (e.g., 50-100 nm thickness).

The nanoscale device can comprise one or a plurality of nanostructures, typically more than 5, 10, 50, 100, 500, 1000, 10,000 and 100,000 nanostructures for binding, holding, streaming, flowing, washing, flushing, or stretching samples. The samples can include the nanoparticles, polymerase, nucleotides, target nucleic acid molecules, primers and/or oligonucleotides. The fluid which runs through the nanoscale device can be liquid, gas or slurry. Nanoscale devices are also known as nanofluidic devices.

Nanoscale devices and/or their component nanostructures may be fabricated from any suitable substrate including: silicon, carbon, glass, polymer (e.g., polydimethylsiloxane), metals, boron nitrides, nickel, platinum, copper, tungsten, titanium, aluminum, chromium, gold, synthetic vesicles, carbon nanotubes, or any combination thereof.

The nanoscale devices and and/or nanostructures may be fabricated using any suitable method, including: lithography; photolithography; diffraction gradient lithography (DGL); nanoimprint lithography (NIL); interference lithography; self-assembled copolymer pattern transfer; spin coating; electron beam lithography; focused ion beam milling; plasma-enhanced chemical vapor deposition; electron beam evaporation; sputter deposition; bulk or surface micromachining; replication techniques such as embossing, printing, casting and injection molding; etching including nuclear track or chemical etching, reactive ion-etching, wet-etching; sacrificial layer etching; wafer bonding; channel sealing; and combinations thereof.

The nanoscale device can be used to react, confine, elongate, mix, sort, separate, flow, deliver, flush, wash, or enrich the nanoparticles or biomolecules, or the intermediates or products of nucleotide incorporation. For example, the target nucleic acid molecule (e.g., nucleic acid molecules, or chromosomal or genomic DNA) can be elongated using pulsed field electrophoresis, or in a nanofluidic device via flow stretching (with or without tethering) or confinement elongation. Elongated nucleic acid molecules can be used to: measure the contour length of a nucleic acid molecule, locate landmark restriction sites along the length of the molecule, or detect sequencing reactions along the molecule (Schwartz, U.S. Pat. Nos. 6,221,592, 6,294,136 and U.S. Published App. Nos. 2006/0275806 and 2007/0161028). In one aspect, the nanostructure can be one or more nanochannels, which are capable of transporting a macromolecule (e.g., nucleic acid molecule) across its entire length in elongated form. In another aspect, the nanostructure can detect an elongated macromolecule, or detect sequencing of a single nucleic acid molecule.

The nanochannels can be enclosed by surmounting them with a sealing material using suitable methods. See, for example, U.S. Publication No. 2004/0197843. The nanoscale device can comprise a sample reservoir capable of releasing a fluid, and a waste reservoir capable of receiving a fluid, wherein both reservoirs are in fluid communication with the nanofluidic area. The nanoscale device may comprise a microfluidic area located adjacent to the nanofluidic area, and a gradient interface between the microfluidic and nanofluidic area which reduces the local entropic barrier to nanochannel entry. See, for example, U.S. Pat. No. 7,217,562.

The nanoscale device comprising a nanochannel array can be used to isolate individual nucleic acid molecules prior to sequencing, wherein the sample population of nucleic acid molecules is elongated and displayed in a spatially addressable format. Isolation of the nucleic acid molecules to be sequenced may be achieved using any suitable nanoscale device which comprises nanostructures or nanofluidic constrictions of a size suited to achieve isolation and separation of the test nucleic acid molecule from other sample components in a manner which will support direct sequencing of the test molecule in situ. For example, a nucleic acid molecule, such as a chromosome, is isolated from a sample mixture using a nanofluidic device which is capable of receiving a sample comprising mixed population of nucleic acid molecules and elongating and displaying them in an ordered format without the need for prior treatment or chemical attachment to a support.

The nanoscale device supports analysis of intact chromosomes without the need for fragmentation or immobilization of sequencing components. The nanoscale device comprises at least one nanostructure, typically a nanochannel, which is designed to admit only a single polymeric molecule and elongate it as it flows through the nanostructure. Suitable nanoscale devices have been described, for example, in U.S. Pat. No. 6,635,163 (nanofluidic entropic trapping and sieving devices). Suitable nanoscale devices comprise microfluidic and nanofluidic areas separated by a gradient interface which reduces the local entropic barrier to nanochannel entry thereby reducing clogging of the device at the microfluidic-nanofluidic interface. See, for example, Cao, U.S. Pat. No. 7,217,562 and U.S. Pub. No. 2007/0020772.

The nanoscale device can include an array of nanochannels. Introduction of a sample comprising a mixed population of nucleic acid molecules into the nanoscale device results in the isolation and elongation of a single nucleic acid molecule within each nanostructure, so that an entire population of nucleic acid molecules is displayed in an elongated and spatially addressable format. After the nucleic acid molecules enter and flow through their respective nanochannel, they are contacted with one or more components of a nucleotide incorporation reaction mixture, and the progress of the incorporation reaction is monitored using suitable detection methods. The ordered and spatially addressable arrangement of the population allows signals to be detected and monitored along the length of each nucleic acid molecule. Separate sequencing reactions occur within each nanochannel. The spatially addressable nature of the arrayed population permits discrimination of signals generated by separate priming events, and permitting simultaneous detection and analysis of multiple priming events at multiple points in the array. The emission data can be gathered and analyzed to determine the time-sequence of incorporation events for each individual nucleic acid (DNA) in the nanochannel array. Nanoscale devices can permit the simultaneous observation of macromolecules in multiple channels, thereby increasing the amount of sequence information obtainable from a single experiment and decreasing the cost of sequencing of an entire genome. See, for example, U.S. Pub. No. 2004/0197843, also U.S. Ser. Nos. 61/077,090, filed on Jun. 30, 2008, and 61/089,497, filed on Aug. 15, 2008, and 61/090,346, filed on Aug. 20, 2008.

In one embodiment, the nanoscale device can include a flow cell which includes a two-sided multi-channel flow cell comprising multiple independently-addressable sample channels and removable loading blocks for sample loading (Lawson, U.S. published patent application No. 2008/0219888).

In another embodiment, the nanoscale device can include a light source for directing light to the nucleotide incorporation reaction, a detector (e.g., photon detector), a camera, and/or various plumbing components such as microvalves, micropumps, connecting channels, and microreservoirs for controlled flow (in and/or out) of the reagents of the nucleotide incorporation reactions. The reagents can be pulled through the inlet or outlet ports via capillary action, or by vacuum (Lawson, U.S. published patent application No. 2008/0219890; and Harris, et al., 2008 Science 320:106-109, and Supplemental Materials and Methods from the supporting online material), or moved via a pressure-driven fluidics system. The reagents can be pulled through the inlet or outlet ports using a passive vacuum source (Ulmer, U.S. Pat. No. 7,276,720).

In another embodiment, the nucleotide incorporation methods can be practiced in a nanoscale device such as a patterned metal masked array which includes a metal layer disposed on a glass support, where the metal layer is perforated with holes ranging in size from 50-10,000 nm. The holes can be any shape including round, rectilinear, triangular, slit, and the like. The metal layer can have a thickness of about 50-100 nm. The metal layer can be gold, chrome, silver, aluminum, titanium, nickel, platinum, copper, tungsten, titanium-tungsten, carbon, carbon nanotubes, nanoparticles, or polymers. The surface can be spin-coated with an imaging resist using e-beam or photo resist procedures. The metal can be global-coated using evaporation or sputtering procedures. The exposure step can be achieved using e-beam or photomask lithography. See for example, U.S. Ser. No. 61/245,248, filed Sep. 23, 2009.

The nanoparticles and biomolecules (e.g., polymerases, nucleotides, target nucleic acid molecules, primers, and/or oligonucleotides) can be isolated, modified, sorted, collected, distributed, linked and/or immobilized using suitable procedures and devices.

The nanoparticles and biomolecules (e.g., polymerases, nucleotides, target nucleic acid molecules, primers, and/or oligonucleotides) can be used presently for any procedure described herein, or can be stored or preserved for later use by employing suitable procedures.

Modified Surfaces

The surface can be chemically or enzymatically modified to have one or more reactive groups, including amines, aldehyde, hydroxyl, sulfate or carboxylate groups, which can be used to attach the surface to the nanoparticles, polymerases, nucleotides, target nucleic acid molecules, primers, and/or oligonucleotides.

Attaching Nucleic Acid Molecules to the Surface

Nucleic acid molecules can be attached to a surface. The target nucleic acid molecules, primers, and/or oligonucleotides can be modified at their 5' or 3' end, or internally, to carry a reactive group which can bind to a reactive group on the surface. Typically, the surface is treated or untreated to provide reactive groups such as silanol, carboxyl, amino, epoxide, and methacryl groups. The nucleic acid molecules can be treated or untreated to provide reactive groups including: amino, hydroxyl, thiol, and disulfide. The nucleic acid molecules can include non-natural nucleotides having reactive group which will attach to a surface reactive group. For example, the non-natural nucleotides include peptide nucleic acids, locked nucleic acids, oligonucleotide N3'→P5' phosphoramidates, and oligo-2'-O-alkylribonucleotides.

In one aspect, nucleic acid molecules modified with one or more amino groups at the 5' or 3' end, or internally, can be attached to modified surfaces.

In another aspect, the nucleic acid molecules can be attached at their 5' ends with one or more amino groups, including: a simple amino group; a short or long tethering arm having one or more terminal amino groups; or amino-modified thymidine or cytosine. The tethering arms can be linear or branched, have various lengths, charged or uncharged, hydrophobic, flexible, cleavable, or have one or multiple terminal amino groups. The number of plural valent atoms in a tethering arm may be, for example, 0, 1, 2, 3, 4, 5, 6, 7, 8, 9, 10, 20, 25, 30 or a larger number up to 40 or more.

In another aspect, the 3' end of nucleic acid molecules can be modified to carry an amino group. Typically, the amino group is initially protected by a fluorenylmethylcarbamoyl (Fmoc) group. To expose the amino group, the protecting group can be removed and acylated with an appropriate succinimidyl ester, such as an N-hydroxy succinimidyl ester (NHS ester).

In another aspect, the nucleic acid molecules can carry internal amino groups for binding to the solid surface. For example, 2' amino modified nucleic acid molecules can be produce by methoxyoxalamido (MOX) or succinyl (SUC) chemistry to produce nucleotides having amino linkers attached at the 2' C of the sugar moiety.

In another aspect, the surface can be modified to bind the amino modified nucleic acid molecules. For example, 5' amino-modified nucleic acid molecules can be attached to surfaces modified with silane, such as epoxy silane derivatives (J. B. Lamture, et al., 1994 Nucleic Acids Res. 22:2121-2125; W. G. Beattie et al., 1995 Mol. Biotechnol. 4:213-225) or isothiocyanate (Z. Guo, et al., 1994 Nucleic Acids Res. 22:5456-5465). Acylating reagents can be used to modify the surface for attaching the amino-modified nucleic acid molecules. The acylating reagents include: isothiocyanates, succinimidyl ester, and sulfonyl chloride. The amino-modified nucleic acid molecules can attach to surface amino groups which have been converted to amino reactive phenylisothiocyanate groups by treating the surface with p-phenylene 1,4 diisothiocyanate (PDC). In other methods, the surface amino groups can be reacted with homobifunctional crosslinking agents, such as disuccinimidylcaronate (DCS), disuccinimidyloxalate (DSO), phenylenediisothiocyanate (PDITC) or dimethylsuberimidate (DMS) for attachment to the amino-modified nucleic acid molecules. In another example, metal and metal oxide surfaces can be modified with an alkoxysilane, such as 3-aminopropyltriethoxysilane (APTES) or glycidoxypropyltrimethoxysilane (GOPMS).

In another aspect, succinylated nucleic acid molecules can be attached to aminophenyl- or aminopropyl-modified surfaces (B. Joos et al., 1997 Anal. Biochem. 247: 96-101).

In yet another aspect, a thiol group can be placed at the 5' or 3' end of the nucleic acid molecules. The thiol group can form reversible or irreversible disulfide bonds with the surface. The thiol attached to the 5' or 3' end of the nucleic acid molecule can be a phosphoramidate. The phosphoramidate can be attached to the 5' end using S-trityl-6-mercaptohexyl derivatives.

In another aspect, the thiol-modified nucleic acid molecules can be attached to a surface using heterobifunctional reagents (e.g. cross linkers). For example, the surface can be treated with an alkylating agent such as iodoacetamide or maleimide for linking with thiol modified nucleic acid molecules. In another example, silane-treated surfaces (e.g., glass) can be attached with thiol-modified nucleic acid molecules using succinimidyl 4-(malemidophenyl)butyrate (SMPB).

In another aspect, the nucleic acid molecule can be modified to carry disulfide groups can be attached to thiol-modified surfaces (Y. H. Rogers et al., 1999 Anal. Biochem. 266:23-30).

Still other aspects include methods which employ modifying reagents such as: carbodiimides (e.g., dicyclohexylcarbodiimide, DCC), carbonyldiimidazoles (e.g., carbonyldiimidazole, $CDI_Z$), and potassium periodate. The nucleic acid molecules can have protective photoprotective caps (Fodor, U.S. Pat. No. 5,510,270) capped with a photoremovable protective group. DMT-protected nucleic acid molecules can be immobilized to the surface via a carboxyl bond to the 3' hydroxyl of the nucleoside moiety (Pease, U.S. Pat. No. 5,599,695; Pease et al., 1994 Proc. Natl. Acad. Sci. USA 91(11):5022-5026). The nucleic acid molecules can be functionalized at their 5' ends with activated 1-O-mimethoxytrityl hexyl disulfide 1'-[(2-cyanoethyl)-N,N-diisopropyl)] phosphoramidate (Rogers et al., 1999 Anal. Biochem. 266: 23). Exemplary methods of attaching nucleic acid molecules to suitable substrates are disclosed, for example, in Schwartz, U.S. Pat. Nos. 6,221,592, 6,294,136 and U.S. Published App. Nos. 2006/0275806 and 2007/0161028 (Schwartz et al.). Linking agents, can be symmetrical bifunctional reagents, such as bis succinimide (e.g., bis-N-hydroxy succinimide) and maleimide (bis-N-hydroxy maleimide) esters, or toluene diisocyanate can be used. Heterobifunctional cross-linkers include: m-maleimido benzoyl-N-hydroxy succinimidyl ester (MBS); succinimidyl-4-(p-maleimido phenyl)-Butyrate (SMPB); and succinimidyl-4-(N-Maleimidomethyl)Cyclohexane-1-Carboxylate (SMCC) (L. A. Chrisey et al., 1996 Nucleic Acids Res. 24:3031-3039). In one example, a glass surface can be layered with a gold (e.g., about 2 nm layer) which is reacted with mercaptohexanoic acid. The mercaptohexanoic acid can be placed in a patterned array. The mercaptohexanoic acid can be reacted with PEG. The PEG can be reacted to bind nucleic acid molecules such as the target nucleic acid molecules.

In another aspect, the target nucleic acid molecule can be linked to an amine-functionalized solid surface. In one embodiment, the amine-functionalized solid surface can be a spot surrounded by PEG molecules, where the target molecule preferentially binds the amine-functionalized spots (see Fry, et al., U.S. Ser. No. 61/245,248, filed on Sep. 23, 2009).

Capture Probes:

The surfaces, nanoparticles, polymerases, nucleotides, target nucleic acid molecules, primers, and/or oligonucleotides can be attached to each other in any combination via capture nucleic acid probes.

For example, the surface may comprise capture nucleic acid probes which form complexes with single or double stranded nucleic acid molecules. In one embodiment, the capture probes anneal with target nucleic acid molecules. The capture probes include oligonucleotide clamps (U.S. Pat. No. 5,473,060). The parameters for selecting the length and sequence of the capture probes are well known (Wetmur 1991 Critical Reviews in Biochemistry and Molecular Biology, 26: 227-259; Britten and Davidson, chapter 1 in: Nucleic Acid Hybridization: A Practical Approach, Hames et al, editors, IRL Press, Oxford, 1985). The length and sequence of the capture probes may be selected for sufficiently stability during low and/or high stringency wash steps. The length of the capture probes ranges from about 6 to 50 nucleotides, or from about 10 to 24 nucleotides, or longer.

Attaching Proteins to the Solid Surface

In one aspect, the surface can be modified to attach the protein molecules (e.g., polymerases) via covalent or non-covalent linkage. The polymerases may be attached to the surface via covalent cross-linking bridges, including disulfide, glycol, azo, sulfone, ester, or amide bridges. Some exemplary methods for attaching polymerases to a surface are disclosed in U.S. Pat. Nos. 7,056,661, 6,982,146, 7,270, 951, 6,960,437, 6,255,083, 7,229,799 and published application U.S. No. 2005/0042633.

The polymerases can be modified at their amino- or carboxyl-terminal ends, or internally, to carry a reactive group which can bind to a reactive group on the surface.

The polymerases can be attached to the modified surfaces using standard chemistries including: amination, carboxylation or hydroxylation. The attachment agents can be cyanogen bromide, succinimide, aldehydes, tosyl chloride, photo-crosslinkable agents, epoxides, carbodiimides or glutaraldehyde (in: Protein immobilization: Fundamentals and Applications, Richard F. Taylor, ed. (M. Dekker, New York, 1991). The surface can be treated or untreated to provide reactive groups such as silanol, carboxyl, amino, epoxide, and methacryl groups. The protein molecules can be treated or untreated to provide reactive groups including: amino, hydroxyl, thiol, and disulfide. The surface can be coated with an electron-sensitive compound such as polymethyl methacrylate-like material (PMMA).

The polymerases can be attached to a surface which is untreated or modified via physical or chemical interaction. See Nakanishi for a review of protein immobilization methods (K. Nakanishi, 2008 Current Proteomics 5:161-175).

The polymerases can be adsorbed onto a surface. The adsorption can occur via ion exchange, charge-charge interaction, or hydrogen bond interactions. The adsorption can occur on to untreated surfaces, including polystyrene, polyvinylidene fluoride (PVDF), glass coated with poly-lysine (H. Ge 2000 Nucl. Acids Res. 28: e3; B. B. Haab, et al., 2001 Genome Biol. 2: R4-13; Zhu and Snyder 2003 Curr. Opin. Chem. Biol. 7: 55-63), or onto surfaces having hydrophobic properties (Y. Sanghak, et al., 2006 Curr. Appl. Phys. 6: 267-70).

The polymerases can be attached to the surface using a hydrogel (P. Arenkov, et al., 2000 Anal. Biochem. 278: 123-31; S. Kiyonaka, et al., 2004 Nat. Mater. 3: 58-64).

The polymerases can be linked to an affinity His-tag (e.g., 6×His-tag (SEQ ID NO: 63)) which interacts with $Ni^{2+}$, $Co^{2+}$, or $Cu^{2+}$ surfaces (T. Nakaji-Hirabayashi, et al., 2007 Biomaterials 28: 3517-29; R. Vallina-Garcia, et al., 2007 Biosens. Bioelectron. 23: 210-7; T. Cha, et al., 2004 Proteomics 4: 1965-76; T. Cha, et al., 2005 Proteomics 5: 416-9). For example, the polymerases can be a fusion protein which includes the His-tag sequence. The glass surface can be functionalized with a chelate group by treating with nitrotriacetic acid (NTA) or imidoacetic acid (IDA) and reacted with $Ni^{2+}$ or $Cu^{2+}$, respectively.

The polymerases can be attached to the surface via chemisorption between a thiol (e.g., SH group of cysteines) on the polymerase and a gold surface (S. V. Rao, et al., 1998 Mikrochim Acta 128: 127-43).

The polymerases can be attached to the surface via a Schiff's base linkage reaction. For example, a glass surface can be silanized with silane, polysilane, trimethoxysilane, or aminosilane. The silanized glass surface can interact with amino groups (e.g., lysine) on the polymerase (MacBeath and Schreiber 2000 Science 289: 1760-1763; H. Zhu, et al., 2000 Nat. Genet. 26: 283-289). Metal and metal oxide surfaces can be modified with an alkoxysilane, such as 3-aminopropyltriethoxysilane (APTES) or glycidoxypropyltrimethoxysilane (GOPMS).

The polymerases can be immobilized via protein coil-coil interaction between a heterodimeric Leu zipper pair (J. R. Moll, et al., 2001 Protein Sci. 10: 649-55; K. Zhang, et al., 2005 J. Am. Chem. Soc. 127: 10136-7). For example, the surface can be functionalized to bind one of the zipper proteins, and the polymerases can be linked with the other zipper protein. The polymerases can be fusion proteins which include a zipper protein sequence. The glass surface can be coated with a bifunctional silane coupling reagent comprising aldehyde (e.g., octyltrichlorosilane (OTC)) and functionalized with a hydrophobic elastin mimetic domain (ELF) as a hydrophobic surface anchor which serves to bind a leucine zipper sequence. The anchored zipper sequence can interact with a partner leucine zipper sequence linked to the polymerases.

The polymerases can be immobilized via an acyl transfer reaction. For example, transglutaminase (TGase) can catalyze an acyl transfer reaction between a primary amino group and a carboxyamide group (J. Tominaga, et al., 2004 Enz. Microb. Technol. 35: 613-618). In one embodiment, carboxyamide groups from a casein-coated surface can react with the primary amine groups (e.g., lysine as a peptide tag or part of the polymerase) on the polymerases. In another embodiment, the amine groups on the surface can react with carboxyamide groups (e.g., glutamine-tag or glutamine groups on the polymerases).

The polymerases can be immobilized via interaction between an affinity peptide sequence (e.g., motif) and its cognate peptide binding partner. For example, the affinity motif could bind a protein kinase. In one embodiment, the affinity motif comprises the "minimal" motif, R—X—X—S*/T* (T. R. Soderling 1996 Biochim Biophys. Acta 1297: 131-138), including peptide motifs RRATSNVFA (SEQ ID NO:17), RKASGPPV (SEQ ID NO:18), or LRRASLG (SEQ ID NO:19), which bind a calmodulin-dependent protein kinase.

Oriented poly-His tagged protein molecules can be immobilized on to a glass surface modified with PEG and reacted with a chelate group such as iminodiacetic acid (IDA) or nitrolotriacetic acid (NTA), and metal ions such as $Ni^{2+}$ or $Cu^{2+}$ (T. Cha, et al., 2004 Proteomics 4:1965-1976).

EDAC chemistry can be use to link a carboxylated silica surface to an avidin. The avidin can bind to a biotinylated protein (e.g., polymerase). The avidin-silica surface can bind one or more biotinylated protein molecules, or bind more than one type of biotinylated protein (e.g., binds biotinylated polymerase).

In one aspect, a peptide linker can be used to attach the protein molecules (e.g., polymerases) to the nanoparticle or to the solid surface. The peptide linkers can be part of a fusion protein comprising the amino acid sequences of the polymerases. The fusion protein can include the peptide linker positioned at the N- or C-terminal end or in the interior of the fusion protein. In another embodiment, the peptide linkers can be separate linkers which are attached to the protein and the solid surface or nanoparticle.

For example, the peptide linker can be a flexible linker comprising the amino acid sequence GGGGSGGGGSAAAGSAA (SEQ ID NO:20). In another example, the peptide linker can be a rigid linker comprising the amino acid sequence GAAAKGAAAKGSAA (SEQ ID NO:21). In another example, the peptide linker can be a poly-lysine linker, comprising between about 4-15 lysine residues (e.g., 12 lysine residues). BS3 coupling (bis(sulfosuccinimidyl)suburate) can be used to attach the poly-lysine linkers to PEG-amine groups on the solid surfaces or on nanoparticles. In yet another example, the peptide linker can be a poly-cysteine linker comprising between about 4-15 cysteine residues (e.g., 12 cysteine residues). SMCC coupling (succinimidyl-4-(N-maleimidomethyl)cyclohexane-1-carboxylate) can be used to attach the poly-cysteine linkers to PEG-amine groups on solid surfaces or on nanoparticles. In yet another example, the peptide linker can be a transglutaminase tag comprising the amino acid sequence PKPQQF (SEQ ID NO:22) or PKPQQFM (SEQ ID NO:23). The transglutaminase tag can provide site specific attachment of the protein (polymerase) to the solid surface or nanoparticle. Transglutaminase enzyme can catalyze an acyl transfer reaction between the γ-carboxyamide group of an acceptor glutamine residue and a primary amine donor on the solid surface or nanoparticles. In yet another example, the peptide linker can be a protein kinases (PKA) tag comprising the amino acid sequence LRRASL (SEQ ID NO: 62). The PKA tag can provide site specific attachment of the protein (polymerase) to the solid surface or nanoparticle. SPDP (N-succinimidyl 3-(2-pyridyldithio) propionate) and iodoacetic acid are heterobifunctional cross-linking agents which can react with amines and sulfhydryl groups to link proteins to the solid surfaces or nanoparticles.

In yet another embodiment, the peptide linker can include a poly-histidine tag: MNHLVHHHHHHIEGRHMEL-GTLEGS (SEQ ID NO:14), or MSHHHHHHSMSGLN-DIFEAQKIEWHEGAPGARGS (SEQ ID NO:15), or MHHHHHHLLGGGGSGGGGSAAAGSAAR (SEQ ID NO:16).

In one embodiment, the solid surface can be modified to provide avidin (or avidin-like) binding groups. In one embodiment, the surface material is glass. In another embodiment, the glass surface is reacted with silane or its derivative. In another embodiment, the glass surface is reacted with PEG, biotin, and avidin (or avidin-like protein) to provide avidin (or avidin-like) binding sites. In yet another embodiment, the glass surface is reacted with PEG and avidin (or avidin-like protein) to provide avidin (or avidin-like) binding site. The binding sites on the glass slide can attach to the nanoparticles, proteins (e.g., polymerases, or any fusion proteins thereof), target nucleic acid molecules, primers, or oligonucleotides.

In another embodiment, the polymerase (or polymerase fusion protein) is linked to the surface. In another embodiment, the solid surface can be modified for binding to a His-tagged protein. In another embodiment, the polymerase can be a biotinylated protein bound to a surface which is coated with avidin or avidin-like protein. In another embodiment, the polymerase can be a poly-His-tagged protein bound to a nickel-conjugated surface. In another embodiment, the polymerase (or polymerase fusion protein) can be linked to a nanoparticle. In another embodiment, polymerase and nanoparticle can be separately linked to the surface. The immobilized polymerase can bind the target nucleic acid molecule, which may or may not be base-paired with the polymerization initiation. The immobilized polymerase can bind the nucleotide and/or can incorporate the nucleotide onto the polymerization initiation site.

Reducing Non-Specific Binding

In one aspect, the surfaces, nanoparticles, polymerases, nucleotides, target nucleic acid molecules, primers, and/or oligonucleotides can be modified to reduce non-specific binding by dyes or nucleotides. For example, the surface can be coated with sugar molecules (e.g., mono or disaccharides as described in Jogikalmath, U.S. 2008/0213910), silane (Menchen, U.S. Ser. No. 11/943,851), and/or PEG to reduce non-specific binding with dyes and/or nucleotides. Silane includes: N-(3-aminopropyl)3-mercapto-benzamide; 3-aminopropyl-trimethoxysilane; 3-mercaptopropyl-trimethoxysilane; 3-(trimethoxysilyl)propyl-maleimide; and 3-(trimethoxysilyl)propyl-hydrazide. In another example, the nanoparticles can be reacted with bovine serum albumin (BSA) to reduce non-specific binding to polymerases.

Linking Methods

In some embodiments, the surfaces, reporter moieties (including, e.g., energy transfer moieties, nanoparticles and organic dyes), polymerases, nucleotides, and nucleic acid molecules (including, e.g., targets, primers and/or oligonucleotides) can be linked to each other, in any combination and in any order, using well known linking chemistries. Such linkage can optionally include a covalent bond and/or a non-covalent bond selected from the group consisting of an ionic bond, a hydrogen bond, an affinity bond, a dipole-dipole bond, a van der Waals bond, and a hydrophobic bond.

In some embodiments, the linking procedure used to link the biomolecules, reporter moieties and/or surfaces of the present disclosure comprises a chemical reaction that includes formation of one or more covalent bonds between a first and second moiety, resulting in the linkage of the first moiety to the second moiety. In some embodiments, the chemical reaction occurs between a first group of the moiety and a second group of the second moiety. Such chemical reaction can include, for example, reaction of activated esters, acyl azides, acyl halides, acyl nitriles, or carboxylic acids with amines or anilines to form carboxamide bonds. Reaction of acrylamides, alkyl halides, alkyl sulfonates, aziridines, haloacetamides, or maleimides with thiols to form thioether bonds. Reaction of acyl halides, acyl nitriles, anhydrides, or carboxylic acids with alcohols or phenols to form an ester bond. Reaction of an aldehyde with an amine or aniline to form an imine bond. Reaction of an aldehyde or ketone with a hydrazine to form a hydrazone bond. Reaction of an aldehyde or ketone with a hydroxylamine to form an oxime bond. Reaction of an alkyl halide with an amine or aniline to form an alkyl amine bond. Reaction of alkyl halides, alkyl sulfonates, diazoalkanes, or epoxides with carboxylic acids to form an ester bond. Reaction of an alkyl halides or alkyl sulfonates with an alcohol or phenol to form an ether bond. Reaction of an anhydride with an amine or aniline to form a carboxamide or imide bond. Reaction of an aryl halide with a thiol to form a thiophenol bond. Reaction of an aryl halide with an amine to form an aryl amine bond. Reaction of a boronate with a glycol to form a boronate ester bond. Reaction of a carboxylic acid with a hydrazine to form a hydrazide bond. Reaction of a carbodiimide with a carboxylic acid to form an N-acylurea or anhydride bond. Reaction of an epoxide with a thiol to form a thioether bond. Reaction of a haloplatinate with an amino or heterocyclic group to form a platinum complex. Reaction of a halotriazine with an amine or aniline to form an aminotriazine bond. Reaction of a halotriazines with an alcohol or phenol to form a triazinyl ether bond. Reaction of an imido ester with an amine or aniline to form an amidine bond. Reaction of an isocyanate with an amine or aniline to form a urea. Reaction of an isocyanate with an alcohol or phenol to form a urethane bond. Reaction of an isothiocyanate with an amine or aniline to form a thiourea bond. Reaction of a phosphoramidate with an alcohol to form a phosphite ester bond. Reaction of a silyl halide with an alcohol to form a silyl ether bond. Reaction of a sulfonate ester with an amine or aniline to form an alkyl amine bond. Reaction of a sulfonyl halide with an amine or aniline to form a sulfonamide bond. Reaction of a thioester with thiol group of a cysteine followed by rearrangement to form an amide bond. Reaction of an azide with an alkyne to form a 1,2,3-traizole.

In some embodiments, water-insoluble substances can be chemically modified in an aprotic solvent such as dimethylformamide, dimethylsulfoxide, acetone, ethyl acetate, toluene, or chloroform. Similar modification of water-soluble substances can be accomplished using reactive compounds to make them more readily soluble in organic solvents.

Linkage to Surface

In some embodiments the biomolecules and/or reporter moieties of the present disclosure are linked to a surface. Optionally, such linkage can result in reversible or non-reversible immobilization of the nanoparticles, polymerases, nucleotides, nucleic acid molecules, primers, and/or oligonucleotides onto the surface. Non-limiting examples of such linkage can include: nucleic acid hybridization, protein aptamer-target binding, non-specific adsorption, and solvent evaporation. In some embodiments, the biomolecule that is linked to a surface is a polymerase (such as, for example, a polymerase fusion protein). The polymerase can be attached to a surface via a linker comprising an anchor or tethering moiety. The anchor or tethering moiety can be flexible or rigid. The anchor or tether can orient the polymerase, or polymerase fusion protein, in a manner that does not interfere with the nucleotide binding and/or polymerase activity.

Conjugation Methods—Biomolecules

Linkage of biomolecules to reporter moieties, surfaces and/or to each other can be accomplished by any suitable method (for example, Brinkley et al., 1992 Bioconjugate Chem. 3: 2). In some embodiments, a biomolecule can comprise a single type of reactive site (as is typical for polysaccharides), or it can comprise multiple types of reactive sites, e g, amines, thiols, alcohols, phenols, may be available (as is typical for proteins). Conjugation selectivity can be obtained by selecting an appropriate reactive moiety. For example, modification of thiols with a thiol-selective reagent such as a haloacetamide or maleimide, or modification of amines with an amine-reactive reagent such as 1-ethyl-3-(3-dimethyl-aminopropyl) carbodiimide (variously known as EDC or EDAC), an activated ester, acyl azide, isothiocyanate or 3,5-dichloro-2,4,6-triazine. Partial selectivity can also be obtained by careful control of the reaction conditions.

In some embodiments, the biomolecule can be linked to the reporter moiety through a bond selected from group consisting of: a covalent bond, a hydrogen bond, a hydrophilic bond, a hydrophobic bond, an electrostatic bond, a Van der Waals bond, and an affinity bond.

In some embodiments, the biomolecule comprises a peptide and the bond is a covalent bond formed between an amine group of a lysine residue of the biomolecule and an amine-reactive moiety, wherein the amine reactive moiety is linked to the reporter moiety. In some embodiments, the biomolecule comprises a peptide and the bond is a covalent bond formed between a carboxy group of an amino acid residue of the biomolecule and a maleimide moiety, wherein the maleimide moiety is linked to the reporter moiety.

In some embodiments, the biomolecule can be linked to a reporter moiety, such as, for example a nanoparticle. Optionally, the nanoparticle further comprises at least one carboxyl group on its surface, and the one or more biomolecules or fragments at least one primary amine group, and the cross-linking agent EDC is employed to form a covalent amide bond between the at least one nanoparticle and the one or more biomolecules or fragments.

In some embodiments, the biomolecule can be attached to a reporter moiety (including, e.g., a FRET donor or acceptor moiety) using any suitable chemical linking procedure, including chemical linking procedures that are known in the art. In some embodiments, the at least one biomolecule or biologically active fragment can be operably linked to the nanoparticle via chemical linking procedures. Many linking procedures are well known in the art, including: maleimide, iodoacetyl, or pyridyl disulfide chemistry which targets thiol groups on polypeptides; or succinimidyl esters (NHS), sulfonyl chlorides, iso(thio)cyanates, or carbonyl azide chemistry which targets primary amines in a polypeptide, and dichlorotriazine-based linking procedures. Additional exemplary linking procedures are described in more detail herein.

In some embodiments, the appropriate reactive compounds can be dissolved in a nonhydroxylic solvent (usually DMSO or DMF) in an amount sufficient to give a suitable degree of conjugation when added to a solution of the protein to be conjugated. These methods have been used to prepare protein conjugates from antibodies, antibody fragments, avidins, lectins, enzymes, proteins A and G, cellular proteins, albumins, histones, growth factors, hormones, and other proteins. The resulting protein (e.g., polymerase) attached to the energy transfer or reporter moiety can be used directly or enriched, e.g., chromatographically enriched to separate the desired linked compound from the undesired unlinked compound. Several linking procedures are described in U.S. Pat. No. 5,188,934. Other suitable linking procedures are also known in the art.

When conjugating biomolecules to nanoparticles, the residual, unreacted compound or a compound hydrolysis product can be removed by dialysis, chromatography or precipitation. The presence of residual, unconjugated moieties can be detected by methods such as thin layer chromatography which elutes the unconjugated forms away from its conjugate. In some embodiments, the reagents are kept concentrated to obtain adequate rates of conjugation.

Modification to Facilitate Linkage

In some embodiments, the surfaces, reporter moieties (including, e.g., dyes and/or nanoparticles) and/or biomolecules (including, e.g., polymerases, nucleotides and nucleic acid molecules) disclosed herein can be modified to facilitate their linkage to each other. Such modification can optionally include chemical or enzymatic modification. The modification can be practiced in any combination and in any order. In some embodiments, the modification can mediate covalent or non-covalent linkage of the surfaces, reporter moieties and/or biomolecules with each other.

In some embodiments, the biomolecule can be attached, fused or otherwise associated with a moiety that facilitates purification and/or isolation of the biomolecule. For example, the moiety can be an enzymatic recognition site, an epitope or an affinity tag that facilitates purification of the biomolecule.

In some embodiments, the polymerase can include an amino acid analog which provides a reactive group for linking to the nanoparticle, target, substrate and/or surface. For example, the amino acid analog can be produced using a cell (e.g., bacterial cell) which is genetically engineered to have a 21 amino acid genetic code which is capable of inserting the amino acid analog into the encoded polymerase (or fusion protein). The inserted amino acid analog can be used in a linking chemistry procedure to attach the polymerase (or fusion protein) to the energy transfer donor moiety, biomolecule or the surface.

His Tag Modification

In some embodiments, the biomolecule is a protein and is modified with a His tag. In some embodiments, the His tag may be fused directly with the protein; alternatively, a linker comprising various lengths of amino acid residues can be placed between the protein and the His tag. The linker can be flexible or rigid.

Optionally, the presence of the His tag can facilitate purification of the protein. For example, His tagged protein can be purified from a raw bacterial lysate by contacting the lysate with any suitable affinity medium comprising bound metal ions to which the histidine residues of the His-tag can bind, typically via chelation. The bound metal ions can comprise, e.g., zinc, nickel or cobalt, to which the His tag can bind with micromolar affinity. Suitable affinity media include Ni Sepharose, NTA-agarose, HisPur® resin (Thermo Scientific, Pierce Protein Products, Rockford, Ill.), or Talon® resin (Clontech, Mountain View, Calif.). The affinity matrix can then be washed with suitable buffers, e.g., phosphate buffers, to remove proteins that do not specifically interact with the cobalt or nickel ion. Washing efficiency can be improved by the addition of 20 mM imidazole. The biomolecule can optionally be eluted from the proteins are usually eluted with 150-300 mM imidazole). The purity and amount of purified biomolecule can then be assessed using suitable methods, e.g., SDS-PAGE and Western blotting.

Optionally, the His tag can be fused to a suitable amino acid sequence that facilitates removal of the His-tag using a suitable endopeptidase. Alternatively, the His tag may be removed using a suitable exopeptidase, for example the Qiagen TAGZyme exopeptidase.

In some embodiments, the His tag can facilitate linkage of the biomolecule to a metal surface, for example, a surface comprising $Zn^{2+}$, $Ni^{2+}$, $Co^{2+}$, or $Cu^{2+}$ ions. Optionally, the His-tag can facilitate linkage of the biomolecule to the surface of a nanoparticle comprising one or more metal ions, typically via chelation interactions, as described in more detail herein.

Linkers

Suitable linkers can be used to link the biomolecules (including, e.g., the polymerases, nucleotides and nucleic acid molecules), the labels (including, e.g., nanoparticles, organic dyes, energy transfer moieties and/or other reporter moieties) and/or the surfaces of the present disclosure to each other, in any combination. The linkers can be attached (to the surfaces, nanoparticles, polymerases, nucleotides, target nucleic acid molecules, primers, oligonucleotides, reporter moieties, and/or energy transfer moieties) via covalent bonding, non-covalent bonding, ionic bonding, hydrophobic interactions or any combination thereof. The type and length of the linker can be selected to optimize tethering, proximity, flexibility, rigidity, or orientation. The attachment can be reversible or non-reversible.

Suitable linkers include without limitation homobifunctional linkers and heterobifunctional linkers. For example, heterobifunctional linkers contain one end having a first reactive functionality to specifically link to a first molecule, and an opposite end having a second reactive functionality to specifically link to a second molecule. Depending on such factors as the molecules to be linked and the conditions in which the method of strand synthesis is performed, the linker can vary in length and composition for optimizing properties such as stability, length, FRET efficiency, resistance to certain chemicals and/or temperature parameters, and be of sufficient stereo-selectivity or size to link a nanoparticle to the biomolecule such that the resultant conjugate is useful reporting biomolecular activity such as approach, bonding, fusion or catalysis of a particular chemical reaction. Linkers can be employed using standard chemical techniques and include but not limited to, amine linkers for attaching reporter moieties to nucleotides (see, for example, U.S. Pat. No. 5,151,507); a linker containing a primary or secondary amine for linking a reporter moiety to a nucleotide; and a rigid hydrocarbon arm added to a nucleotide base (see, for example, Science 282:1020-21, 1998).

In some embodiments, the linker comprises a polyethylene glycol (PEG) or PEG derivative. See, e.g., U.S. Provisional Applications 61/086,750; 61/102,709; 61/102,683; and 61/102,666. Such PEG moieties can be functionalized at one or both ends. In some embodiments, functionalization at both ends with the same reactive moiety can be employed to create a homobifunctional PEG derivative. Some examples of homobifunctional PEG derivatives include without limitation COOH-PEG-COOH; NH2-PEG-NH2; and MAL-PEG-MAL (where MAL denotes a maleimide group).

The linker moiety can optionally include: a covalent or non-covalent bond; amino acid tag; chemical compound (e.g., polyethylene glycol); protein-protein binding pair (e.g., biotin-avidin); affinity coupling; capture probes; or any combination of these.

Optionally, the linker can be selected such that they do not significantly interfere with the function or activity of the biomolecules, reporter moieties and/or surfaces that it links to each other. For example, when the biomolecule is a polymerase, the linker can be selected such that it does not significantly interfere with nucleotide binding to the polymerase, or with cleavage of the phosphodiester bonds, or with nucleotide incorporation, or with release of the polyphosphate product, or with translocation of the polymerase or with energy transfer, or with emission of a detectable signal.

In some embodiments, the linker can comprise a single covalent bond or a series of covalent bonds. Optionally, the linker can be linear, branched, bifunctional, trifunctional, homofunctional, or heterofunctional. The linker can be cleavable. The linkers can be rigid or flexible. The linker can be capable of energy transfer. The linker can be a chemical chain or a chemical compound. The linker can be resistant to heat, salts, acids, bases, light and chemicals. The linker can include a short or long spacer, a hydrophilic spacer, or an extended spacer.

In another embodiment, the rigid linker can be used to improve a FRET signal. Examples of rigid linkers include benzyl linkers, proline or poly-proline linkers (S. Flemer, et al., 2008 Journal Org. Chem. 73:7593-7602), bis-azide linkers (M. P. L. Werts, et al., 2003 Macromolecules 36:7004-7013), and rigid linkers synthesized by modifying the so-called "click" chemistry scheme which is described by Megiatto and Schuster 2008 Journal of the Am. Chem. Soc. 130:12872-12873. In yet another embodiment, the linker can be an energy transfer linker synthesized using methods described in U.S. published patent application No. 2006/0057565, which is incorporated in its entirety. In yet another embodiment, the spacer linking moiety can be a cationic arginine spacer or an imidazolium spacer molecule.

In some embodiments, the linker moiety comprises about 1-40 plural valent atoms or more selected from the group consisting of C, N, O, S and P. The number of plural valent atoms in a linker may be, for example, 0, 1, 2, 3, 4, 5, 6, 7, 8, 9, 10, 20, 25, 30, or 40, or more. A linker may be linear or non-linear; some linkers have pendant side chains or pendant functional groups (or both). Examples of such pendant moieties are hydrophilicity modifiers, for example solubilizing groups like, e.g., sulfo (—$SO_3H$— or —$SO^3$—). In some embodiments, a linker is composed of any combination of single, double, triple or aromatic carbon-carbon bonds, carbon-nitrogen bonds, nitrogen-nitrogen bonds, carbon-oxygen bonds and carbon-sulfur bonds. Exemplary linking members include a moiety which includes —C(O)NH—, —C(O)O—, —NH—, —S—, —O—, and the like. Linkers may by way of example consist of a combination of moieties selected from alkyl, alkylene, aryl, —C(O)NH—, —C(O)O—, —NH—, —S—, —O—, —C(O)—, —S(O)$_n$— where n is 0, 1, 2, 3, 4, 5, or 6-membered monocyclic rings and optional pendant functional groups, for example sulfo, hydroxy and carboxy.

In some embodiments, the linker can result from "click" chemistries schemes (see, e.g., Gheorghe, et al., 2008 Organic Letters 10:4171-4174) which can be used to attach any combination of biomolecules, reporter moieties and surfaces as disclosed herein to each other In one aspect, the linker can attach two or more energy transfer or reporter moieties to each other (the same type or different types of moieties). In another aspect, a trifunctional linker (e.g., Graham, U.S. published patent application No. 2006/0003383) can be linked to two fluorescent dye moieties (the same type or different types) to amplify the fluorescent signal upon nucleotide binding or nucleotide incorporation. For example, a trifunctional linker can be linked to two energy transfer acceptor moieties, or to an energy transfer acceptor and a reporter moiety. In another example, multiple trifunctional linkers can be linked to each other, which can be linked to multiple fluorescent dyes for dendritic amplification of the fluorescent signal (e.g., Graham, U.S. published patent application No. 2007/0009980).

In some embodiments, the linker can be a cleavable linker such as, for example, a photocleavable linker, a chemically cleavable linker or a self-cleaving linker.

In some embodiments, the linker is a self-cleaving linker. Optionally, such linker can be a trimethyl lock or a quinone methide linker, which can each optionally link to two energy transfer acceptor and/or reporter moieties and the nucleotide.

In some embodiments, the linkers can be cleavable where cleavage is mediated by a chemical reaction, enzymatic activity, heat, acid, base, or light. For example, photocleavable linkers include nitrobenzyl derivatives, phenacyl groups, and benzoin esters. Many cleavable groups are known in the art and are commercially available. See, for example, J. W. Walker, et al., 1997 Bioorg. Med. Chem. Lett. 7:1243-1248; R. S. Givens, et al., 1997 Journal of the American Chemical Society 119:8369-8370; R. S. Givens, et al., 1997 Journal of the American Chemical Society 119:2453-2463; Jung et al., 1983 Biochem. Biophys. Acta, 761: 152-162; Joshi et al., 1990 J. Biol. Chem., 265: 14518-14525; Zarling et al., 1980 J. Immunol., 124: 913-920; Bouizar et al., 1986 Eur. J. Biochem., 155: 141-147; Park et al., 1986 J. Biol. Chem., 261: 205-210; and Browning et al., 1989 J. Immunol., 143: 1859-1867; see also U.S. Pat. No. 7,033,764. A broad range of cleavable, bifunctional (both homo- and hetero-bifunctional) spacer arms with varying lengths are commercially available.

A rigid linker can be used. In some embodiments, use of a rigid linker can be useful in improving a FRET signal. Examples of rigid linkers include benzyl linkers, proline or poly-proline linkers (S. Flemer, et al., 2008 Journal Org. Chem. 73:7593-7602), bis-azide linkers (M. P. L. Werts, et al., 2003 Macromolecules 36:7004-7013), and rigid linkers synthesized by modifying the so-called "click" chemistry scheme that is described by Megiatto and Schuster 2008 Journal of the Am. Chem. Soc. 130:12872-12873.

In yet another embodiment, the linker can be an energy transfer linker synthesized using methods described in U.S. Published Patent Application No. 2006/0057565.

In yet another embodiment, the linker can comprise a spacer, for example a cationic arginine spacer or an imidazolium spacer molecule.

In some embodiments, the linker can be a fragmentable linker, including non-lamellar "detergent-like" micelles or lamellar vesicle-like micelles such as small unilamellar vesicles or liposomes ("SUVs"), small multilamellar vesicles or liposomes (SMVs"), large unilamellar vesicles or liposomes ("LUVs") and/or large multilamellar vesicles or liposomes ("LMVs") (see U.S. application Ser. No. 11/147, 827) and see U.S. Application Nos. 60/577,995, and Ser. No. 12/188,165.

In some embodiments, the linker can include multiple amino acid residues (e.g., arginine) which serve as an intervening linker between the terminal phosphate group and the reporter moiety. For example, the linker can be can four arginine residues which connect a dye moiety to a nucleotide comprising one or more phosphate groups, wherein the linker links the dye moiety to the terminal phosphate group of the nucleotide.

In some embodiments, linkers can be used to attach energy transfer or reporter moieties to nucleotides using any suitable linking procedure, including: amine linkers for attaching reporter moieties to nucleotides (see, for example, Hobbs, U.S. Pat. No. 5,151,507); a linker comprising a primary or secondary amine for operably linking a reporter moiety to a nucleotide; and a rigid hydrocarbon arm added to a nucleotide base (see, for example, R. F. Service, 1998 Science 282(5391):1020-21). Some exemplary linking procedures for attaching energy transfer or reporters moieties to base molecules are provided in European Patent Application 87310256.0; International Application PCT/US90/05565; Marshall, 1975 Histochemical Journal 7:299-303; and Barone et al., 2001 Nucleosides, Nucleotides, and Nucleic Acids, 20(4-7): 1141-1145. Other examples include linkers for attaching energy transfer or reporter moieties to oligonucleotides synthesized using phosphoramidate to incorporate amino-modified dT (see Mathies, U.S. Pat. No. 5,707, 804).

PEG Linkers

In one aspect, a linker comprising a polymer of ethylene oxide can be used to attach the surfaces, reporter moieties (including, e.g., dyes and nanoparticles), polymerases, nucleotides and/or nucleic acid molecules of the present disclosure to each other in any combination. Non-limiting examples of such polymers of ethylene oxide include polyethylene glycol (PEG), including short to very long PEG, branched PEG, amino-PEG-acids, PEG-amines, PEG-hydrazines, PEG-guanidines, PEG-azides, biotin-PEG, PEG-thiols, and PEG-maleinimides. For example, PEG includes: PEG-1000, PEG-2000, PEG-12-OMe, PEG-8-OH, PEG-12-COOH, and PEG-12-$NH_2$. In some embodiments, the PEG molecule may be linear or branched. In some embodiments, it can have a molecular weight greater than or approximately equal to 1000, 2000, 3000, 4000, 5000 or greater.

In some embodiments, functionalization with different reactive moieties can be used create a heterobifunctional PEG derivative comprising different reactive groups at each end. Such heterobifunctional PEGs can be useful in linking two entities, where a hydrophilic, flexible and biocompatible spacer is needed. Some examples of heterobifunctional PEG derivatives include without limitation Hydroxyl PEG Carboxyl (HO-PEG-COOH): Thiol PEG Carboxyl (HS-PEG-COOH); Hydroxyl PEG Amine (HO-PEG-NH2); t-Boc Amine PEG Amine (TBOC-PEG-NH2); Amine PEG Carboxyl (NH2-PEG-COOH); t-Boc Amine PEG NHS Ester (TBOC-PEG-NHS); FMOC Amine PEG NHS Ester (FMOC-PEG-NHS): Acrylate PEG NHS Ester (ACLT-PEG-NHS); Maleimide PEG Carboxyl (MAL-PEG-COOH); Maleimide PEG Amine (MAL-PEG-NH2), including the TFA Salt thereof; Maleimide PEG NHS Ester (MAL-PEG-NHS); Biotin PEG NHS Ester (BIOTIN-PEG-NHS); Biotin Polyethylene Glycol Maleimide (BIOTIN-PEG-MAL); OPSS PEG NHS Ester (OPSS-PEG-NHS).

Optionally, the PEG derivative can be a multi-arm PEG derivative. In some embodiments, the multi-arm PEG derivative can be a PEG derivative having a core structure comprising pentaerythritol (including, for example, 4arm PEG Amine (4ARM-PEG-NH2); 4arm PEG Carboxyl (4ARM-PEG-COOH); 4arm PEG Maleimide (4ARM-PEG-MAL); 4arm PEG Succinimidyl Succinate (4ARM-PEG-SS); 4arm PEG Succinimidyl Glutarate (4ARM-PEG-SG)); a PEG derivative having a core structure comprising hexaglycerin (including, for example, 8arm PEG Amine (8ARM-PEG-NH2); 8arm PEG Carboxyl (8ARM-PEG-COOH); 8arm PEG Succinimidyl Succinate (8ARM-PEG-SS); 8arm PEG Amine (8ARM-PEG-SG); PEG derivative having a core structure comprising tripentaerythritol (including, for example, 8arm PEG Amine (8ARM(TP)-PEG-NH2); 8arm PEG Carboxyl (8ARM(TP)-PEG-COOH); 8arm PEG Succinimidyl Succinate (8ARM(TP)-PEG-SS); 8arm PEG Amine (8ARM(TP)-PEG-SG)). Optionally, end groups for heterobifunctional PEGs can include maleimide, vinyl sulfones, pyridyl disulfide, amine, carboxylic acids and NHS esters. The activated PEG derivatives can then be used to attach the PEG to the desired biomolecule and/or nanoparticle. Optionally, one or both ends of the PEG derivative can be attached to the N-terminal amino group or the C-terminal carboxylic acid of a protein-comprising biomolecule.

Signal Detection

The methods, compositions, systems and kits disclosed herein can involve the use of a detection system for optical or spectral detection of a signal, or a change in a signal, generated (emitted) by the energy transfer moiety(ies) or reporter moiety(ies) in the nucleotide binding or nucleotide incorporation reactions.

The systems and methods can detect and/or measure a signal, or a change or an amount of change of an optical or spectral characteristic of a signal (e.g., fluorescence or quenching) from a reporter moiety, such as an energy transfer donor and/or acceptor moiety. The change in the signal can include changes in the: intensity of the signal; duration of the signal; wavelength of the signal; amplitude of the signal; duration between the signals; and/or rate of the change in intensity, duration, wavelength or amplitude. The change in the signal can include a change in the ratio of the change of the energy transfer donor relative to change of the energy transfer acceptor signals.

The detection system comprises: excitation illumination, optical transmission elements, detectors, and/or computers.

In one aspect, detecting radiation emitted by an excited energy transfer or reporter moiety during nucleotide binding comprises: the nucleotide, which can be labeled with a FRET acceptor, binds the polymerase which can be labeled with a FRET donor, bringing the FRET acceptor/donor pair in proximity to each other, and the FRET donor can be excited resulting in energy transfer to the FRET acceptor which emits a signal which is detectable by the detection system.

The detection system comprises excitation illumination which can excite the energy transfer or reporter moieties which produce a detectable signal. The excitation illumination can be electromagnetic energy, such as radio waves, infrared, visible light, ultraviolet light, X-rays or gamma rays. The source of the electromagnetic radiation can be a laser, which possesses properties of mono-chromaticity, directionality, coherence, polarization, and/or intensity. The laser can produce a continuous output beam (e.g., continuous wave laser) or produce pulses of light (e.g., Q-switching or mode-locking). The laser can be used in a one-photon or multi-photon excitation mode. The laser can produce a focused laser beam. The wavelength of the excitation electromagnetic radiation can be between about 325-850 nm, or between about 325-752 nm, or between about 330-752 nm, or between about 405-752 nm. The laser can be generated by a mercury, xenon, halogen, or other lamps.

The wavelength and/or power of the excitation illumination can be selected to avoid interfering with or damaging the polymerase enzymatic activities. The excitation illumination can be focused on a stationary position or moved to a different field of view (FOV). The excitation illumination can be directed at a nucleotide incorporation reaction which is: in a liquid volume (e.g., aqueous or oil); on a surface; in or on a nanodevice; in a waveguide; or in an evanescent illumination system (e.g., total internal reflection illumination). The excitation illumination can pass through a transparent or partially transparent surface which is conjugated (covalently or non-covalently) with the components of the nucleotide incorporation reaction.

The energy transfer moiety (e.g., a FRET donor) can be excited by the excitation illumination at a particular wavelength, and transmit the excitation energy to an acceptor moiety which is excited and emits a signal at a longer wavelength. The energy transfer moiety or reporter moiety can undergo multi-photon excitation with a longer wavelength, typically using a pulsed laser.

The detection system comprises suitable optical transmission elements which are capable of transmitting light from one location to another with the desired refractive indices and geometries. The optical transmission elements transmit the excitation illumination and/or the emitted energy in an unaltered or altered form. The optical transmission elements include: lens, optical fibers, polarization filters (e.g., dichroic filters), diffraction gratings (e.g., etched diffraction grating), arrayed waveguide gratings (AWG), optical switches, mirrors, dichroic mirrors, dichroic beam splitter, lenses (e.g., microlens and nanolens), collimators, filters, prisms, optical attenuators, wavelength filters (low-pass, band-pass, or high-pass), wave-plates, and delay lines, or any combination thereof.

The detection system comprises suitable detectors which are capable of detecting and/or distinguishing the excitation illumination and/or the emitted energy. A wide variety of detectors are available in the art, including: single or multiple channel detectors, high-efficiency photon detection systems, optical readers, charge couple devices (CCD), photodiodes (e.g. avalanche photo diodes (APD)), APD arrays, cameras, electron-multiplying charge-coupled device (EMCCD), intensified charge coupled device (ICCD), photomultiplier tubes (PMT), multi-anode PMT, complementary metal oxide semiconductor (CMOS) chip(s), and a confocal microscope equipped with any of the foregoing detectors. The location of the nucleotide incorporation reaction can be aligned, with respect to the excitation illumination and/or detectors, to facilitate proper optical transmission.

Suitable detection methods can be used for detecting and/or distinguishing the excitation illumination (or change in excitation illumination) and/or the emitted energy (or change in emitted energy), including: confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photo-conversion, wide field fluorescence, single and/or multi-photon excitation, spectral wavelength discrimination, evanescent wave illumination, scanning two-photon, scanning wide field two-photon, Nipkow spinning disc, multi-foci multi-photon, or any combinations thereof.

The signals emitted from different energy transfer moieties can be resolved using suitable discrimination methods which are based on: fluorescence resonance energy transfer measurements; photoconversion; fluorescent lifetime measurements; polarization; fluorescent lifetime determination; correlation/anti-correlation analysis; Raman; intensity; ratiometric; time-resolved methods; anisotropy; near-field or far field microscopy; fluorescence recovery after photobleaching (1-RAP); spectral wavelength discrimination; measurement and separation of fluorescence lifetimes; fluorophore identification; background suppression, parallel multi-color imaging, or any combination thereof. See, for example, J. R. Lakowitz 2006, in: "Principles of Fluorescence Spectroscopy", Third Edition. If the different nucleotides are labeled with different energy transfer or reporter moieties, then resolving the emitted signals can be used to distinguish between the different nucleotides which bind the polymerase and/or which are incorporated by the polymerase.

In one embodiment, a system and method for detecting radiation emitted by an excited energy transfer or reporter moiety comprises: an illumination source (e.g., a laser) which produces the excitation energy (e.g., one or multiphoton excitation radiation) which is directed, via a dichroic beam splitter, through a lens, and through a transparent surface or onto a surface, where the nucleotide binding reaction or the nucleotide incorporation reaction is attached to the surface or is in a solution. The excitation illumination excites the energy transfer or reporter moiety (e.g., fluorescent dye and/or nanoparticle) resulting in emitted radiation (or a change in radiation) which passes back through the dichroic beam splitter and is directed to the detector (or an array of detectors) which is capable of identifying and/or resolving the type of emission. Information about the detected emitted signals is directed to the computer where the information is registered and/or stored. The computer can process the registered and/or stored information to determine the identity of the nucleotide which bound the polymerase or the identity of the incorporated nucleotide.

In one aspect, the system and method for detecting radiation emitted by an excited energy transfer or reporter moiety includes a multifluorescence imaging system. For example, the different nucleotides may each be linked to different FRET acceptor moieties. The FRET acceptor moieties can be selected to have minimal overlap between the absorption and emission spectra, and the absorption and emission maxima. The multifluorescence imaging system can simultaneously (or substantially simultaneously) detect signals from the FRET acceptor moieties, and resolve the signals. Such multifluorescent imaging can be accomplished using suitable filters, including: band pass filters, image splitting prisms, band cutoff filters, wavelength dispersion prisms, dichroic mirrors, or diffraction gratings, or any combination thereof.

In another aspect, the multifluorescence imaging system is capable of detecting the signals emitted by the different energy transfer and reporter moieties attached to the different nucleotides. Such a system can include special filter combinations for each excitation line and/or each emission band. In one embodiment, the detection system includes tunable excitation and/or tunable emission fluorescence imaging. For tunable excitation, light from a light source can pass through a tuning section and condenser prior to irradiating the sample. For tunable emissions, emissions from the sample can be imaged onto a detector after passing through imaging optics and a tuning section. The tuning sections can be controlled to improve performance of the system.

In yet another aspect, the detection system comprises an optical train which directs signals emitted from an organized array onto different locations of an array-based detector to detect multiple optical signals from multiple locations. The optical trains typically include optical gratings and/or wedge prisms to simultaneously direct and separate signals having differing spectral characteristics from different addressable locations in an array to different locations on an array-based detector, e.g., a CCD.

In another aspect, the detection methods include detecting photon bursts from the labeled nucleotides during incorporation. The photon bursts can be the fluorescent signals emitted by the energy transfer moiety which is linked to the nucleotide. The photon bursts can be a FRET event. The methods can additionally include analyzing the time trace of the photon bursts. The methods can be practiced using time-resolved fluorescence correlation spectroscopy.

Nucleotide incorporation reactions using nucleotides labeled at the terminal phosphate with a fluorescent dye have been previously demonstrated (Sood, U.S. published patent application No. 2004/0152119; and Kumar, U.S. Pat. No. 7,393,640). Furthermore, fluorescence detection of single molecule nucleotide incorporation reactions has been routinely obtained (Kao, U.S. Pat. No. 6,399,335; and Fuller, U.S. Pat. No. 7,264,934).

The nucleotide labeling strategy can be used as a basis for selecting any suitable detection system for detecting and/or resolving signals emitted by the nucleotide binding reaction or the nucleotide incorporation reaction. Exemplary labeling and detection strategies include but are not limited to optical train and TIRF detection methods such as those disclosed in U.S. Pat. No. 6,423,551; and U.S. Pub. Nos. 2006/0176479, 2007/0109536, 2007/0111350, and 2007/0250274.

Sequence Analysis of Detected Signals

Following detection of the sample emissions, the raw emission data can be analyzed to identify events involving nucleotide polymerization. In some embodiments, the emissions can be analyzed in single molecule format to identify nucleotide polymerization.

In one aspect, a labeled enzyme conjugate is a labeled polymerase conjugate, and a time series of nucleotide incorporations by the labeled polymerase conjugate is detected and analyzed to deduce the ordered sequence of nucleotides (identifying the nucleotide bases) in the single nucleic acid substrate that is being replicated by the polymerase.

In one exemplary embodiment, the labeled polymerase conjugate comprises an energy transfer moiety that undergoes FRET with the energy transfer moiety of an incoming labeled nucleotide that is polymerized by the polymerase of the conjugate. Nucleic acid sequence analysis is performed by first analyzing the raw emission data to computationally determine the occurrence of a FRET event. In some embodiments, FRET events i.e., a detectable change in a signal produced from a donor or acceptor resulting from a change in the distance between the donor and acceptor, can be identified using a Hidden Markov Model (HMM)-based or equivalent generalized likelihood ratio test that determines the location of an intensity change point based on individual photon arrival times; this test can then be applied recursively to an entire single molecule intensity trajectory, thus finding each change points. The true number of states accessible to the system is then computed. See, e.g., Watkins et al., "Detection of Intensity Change Points in Time-Resolved Single-Molecule Measurements" J. Phys. Chem. B., 109(1): 617-628 (2005). An exemplary FRET detection method using this technique is described herein in Example 14.

In one aspect, a system can collect and analyze chemical and/or physical event data occurring at one or a plurality of locations within a viewing volume or field of an imaging apparatus. In some embodiments, the system comprises a sample subsystem for containing a sample to be detected and analyzed, where the sample includes at least one moiety (e.g., enzyme, substrate, reporter moiety, etc) having detectable property that undergoes a change before, during or after one or a sequence of chemical and/or physical events involving the moiety. The system can also includes a detection apparatus having a viewing field that permits the detection of changes in the detectable property of the moiety within the viewing field. The system also includes a data processing subsystem connected to the imaging apparatus for collecting, storing and analyzing data corresponding to the chemical and/or physical events occurring at definable locations in the viewing field involving one or more moieties within the viewing field of the imaging subsystem. The data processing subsystem converts the data into classifications of events according the event type determined by a set of parameters defining or characterizing each event type. See, e.g., U.S. Published Patent Application No. 2007/0250274, Volkov et al. which is incorporated herein as if set forth in full.

In one aspect, FRET events can be identified by computationally determining the occurrence of an anti-correlated FRET event (typically involving a correlated decrease in donor signal and increase in acceptor signal). In one exemplary embodiment, FRET events corresponding to interactions between a donor fluorophore associated with a first moiety, e.g., a polymerase and an acceptor fluorophore associated with a second moiety, e.g., a nucleotide can be analyzed by first collecting or receiving data from a viewing volume of an imaging apparatus such as an CCD or iCCD detection system. In some embodiments, the data can be in a single data channel or a plurality of data channels, each data channel representing a different frequency range of emitted fluorescent light, e.g., one channel can include fluorescent light data emitted by a donor, a donor channel, while other channels include fluorescent light data emitted by an acceptor, an acceptor channel, or by another donor, a second donor channel. In certain embodiments, a channel will exit for each different fluorophore being detected simultaneously. In some embodiments, the acceptors are selected so that they can be separately identified based on detectable attributes of their signals e.g., intensity, frequency shifts, signal duration, attenuation, etc. After data collection, the separate data channels are spatially correlated within the viewing volume so that active fluorophores can be spatially and temporally related, called calibration or registration. The goal of calibration is to determine the pixel coordinates in each quadrant that correspond to a single position on the slide or a single location within the viewing field—to make sure that the data in each channel is spatially coincident over the viewing field and through time of detection. After reading the configuration file and the open log file, calibrations, if any, are loaded from the command line. After loading the calibration information, a corresponding directory is read as specified in the command line with all subdirectories, for each one. This read step includes: (1) scanning for calibration stacks, and if there are some not matched by the available calibrations, generate new calibrations out of them; (2) scanning for stacks; if there are some, assume this directory is a slide; and (3) scanning the directory path for a date and slide name comprising reaction conditions such as donor identity, acceptor identity, buffers, etc. See, for example, U.S. Published Patent Application No. 2007/0250274, Volkov et al.

Once FRET events have been identified, they can be analyzed to determine the order and sequence of nucleotide incorporations.

Analysis of Fluorescence Data to Extrapolate Sequence Information

To convert the observed fluorescence emissions detected during the sequencing reaction into nucleotide sequence information, the raw data comprising a movie of observed emissions was first processed by using a Hidden Markov Model (HMM)-based algorithm or equivalent to detect and identify FRET events. The subsequent detected FRET events were filtered and filtered sequences were aligned. Each of these two steps, FRET event detection and sequence analysis, are described in more detail below.

Detection of FRET Events

The analysis underlying FRET event detection is designed to process spatially correlated movie(s) comprising sequence fluorescence emission data, and extract time-series of interest from those data. A movie typically contains one or more channels where each channel represents the same spatial location at different wavelengths. The analysis chain begins with the submission of one or more movies to the analysis machine via a comprehensive user interface. The user interface requires the user to input various parameters that describe the movie(s) (e.g. channel regions, dye emission properties, etc.). Once this data is submitted the movie(s) are then processed by the image analysis software where a sliding window of N frames propagates through the movie calculating a temporal local average of the frames within the window. At each position of the window in the movie, the local average image is then further processed and enhanced using well known image processing algorithms and a record of the maximum projection of all the local average images is recorded to produce a global image of the movie. This global image is the input into a spot identification algorithm which produces a set of spots identified by a unique spot id, its x and y location and its corresponding channel, for the sake convenience referred to as a spot-tuple. Each set of spots for a given channel is then registered to the set of spots in every other channel. In this way a set of spot tuples is constructed. If a detected spot in one channel does not have a corresponding detected spot in another channel, then the position of the undetected spot using the transformation between the two channels and the location of the detected spot is inferred. Once a complete set of spot tuples is constructed the movie is iterated over and at each frame the amplitude of each spot is calculated and appended to the appropriate time-series.

The collection of time-series from a spot tuple consists of time-series from donor and corresponding acceptor channels. This collection is called a Vector Time-Series (VTS). The FRET detection process starts with a data segmentation step using a Markov Chain Monte-Carlo (MCMC) algorithm. Each segment of VTS is modeled by a multivariate Gaussian model, with each of the channel modeled by a mean and a standard deviation. This model establishes a baseline for each channel, from which quantities such as "Donor Down" and "Acceptor Up" can be calculated. A Hidden Markov Model (HMM) or equivalent algorithm is used to model the observed data. The underlying states consist of a null state, a blink state and a number of FRET states (one for each acceptor channel). Each state has its emission probability, which reflects the state's corresponding physical concept. FRET states are characterized by significant "donor down" and "acceptor up" signals. Blink state is characterized by significant "donor down" with no "acceptor up". Null state is characterized by no "donor down" and no "acceptor up". Given the observed VTS signal, the emission matrix, and a state transition probability matrix, the most probable state path can be computed using the Viterbi algorithm. This state path assigns each of the frames to a state. Temporally neighboring FRET frames are grouped into FRET events. For each of the detected FRET events, a list of event features are calculated, including event duration, signal average, signal to noise ratio, FRET efficiency, probability of event, color calling and other features. This list of events and corresponding features are stored in a file.

The final stage of the automated analysis generates a report summarizing the results in the form of a web page containing summary image, statistics of the spots and FRET detection, together with line intensity plots and base call plots.

Using the above process, the movie data obtained from the sequencing reactions was analyzed to detect and identify FRET events according to the process described above. The FRET events were then processed to identify sequences as described below.

Sequence Analysis

The string of FRET events from the same spot-tuple are then aligned to a reference sequence. Each color call in the string is associated with a nucleotide, creating a DNA sequence. That DNA sequence and a reference sequence are fed into a Smith-Waterman alignment or equivalent algorithm to determine where the read comes from in the template sequence and the similarity between the sequences.

Kits

Provided herein are kits for conducting the nucleotide binding reactions and/or the nucleotide incorporation reactions described herein. The kits can include, in one or more containers, the components of nucleotide binding and/or nucleotide incorporation disclosed herein, including: the solid surfaces, energy transfer moieties, reporter moieties, nanoparticles, polymerases, nucleotides, target nucleic acid molecules (e.g., a control test target molecules), primers, and/or oligonucleotides.

In the kits, the solid surfaces, energy transfer moieties, reporter moieties, nanoparticles, polymerases, nucleotides, target nucleic acid molecules, primers, and/or oligonucleotides can be attached to each other in any combination, and/or be unattached. The kits can include positive and/or negative control samples.

Additional components can be included in the kit, such as buffers and reagents. For example, the buffers can include Tris, Tricine, HEPES, or MOPS, or chelating agents such as EDTA or EGTA. In another example, the reagents can include monovalent ions, such as KCl, K-acetate, $NH_4$-acetate, K-glutamate, $NH_4Cl$, or ammonium sulfate. In yet another example, the reagents can include divalent ions, such as $Ca^{2+}$, $CaCl_2$, $Mg^{2+}$, $MgCl_2$, Mg-acetate, $Mn^{2+}$, $MnCl_2$, and the like. The kits can include the components in pre-measured unit amounts. The kits can include instructions for performing the nucleotide binding reactions and/or the nucleotide incorporation reactions. Where the kit is intended for diagnostic applications, the kits may further include a label indicating regulatory approval for the diagnostic application.

EXAMPLES

All of the compositions and methods disclosed and claimed herein can be made and executed without undue experimentation in light of the present disclosure. In some cases, the compositions and methods of this invention have been described in terms of embodiments, however these embodiments are in no way intended to limit the scope of the claims, and it will be apparent to those of skill in the art that variations may be applied to the compositions and/or methods and in the steps or in the sequence of steps of the methods described herein without departing from the concept, spirit and scope of the invention. More specifically, it will be apparent that certain components which are both chemically and physiologically related may be substituted for the components described herein while the same or similar results would be achieved. All such similar substitutes and modifications apparent to those skilled in the art are deemed to be within the spirit, scope and concept of the invention as defined by the appended claims.

Example 1

Synthesis of Nucleotide Tetraphosphate Molecules Labeled with Alexa Dyes

The synthesis scheme of amino-dN tetraphosphate is illustrated in scheme 1 using amino-dG4P as an illustrative example. Amino-attached dA4P, dC4P and dT4P were synthesized by the same method.

1.) Synthesis of Compound 2

Compound 1 (678 mg, 2 mmol) was suspended in trimethyl phosphate (5 mL) and cooled to 0° C. $POCl_3$ (280 μL) was added to the stirred mixture under argon. The mixture was warmed up and stirred at room temperature overnight. The reaction was quenched by adding slowly 4 mL of TEAB buffer (1 M) at 0° C. Triethylamine was added to adjust to pH 7. The solvent was evaporated and the residue was purified by column chromatography on silica gel, eluting with 10% $H_2O/CH_3CN$. After evaporation of the solvent, the solid was dissolved in water. The pH of the solution was adjusted to pH 7 with TEAB buffer (1 M), followed by coevaporation with methanol. Yield: 400 mg of compound 2.

Scheme 1

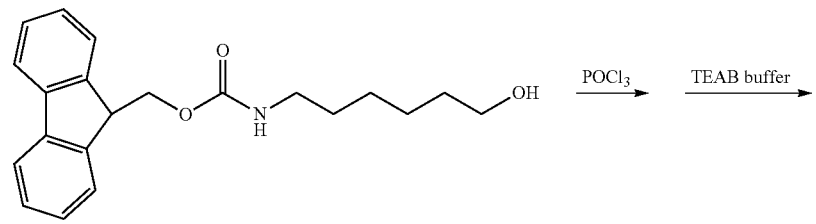

1

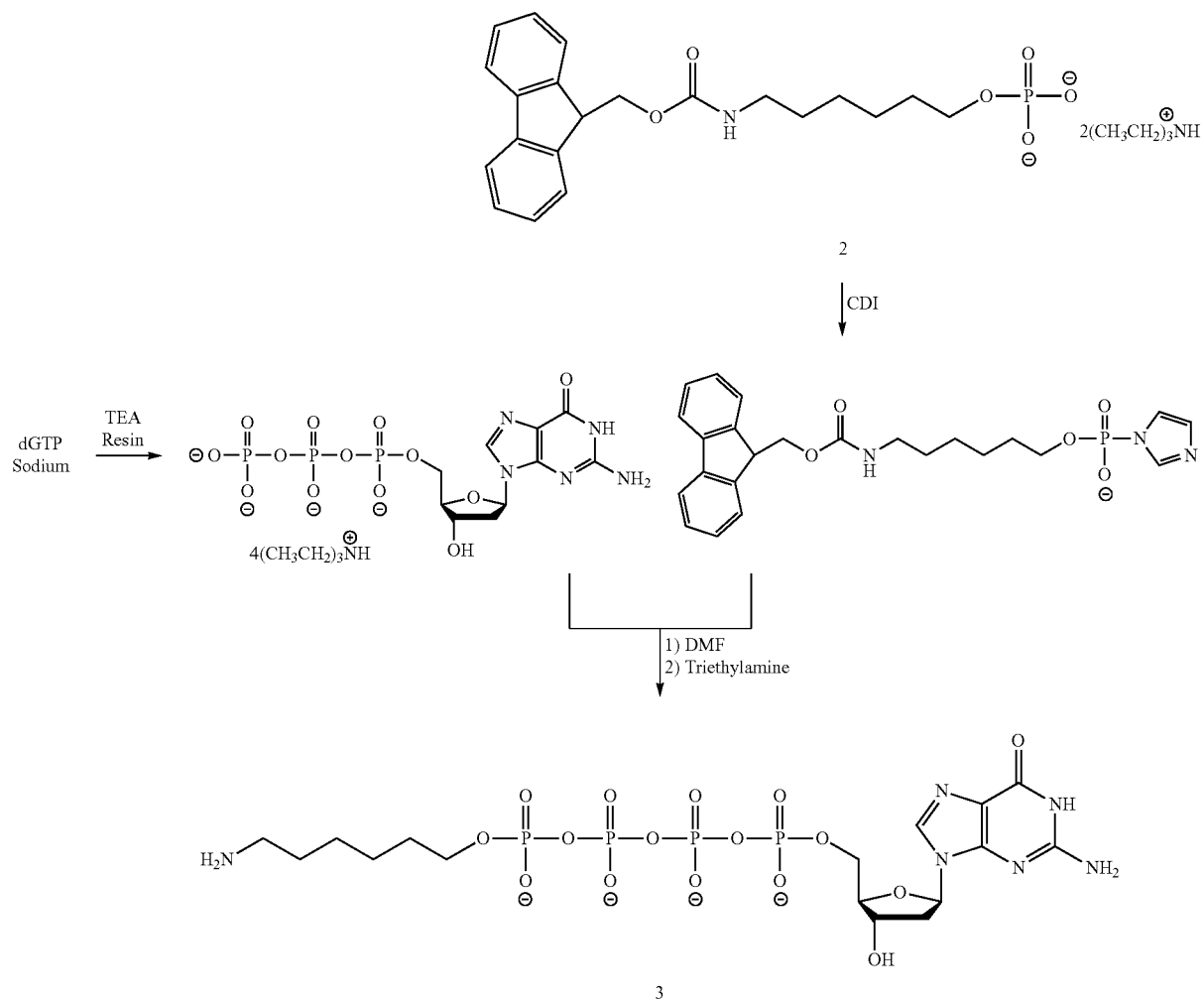

2.) Synthesis of Compound 3

The sodium salt of dGTP (20 mg) was converted into its triethylammonim salt by passing a trethylammonium resin and dried in high vacuum. Compound 2 (42 mg) was dissolved in 2 mL of dry DMF. arbonyldiimidazole (CDI) (65 mg) was added and the solution was stirred for 4 hours at room temperature, followed by the addition of anhydrous methanol (18 μL) and stirred for a further hour. The dried dGTP triethylammonium salt was dissolved in dry DMF (2 mL), and to this solution was added the prepared phospoimidazolate solution of 2 under argon. The mixture was stirred under argon overnight. Triethylamine (1 mL) was added and stirred for 4 hours. The solvent was evaporated, washed with $CHCl_3$, dissolved in water and purified by sephadex A-25 DEAE ion exchange chromatography, eluting with a linear gradient of 0.05 M to 0.6 M TEAB buffer. After coevaporation with methanol and lyophilization, ca. 5 mg of compound 3 was obtained. The reaction was checked by TLC (Dioxane/IPA/$H_2O$/$NH_4OH$=40/20/40/36).

3.) Synthesis of Amino-Attached dA4P (4), dC4P (5) and dT4P (6)

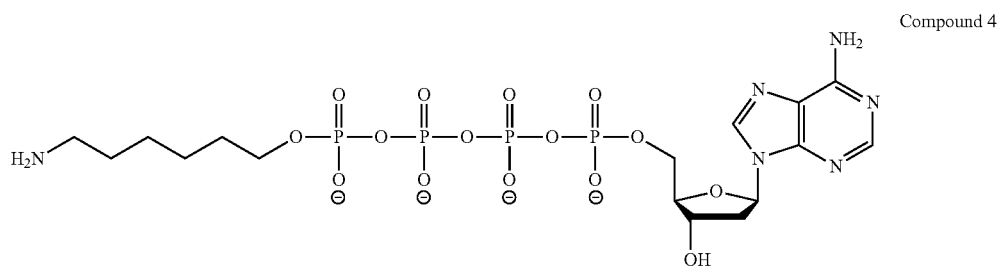

Compound 4

Compound 5

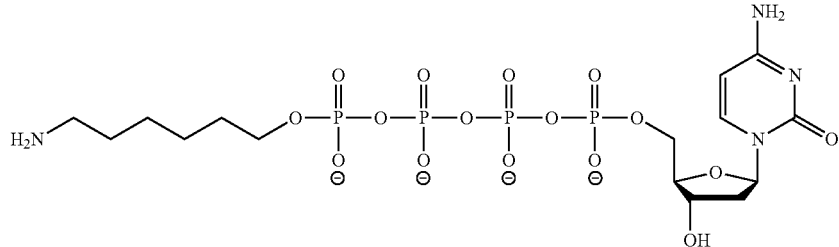

Compound 6

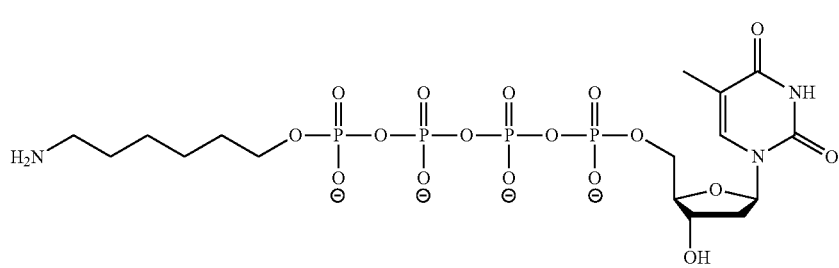

These compounds were synthesized by the same method as described for amino-dG4P (3).

4.) Labeling Amino-dGP4 with Alexa Dyes

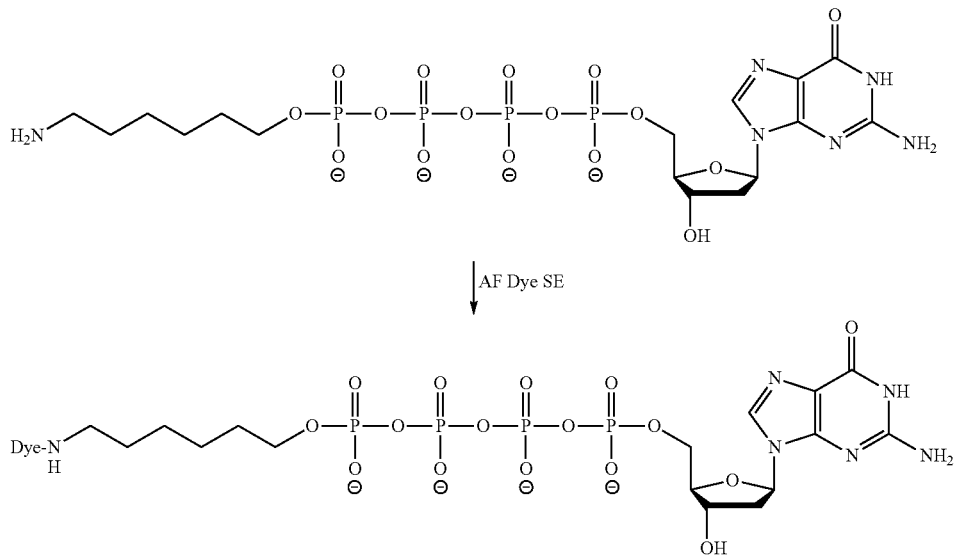

A solution of amino-dG4P (3) (0.5 mg) in DMF-water (2:1, 300 μL) was mixed with 50 μL of saturated sodium bicarbonate solution. To this solution was added the Alexa dye SE (2 mg). The solution was stirred at room temperature until the completion of the reaction (ca. 1 hour). The product was purified by column chromatography on sephadex LH-20, eluting with water. The desired fraction was concentrated to ca. 300 μL and stored at −20° C.

The Alexa dye SE used includes AF633 SE, AF647 SE, AF660 SE, AF680 SE, AF700 SE and AF750 SE.

5.) Labeling Amino-dAP4, Amino-dC4P and Amino-dT4P with Alexa Fluor Dyes

These amino-dN tetraphosphates were labeled with Alexa dyes by the same method as described in procedure 4.

Example 2

Preparing PEG and Biotin-Streptavidin Coated Surfaces

Low-Density Streptavidin Coating

Low density streptavidin layers were coated on the surface of glass coverslips using a flowcell. PEG/PEG-biotin coated glass cover slips (MicroSurfaces, Inc., Minneapolis, Minn.) were assembled into 8-lane reaction chambers with laser-cut 3M double-sided adhesive and custom fabricated plastic superstructures with inlet/outlet ports for fluid addition. The surface was wetted by flowing 1 milliliter of TBSB solution which contains Tris-buffered saline (50 mM Tris, pH 7.5, 150 mM NaCl) and 0.5% bovine serum albumin (Sigma, catalog #A8577). 250 microliters of 1% BSA/TBS (50 mM Tris, pH 7.5, 1% BSA) was flowed across the chip and allowed to incubate at room temperature for 5 minutes. The surface was coated with streptavidin by flowing 100 microliters of 60 pM streptavidin, (Zymed, Cat #43-4302) diluted in TBSB, and incubating for 30 minutes at room temperature. The lanes were washed with 1 milliliter of TBSB and passivated for a second time with 250 microliters of 1% BSA/TBS-biotinylated DNA, in the form of a self-annealing 5'-overhanging hairpin molecule, was diluted to 10-100 pM in 1% BSA/TBS and 100 microliters was flowed into the reaction chamber and incubated 30 minutes at room temperature. The lanes were washed with 1 milliliter of TBSB. The density of the DNA bound to the low density PEG-biotin-streptavidin coated glass surface was imaged using total internal reflection microscopy (TIRF) and a 633 nm laser.

High-Density Streptavidin Coating

High density streptavidin layers were coated on the surface of glass coverslips using a flowcell. PEG/PEG-biotin coated cover slips (MicroSurfaces, Inc., Minneapolis, Minn.) were assembled into 8-lane reaction chambers with laser-cut 3M double-sided adhesive and custom fabricated plastic superstructures with inlet/outlet ports for fluid addition. The surface was wetted by flowing 1 milliliter of TBSB solution which contains Tris-buffered saline (50 mM Tris, pH 7.5, 150 mM NaCl) containing 0.5% bovine serum albumin (Sigma, catalog #A8577). 250 microliters of 1% BSA/TBS (50 mM Tris, pH 7.5, 1% BSA) was flowed across the chip and allowed to incubate at room temperature for 5 minutes. The surface was coated with streptavidin by flowing 100 microliters of 200 µg/ml streptavidin, (Zymed, Cat #43-4302) diluted in TBSB, and incubating for 10 minutes at room temperature. The lanes were washed with 1 milliliter of TBSB and passivated for a second time with 250 microliters of 1% BSA/TBS. Biotinylated DNA, in the form of a self-annealing 5'-overhanging hairpin molecule, was diluted to 10-100 pM in 1% BSA/TBS and 100 microliters was flowed into the reaction chamber and incubated 30 minutes at room temperature. The lanes were washed with 1 milliliter of TBSB. The density of the DNA bound to the high density PEG-biotin-streptavidin coated glass surface was imaged using total internal reflection microscopy (TIRF) and a 633 nm laser.

Example 3

Linking Chemistries for Attaching Nanoparticles with Polymerases

Preparing Phosphorothiolated Phi29 Polymerases

Phi29 polymerase protein, comprising the protein kinase A recognition sequence LRRASLG (SEQ ID NO:19) at the N-terminus (SEQ ID NO:7), was incubated with kinase and ATP-γS to form a phosphorothioate functional group on the serine residue of the recognition sequence.

Modifying the Nanoparticles with Adipic Dihydrazide

C8 Nanoparticles having outer shells which are pre-modified with methoxy-terminated PEG were obtained from Molecular Probes. These nanoparticles have residual carboxylate functional groups. 300 µl of 4.1 µM the nanoparticles were buffer exchanged into 100 mM MES, 300 mM NaCl, pH 5.5 using ultrafiltration (VivaSpin 100K MWCO spin filters). The reaction was started by adding: 260 µl of 4.08 µM buffer exchanged nanoparticles, 10.6 µl of 20 mM adipic dihydrazide (dissolved in water) and 13.5 µl of 10 mM EDC (1-ethyl-3-(3-dimethylaminopropyl) carbodiimide hydrochloride dissolved in water). 25 minutes after the start of the reaction another 13.5 µl aliquot of 10 mM EDC was added to the reaction mix. After two hours incubation at room temperature, the reaction mix was concentrated by ultrafiltration (VivaSpin 100K MWCO) then washed three times with 200 µl of 100 mM MES, 300 mM NaCl, pH 7.5 using the same ultrafiltration unit. The nanoparticles have hydrazide functional groups.

Reacting the Nanoparticles with Iodoacetic Acid

The nanoparticles (having hydrazide reactive groups) were modified with iodoacetic acid. The following reagents were added: 185 µl of 3.98 µM hydrazide-modified nanoparticles, 14.7 µl of 10 mM iodoacetic acid (sodium salt, dissolved in water) and 10 µl of 10 mM EDC (dissolved in water). 25 minutes after the start of the reaction another 10 µl aliquot of 10 mM EDC was added to the reaction mix. The reaction mix was allowed to incubate at room temperature, in the dark for three hours. After incubation, the reaction mix was concentrated by ultrafiltration and washed 5×200 µl with 100 mM MES, 300 mM NaCl, pH 5.5 also using ultrafiltration. The nanoparticles have iodoacetyl functional groups.

Attaching Iodoacetyl Nanoparticles with Phi29 Polymerases

The phosphorothioated phi29 polymerase was buffer exchanged into 100 mM MES, 300 mM NaCl, pH 5.5 using a NAPS column (GE Healthcare). For the conjugation reaction, 392 µl of 13.2 µM phosphorothioated phi29 polymerase was added to 95 µl of 2.73 µM iodoacetyl nanoparticles. The reaction mix was allowed to incubate overnight at room temperature in the dark. The reaction mix was concentrated to approximately 30 µl then purified over a SUPERDEX 200 (GE Healthcare) 8 mm×5.5 cm column (2 mL disposable column from Thermo Scientific) using 100 mM TRIS, 300 mM NaCl, pH 7.5 as the elution buffer. Three fractions were collected and assayed for concentration, extension activity and template binding.

Materials:

Hairpin oligonucleotide 221 sequence:

(SEQ ID NO: 24)
5'-TTTTTTTGCAGGTGACAGGTTTTTCCTGTCACCXGC-3' where X=fluorescein dT.

Hairpin oligonucleotide ALEXA FLUOR-647-labeled 199 sequence:

(SEQ ID NO: 25)
5'-TTATCTTTGTGGGTGACAGGTTTTTCCTGTCACCX-3' where X=ALEXA FLUOR 647-dC

1× extension buffer: 50 mM Tris (pH 8), 50 mM NaCl, and 10 mM $MgCl_2$.

Activity Assay

A 150 nM master mix solution of a labeled hairpin oligonucleotide 221 was prepared by diluting the appropriate quantity of a 50 µM stock solution with extension buffer (50 mM TRIS, pH 8, 50 mM NaCl, 10 mM $MgCl_2$). 450 µl of a master mix was prepared for each sample being tested.

The conjugate being tested was diluted in 450 µl of the master mix such that the final concentration of the conjugate is in the range of 10 nM to 50 nM. The positive control samples of free PKAΦ29 were similarly diluted. The sample solution was deposited in four microtiter plate wells, at 100 µl/well.

The microtiter plate was placed in a plate reader (Molecular Devices, SpectraMax M5) and set up to monitor the fluorescence as function of time (excitation 490 nm, emission 535 nm, cutoff filter 515 nm). Just prior to starting the plate reader, 2 µl of 1 mM dATP was added to each of two microtiter wells to start the extension reaction. The other two microtiter wells with sample represent no extension controls. The plate was read for an hour or until the samples reached saturation. The results indicate that phi29 polymerase, attached to nanoparticles, can incorporate nucleotides.

Binding Assay

Each sample to be tested was diluted to 20 nM in 650 µl of extension buffer. 50 µl of the sample was pipetted into each well of the top row of a microtiter plate.

A 2 µM solution of an ALEXA FLUOR-labeled hairpin oligonucleotide JX338 was prepared by dissolving the appropriate amount of stock oligonucleotide in extension buffer. 140 µl of each sample to be tested was prepared. The hairpin primer/template solution was pipetted into the first well of the second row in the microtiter plate. Into the remaining 11 wells of the second row of the microtiter plate, 70 µl of extension buffer was pipetted. 70 µl of the hairpin primer/template was removed from the first well of the second row and mixed with the extension buffer in the second well. 70 µl from the second well was removed and mixed with the extension buffer in the third well. The serial dilution was prepared up to the last well in row two.

50 µl of the primer/template was transferred from each well of row two into 50 µl of the sample in each well of row one.

The microtiter plate was placed on the plate reader which was set to measure fluorescence at 605 nm and 670 nm with excitation at 450 nm. The results showed an increase in FRET acceptor signal with an increase in the amount of the labeled oligonucleotide-199, or a decrease in FRET donor signal.

Example 4

Preparing Nanoparticles Attached with His-Tagged Polymerases

Materials:
Hairpin ALEXA FLUOR 647 labeled-oligonucleotide 192 sequence:

(SEQ ID NO: 26)
5'-TTTTTTTGCCCCCAGGGTGACAGGTTTTTCCTGTCACCC-3' where the 192 oligo is labeled at the 3' end with ALEXA FLUOR 647.
Hairpin ALEXA FLUOR 647 labeled-oligonucleotide 199 sequence:

(SEQ ID NO: 25)
5'-TTATCTTTGTGGGTGACAGGTTTTTCCTGTCACCX-3' where X=ALEXA FLUOR 647-dC.
Hairpin fluorescein labeled-oligonucleotide 221 sequence:

(SEQ ID NO: 24)
5'-TTTTTTTGCAGGTGACAGGTTTTTCCTGTCACCXGC-3' where X=fluorescein dT.
Hairpin ALEXA FLUOR 647 labeled-oligonucleotide 229 sequence:

(SEQ ID NO: 27)
5'-TTTTTGCGGGTGACAGGTTTTTCCTGTCACCC-3' where the 229 oligo is labeled at the 3' end with ALEXA FLUOR 647.
1× extension buffer: 50 mM Tris (pH 7.5), 50 mM NaCl, 10 mM $MgCl_2$, and 0.5 mM $MnCl_2$.
Preparing Nanoparticles Attached with Phi29 Polymerase 300 µL, of a stock solution of His-tagged phi29 polymerase (SEQ ID NO:8) (56 µM) which is exonuclease minus (flexible linker: GGGGSGGGGSAAAGSAA, SEQ ID NO:20) (stock solution in: 10 mM Tris (pH 7.5) buffer with 100 mM NaCl, 1 mM DTT, 0.5% Tween-20, 0.1 mM EDTA and 50% v/v glycerol) was buffer exchanged into 100 mM Tris (pH 7.5) buffer with 300 mM NaCl using an NAP-5 column.

C8 Nanoparticles (160 µL, 4.9 µM in 50 mM borate buffer pH 8.0) was concentrated to approximately 30 µL by ultrafiltration (VivaSpin, at 100K MWCOO, and mixed with the buffer exchanged phi29 polymerase (440 µL, 26.9 µM in 100 mM Tris (pH 7.5) buffer with 300 mM NaCl n a 1:15 molar ratio (nanoparticle to polymerase). The resulting solution was incubated overnight at 4° C., concentrated to ~30 µL by ultra-filtration with a 100K MWCO VivaSpin centrifugal concentrator, further purified on SUPERDEX 200 column using 100 mM Tris (pH 7.5) buffer with 300 mM NaCl as the eluent.

The conjugated nanoparticle-phi29 was assayed to determine nucleotide incorporation activity and DNA binding by detecting FRET signals. The incorporation reaction contained: 1× extension buffer, 10 nM nanoparticle-phi29 conjugates (or non-conjugated phi29 as a control), 150 nM oligonucleotide 221, and 20 µM dATP.

The results indicate that phi29 polymerase, attached to nanoparticles, can incorporate nucleotides.

The binding reactions contained: 1× extension buffer, C8 nanoparticles-phi29 conjugates (or phi29 non-conjugated), oligonucleotide 199, and dATP. The binding reactions were serially diluted. The results showed an increase in FRET acceptor signal with an increase in the amount of the labeled oligonucleotide-199, or a decrease in FRET donor signal.

Preparing GST-Nanoparticles Attached with Phi 29 Polymerase

C8 Nanoparticles (50 µL, 3.5 µM in 50 mM borate buffer pH 8.0) was diluted with 100 µL of 100 mM Tris buffer pH 7.5 with 300 mM NaCl and concentrated to ~20 µL by ultrafiltration (VivaSpin, 100K MWCO). The concentrated nanoparticle solution was mixed with His-tagged-GST (184 µL, 19 µM in 50 mM Tris pH7.5 with 200 mM NaCl) in a 1:20 molar ratio (nanoparticle to His-tagged-GST). The resulting solution was incubated at room temperature for 5 hours. Phi29 polymerase (SEQ ID NO:8) (60 µL, 14.5 µM in 100 mM Tris (pH 7.5) buffer with 300 mM NaCl) was added to the nanoparticles in a 5:1 molar ratio (phi29 to nanoparticle). The resulting solution was incubated overnight at 4° C., concentrated to ~30 µL by ultra-filtration with 100K MWCO VivaSpin centrifugal concentrator, purified on a SUPERDEX 200 column using 100 mM Tris (pH 7.5) buffer with 300 mM NaCl as the eluent.

The conjugated GST-nanoparticle-phi29 were assayed to determine template extension activity and DNA binding by detecting FRET signals. The incorporation reaction contained: 1× extension buffer, 10 nM nanoparticle-phi29 conjugates (or non-conjugated phi29 as a control), 150 nM oligonucleotide 221, and 20 µM dATP.

The results indicated that phi29 polymerase, attached to GST-treated nanoparticles, can incorporate nucleotides.

The binding reactions contained: 1× extension buffer, C8 nanoparticles-phi29 conjugates (or phi29 non-conjugated), oligonucleotide 199, and dATP. The binding reactions were serially diluted. The results showed an increase in FRET acceptor signal with an increase in the amount of the labeled oligonucleotide-199, or a decrease in FRET donor signal.

Preparing UDG-Ugi-Nanoparticles Attached with Phi29 Polymerase

His-tagged UDG protein (uracil DNA glycosylase) (500 µL, 27 mM in 30 mM Tris buffer (pH 7.5) with 200 mM NaCl) was mixed ugi (uracil-DNA glycosylase inhibitor) (50 µL, 347 µM in 30 mM Tris buffer (pH 7.5) with 200 mM NaCl) in 1:1.2 molar ratio (His-tagged-UDG to ugi protein), and incubated at 4° C. overnight.

C8 Nanoparticles (140 µL, 4.9 µM in 50 mM borate buffer pH 8.0) was diluted by 200 µL of 100 mM Tris buffer (pH 7.5) with 300 mM NaCl and concentrated to ~30 µL by ultrafiltration (VivaSpin, 100K MWCO). The concentrated nanoparticle solution was mixed with the His-tagged-UDG-ugi protein conjugate (550 µL, 24.7 µM in 30 mM Tris buffer (pH 7.5) with 200 mM NaCl) in a 1:20 molar ratio (nanoparticle to His-tagged-UDG-ugi) to prepare the UDG-ugi-nanoparticles. The resulting solution was incubated at room temperature for 5 hours.

The phi29 polymerase (SEQ ID NO:8) was added (220 µL, 15.4 µM in 100 mM Tris (pH 7.5) buffer with 300 mM NaCl) in a 1:5 molar ratio (UDG-ugi-nanoparticle to phi29). The resulting solution was incubated overnight at 4° C., concentrated to ~30 µL by ultra-filtration with 100K MWCO VivaSpin centrifugal concentrator, and purified on a SUPERDEX 200 column using 100 mM Tris (pH 7.5) buffer with 300 mM NaCl as the eluent.

The conjugated UDG-ugi-nanoparticle-phi29 was assayed to determine template extension activity and DNA binding by detecting FRET signals. The incorporation reaction contained: 1× extension buffer, 10 nM nanoparticle-phi29 conjugates (or non-conjugated phi29 as a control), 150 nM oligonucleotide 199, and 20 µM dATP.

The results showed that phi29 polymerase, attached to UDG/ugi-treated nanoparticles, can incorporate nucleotides.

The binding reactions contained: 1× extension buffer, C8 nanoparticles-phi29 conjugates (or phi29 non-conjugated), oligonucleotide 199, and dATP. The binding reactions were serially diluted. The results showed an increase in FRET acceptor signal with an increase in the amount of the labeled oligonucleotide-199, or a decrease in FRET donor signal.

Preparing BSA-Nanoparticles Attached with Phi29 Polymerase

Bovine serum albumin (BSA) (20 mg, catalog # B4287, Sigma) was dissolved in 2 mL deionized water. The BSA solution (200 µL, 10 mg/mL in H₂O was mixed with DTT (8 µL, 1M), and incubated at room temperate overnight. The resulting solution was purified on an NAP-5 column using deionized water as the eluent.

A1 Nanoparticles (100 µL, 1.0 µM in 50 mM Tris buffer (pH 8)) was diluted by 100 µL of 100 mM Tris buffer (pH 7.5) with 300 mM NaCl and concentrated to ~30 µL by ultrafiltration (VivaSpin, 100K MWCO).

The concentrated nanoparticle solution was mixed with DTT (1.0 µL, 100 mM), and with the above-described BSA solution (27 µL, 75.8 µM in deionized water) in a 1:20 molar ratio (nanoparticle to BSA). The resulting solution was incubated at room temperature overnight, concentrated to ~30 µL by ultra-filtration 100K MWCO VivaSpin centrifugal concentrator.

The concentrated nanoparticle-BSA solution was mixed with the phi29 polymerase (SEQ ID NO:8) (48 µL, 20.8 µM in 100 mM Tris (pH 7.5) buffer with 300 mM NaCl) in a 1:10 molar ration (BSA-nanoparticles to phi29). The resulting solution was incubated overnight at 4° C., concentrated to ~30 µL by ultra-filtration with 100K MWCO VivaSpin centrifugal concentrator, and purified on a SUPERDEX 200 column using 100 mM Tris (pH 7.5) buffer with 300 mM NaCl as the eluent.

The conjugated BSA-nanoparticle-phi29 was assayed to determine template extension activity and DNA binding by detecting FRET signals. The incorporation reaction contained: 1× extension buffer, 10 nM nanoparticle-phi29 conjugates (or non-conjugated phi29 as a control), 150 nM oligonucleotide 229, and 20 µM dATP.

The results showed that phi29 polymerase, attached to BSA-treated nanoparticles, can incorporate nucleotides.

The binding reactions contained: 1× extension buffer, C8 nanoparticles-phi29 conjugates (or phi29 non-conjugated), oligonucleotide 229, and dATP. The binding reactions were serially diluted. The results showed an increase in FRET acceptor signal with an increase in the amount of the labeled oligonucleotide-229, or a decrease in FRET donor signal.

Example 5

Nucleotide Polymerization Using Polymerases Attached to Nanoparticles

Materials

Nanoparticle shapes: A1 are spherical, and A2 and A4 are rod-shaped. The spherical nanoparticles are about 8 nm in diameter, and the rod-shaped ones are about 5×12 nm (width×length). These nanoparticles have ligand coatings which include: L-carnosine; dipeptides (e.g., His-Leu and Gly-His); 4-aminobenzophenone; citric acid; glycine; tris (hydroxymethyl)phosphine; and amino-dPEG24-acid.

The nanoparticles were reacted with HRP, BSA, biotin, and conjugated with one of three different phi29 polymerases: HP1, HP1-Q380A or HP1-S388G.

HP1 is a 6×His-tagged phi29 polypeptide ('6×His' disclosed as SEQ ID NO: 63) which is exonuclease-minus (SEQ ID NO:9). HP1-Q380A is a 6×His-tagged phi29 mutant polypeptide ('6×His' disclosed as SEQ ID NO: 63) which is exonuclease-minus (SEQ ID NO:10). HP1-S388G is a 6×His-tagged phi29 mutant polypeptide ('6×His' disclosed as SEQ ID NO: 63) which is exonuclease-minus (SEQ ID NO:11).

Attaching Nanoparticles Attached with Polymerases

Horseradish peroxidase (HRP; Invitrogen; Cat#01-2001) reduction reaction: 3 mg of HRP was reacted with 150 mg of Cleland's REDUCTACRYL Reagent (VWR; Cat#80056-208) in 600 µl of 50 mM sodium borate buffer, pH 8.2 for 45 minutes at room temperature. The reaction was filtered through a Micro Bio-Spin Empty Column (Bio-Rad; Cat#732-6204). 360 pmol of spherical (A1) or rod-shaped (A2 or A4) nanoparticles (1 eq.) were added in 50 µl of 50 mM sodium borate buffer, pH 8.2 containing 5 µL of 10% BSA (Invitrogen; Cat#P2489) for 1 hour at room temperature. The reaction mixture was concentrated using a VivaSpin 500 100 KDa MWCO ultrafiltration unit (VWR; Cat#14005-008) and washed (5 times) with 50 mM sodium borate buffer (pH 8.2). 3 mg of LC-sulfo-NHS-Biotin (Molecular Biosciences; Cat#00598) was added in 300 µl of 50 mM sodium borate buffer, pH 8.2 for 30 min at room temperature. The reaction was filtered and washed again as above (5 times), diluted with 100 µl of sodium borate buffer containing 300 mM NaCl (final concentration in a final reaction volume). Phi29 polymerase (HP1 or HP1-Q380A (15 eq.) was added and incubated at 4° C. overnight. Reaction mixtures were purified using a SUPERDEX column (VWR; Cat#95017-068) eluting with a borate buffer containing 300 mM NaCl and concentrated to 1-2 µM of conjugation products using VivaSpin 500 100 KDa MWCO filters and centrifugation at 6,000×G.

Assay: Confirming Nanoparticles are Conjugated with Polymerases

Assays were performed to confirm that the phi29 polymerases were attached to the nanoparticles. The assay included 250 nM of ALEXA FLUOR 647 labeled oligonucleotide:

(SEQ ID NO: 64)
(5'-TTATCTTTGTGGGTGACAGGTTTTTCCTGTCACC-3'-ALEXA

FLUOR 647)

and 40 nM of the nanoparticle-polymerase conjugates in 50 mM Tris, 50 mM NaCl and 10 mM $MgCl_2$. The reaction was excited at 450 nm and emission (e.g., FRET) was detected as a ratio of intensities at 605/670 (nanoparticle emission/ALEXA FLUOR 647 emission). Control nanoparticles were reacted with HRP, BSA, biotin, and ALEXA FLUOR 647, but no phi29 polymerase.

The results showed that the control nanoparticles exhibit a higher intensity peak compared to the nanoparticles conjugated with phi29 polymerase and dye-labeled oligonucleotides at the same concentration, and the signal intensity peaks at 670 nm. This demonstrates that the nanoparticles are bound with the phi29 polymerase and with the ALEXA FLUOR 647-labeled oligonucleotide.

Assay: Nucleotide Incorporation

Assays were performed to determine if the polymerases, which are attached to the nanoparticles, could incorporate nucleotides. The assay included 150 nM of a hairpin oligonucleotide, fluorescein-labeled oligo-221:

(5'-TTTTTTTGCAGGTGACAGGTTTTTCCTGT-CACC(fluorescein-T)GC-3') (SEQ ID NO:28), and 40 nM of the nanoparticle-polymerase conjugates, 20 dATP in 50 mM Tris, 50 mM NaCl, and 10 mM $MgCl_2$ buffer. The reaction was excited at 490 nm and emission was detected at 525 nm. Control nanoparticles were reacted with HRP, BSA, biotin, and ALEXA FLUOR 647, and no phi29 polymerase.

The results showed that the control nanoparticles exhibit baseline intensity fluorescence levels compared to nanoparticles bound with phi29 polymerase and dye-labeled oligonucleotides. These results demonstrate that phi29 enzyme conjugated with a nanoparticle retains its nucleotide incorporation activity.

Assay: Nucleotide Incorporation and DNA Extension

Assays were performed to determine if the polymerases, which are attached to the nanoparticles, could polymerize nucleotides. The assay included 50 mM Tris (pH 7.0), 2 mM $MnCl_2$, 62.5-70 mM NaCl (from the various nanoparticle-polymerase conjugate stocks), 0.5% BSA, 1 µM each dNTP, 50 nM duplex (primer Top: 5'-GGTACTAAGCGGCCG-CATG-3' (SEQ ID NO:29) with template C6gOV: 5'-TAAAGCCCCCCCATGCGGCCGCTTAGTACC-3' (SEQ ID NO:30) or template T6gOV: 5'-TAAAGTTTTTTCATGCGGCCGCTTAGTACC-3') (SEQ ID NO:31), and 100 nM of HP1 phi29 polymerase (no nanoparticles), 100 nM A1/HRP-HP1 (A1 spherical nanoparticles conjugated with phi29 polymerase), or 100 nM A4/HRP-HP1 (A4 rod-shaped nanoparticles conjugated with phi29 polymerase). The reaction was initiated with the addition of dNTPs (1 µM) including dA4P labeled at the terminal phosphate group with one ALEXA FLUOR 647, dG4P labeled at the terminal phosphate group with ALEXA FLUOR 680, and dCTP labeled at the nucleo-base with Cy5 dye (GE Healthcare Biosciences; catalog #PA55021). The reaction was quenched with EDTA and analyzed by electrophoresis in a 20% 7M urea denaturing gel followed by fluorescence imaging. The results showed extension products from phi29 polymerase in all three forms (unbound; bound to spherical nanoparticles (A1); and bound to rod nanoparticles (A4)). The results also showed extension products produced by phi29 polymerase, bound to nanoparticles, and incorporating fluorescent dye labeled deoxynucleotide tetraphosphate molecules (dA4P and dG4P).

Assay: Nucleotide Incorporation and DNA Extension

Assays were performed to determine if the polymerases, which are attached to the nanoparticles, could polymerize nucleotides. The assay included 50 mM Tris (pH 7.0), 2 mM $MnCl_2$, 42.5-167.5 mM NaCl (from various nanoparticle-polymerase conjugate stocks), 0.5% BSA, 1 µM each dNTP, 100 nM duplex (primer Top: 5'-GGTACTAAGCGGCCG-CATG-3' (SEQ ID NO:29) with template C6gOV: 5'-TAAAGCCCCCCCATGCGGCCGCTTAGTACC-3' (SEQ ID NO:30) or template A6A: 5'-GGTACTAAGCG-GCCGCATGAAAAAAA-3') (SEQ ID NO:32), and 200 nM of HP1 phi29 polymerase (no nanoparticles) or 200 nM of A2/HRP-HP1 (rod-shaped nanoparticles conjugated with phi29 polymerase). The reaction was initiated with the addition of 1 µM of dNTPs, including dCTP labeled at the nucleo-base with Cy5 dye (GE Healthcare Biosciences; catalog #PA55021) in combination with dG4P labeled at the terminal phosphate group with ALEXA FLUOR 680 or with dGTP. For the A6A template, the reaction was conducted in the presence of dU4P labeled at the terminal phosphate group with ALEXA FLUOR 680 and labeled at the nucleo-base with ALEXA FLUOR 647. The reactions were quenched with EDTA and analyzed by gel electrophoresis in a 20% 7M urea denaturing gel followed by fluorescence imaging. The results showed extension products from phi29 polymerase in four forms: (1) unbound HP1 polymerase, (2) HP1 polymerase bound to A2 rod-shaped nanoparticles (A2-HP1), (3) HP1 polymerase mutant Q380A bound to A2 rod-shaped nanoparticles A2-HP1-Q380A), and (4) HP1 polymerase mutant S388G bound to A2 rod-shaped nanoparticles (A2-S388G-Phi29). The results also showed extension products produced by phi29 polymerase bound to nanoparticles and incorporating deoxynucleotide tetraphosphate molecules (dG4P) and fluorescent-dye labeled deoxynucleotide tetraphosphate molecules (dG4P-Alexa 680).

Detecting FRET Signals in a Single Molecule Assay

Chambered glass cover slips were prepared to facilitate injection and multiple experiments data collection from several chambers using a single slide. The PEG-neutravidin glass coverslips were functionalized as described by Taekjip Ha (2002 Nature 419:638-641) but using neutravidin instead of streptavidin. Duplexes of primer/template strands were prepared by reacting 1 µM of the template and 1 µM of the primer strands in 1× Duplexing buffer (50 mM Tris (pH 7.2), 10 mM NaCl).

Reaction 1:
Primer:

(SEQ ID NO: 33)
5'-TGATAGAACCTCCGTGT-3'

Template:

(SEQ ID NO: 34)
5'-GGAACACGGAGGTTCTATCATCGTCATCGTCATCGTCATCG-3';

-continued

Reactions 2 and 3:
Primer:
(SEQ ID NO: 35)
5'-GGTACTAAGCGGCCGCATG-3'

Template:
(SEQ ID NO: 36)
5'-TTTTACCCATGCGGCCGCTTAGTACC-3';

Reaction 4:
Primer:
(SEQ ID NO: 37)
5'-GGTACTAAGCGGCCGC-dd-3'

Template:
(SEQ ID NO: 38)
5'-TTTTACCCATGCGGCCGCTTAGTACC-3'.

10 nM of the nanoparticles (which were conjugated with phi29 polymerase mutant Q380A) were reacted with 300 nM of the DNA primer/template duplex on ice for 30 minutes in 1× pre-complexing buffer (50 mM Tris (pH 7.2), 100 mM NaCl) in a total volume of 100 µL. This reaction forms the binary complex of nanoparticle/polymerase bound with template/primer.

The binary complex was diluted to a nanoparticle/polymerase (100 µM) and template/primer duplex (3000 µM) to a ratio of 1:30. 100 µL of the diluted binary complex was injected into a chamber and was allowed to immobilize on the PEG-neutravidin surface for 5 minutes. An extension mix was injected and the reaction was allowed to occur for 2 minutes, followed by a 200 µL of EDTA and an oxygen scavenging system containing buffer wash. The extension mix consisted of 50 mM Tris (pH 7.2), 2 mM $MnCl_2$, 100 mM NaCl, 0.5% BSA and natural dNTPs (dGTP) or dye-labeled dNTPs (dG4P labeled at the terminal phosphate group with ALEXA FLUOR 680 and Cy5 base-labeled dUTP) at 1 µM each. The oxygen scavenging system consisted of 50 nM protocatechuate-3,4-dioxygenase, 2.5 mM protocatechuic acid and 1 mM TROLOX (6-Hydroxy-2,5,7,8-tetramethylchroman-2-carboxylic Acid; Hoffmann-La-Roche).

Four separate reactions were performed: Reaction #1 included Cy5 base-labeled dUTP (GE Healthcare Biosciences; catalog # PA55022). Reaction #2 included dGTPs and Cy5 base-labeled dUTP (GE Healthcare Biosciences; catalog # PA55022). Reaction #3 included dG4P labeled at the terminal phosphate group with ALEXA FLUOR 680 and Cy5 base-labeled dUTP (GE Healthcare Biosciences; catalog # PA55022). Reaction #4 included dG4P labeled at the terminal phosphate group with ALEXA FLUOR 680 and Cy5 base-labeled dUTP (GE Healthcare Biosciences; catalog # PA55022), and the primer having a ddG at the 3' end (negative control).

The data were collected on the single molecule detection system, which included an ANDOR back-illuminated EMCCD camera (iXonEM), and an inverted Olympus microscope (IX71), with a 100×TIRF objective. The samples were excited using a 405 nm laser (Coherent; Cat#1069413) at 460 µW, and the data was collected at 100 ms integration time for 2000 frames and 3 to 5 consecutive streams were collected by moving to new fields of views (FOVs). The signals were separated using dichroics (535 nm, 667 nm) before forming an image on the camera.

FRETAN software (Volkov et al., U.S. Ser. No. 11/671,956) was used to obtain donor and acceptor FRET traces. Custom-designed MATLAB scripts were used to extract the data and obtain percent FRET or percent activity data. Only acceptor donor type signals and acceptors with S/N greater than 2 were counted for the percent activity numbers.

Example 6

Preparation of Core-Shell Nanoparticle CdSe/4CdS–3.5ZnS
Core Synthesis

Cores are prepared using standard methods, such as those described in U.S. Pat. No. 6,815,064, the only change being that the growth is halted at 535 nm emission. These cores were precipitated and cleaned in the standard methods and resuspended into hexane for use in the shell reaction.

Shell Synthesis:

A 1:1 (w:v) mixture of tri-n-octylphosphine oxide (TOPO) and tri-n-octylphosphine (TOP) was introduced into a flask. Tetradecylphosphonic acid (TDPA) was added to the flask in an amount suitable to fully passivate the final material, as can be calculated from the reaction scale and the expected final nanoparticle size. The contents of the flask were heated to 125° C. under vacuum and then the flask was refilled with $N_2$ and cooled.

Inside the glovebox, a solution of a suitable cadmium precursor (such as dimethylcadmium or cadmium acetate) in TOP was prepared in a quantity sufficient to produce a desired thickness of shell, as can be calculated by one of ordinary skill in the art. When a zinc shell was also desired, a solution of a suitable zinc precursor (such as diethylzinc or zinc stearate) was prepared in TOP in a quantity sufficient to produce the desired shell thickness. Separately, a solution of trimethylsilylsulfide [$(TMS)_2S$] in TOP was prepared in a quantity sufficient to produce the desired shell thickness. Each of these solutions was taken up in separate syringes and removed from the glove box.

Of the previously prepared core/hexane solution, 17 mL (at an optical density of 21.5 at the band edge) was added to the reaction flask and the hexane was removed by vacuum; the flask was then refilled with $N_2$. The flask was heated to the desired synthesis temperature, typically about 200 to about 250° C. During this heat-up, 17 mL of decylamine was added.

The cadmium and sulfur precursor solutions were then added alternately in layer additions, which were based upon the starting size of the underlying cores. So this means that as each layer of shell material was added, a new "core" size was determined by taking the previous "core" size and adding to it the thickness of just-added shell material. This leads to a slightly larger volume of the following shell material needing to be added for each subsequent layer of shell material.

After a desired thickness of CdS shell material was added, the cadmium precursor solution was replaced with the zinc precursor solution. Zinc and sulfur solutions were then added alternately in layer additions until a desired thickness of ZnS was added. A final layer of the zinc solution was added at the end, the reaction flask was cooled, and the product was isolated by conventional precipitation methods.

Example 7

Exchange Process Using Dipeptide Ligands and Butanol as a Cosolvent

Core/shell nanocrystals (quantum dots) were prepared by standard methods, and were washed with acetic acid/toluene several times, and suspended in hexanes. 10 nmol of core/shell nanocrystals were suspended in 40 mL hexane. This was mixed with 10 mL of a 300 mM solution of carnosine and 10 mL of 1 M sodium carbonate solution. n-Butanol (14 mL) was added, and the vessel was flushed with argon. The mixture was mixed vigorously overnight at room temperature. The mixture was then heated and allowed to cool to room temperature. The aqueous phase was then removed and filtered through a 0.2/0.8 micron syringe filter.

Excess carnosine was removed by dialyzing against 3.5 L of 25 mM NaCl for one hour. The solution was concentrated to 1 mL using a 10K MWCO (10,000 molecular weight cut-off) Amicon centricon. A solution was then prepared with 568 mg of His-Leu dipeptide plus 212 mg of Gly-His dipeptide in 9 mL sodium carbonate solution, and this solution was combined with the aqueous solution of quantum dots. This mixture was stirred overnight at room temperature. The mixture of water-soluble quantum dots was then dialyzed against 3.5 L of 25 mM NaCl for one hour.

To crosslink the peptide ligands (clarify) A solution of 0.5 mM 4-aminobenzophenone in ethanol was then added to the aqueous quantum dots mixture, and the mixture was irradiated at 365 nm for 4 hours to effect reaction of the aminobenzophenone with the surface molecules on the quantum dots. To this, 5 mmol of THP (tris(hydroxymethyl)phosphine) was added, and the mixture was stirred at RT overnight, to induce crosslinking. Another 5 mmol of THP was added, and again the mixture was stirred overnight at RT. Another 5 mmol of THP was added the next day, along with 300 micromoles of PEG1000-COOH. This was mixed overnight at room temperature, then another 5 mmol of THP was added along with 30 mmol of glycine, and the mixture was stirred overnight at RT.

The material was purified by dialysis using the 10K MWCO Amicon centricon, and was washed with 50 mM borate buffer (pH 9). The final material was dispersed into 50 mM borate buffer to a final concentration of 2.5 micromolar for storage.

Example 8

Exchange Process Using Trithiol Ligands

A solution of hydrophobic phosphonate-coated quantum dots in organic solvent (e.g. toluene, chloroform, etc) with a concentration of between about 0.1 and 10 micromolar quantum dots was prepared. Approximately 1000 to 1000000 equivalents of a suitable trithiol ligand was added, optionally as a solution in a suitable organic solvent (e.g. acetone, methanol, etc). The reaction mixture was stirred for 1-48 hours and then the solution was basicified by addition of an organic base (e.g. tetramethylammonium hydroxide, tetrabutylammonium hydroxide, etc). After a shorter second stirring period, water or aqueous buffer was used to extract the dots with hydrophilic ligands. The aqueous solution was washed with additional organic solvent (e.g. toluene, chloroform, etc) and purified by filtration.

Example 9

Two-Step Ligand Exchange: Process for Exchanging Phosphonate Ligands with Sulfonate (Triflate) Ligands A nanoparticle comprising a core/shell nanocrystal having TDPA ligands on its surface is dissolved in dichloromethane, and excess TMS triflate is added to it. After 1-2 hours at room temperature, analysis indicates that the TDPA ligands have been removed, and the nanoparticle remains dispersed in the solvent. It is dialyzed against dichloromethane using a 10K MWCO (10,000 molecular-weight cut-off) dialysis membrane to remove excess TMS triflate and the TMS-TDPA produced by the reaction of TMS triflate with the TDPA ligands. This produces a solution/suspension of nanoparticles comprising triflate ligands on the surface of nanocrystals. These triflate-containing nanoparticles are soluble in many organic solvents, but may not be readily soluble in hexanes, depending upon the complement of ligands present.

Two-Step Process for Exchanging Sulfonate (Triflate) Ligands with PEG Conjugated Dithiol (DHLA) Ligands Using n-Butanol as an Intermediate Ligand and DMF as a Co-Solvent The triflate-containing nanoparticle solution, described above, can be contacted with excess n-butanol in acetonitrile, using DMF as a co-solvent, to provide an intermediate nanoparticle believed to comprise butanol ligands in place of the triflates which were on the nanoparticle. This intermediate nanoparticle can be isolated from the medium, or it can be further modified without isolation. This intermediate nanoparticle is contacted with an excess of a dihydrolipoic acid-PEG conjugate of this formula:

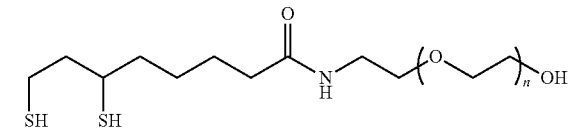

where n is 1-100.

The product is a water-soluble, stable nanoparticle. It can be collected by extraction into a pH 9 buffer, and isolated by conventional methods, including dialysis with a 10K MWCO dialysis filter, or by size exclusion (gel filtration) chromatography.

Two-Step Process for Exchanging Sulfonate (Triflate) Ligands with Nucleophilic Reactant Group Containing Ligands Using n-Butanol as an Intermediate Ligand and DMF as a Co-Solvent The triflate-containing nanoparticle solution from can be contacted with excess n-butanol in acetonitrile, using DMF as a co-solvent, to provide an intermediate nanoparticle believed to comprise butanol ligands in place of the triflates which were on the nanoparticle. This intermediate nanoparticle can be isolated from the medium, or it can be further modified without isolation. To further modify it, it is treated with a new ligand containing at least one nucleophilic reactant group: suitable ligands include HS—$CH_2$—$CH_2$—PEG; aminomethyl phophonic acid; dihydrolipoic acid; omega-thio-alkanoic acids, and carboxymethylphosphonic acid. The mixture is then treated with TMEDA (tetramethylethylene diamine), and monitored until triflate is displaced, then the nanocrystal product is extracted into pH 9 buffer and purified by conventional methods.

Process for Exchanging Sulfonate (Triflate) Ligands with Carboxylate Functionalized Dithiol (DHLA) Ligands The triflate-containing nanoparticle is contacted with neat dihydrolipoic acid (DHLA) for an hour at room temperature, and is then dispersed into pH 9 buffer and isolated by conventional methods. This provides a nanoparticle having carboxylate groups to provide water solubility, and having two thiol groups binding the carboxylate to the nanocrystal surface. The product is water soluble and stable in aqueous buffer. It provides good colloidal stability, and a moderate quantum yield. This composition containing DHLA as a ligand contains free carboxyl groups which can be used to attach other groups such as a PEG moiety, optionally linked to a functional group or a biomolecule. The same reaction can be performed to replace triflate groups on a nanoparticle with thioglycolic acid (HS—CH$_2$—COOH) ligands. This provides a highly stabilized nanoparticle which produces a high quantum yield, but has lower colloidal stability than the product having DHLA on its surface.

Process for Exchanging Sulfonate (Triflate) Ligands with Amine Ligands

The triflate-containing nanoparticle is dispersed in dichloromethane plus hexanes, and an alkylamine is added. Suitable alkylamines are preferably primary amines, and include, e.g., H$_2$N—(CH$_2$)$_r$—PEG (r=2-10), p-aminomethylbenzoic acid, and lysine ethyl ester. After an hour at room temperature, the exchange process is completed, and the nanoparticle product can be isolated by conventional methods.

Process for Pre-Treating Phosphonate Coated Nanocrystals with Toluene Acetic Acid to Remove Impurities Prior to Exchanging with Sulfonate (Triflate) Ligands TDPA-covered nanocrystals were synthesized which emitted light at 605 nm and had shells of CdS and of ZnS. These when treated with 200,000 equivalents of TMS triflate in hexanes did not produce a precipitate. This was attributed to excess TDPA-derived impurities in the nanocrystals. This was alleviated by dissolving the nanocrystals in toluene-acetic acid and precipitating them with methanol, to remove TDPA salts or related by-products. The resultant TDPA nanocrystals behaved as described above, demonstrating that impurities were causing the nanocrystals to behave differently when made with excess TDPA present, and that those impurities can be removed by precipitation under conditions better suited to dissolving TDPA-related impurities.

Process for Exchanging Activated (Sulfonate Coated) Nanocrystals with Dithiol (DHLA) Ligands Using Butanol, DMF or Isopropyl Alcohol as Dispersants Three different methods of depositing the DHLA ligands were employed, each of which was considerably more rapid than the classic approach using non-activated dots. In the first approach, the activated dot powder was dispersed in butanol and stirred with DHLA, then precipitated with hexane and collected in aqueous buffer. In the second approach, the activated dot powder was dispersed in dimethylformamide (DMF) and stirred with DHLA, then precipitated with toluene and collected in aqueous buffer. In the third approach, the activated dot powder was stirred as a slurry in neat DHLA, then dispersed in isopropyl alcohol, precipitated with hexane, and collected in aqueous buffer and purified with a filtration membrane.

These three samples, plus a sample derived from non-activated dots were diluted to 60 nM for a colloidal stability challenge, wherein the absorbance is monitored over the course of days to watch for precipitation. Samples 1 (butanol-mediated), 2 (DMF-mediated), and 4 (classic) all precipitated on day 3 or 4 of the stability challenge, but sample 3 (neat DHLA) lasted twice as long, coming out of solution on day 7. HPLC measurements indicated that the DHLA-coated particles produced from activated dots showed even less aggregation than the classic DHLA particles made by the displacement of TOPO or pyridine ligands from nanocrystals. Thus the invention provided rapid reactions leading to improved colloidal stability and comparable or lower aggregation levels than conventional ligand replacement methods of putting DHLA on a nanocrystal. Similar treatment with other thiol ligands like mercaptoundecanoic acid (MUA) or the PEGylated thiol also provided water-dispersible nanocrystals. Reacting triflate-coated nanoparticles with MUA or PEG-thiol gave particles which were readily dispersible in water, indicating that ligand exchange had occurred. The observed quantum yield was over 70% in each case.

Process for Exchanging Activated (Sulfonate Coated) Nanocrystals with Hydrophilic Phosphonate Ligands Triflate-coated dots were dispersed in butanol and then stirred with phosphonoacetic acid. Triethylamine was added to form the triethylammonium salt of both the phosphonate and carboxylate functionalities, and then pH 9 aqueous borate buffer was added to extract the hydrophilic particles. The result was a bright orange aqueous dispersion of quantum dots, with no remaining color observed in the butanol layer. The particles were purified by centrifugal filtration and the quantum yield was measured to be 72%. Multiple batches of particles were prepared and remained in solution through room temperature storage for at least eight weeks. The same method can be successfully employed with DHLA, MUA, and PEGylated thiol ligands.

Process for Exchanging Activated (Sulfonate Coated) Nanocrystals with a Variety of Hydrophilic Phosphonate Ligands Via Biphasic Exchange Using a biphasic exchange method, dispersing the quantum dots in organic solvents such as chloroform and the exchangeable ligands in aqueous solution, quantum dots were made water soluble and stable after ligand exchange with N,N-Bis(phosphonomethyl)glycine (1) or phosphonoacetic acid (2). In a typical bi-phasic ligand exchange experiment, 1 nmol of quantum dots were dispersed in 1 mL of chloroform and placed in a vial with 2 mL of 300 mM phosphonic acid in basic buffer and the mixture was rapidly stirred at room temperature for 2 days. Quantum yields as high as 53% were achieved; however the quantum yields achieved were dependent on core-shell batch employed, probably as a result of variable amounts of long-chain alkyl phosphonates remaining on the nanocrystal surface post-ligand exchange. This demonstrated that complete removal of TDPA from nanocrystals is important for successful modification of the surface. Though the dots were rendered water stable by the above phosphonate-containing ligands, they were not successfully modified with PEG2000-diamine using standard EDC condensation chemistry.

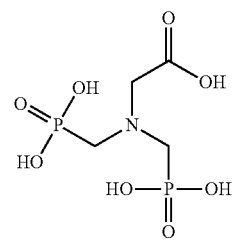

1

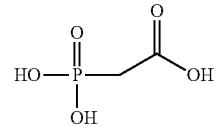

2

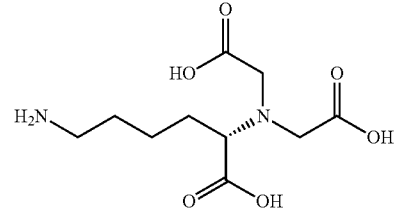

3

Nanocrystals coated with compounds 1, 2, or 3 were readily prepared by this method, as well as nanocrystals having a mixture of compounds 1 and 2, or 1 and 3, or 2 and 3. In each case, the nanocrystals were stable, bright and water-soluble. Using mixed ligands, it was found that PEGylation (with PEG2000-diamine using standard EDC condensation chemistry) could be achieved with these phosphonate-containing ligands to produce highly stable, bright, water soluble nanoparticles. These nanoparticles can be further stabilized by at least partially cross-linking the ligands using a diamine such as putrescine, cadaverine, 1,2-diaminoethane, bis(hexamethylene)triamine, PAMAM dendrimer, and cystamine.

Two-Step Ligand Exchange Process with Tridentate Thiol Ligands

Triflate exchange step was performed following the procedure described above. Next, the triflate nanoparticles were dispersed in organic solvent (e.g. toluene, chloroform, etc) with a concentration of between about 0.1 and 10 micromolar quantum dots. Approximately 1000 to 1000000 equivalents of a suitable tridentate thiol ligand was added, optionally as a solution in a suitable organic solvent (e.g. acetone, methanol, etc). The reaction mixture was stirred for 1-48 hours and then the solution was basicified by addition of an organic base (e.g. tetramethylammonium hydroxide, tetrabutylammonium hydroxide, etc). After a shorter second stirring period, water or aqueous buffer was used to extract the dots with hydrophilic ligands. The aqueous solution was washed with additional organic solvent (e.g. toluene, chloroform, etc) and purified by filtration.

Example 10

Functionalized Ligands on Nanoparticles
General Core Reaction Procedure

Into a 25 mL 3 neck flask with 14/20 joints, 1.575 g of >99% tri-n-octylphosphine oxide (TOPO) was weighed. To this, 1-1000 micromoles of a bi-functional phosphonate ligand was added. A stir bar was added to this flask. The flask was connected to an inert atmosphere manifold and evacuated thoroughly, then refilled with nitrogen. A solution of a suitable cadmium salt in tri-n-octylphosphine (TOP) was prepared with a concentration of 0.5 mol Cd per kg solution. A desired amount of cadmium as required for growth of nanoparticles of a desired size was extracted from this solution, diluted with 0.9 mL of additional TOP, and added to the flask. The flask was stirred and heated to ~200-350° C. under nitrogen flow. A 1 molar solution of selenium in TOP was prepared and a desired amount as required for growth of nanoparticles of a desired size was added to the solution, optionally with addition of a reaction promoter to achieve desired levels of particle nucleation. One minute after the reaction was initiated by adding these final reagents, a 20 microliter sample was removed from the reaction, mixed with 5 mL of hexane, and an emission spectrum was collected. This aliquot removal and measurement process was repeated after 2, 3, 4, 5, 6, 7, 8, 10, 12, and 14 minutes. After 14 minutes, the reaction was rapidly cooled and the products were isolated by methods understood in the art.

Control Core Reaction with Tetradecylphosphonic Acid [TDPA]

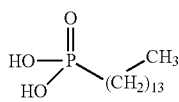

TDPA

The core reaction using TDPA as the phosphonate ligand was demonstrated as a control reaction. This reaction proceeded with an initial emission reading at 1 minute of ~490 nm and progressing to a final emission reading of ~544 nm at 14 minutes. The full width at half maximum intensity (FWHM) never got above 28 nm. The final "growth solution" of the cores was yellow/light orange in appearance by eye. The aliquoted samples of this reaction remained dispersed and clear solutions in hexane.

Core Reaction with 11-methoxy-11-oxo-undecylphosphonic acid

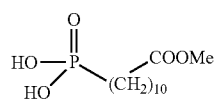

The reaction using 11-methoxy-11-oxo-undecylphosphonic acid as the phosphonate ligand proceeded with an initial emission reading at 1 minute was ~560 nm; this was redder than the final emission of the control reaction. The final emission of this reaction was ~610 nm. The FWHM of this reaction started at ~35 nm and steadily got more broad throughout the reaction for a final FWHM of ~50 nm.

The aliquoted samples were not soluble in hexane, and became almost instantly flocculated and settled to the bottom of the vials within minutes.

Core Reaction with 6-ethoxy-6-oxohexylphosphonic acid

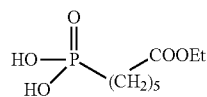

The core reaction using 6-ethoxy-6-oxohexylphosphonic acid as the phosphonate ligand had an initial emission reading at 1 minute of ~560 nm and a final emission reading of ~606 nm. The FWHM of this reaction started out at 1 minute at ~43 nm and narrowed to a final FWHM of ~40.5 nm.

The solubility of the aliquoted samples was observed. The hexane samples were immediately cloudy, however the flocculation did not settle to the bottom of the vials. Six of the aliquoted samples were centrifuged and the resulting clear, colorless supernatants were discarded. The pellets were soluble in toluene, dichloromethane ($CH_2Cl_2$), dimethylformamide (DMF), and methanol (MeOH). The pellets were not soluble in water, 50 mM borate buffer at pH=8.3 or hexane.

Particles synthesized in the presence of TDPA are soluble in hexane, toluene, $CH_2Cl_2$, DMF and hexane. The 6-ethoxy-6-oxohexylphosphonic acid itself is not soluble in hexane, and neither were the resulting particles from this reaction, suggesting that the ligand was indeed coating the nanoparticles—a suggestion which was confirmed with infrared and NMR spectroscopy indicating the expected ester functionality. Using a solvent system of toluene as the solubilizing solvent and hexane as a precipitating solvent, a pellet can be formed along with a clear, colorless supernatant. The resulting pellet can be re-solubilized in toluene.

This resulting toluene solution allowed an absorbance spectrum of these cores to be obtained.

These data suggest that quantum confined nanoparticles have been formed with 6-ethoxy-6-oxohexylphosphonic acid on the particle surface. The resulting core particles were taken further into a shell reaction.

Shell Reaction Procedure Using
6-ethoxy-6-oxohexylphosphonic acid

Core Precipitation

Three (3) mL of growth solution cores using 6-ethoxy-6-oxohexylphosphonic acid ligand (prepared according to the procedure of Example 4) was solubilized into 3 mL toluene in a 250 mL conical bottom centrifuge tube. A total of 135 mL of hexane was added to precipitate the cores. The tube was centrifuged at 3000 RPM for 5 min. The resulting clear, colorless supernatant was discarded and the pellet was dispersed into 3 mL of toluene.

Shell Reaction

Into a 25 mL 3 neck flask with 14/20 joints, 1.4 g of TOPO was weighed. To this, 1-1000 mg of 6-ethoxy-6-oxohexylphosphonic acid was added. A stir bar and 1.4 mL of TOP were added to the flask. The flask was connected to an inert atmosphere manifold and evacuated thoroughly, then refilled with nitrogen. 2.6 mL of the toluene solution of cores was added to the flask and the flask was warmed and evacuated to remove the toluene, then refilled with nitrogen. Approximately 1 mL of a suitably high-boiling amine was added to the flask and the flask was heated to 200-350° C. Solutions of suitable cadmium and zinc precursors in TOP were prepared with a concentration of 0.5 mol metal ion per kg of solution. A solution of 10% trimethylsilylsulfide in TOP by weight was prepared as well. The metal and sulfur precursor solutions were added slowly over the course of several hours to minimize additional nanoparticle nucleation. Sufficient shell precursors were added to grow a shell of a desired thickness, as can be calculated by one of ordinary skill in the art. When the desired shell thickness was reached, the reaction was cooled and the core/shell nanoparticles were isolated by conventional means. Aliquots taken during the reaction permitted monitoring of the progress of the shell reaction. It was observed that the emission maximum after heating but before addition of shell precursors was very similar to that of the initial cores (~600 nm), suggesting that the bi-functional phosphonate was sufficiently strongly coordinated to the nanoparticle surface to minimize Ostwald ripening. A red-shift during shell precursor addition of ~50 nm was typical of a shell as deposited in a reaction employing TDPA, suggesting that the shell formed as expected. In addition, the nanoparticle solution became much more intensely emissive, as would be expected of successful deposition of an insulating shell. Infrared and NMR spectroscopy confirmed that the functionalized phosphonates were present on the nanoparticles.

Example 11

Conjugates of Active Polymerase and Nanocrystals
Preparing Phi29 Polymerase Conjugated with UDG-Ugi-C8 Nanoparticles His-tagged UDG protein (uracil DNA glycosylase) (2.02 mL, 53.4 µM in 30 mM Tris buffer (pH 8) with 200 mM NaCl, 0.5 mM EDTA and 1 mM DTT) was mixed with ugi (uracil-DNA glycosylase inhibitor) (748 µL, 173 µM in 10 mM Tris (pH 7.5) buffer with 100 mM NaCl, 4 mM DTT, 0.5% v/v Tween-20, 0.1 mM EDTA and 50% v/v glycerol) in 1:1.2 molar ratio (His-tagged-UDG to ugi protein), and incubated at 4° C. overnight. The resulting His-tagged-UDG-ugi protein complex was stored at 4° C. without further purification for future use.

C8 Nanoparticles (100 µL, 5.3 µM in 50 mM borate buffer pH 8 with 1.0 M Betaine which is frozen at -20° C. immediately after synthesis) was thawed and mixed with the His-tagged-UDG-ugi protein complex (132 µL, 40.0 µM in 30 mM Tris buffer (pH 8) with 200 mM NaCl, 0.5 mM EDTA and 1 mM DTT) and 389 µL of 100 mM Tris (pH 7.5) buffer with 300 mM NaCl and 1 mM DTT in a 1:10 molar ratio (nanoparticle to His-tagged-UDG-ugi). The solution was incubated for 1 hour at 4° C. The resulting UDG-ugi-nanoparticles solution was mixed with stock His-tagged HP1-Phi29 mutant polymerase (SEQ ID NO:9) (115 µL, 46 µM in 10 mM Tris (pH 7.5) buffer with 100 mM NaCl, 4 mM DTT, 0.5% v/v Tween-20, 0.1 mM EDTA and 50% v/v glycerol) in a 1:10 molar ratio (nanoparticle to polymerase). The conjugation solution was incubated overnight at 4° C., centrifuged for 5 minutes at 16.8K rcf, purified on $Ni^{2+}$-NTA Agarose column using 100 mM Tris (pH 7.5) buffer with 300 mM NaCl and 1 mM DTT as the eluent. The purified conjugate solution was centrifuged for 5 minutes at 16.8K rcf, transferred into a 10K MWCO dialysis cassette, then dialyzed into 50 mM Tris buffer pH7.5 with 150 mM NaCl, 0.2 mM EDTA, 0.5% v/v Tween-20, 5 mM DTT and 50% v/v glycerol. The resulting UDG-ugi-nanoparticle-HP1-Phi29 conjugate was assayed to determine concentration, template extension activity, and active number of Phi29 per conjugate and DNA binding by FRET signal detection (see Table 1 below).

TABLE 1

| Conjugate | Activity |
| --- | --- |
| C8-UDG-ugi-HP1 Phi29 mutant | 0.50 base/sec/conj |
| Stock HP1 Phi29 mutant | 0.10 base/sec/enz |

The FRET signals from the mutant Phi29-nanoparticle conjugate binding to oligonucleotide 199 labeled at the 3' end with ALEXA FLUOR 647 (conjugate and C8 dot concentration: 10 nM; AF647-3'-oligo 199 concentration: 1000 nM) were compared to non-conjugated C8 nanoparticles. The 605/670 ratio is the fluorescence intensity at 605 nm divided by fluorescence intensity at 670 nm with 450 nm excitation for both the conjugate and the unconjugated C8 nanoparticles. The low 605/670 ratio for the conjugate indicated the conjugate binding to the dye labeled oligo and showing FRET signal.

Figures 9A, 9B:
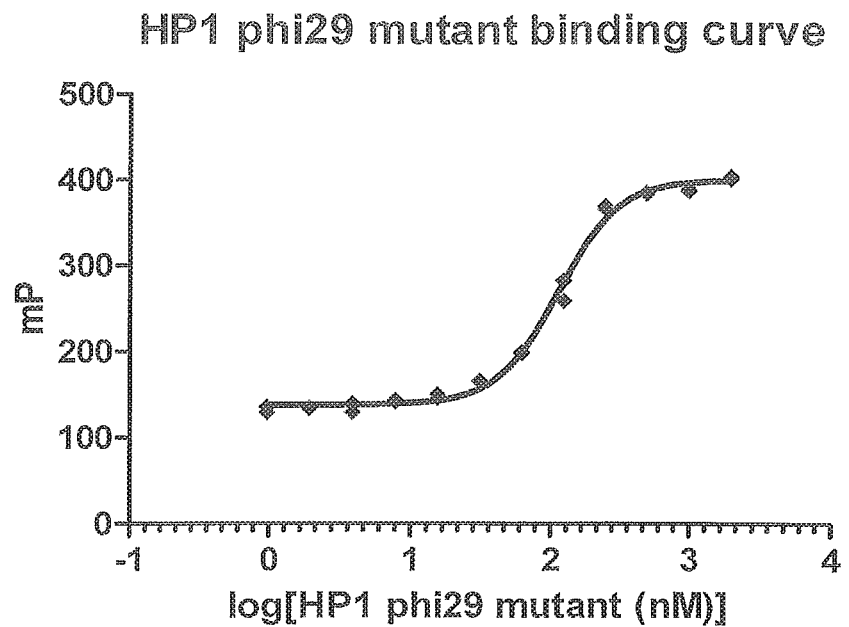
FIG. 9A is a graph showing the binding curve of labeled oligonucleotides binding to UDG-ugi-C8 nanoparticle-HP1-phi29 polymerase conjugates. In this graph, mP is millipolarization units.
FIG. 9B is a mathematical equation that describes the binding curve shown in FIG. 9A, and was used to calculate the number of active phi29 polymerases per nanoparticle. The concentration of the nanoparticles contained in the polymerase-nanoparticle conjugates is known, but the number of phi29 polymerases (X) per nanoparticle is unknown.

The active number of polymerases per conjugate for C8-UDG-ugi-HP1 Phi29 mutant conjugate are shown in FIGS. 9A, B and C.

Preparing B103 Polymerase Conjugated with UDG-Ugi-C8 Nanoparticles

His-tagged UDG protein (uracil DNA glycosylase) (2.02 mL, 53.4 µM in 30 mM Tris buffer (pH 8) with 200 mM NaCl, 0.5 mM EDTA and 1 mM DTT) was mixed with ugi (uracil-DNA glycosylase inhibitor) (748 µL, 173 µM in 10 mM Tris (pH 7.5) buffer with 100 mM NaCl, 4 mM DTT, 0.5% v/v Tween-20, 0.1 mM EDTA and 50% v/v glycerol) in 1:1.2 molar ratio (His-tagged-UDG to ugi protein), and incubated at 4° C. overnight. The resulting His-tagged-UDG-ugi protein complex was stored at 4° C. without further purification for future use.

C8 nanoparticle s (100 µL, 4.5 µM in 50 mM borate buffer pH 8.0 with 1.0 M Betaine which were frozen at ~20° C.

immediately after synthesis) was thawed and mixed with stock His-tagged HP1-B103 polymerase (SEQ ID NO:4) (40.5 µL, 111 µM in 10 mM Tris (pH 7.5) buffer with 100 mM NaCl, 4 mM DTT, 0.5% v/v Tween-20, 0.1 mM EDTA and 50% v/v glycerol) and 309 µL of 100 mM Tris (pH 7.5) buffer with 300 mM NaCl and 1 mM DTT in a 1:10 molar ratio (nanoparticle to polymerase). The conjugation solution was incubated overnight at 4° C. The resulting B103 polymerase-C8 nanoparticle conjugate was mixed with the His-tagged-UDG-ugi protein complex (112 µL, 40.0 µM in 30 mM Tris buffer (pH 8) with 200 mM NaCl, 0.5 mM EDTA and 1 mM DTT) in a 1:10 molar ratio (nanoparticle to His-tagged-UDG-ugi). The mixture was incubated for 5 hours at 4° C. to prepare the UDG-ugi-nanoparticle s-B103 conjugate. The resulting conjugate solution was centrifuged for 5 minutes at 16.8K rcf, purified on $Ni^{2+}$-NTA agarose column using 100 mM Tris (pH 7.5) buffer with 300 mM NaCl and 1 mM DTT as the eluent, centrifuged and transferred into a 10K MWCO dialysis cassette. The conjugate was dialyzed into 50 mM Tris buffer pH 7.5 with 150 mM NaCl, 0.2 mM EDTA, 0.5% v/v Tween-20, 5 mM DTT and 50% v/v glycerol. The resulting UDG-ugi-nanoparticle-HP1-B103 conjugate was assayed to determine concentration, template extension activity, active number of Phi29 per conjugate and DNA binding by FRET (see Table 2 below).

TABLE 2

| Conjugate | Activity |
|---|---|
| C8-HP1 B103 -UDG-ugi | 1.41 base/sec/conj |
| Stock HP1 B103 | 0.41 base/sec/enz |

The FRET signals from the B103-nanoparticle conjugate binding to oligonucleotide 199 labeled at the 3' end with ALEXA FLUOR 647 (conjugate and C8 dot concentration: 10 nM; AF647-3'-oligo 199 concentration: 1000 nM) were compared to non-conjugated C8 nanoparticles. The 605/670 ratio is the fluorescence intensity at 605 nm divided by fluorescence intensity at 670 nm with 450 nm excitation for both the conjugate and the unconjugated C8 nanoparticles. The low 605/670 ratio for the conjugate indicated the conjugate binding to the dye labeled oligo and showing FRET signal.

Figures 10A, 10B:
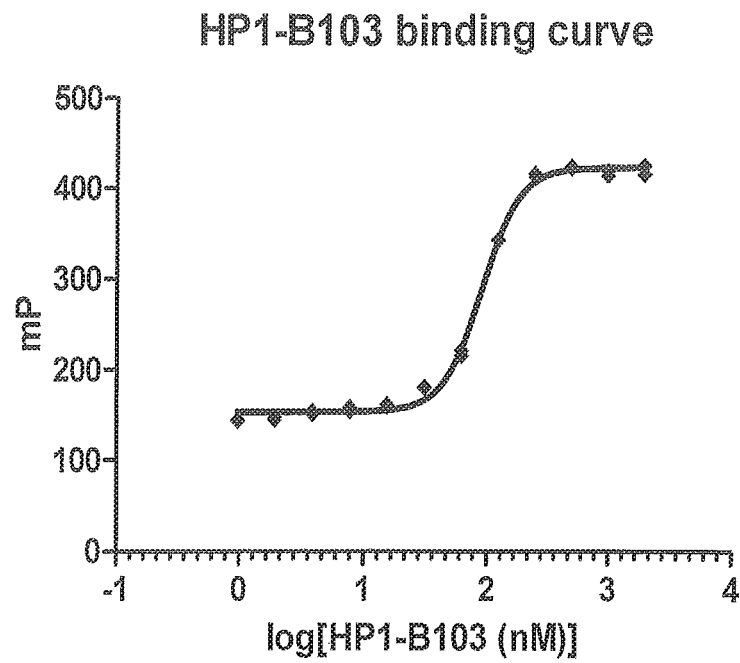
FIG. 10A is a graph showing the binding curve of labeled oligonucleotides binding to UDG-ugi-C8 nanoparticle-HP1-B103 polymerase conjugates. In this graph, mP is millipolarization units.
FIG. 10B is a mathematical equation that describes the binding curve shown in FIG. 10A, and was used to calculate the number of active B103 polymerases per nanoparticle. The concentration of the nanoparticles contained in the polymerase-nanoparticle conjugates is known, but the number of B103 polymerases (X) per nanoparticle is unknown.

Active number of polymerase per conjugate for C8-HP1 B103-UDG-ugi conjugate are shown in FIGS. 10A, B and C.

Example 12

FRET Detection of Incorporated Nucleotides Using Polymerase-Dye Conjugates
Preparing PEG-Biotin Surfaces:
Glass coverslips surfaces were plasma cleaned and treated with a mixture of poly-ethyleneglycol (PEG) and biotin-PEG to produce a low density biotin surface with a PEG coating to prevent non-specific background of proteins and macromolecules.
Fluidic Chamber Assembly:
Fluidic cassettes were assembled with glass coverslips to create fluidic chambers capable of containing approximately 2 µl of fluid.
Attaching Biotinylated DNA to Low Density PEG-Biotin Surfaces:
Streptavidin protein was diluted to 200 pM in Incubation Buffer (50 mM NaCl; 50 mM Tris-Cl pH=7.5; 0.5% BSA). Diluted streptavidin was flowed into fluidic chamber and streptavidin was incubated for 10 minutes. Chambers were washed 1× with 1 ml Incubation Buffer. Biotinylated-DNA templates were diluted to 200 pM in Incubation Buffer and allowed to bind for 5 minutes. Surfaces were washed 1× with 1 ml Incubation Buffer.
SA-Polymerase Preparation:
Streptavidin was labeled with Cy3 (Life Technologies). Streptavidin-Cy3 was mixed with a biotinylated mutant Phi29 (b-Phi29)(SEQ ID NO:12) at a 1:1 ratio of SA-protein:biotinylated-Phi29 in 1×PBS.
SA-Cy3-b-Phi29 Binding to Templates:
SA-Cy3-b-Phi29 was diluted to 1 nM in binding buffer (50 mM Tris-Cl; pH=7.5; 0.3% BSA; 100 mM NaCl). Conjugates were flowed into fluidic chamber which were previously loaded with DNA templates on the surface. Surfaces were incubated for 5 minutes with 1 nM SA-Cy3-b-Phi29. Surfaces were washed with 1×1 ml Incubation Buffer.
Fluorescence Imaging:
The Olympus microscope body was outfitted with a TIRF objective lens (100×; 1.45 NA). The excitation light passes through an excitation filter (EX FT—543/22), and dichroic mirror (DM—532) and the sample is epi-illuminated (Coherent) using TIR at typically 100 W/cm². Upon excitation, resulting epifluorescence emission passes an emission filter (EM FT—540LP) and the resulting emission is split into three paths (triview) using 2 dichroic mirrors and the appropriate bandpass filters for the dye sets of choice. The emission was imaged on a CCD camera. Images were collected at a frame rate of approximately 30 ms. Images depict single DNA strands complexed with single SA-Cy3-b-Phi29 conjugates (donor molecules in this example) and FRET signals from acceptor species (hexaphosphate nucleotides labeled with ALEXA FLUORE 647, 676 or 680) bound in the enzyme active site.
Nucleotide Polymerization with SA-DonorDye-Phi29 or B103 Conjugates:
Homopolymer Template Sequence:
Hexa-phosphate dye-labeled nucleotides were diluted to 200 nM in extension buffer. (50 mM MOPS pH=7.1; 75 mM potassium acetate (pH=7.0); 0.3% BSA; 1 mM $MnCl_2$; 300 nM procatuate dioxygenase; 4 mM 3,4 dihydroxyl benzoic acid; 1 mM 2-nitrobenzoic acid; 400 mM 1,2 phenylenediamine; 100 mM ferrocene monocarboxylic acid; 0.02% cyclooctratetraene; 6 mM Trolox). Nucleotide mix was flowed into channel with SA-Cy3-b-Phi29 or SA-Cy3-b-B103 (SEQ ID NO:5) bound to DNA template and images were recorded for approximately 2 minutes at approximately 20 ms frame rates.

As one example, the DNA template sequence extends with the following sequence $(G)_{15}(A)_{15}(G)_{15}(A)_{15}$ (SEQ ID NO:39). Using 200 nM hexaphosphate-nucleotide 647-dGTP and 200 nM hexaphosphate-nucleotide 676-dATP, patterns were identified with spectral signatures for 647 dye emission (G signal) preceding spectral signatures for 676 dye emission (e.g. the A signal) which resulted from fluorescence resonance energy transfer (FRET) from the donor molecule SA-Cy3-b-Phi29, or SA-Cy3-b-B103.
Random Template Sequence:
Hexa-phosphate nucleotides which were dye-labeled at the terminal phosphate group were diluted to 200 nM in extension buffer. (50 mM MOPS pH=7.1; 75 mM potassium acetate (pH=7.0); 0.3% BSA; 1 mM $MnCl_2$; 300 nM procatuate dioxygenase; 4 mM 3,4 dihydroxyl benzoic acid; 1 mM 2-nitrobenzoic acid; 400 mM 1,2 phenylenediamine; 100 mM ferrocene monocarboxylic acid; 0.02% cyclooctratetraene; 6 mM Trolox). Nucleotide mix was flowed into channel with SA-Cy3-b-Phi29 bound to DNA template and images were recorded for approximately 2 minutes at approximately 20 ms frame rates. The DNA template sequence extended with the following sequence:
Random Oligonucleotide:

(SEQ ID NO: 40)
5'-TTGAACGGATGAGGACCAGACACCACTTGAACGGATGAGGAAAAAA
AAAATCA-3'.

Using 200 nM hexaphosphate-647-dGTP and 200 nM hexaphosphate-676-dATP, 2 µM dCTP and 2 µM dTTP, patterns were identified with spectral signatures for 647 dye emission (G signal) and 676 dye emission (A signal) which resulted from fluorescence resonance energy transfer (FRET) using SA-Cy3-b-Phi29 or SA-Cy3-b-B103 as the donor molecule, respectively.

Analysis of Homopolymer Sequencing Results.

The resulting pattern sequencing data acquired using the methodologies described in Example 12 herein was processed. The subsequent detected FRET events were filtered and sequences were aligned.

In one exemplary experiment, 200 nM hexaphosphate-647-dGTP and 200 nM hexaphosphate-676-dATP was used along with SA-Cy3-b-Phi29 as the donor molecule. The alignment algorithm found 55 molecules in the field of view, which clearly demonstrated the completion of at least 30 base pairs of the full 60 base pair sequence. As a result, the number of events detected for the first 15 G insertions was approximately 15 and the number of events for the subsequent 15 A insertions was approximately 15.

In another exemplary experiment, 200 nM hexaphosphate-647-dGTP and 200 nM hexaphosphate-676-dATP was used along with SA-Cy3-b-B103 as the donor molecule.

Analysis of Random Sequencing Results.

Resulting pattern sequencing data acquired using the methodologies described in Example 13 herein was processed. The subsequent detected FRET events were filtered and sequences were aligned. Results are represented by the aligning the sequence, whereby light gray blocks represents the G insertion signals and dark gray indicates A insertion signals. The alignment algorithm found 95 molecules in the field of view, which demonstrated the matching of detected events with the actual sequence.

Enzyme Kinetics and Extension Speeds for Polymerase Conjugates:

Using the conditions and template described above in the homopolymer sequence example, various SA-Cy3-labeled mutant polymerase conjugates were tested to determine on-chip single molecule kinetics and extension speeds.

Distributions of the start times were shown for all of the events from all of the molecules which were successfully aligned with the algorithm from their respective blocks, whereby a block refers to 1 of the 4 homopolymer stretches. This analysis demonstrates the nearly uniform extension speed of the population of SA-Cy3-polymerase conjugates. In addition, the distributions for event duration from each of the blocks for all of molecules with correct sequence alignment was also determined and found to provide strong correlation with stopped-flow experiments.

Example 13

Analysis of Fluorescence Data to Extrapolate Sequence Information

To convert the observed fluorescence emissions detected during the nucleotide incorporation reaction into nucleotide sequence information, the raw data comprising a movie of observed emissions was first processed by using a Hidden Markov Model (HMM)-based algorithm to detect and identify FRET events. The subsequent detected FRET events were filtered and filtered sequences were aligned. Each of these two steps, FRET event detection and sequence analysis, are described in more detail below. The HMM-based algorithm was used to analyze the data in Example 14 below.

Detection of FRET Events

The analysis underlying FRET event detection is designed to process spatially correlated movie(s) comprising real time sequence fluorescence emission data, and extract time-series of interest from those data. A movie typically contains one or more channels where each channel represents the same spatial location at different wavelengths. The analysis chain begins with the submission of one or more movies to the analysis machine via a comprehensive user interface. The user interface requires the user to input various parameters which describe the movie(s) (e.g. channel regions, dye emission properties). Once this data is submitted the movie(s) are then processed by the image analysis software where a sliding window of N frames propagates through the movie calculating a temporal local average of the frames within the window. At each position of the window in the movie, the local average image is then further processed and enhanced using well known image processing algorithms and a record of the maximum projection of all the local average images is recorded to produce a global image of the movie. This global image is the input into a spot identification algorithm which produces a set of spots identified by a unique spot identification, its x and y location and its corresponding channel. Each set of spots for a given channel is then registered to the set of spots in every other channel. In this way a set of spot tuples is constructed. If a detected spot in one channel does not have a corresponding detected spot in another channel, then the position of the undetected spot using the transformation between the two channels and the location of the detected spot is inferred. Once a complete set of spot tuples is constructed the movie is iterated over and at each frame the amplitude of each spot is calculated and appended to the appropriate time-series.

The collection of time-series from a spot tuple consists of time-series from donor and corresponding acceptor channels. This collection is called a Vector Time-Series (VTS). The FRET detection process starts with a data segmentation step using a Markov Chain Monte-Carlo (MCMC) algorithm. Each segment of VTS is modeled by a multivariate Gaussian model, with each of the channel modeled by a mean and a standard deviation. This model establishes a baseline for each channel, from which quantities such as "Donor Down" and "Acceptor Up" can be calculated. A Hidden Markov Model (HMM) was used to model the observed data. The underlying states consist of a null state, a blink state and a number of FRET states (one for each acceptor channel). Each state has its emission probability, which reflects the state's corresponding physical concept. FRET states are characterized by significant "donor down" and "acceptor up" signals. Blink state is characterized by significant "donor down" with no "acceptor up". Null state is characterized by no "donor down" and no "acceptor up". Given the observed VTS signal, the emission matrix, and a state transition probability matrix, the most probable state path can be computed using the Viterbi algorithm. This state path assigns each of the frames to a state. Temporally neighboring FRET frames are grouped into FRET events. For each of the detected FRET events, a list of event features are calculated, including event duration, signal average, signal to noise ratio, FRET efficiency, probability of event, color calling and other features. This list of events and corresponding features are stored in a file.

The final stage of the automated analysis generates a report summarizing the results in the form of a web page containing summary image, statistics of the spots and FRET detection, together with line intensity plots and base call plots. See for example, Watkins et al., "Detection of Intensity Change Points in Time-Resolved Single-Molecule Measurements" J. Phys. Chem. B., 109(1):617-628 (2005).

Using the above process, the movie data obtained from the sequencing reactions was analyzed to detect and identify FRET events according to the process described above. The FRET events were then processed to identify sequences as described below.

Sequence Analysis

Beginning with the set of detected Forster resonance energy transfer (FRET) events, a data overview was constructed in the form of a color image interpreted as a sequencing plot. To generate the plot, the original FRET event data was pre-processed using a set of filters constructed by a priori knowledge of the sequence. For each reaction site (each molecule) an ordered sequence of FRET events was constructed. The base call letters for each FRET event (e.g. "A", "C", "G" or "T") were concatenated to form a sequence ASCII string. The order of letters in the string reflects the temporal relationship of the events. Given that the expected sequence was known a priori, a regular expression was then constructed which represented the full or partial expected sequence or sequence pattern. Matching against the regular expression (expected sequence) was then computed for each sequence in the set and the start and stop indices of the match were recorded. A color plot image was then constructed where each row corresponds to a sequence in the set. The plot image was padded to accommodate sequences of different lengths. A color map of 2*N+1 colors was constructed, where N denotes the number of possible base calls in each sequence (N=2 for the plot of this Example). N colors were assigned to the base characters which fell within the pattern, N colors were assigned to the base characters which did not fall within the pattern (muted color), and finally a color was assigned to the padding (background) of the image. The rows of the image were then sorted according to the number of base calls in the first part of the sequence pattern. The rows of the image were also aligned such that the start of the expected sequence is in the same column for all rows of the plot.

Example 14

Nucleotide Incorporation with B103 Polymerase-Nanoparticle Conjugates:

Template oligonucleotide:
(SEQ ID NO: 41)
5' TTTTGA TT CCCCC TT CCCCC G ACA CGG AGG TTC TAT CAT CGT CAT CGT CAT CGT CAT CG-Biotin TEG-T-3'

Primer oligonucleotide:
(SEQ ID NO: 42)
5'-CGATGACGATGACGATGACGATGATAGAACCTCCGTGTC-3'

The expected sequence is: GGGGGAAGGGGGAA (SEQ ID NO:55)

A template/primer duplex was formed by mixing 1 µL template (100 µM) and 0.5 µL of primer (250 µM) in 48.5 µL of buffer composed of 50 mM Tris pH 7.5, 50 mM NaCl and 10 mM $MgCl_2$. The mixture was incubated at 98° C. for 2 minutes. The mixture was incubated for 30 minutes at room temperature.

Polymerase/Nanoparticle stocks: C8 nanoparticles-UDG-ugi-HP1-Phi29 mutant A, 0.17 µM stock concentration. C8 nanoparticles-44-UDG-UGi-Phi 29 mutant B; 0.38 µM stock concentration. C8 nanoparticles-38-L-B103-UDG-Ugi (SEQ ID NO:4); 0.38 µM stock concentration.

Functionalized nanoparticles were diluted to 2 nM in 100 µL of buffer composed of 50 mM MOPS pH 6.8, 200 mM NaCl, and 0.3% BSA.

The chip was prepared as follows: dd H2O (1 mL/lane). Wash buffer wash (0.2 mL/lane). Inject lane w/5 nM SA and incubate for ~10 minutes. Wash buffer wash (0.4 mL/lane). Inject 200 µM 355/366 duplex for and incubate for ~5 minutes. Wash buffer wash (0.4 mL/lane). Polymerase binding buffer wash (0.2 mL/lane). Mount on scope. Inject 2-5 nM of conjugate and incubate until desired density is reached (<700 spots/FOV). Polymerase binding buffer wash (0.2 mL/lane). Inject 1× extension mix (w/o nucleotides) ~3 min (0.1 mL/lane). Inject 1× extension mix with nucleotides (0.1 mL/lane).

The template/primer duplex (200 µM) was immobilized on biotin-embedded, PEG-coated glass slides purchased from Microsurfaces, Inc. (Bio-01 PEG, Austin, Tex.) using 5 nM streptavidin. The functionalized nanoparticle (2 nM) were conjugated to the surface immobilized duplexes. The conjugates were washed with 100 µL of buffer composed of 50 mM MOPS pH 6.8, 50 mM potassium-OAc, 2 mM $MnCl_2$, 0.3% BSA, 100 U/mL glucose oxidase, 10 U/µL Katalase, 10 mM Trolox (dissolved in 24 mM MOPS pH 6.8), 0.1% Tween-20, 2 mM $(Asp)_4$ (SEQ ID NO: 67), and 0.5% glucose.

The extension reaction was initiated by injecting 100 µL of buffer composed of 50 mM MOPS pH 6.8, 50 mM potassium-OAc, 2 mM $MnCl_2$, 0.3% BSA, 100 U/mL glucose oxidase, 10 U/µL katalase, 10 mM Trolox, 0.1% Tween-20, 2 mM $(Asp)_4$ (SEQ ID NO: 67), 0.5% glucose, 0.2 µM AF647-terminal phosphate labeled dG6P, and 0.2 µM AF680-terminal phosphate labeled dA6P. Laser excitation: 405 nm, ~19 W/cm2, 16 ms.

As described in Example 13 above, the fluorescent signals emitted by the nucleotide incorporation reaction were captured in a movie, and the images were processed using the Hidden Markov Model (HMM).

Example 15

Nucleotide Incorporation with B103 Polymerase-Nanoparticle Conjugates:

Template 404 sequence:
(SEQ ID NO: 43)
5'-TGATTTTTTTTTTCCTCATCCGTTCAAGTGGTGTCTGG TCCTCATCCGTTCAAGACA CGG AGG TTC TAT CAT CGT CAT CGT CAT-biotin TEG-T-3'

Primer 317 sequence:
(SEQ ID NO: 44)
5' TGA TAG AAC CTC CGT GT 3'

Duplex Template/Primer Preparation:

The template oligonucleotide, at 100 nanomolar concentration, and the primer oligonucleotide, at 1 micromolar concentration, were heated to 98° C. in annealing buffer (50 mM Tris, pH 7.5, 50 mM NaCl) for 5 minutes and allowed to cool to room temperature.

Flow Chamber Preparation

PEG/PEG-biotin coated cover slips (MicroSurfaces, Inc., Minneapolis, Minn.) were assembled into 9-lane reaction chambers with laser-cut 3M adhesive and custom fabricated plastic superstructures with inlet/outlet ports for fluid addition. The surface was wetted by flowing 1 milliliter of Tris-buffered saline (50 mM Tris, pH 7.5, 150 mM NaCl) containing 0.1% Tween-20 and 0.5% bovine serum albumin (Sigma, Cat. # A8577) (TBST-B) into each chamber and incubating at room temperature for 5 minutes. The surface was coated with streptavidin by flowing 100 microliters of 5 nM streptavidin, (Zymed, Cat #43-4302) diluted in TBST-B, and incubating for 30 minutes at room temperature. The lanes were washed with 1 milliliter of TBST-B. The duplex template/primer was diluted to 5 μM in TBST-B and 100 microliters was flowed into the reaction chamber and incubated 30 minutes at room temperature. The lanes were washed with 1 milliliter of TBSB.

Nucleotide Incorporation Reaction

Polymerase-nanoparticle conjugates are bound to the templates in the flow chamber for one minute in binding buffer (50 mM MOPS, pH 7.0, 2 mM 4-Aspartate (SEQ ID NO: 67), 50 mM Potassium Acetate, 0.3% BSA, 2 mM $MnCl_2$, 0.1% tween-20, 0.5 mg/ml glucose Oxidase, 10 U/ul Katalase, 10 mM Trolox (in ethanol), 0.5% glucose) at a concentration of 10 nM. The polymerase was exo-minus Phi29 (SEQ ID NO:9). Excess unbound conjugate is washed off with 200 microliters of TBST-B. Image acquisition is initiated and 100 microliters of extension buffer (binding buffer with 200 nanomolar each 680-dG6P and 647-dA6P and 1 micromolar each dTTP and dCTP) was flowed through the chamber. Images are acquired for 90 seconds and exposure time was 16 ms. 405 nanometer laser power density was 20 $W/cm^2$.

As described in Example 13 above, the fluorescent signals emitted by the nucleotide incorporation reaction were captured in a movie, and the images were processed using the Hidden Markov Model (HMM).

Example 16

Nucleotide Incorporation with B103-Fluorescent Dye Conjugates

Preparing NHS-Ester Surfaces:

Glass coverslips surfaces were plasma cleaned and treated with a mixture of poly-ethyleneglycol (PEG) and NHS-ester to produce a low density NHS-ester surface with a PEG coating to prevent non-specific background of proteins and macromolecules.

Fluidic Chamber Assembly:

Fluidic cassettes were assembled with glass coverslips to create fluidic chambers capable of carrying approximately 2 μl of fluid.

Attaching Amine Terminated Hairpin DNA to Low Density NHS-Ester Surfaces:

```
Target DNA hairpin sequence:
          (SEQ ID NOS 45 and 65, respectively)
5'-TTTTTTTT ACCCCCGGGTGACAGGTTXTTCCTGTCACCC-3'
``` where "X" is an amine group.

The target DNA was diluted to 500 nM in 1 M $NaHCO_3$. The diluted target molecules were flowed into the fluidic chamber and incubated for 1 hour. Chambers were washed 1× with 1 ml deactivating buffer (ethanolamine) Surfaces were washed 1× with 1 ml incubation buffer (50 mM Tris-Cl, pH=7.5; 50 mM NaCl; 0.3% BSA).

SA-Polymerase Conjugate Preparation:

Streptavidin was labeled with Cy3. Streptavidin-Cy3 was mixed with biotinylated-B103 (b-B103-exo minus)(SEQ ID NO:5) at a 1:1 ratio of SA-protein:biotinylated-B103 in 1×PBS.

SA-Cy3-b-B103 Binding to Templates:

The SA-Cy3-b-B103 conjugates were diluted to 1 nM in binding buffer (50 mM Tris-Cl; pH=7.5; 0.3% BSA; 100 mM NaCl). The conjugates were flowed into the fluidic chamber which were previously loaded with DNA templates on the surface. Surfaces were incubated for 5 minutes with 1 nM SA-Cy3-b-B103. Surfaces were washed with 1×1 ml incubation buffer.

Fluorescence Imaging:

The microscope body was purchased from Olympus and was outfitted with a TIRF objective lens (100×; 1.45 NA). The excitation light passes through an excitation filter (EX FT—543/22), and dichroic mirror (DM—532) and the sample was epi-illuminated (Coherent) using TIR at typically 100 $W/cm^2$. Upon excitation, the resulting epifluorescence emission passed through an emission filter (EM FT—540LP) and the resulting emission was split into three paths (tri-view) using 2 dichroic mirrors and the appropriate bandpass filters for the dye sets of choice. Using this filter combination, we were able to spectrally resolve 1 donor dye and 3 acceptor dyes in 3 detection channels.

In separate experiments, 1 donor dye and 4 different acceptor dyes could be resolved in 4 detection channels. The optical detection scheme was as follows: DC1=635, F1 640LP; DC2=675, F2=688/31; DC3=705, F3=700 LP. The donor dye used in this case was CY3 and the 4 acceptor dyes are as follows DY634, AF647, AF676, AF700

The emissions resulting in each experiment were imaged on a CCD camera. Images were collected at a frame rate of approximately 20 ms.

Three-Color Nucleotide Incorporation Reaction:

Hexa-phosphate dye-labeled nucleotides were diluted to 200 nM in extension buffer (50 mM MOPS pH=7.1; 75 mM potassium acetate (pH=7.0); 0.3% BSA; 1 mM $MnCl_2$; 300 nM procatuate dioxygenase; 4 mM 3,4 dihydroxyl benzoic acid; 1 mM 2-nitrobenzoic acid; 400 μM 1,2 phenylenediamine; 100 μM ferrocene monocarboxylic acid; 0.02% cyclooctratetraene; 6 mM TROLOX). Nucleotide mix was flowed into channel with SA-Cy3-b-B103 bound to DNA template and images are recorded for approximately 2 minutes at approximately 20 ms frame rates. In this example, the synthesized strand is expected to have the following sequence: $(G)_5T(A)_8$ (SEQ ID NO: 66). Terminal phosphate-labeled nucleotides and 125 nM cold dC6P were used for the nucleotide incorporation reaction. The labeled nucleotides included 125 nM 647-dT6P, 125 nM 676-dG6P, 125 nM 700-dA6P. The spectral signatures for the ALEXA FLUOR-676 G signal, AF-647 T signal, and AF-700 A signal were identified that resulted from fluorescence resonance energy transfer (FRET) from the Cy3 donor molecule, and corresponded to the correct insertion sequence pattern.

Analysis of Three-Color Sequencing Results

Resulting pattern sequencing data was processed using an alignment algorithm. The alignment algorithm found 100 molecules in the field of view, which demonstrated completion of the full 14-nucleotide sequence $((G)_5T(A)_8$ (SEQ ID NO: 66), which represented approximately 20% of the total single molecule donor population. The consensus sequence was determined using an HMM alignment algorithm (e.g., see Example 14). By plotting the accuracy definition (measured as a percentage value) against the HMM score (X axis), a linear relationship was detected. Various measurements of accuracy can be devised that can be suitable for such analysis. In one exemplary experiment, the accuracy was estimated according to the following equation:

$$\alpha(T, A) = \frac{\beta - \delta - \eta + \lambda}{2\lambda}$$

The measurement of accuracy in the above equation is intended to provide some measure of similarity between some given template, T, and some alignment, A, of an observed sequence O. It should be noted that alphabet of T, A, and O are identical. The length of T is denoted by $\lambda$, the number of deletions in the alignment A by $\delta$, the number of insertions in the alignment by $\eta$, and the number of matches in the alignment by $\beta$. Equation (1) is normalized by $\lambda$ such that a an accuracy of 1 indicates a total agreement, and an accuracy of 0 indicates no agreement between T and A. The above definition of accuracy is provided as an example only and is in no way intended to limit the disclosure to any particular theory or definition of accuracy; alternative definitions of accuracy are also possible and it may be suitable to use such alternative definitions in some contexts.

The accuracy in this system using an HMM alignment threshold of 0 was estimated to be approximately 80%.

Four-Color Nucleotide Incorporation Reaction:

```
Template molecule:
                                       (SEQ ID NO: 46)
TTTTTCCCCGACGATGCCTCCCC g ACA Cgg Agg TTC TAT CAT CgT CAT CgT CAT CgT CAT Cg-Biotin TEG-T-3

Primer for the template:
                                       (SEQ ID NO: 47)
5' TGA TAG AAC CTC CGT GTC 3'
```

In this example, the synthesized strand is expected to have the following sequence: GGGGAG-GCATCGTCGGGAAAA (SEQ ID NO:48)

Nucleotide Incorporation Reaction:

Hexa-phosphate dye-labeled nucleotides were diluted to 200 nM in extension buffer (50 mM MOPS pH=7.1; 75 mM potassium acetate (pH=7.0); 0.3% BSA; 1 mM MnCl$_2$; 300 nM procatuate dioxygenase; 4 mM 3,4 dihydroxyl benzoic acid; 1 mM 2-nitrobenzoic acid; 400 µM 1,2 phenylenediamine; 100 µM ferrocene monocarboxylic acid; 0.02% cyclooctratetraene; 6 mM TROLOX). Nucleotide mix was flowed into channel with SA-Cy3-b-B103 bound to DNA template and images are recorded for approximately 2 minutes at approximately 20 ms frame rates.

The terminal phosphate-labeled nucleotides used for the nucleotide incorporation reaction included 125 nM DY634-dA6P, 125 nM AF647-dT6P, 125 nM AF676-dG6P, 125 nM AF700-dC6P. The spectral signatures for the DY-634 A signal, and the ALEXA FLUOR G, T and C signals (AF-676 G signal, AF-647 T signal, and AF-700 C signal) were identified that resulted from fluorescence resonance energy transfer (FRET) from the Cy3 donor molecule, and corresponded to the correct insertion sequence pattern. 4-color sequence alignment was obtained by visual inspection.

The observed FRET event durations for various SA-Cy3-b-B103 conjugates, the event count distributions, and the observed extension speeds of various SA-Cy3-b-B103 conjugates were calculated.

Example 17

Nucleotide Incorporation Reactions

```
Template oligonucleotide:
                                       (SEQ ID NO: 49)
5'-TTTTTCCCCGCGTAACTCTTTACCCC g ACA Cgg Agg TTC

TAT CA-3'

Primer oligonucleotide:
                                       (SEQ ID NO: 50)
5'-TGATAGAACCTCCGTGTC-3'
```

A duplex was formed by mixing 1 µL template (100 µM) and 4 µL of primer (50 µM) in 21 µL of buffer composed of 50 mM Tris pH 7.5, 50 mM NaCl and 10 mM MgCl$_2$. The mixture was incubated at 98° C. for 2 minutes. The mixture was incubated for 30 minutes at room temperature.

Dye-polymerase conjugate: Cy3(9.3)-SAV-biotin-(HBP1)-(B103H370R)-(exo) (SEQ ID NO:3), 0.60 µM stock concentration. The polymerase is HBP1-B103(exo−) conjugated to Cy3 via streptavidin/biotin.

The polymerase conjugate was diluted to 0.75 nM in 100 µL of buffer composed of 50 mM MOPS pH 7.03, 100 mM NaCl, and 0.3% BSA. The duplex (200 pM) was immobilized on biotin-embedded, PEG-coated glass slides purchased from Microsurfaces, Inc. (Bio-01 PEG, Austin, Tex.) using 0.3 nM streptavidin. The dye-polymerase conjugate (0.75 nM) was conjugated to the surface-immobilized duplexes. The conjugate was washed with 100 µL of buffer composed of 50 mM MOPS pH 7.1, 50 mM KOAc pH 6.85, 2 mM Trolox, 0.02% cyclo-octatetraene (COT), 200 U/mL glucose oxidase, 19.9 U/µL katalase and 0.4% glucose.

The extension reactions were initiated by injecting 100 µL of one of the following buffers composed of 50 mM MOPS pH 7.1, 50 mM KOAc pH 6.85, 2 mM Trolox, 0.02% cyclo-octatetraene (COT), 200 U/mL glucose oxidase, 19.9 U/µL katalase, 0.4% glucose, 0.5 mM MnCl$_2$ and one of the three following nucleotides combinations: (1) 120 nM 647G (AF647-terminal phosphate labeled dG6P), 150 nM 676A (AF676-terminal phosphate labeled dA6P), 3 µM dTTP; (2) 24 nM 647G (AF647-terminal phosphate labeled dG6P), 24 nM 676A (AF676-terminal phosphate labeled dA6P), 24 nM dTTP; and (3) 30 nM 647T (AF647-terminal phosphate labeled dT6P), 24 nM 676G (AF676-terminal phosphate labeled dG6P), 24 nM 700A (AF700-terminal phosphate labeled dA6P).

The HMM-based algorithm described in Example 14 was used to analyze the data.

Example 18

Nucleotide Incorporation Reactions

```
Target oligonucleotide:
                                       (SEQ ID NO: 49)
5'-TTTTTCCCCGCGTAACTCTTTACCCC g ACA Cgg Agg TTC

TAT CA-3'

Primer oligonucleotide:
                                       (SEQ ID NO: 50)
5'-TGATAGAACCTCCGTGTC-3'
```

A DNA duplex was formed by mixing 1 µL template (100 µM) and 4 µL of primer (50 µM) in 21 µL of buffer (50 mM Tris pH 7.5, 50 mM NaCl and 10 mM MgCl$_2$) and incubated at 98° C. for 2 minutes. And the mixture was incubated for 30 minutes at room temperature.

A dye-conjugated, exo minus, B103 mutant polymerase (B103-H370R) (SEQ ID NO:3) (60 µM stock concentration) was used. The polymerase-dye conjugate was diluted to 0.75 nM in 100 µL of buffer (50 mM MOPS pH 7.03, 100 mM NaCl, and 0.3% BSA).

The DNA duplex (200 pM) was immobilized on biotin-embedded, PEG-coated glass slides purchased from Microsurfaces, Inc. (Bio-01 PEG, Austin, Tex.) using 0.3 nM streptavidin. The polymerase-dye conjugate (0.75 nM) was reacted with the surface-immobilized DNA duplexes. The DNA duplex/polymerase complex was washed with 100 µL of buffer (50 mM ACES pH 7.1, 50 mM KOAc pH 6.85, 2 mM Trolox, 0.02% cyclo-octatetraene (COT), 200 U/mL glucose oxidase, 19.9 U/µL katalase and 0.4% glucose).

The extension reactions were initiated by injecting 100 µL of one of the following buffers composed of 50 mM MOPS pH 7.1, 50 mM KOAc pH 6.85, 2 mM Trolox, 0.02% cyclo-octatetraene (COT), 200 U/mL glucose oxidase, 19.9 U/µL katalase, 0.4% glucose, 0.5 mM $MnCl_2$ following nucleotides combinations: 30 nM 647T (AF647-terminal phosphate labeled dT6P), 24 nM 676G (AF676-terminal phosphate labeled dG6P), 24 nM 700A (AF700-terminal phosphate labeled dA6P).

The HMM-based algorithm described in Example 14 was used to analyze the data.

Example 19

Nucleotide Incorporation with Polymerase-Tripod Nanoparticle Conjugates
Preparing Tripod Nanoparticle-his-B103-H370R(Exo-) Polymerase Conjugates Tripod Nanocrystals (50 µL, 2.7 µM in 50 mM borate buffer pH 8.0) were mixed with stock His-tagged HP1-B103 H370R exo– polymerase (SEQ ID NO:3) (25 µL, 16 µM in 10 mM Tris (pH 7.5) buffer with 100 mM NaCl, 4 mM DTT, 0.5% v/v Tween-20, 0.1 mM EDTA and 50% v/v glycerol) and 40 µL of 100 mM Tris (pH 7.5) buffer with 300 mM NaCl and 1 mM DTT in a 1:3 molar ratio (nanocrystal to polymerase). The conjugation solution was incubated overnight at 4° C. The resulting conjugate solution was centrifuged for 5 minutes at 16.8K rcf, purified on $Ni^{2+}$-NTA Agarose column using 100 mM Tris (pH 7.5) buffer with 300 mM NaCl and 1 mM DTT as the eluent, centrifuged and transferred into a 10K MWCO dialysis cassette. The conjugate was dialyzed into 50 mM Tris buffer pH7.5 with 150 mM NaCl, 0.2 mM EDTA, 0.5% v/v Tween-20, 5 mM DTT and 50% v/v glycerol. The resulting Tripod-nanocrystal-HP1-B103 H370R exo– conjugate was assayed to determine concentration, template extension activity, active number of Phi29 per conjugate and DNA binding by FRET. In a DNA extension assay, the Tripod-nanoparticle-HP1-B103-H370R (exo–) conjugates exhibited 0.35 base/sec/conjugate, and the stock HP1-B104-H370R (exo–) polymerase exhibited 0.29 base/sec/enzyme.
Nucleotide Incorporation using the Conjugates To a 50 µL solution of 10 µM template DNA: Biotin-5'-TTTTTCCCCGCGTAACTCTTTACCCCgACACAggAggT-TCTATCA-3'-amine) (SEQ ID NO:49), was mixed in 50 µL of 50 µM primer DNA (5'-TGATAGAACCTCCGTGTC-3' (SEQ ID NO:50)). The mixture was heated at 98° C. for 1 minute and chilled on ice. The annealed template/primer was diluted to 200 µM using 500 mM borate buffer (pH 8.2), and injected into lanes of a microfluidic device with coverslip containing NHS ester reactive groups on the surface, incubated at room temperature for 10 minutes. The coverslip surface was deactivated by incubating with 50 mM glycine in 500 mM borate buffer (pH 8.2) for 10 minutes, washed with 50 mM Tris buffer (pH 7.5) with 50 mM NaCl, 0.5% BSA and 0.05% Tween-20.

The microfluidic device was secured on a TIRF (total internal reflection fluorescence) microscope. The TIRF microscope was setup on TIRF mode with power density at ~15 W/$cm^2$ for the 405 nm excitation laser. Nanoparticle-polymerase conjugate solution (10 nM in GO-Cat OSS buffer system, 50 mM MOPS buffer pH 7.2 with 50 mM KOAc, 0.1% Tween-20, 10 mM Trolox, 0.3% BSA, 0.5 mg/mL glucose oxidase, 10 unit/uL catalase, 2 mM tetra-aspartic acid (SEQ ID NO: 67) and 0.5% freshly added glucose) was injected into a lane of the microfluidic, incubated at room temperature for ~1 minute, then washed with the GO-Cat OSS buffer system (50 mM MOPS buffer pH 7.2 with 50 mM KOAc, 0.1% Tween-20, 10 mM Trolox, 0.3% BSA, 0.5 mg/mL glucose oxidase, 10 unit/uL catalase, 2 mM tetra-aspartic acid (SEQ ID NO: 67) and 0.5% freshly added glucose). The successive nucleotide incorporation was captured on a movie, which was recorded for 100 seconds at 30 ms per frame rate on a new FOV (field of view) when injecting into the lane of a primer extension reaction mixture (e.g. 150 nM dG6P-C6-AF647, 150 nM dA6P-C6-AF680, 1000 nM dTTP, 1000 nM dCTP and 0.5 mM $MnCl_2$ in GO-Cat OSS buffer system containing freshly added 0.5% glucose. The movie was analyzed to identify the incorporated nucleotides using time series extraction and base calling software.

Example 20

Reagent Exchange Reactions

Target molecule:
(SEQ ID NO: 51)
5'TTTTGA TTTTTTTTTTT CCCCCCCCCCC TTTTTTTTTTT

CCCCCCCCCCC g ACA Cgg Agg TTC TAT CAT CgT CAT

CgT CAT CgT CAT Cg -amine-3'

Primer molecule A for cycle 1:
(SEQ ID NO: 52)
5' TGA TAG AAC CTC CGT GTC 3'

Primer Molecule B for Cycle 2:
5' TGA TAG AAC CTC YGT GTC 3' (Y=amino modifier C6, C is base, labeled with AF647) (SEQ ID NO:53)
1×TBST/BSA Wash buffer: 50 mM Tris pH 7.5; 50 mM NaCl; 0.05% Tween-20; 0.5% BSA.
1× Polymerase binding buffer: 50 mM MOPS pH 6.8; 100 mM NaCl; 0.1% BSA.
Pre-Extension mix G.O./Cat OSS:
50 mM MOPS pH 7.2 w/KOH; 50 mM potassium acetate (KOAc) pH 7.0; 2 mM Trolox (dissolved 24 mM MOPS pH 6.8; stored at –20° C.); 0.2 cyclooctratetraene; 100 U/mL glucose oxidase; 10 U/µL Catalase; 0.4% glucose.
Extension Mix G.O./Cat OSS:
50 mM MOPS pH 7.2 w/KOH; 50 mM KOAc pH 7.0; 2 mM Trolox (dissolved 24 mM MOPS pH 6.8; stored at –20° C.); 0.2% cyclooctratetraene; 100 U/mL glucose oxidase; 10 U/µL Catalase; 0.4% glucose; 0.6 mM $MnCl_2$; 100 nM AF647-dG6P; 100 nM AF676-dA6P.
Covalent-DNA Immobilization and Chip Preparation:
Coverslips from MicroSurfaces, Inc. were prepared as follows. The lane was injected with 300 µM the target molecules primed with primer A, dissolved in 500 mM borate pH 8.2 and incubated for approximately 5 minutes. The reaction was terminated with 0.1 mL wash (500 mM Borate, pH 8.2). NHS deactivation was conducted using Deactivation buffer supplied by MicroSurfaces, Inc., by injecting 0.08 mL/lane and incubated for more than 5 minutes. The chip was washed with 1×TBST/BSA (1 mL/lane). The chip was mounted on the scope.

Cycle 1 Nucleotide Incorporation Reaction:

Polymerase binding buffer wash (0.3 mL/lane) was injected. 2-5 nM of the polymerase conjugate (Cy3-SA-Phi29 mutant) was injected and incubated until desired density was reached (~900 spots/FOV).

Polymerase binding buffer wash (0.2 mL/lane) was injected. Pre-extension mix (without nucleotides) ~3-5 min (0.1 mL/lane) was injected. 1× extension mix with nucleotides (0.1 mL/lane) was injected. For cycle 1, AF647-dG6P and AF676-dA6P terminal phosphate labeled nucleotides were used. Cycle 1 donors were mapped visually.

Removal of Polymerase and Synthesized Strand:

The polymerase used in cycle 1 was removed using 6.3 M guanidine isothiocyanate, 160 mM Tris pH 9.7, and 2.6 mM EGTA. The synthesized strand was removed using 25% Formamide, 50 mM NaOH.

Cycle 2 Exchanged Polymerase and Primer:

For cycle 2, 500 nM of fresh, AF647-labeled primer B was added in 1×TBST/BSA, and incubated for 5 minutes.

Polymerase binding buffer wash (0.3 mL/lane) was injected. Approximately 2-5 nM of the polymerase conjugate (Cy3-SA-Phi29 mutant) was injected.

Polymerase binding buffer wash (0.2 mL/lane) was injected. Pre-extension mix (without nucleotides) ~3-5 min (0.1 mL/lane) was injected. 1× extension mix with nucleotides (0.1 mL/lane) was injected. For cycle 2, AF676-dG6P and AF700-dA6P terminal phosphate labeled nucleotides were used. Cycle 2 donors were mapped visually (same field of view as for cycle 1). Time traces of the fluorescent acceptor signals for cycle 1 and 2 were obtained. The number of donors mapped in the same field of view for cycle 1 and 2 were analyzed.

Example 21

Reagent Exchange Reactions:

In a first cycle, nucleotide incorporation reactions were conducted on a target nucleic acid molecule with 3 types of nucleotides. The reagents were exchanged, and a second cycle of nucleotide incorporation reactions were conducted using 4 types of nucleotides. Accordingly, reagent exchange reactions were performed to continue nucleotide incorporation reactions on the same target nucleic acid molecules.

In this experiment, the nucleotide incorporation reaction proceeded towards the solid surface.

Target hairpin oligonucleotide:
(SEQ ID NOS 54 and 65, respectively)
5'TTTTTCCCCGACGATGCCTCCCCTTTTTTTTACCCCCGGGTGACAGGT

TXTTCCTGTCACCC-3', where X=amino modifier C6 dT; 5' biotin.
Polymerase conjugated to a Cy3 dye:
Cy3(9.3)-SAV-biotin(HBP1)(B104H370R)(exo⁻), 0.60 μM stock concentration.

The polymerase-dye conjugate was diluted to 0.75 nM in 100 μL of buffer (50 mM MOPS pH 7.03, 100 mM NaCl, and 0.3% BSA).

The hairpin oligonucleotide (300 μM) was surface-immobilized on biotin-embedded, PEG-coated glass slides purchased from Microsurfaces, Inc. (Bio-01 PEG, Austin, Tex.) using 0.5 nM streptavidin. The polymerase-dye conjugate (0.75 nM) was reacted with the surface-immobilized hairpin oligonucleotide (i.e., target nucleic acid molecule) to produce a polymerase/target complex. The complex was washed with 100 μL of a pre-extension buffer (50 mM ACES pH 7.1, 50 mM KOAc pH 6.85, 2 mM Trolox, 0.02% cyclo-octatetraene (COT), 200 U/mL glucose oxidase, 19.9 U/μL katalase and 0.4% glucose).

The first cycle was initiated by injecting 100 μL of extension buffer: 50 mM ACES pH 7.1, 50 mM KOAc pH 6.85, 2 mM Trolox, 0.02% cyclo-octatetraene (COT), 200 U/mL glucose oxidase, 19.9 U/μL katalase, 0.4% glucose, 0.5 mM MnCl₂ supplemented with the following nucleotides combinations: 25 nM 647T (AF647-terminal phosphate labeled dT6P), 50 nM 676G (AF676-terminal phosphate labeled dG6P), and 25 nM 700A (AF700-terminal phosphate labeled dA6P).

A reagent exchange reaction was performed to remove the polymerase, using 200 μL a solution (4.8 M guanidine isothiocyanate and 200 mM Tris pH 9.7). The immobilized hairpin oligonucleotide was washed with 200 μL wash buffer (50 mM Tris pH 7.5, 50 mM NaCl, and 0.3% BSA).

In the second cycle, a fresh supply of the polymerase-dye conjugate (Cy3(9.3)-SAV-biotin(HBP1)(B104H370R)(exo⁻)) was reacted with the immobilized hairpin oligonucleotide and washed with pre-extension buffer (50 mM ACES pH 7.1, 50 mM KOAc pH 6.85, 2 mM Trolox, 0.02% cyclo-octatetraene (COT), 200 U/mL glucose oxidase, 19.9 U/μL katalase and 0.4% glucose). The second extension was conducted using the extension buffer supplemented with the nucleotide combination: 25 nM 634A (Dy634-terminal phosphate labeled dA6P) 25 nM 647T (AF647-terminal phosphate labeled dT6P), 50 nM 676G (AF676-terminal phosphate labeled dG6P), and 25 nM 700C (AF700-terminal phosphate labeled dC6P).

The full length of the expected extendible sequence is:

(SEQ ID NO: 56)
GGGGGTAAAAAAAAGGGGAGGCATCGTCGGGGAAAAA

In the first cycle, the nucleotide incorporation reaction was expected to produce the underlined sequence shown above. In the second cycle, the nucleotide incorporation reaction was expected to produce the non-underlined sequence shown above. A time trace of fluorescent signals from cycle 1 and 2 reactions was obtained.

Example 22

Reagent Exchange Reactions:

Reagent exchange reactions were conducted using a polymerase labeled with a fluorescent donor dye, 4 types of nucleotides each labeled with a different fluorescent acceptor dye, and 2 types of non-hydrolyzable nucleotides (unlabeled).

Template oligonucleotide:
(SEQ ID NO: 49)
5'-TTTTTCCCCGCGTAACTCTTTACCCC g ACA Cgg Agg TTC

TAT CA-3'

-continued

```
Primer oligonucleotide:
                                          (SEQ ID NO: 47)
5'-TGATAGAACCTCCGTGTC-3'
```

A duplex was formed by mixing 1 µL template (100 µM) and 4 µL of primer (50 µM) in 21 µL of buffer (50 mM Tris pH 7.5, 50 mM NaCl and 10 mM MgCl$_2$). The mixture was incubated at 98° C. for 2 minutes. The mixture was then incubated for 30 minutes at room temperature.

Polymerase conjugated to a Cy3 dye: Cy3(9.3)-SAV-biotin(HBP1)(B104H370R)(exo$^-$), 0.60 µM stock concentration.

The polymerase-dye conjugate was diluted to 0.75 nM in 100 µL of buffer (50 mM MOPS pH 7.03, 100 mM NaCl, and 0.3% BSA).

The duplex (300 µM) was immobilized on biotin-embedded, PEG-coated glass slides purchased from Microsurfaces, Inc. (Bio-01 PEG, Austin, Tex.) using 0.5 nM streptavidin.

The nucleotide incorporation and reagent exchange reactions were repeated 5× on the same target DNA molecules according to the following protocol:

The polymerase-dye conjugate (0.75 nM) was reacted with the surface-immobilized DNA duplex (i.e., target nucleic acid molecule) to produce a polymerase/target complex. The complex was washed with 100 µL of a pre-extension buffer (50 mM ACES pH 7, 50 mM KOAc pH 6.85, 2 mM Trolox, 0.02% cyclo-octatetraene (COT), 200 U/mL glucose oxidase, 19.9 U/µL katalase and 0.4% glucose).

The extension reactions were initiated by injecting 100 µL of extension buffer (50 mM ACES pH 7, 50 mM KOAc pH 6.85, 2 mM Trolox, 0.02% cyclo-octatetraene (COT), 200 U/mL glucose oxidase, 19.9 U/µL katalase, 0.4% glucose, 0.5 mM MnCl$_2$, 25 nM 634C (Dy634-terminal phosphate labeled dC6P), 38 nM 647T (AF647-terminal phosphate labeled dT6P), 32 nM 676G (AF676-terminal phosphate labeled dG6P), 38 nM 700A (AF700-terminal phosphate labeled dA6P), 25 nM dApCpp (2'-Deoxy-adenosine-5'-[(α,β)-methyleno]triphosphate, sodium salt) (Jena Bioscience, Germany) and 25 nM dUpCpp (2'-Deoxy-uridine-5'-[(α,β)-methyleno]triphosphate, Sodium salt) (Jena Bioscience, Germany).

Upon completion of each extension cycle, the polymerase-dye conjugate was removed with a 200 µL solution (4.8 M guanidine isothiocyanate and 200 mM Tris pH 9.7). The immobilized target DNA (now having synthesized strands) was washed with 200 µL wash buffer (50 mM Tris pH 7.5, 50 mM NaCl, and 0.3% BSA). The target DNA and synthesized strands were separated using a solution (25% v/v formamide and 50 mM NaOH). The strand separation reaction was terminated by injecting 200 µL of wash buffer (50 mM Tris pH 7.5, 50 mM NaCl, and 0.3% BSA).

The immobilized target DNA molecules were re-hybridized with primers by injecting 100 µL of 500 nM the primer dissolved in wash buffer and incubated for 30 minutes. The re-hybridization was terminated by injecting 200 µL of wash buffer (50 mM Tris pH 7.5, 50 mM NaCl, and 0.3% BSA). A time trace of fluorescent signals from cycle 2 and 3 reactions were obtained.

Example 23

Nucleotide Incorporation of B103 Polymerase: Stopped Flow Analysis

1) B103 Polymerase: Stopped-Flow Measurements of $t_{pol}$

```
Template C sequence:
5'-CGTTAACCGCCCGCTCCTTTGCAAC-3'    (SEQ ID NO: 57)

Primer sequence:
5'-GTTGCAAAGGAGCGGGCG-3'           (SEQ ID NO: 58)
```

The kinetics of nucleotide incorporation by B103 (exo−) (SEQ ID NO:5) and an H370R mutant (SEQ ID NO:3) DNA polymerases were measured in an Applied Photophysics SX20 stopped-flow spectrometer by monitoring changes in fluorescence from a duplex Alexa fluor 546 dye-labeled-DNA template following the mixing of the enzyme-DNA complex with dye-labeled nucleotides (AF647-C6-dG6P) in the reaction buffer containing 50 mM Tris-HCl, pH 7.5, 50 mM NaCl, 4 mM DTT, 0.2% BSA, and 2 mM MnCl$_2$. The reactions included 330 nM recombinant DNA polymerase, 100 nM template/primer duplex, and 7 µM labeled nucleotides.

The averaged (5 traces) stopped-flow fluorescence traces (>1.5 ms) were fitted with a double exponential equation (1) to extrapolate the rates of the nucleotide binding and product release, $$\text{Fluorescence} = A_1 * e^{-k1*t} + A_2 * e^{-kpol*t} + C \qquad \text{(equation 1)}$$

where $A_1$ and $A_2$ represent corresponding fluorescence amplitudes, C is an offset constant, and k1 and kpol are the observed rate constants for the fast and slow phases of the fluorescence transition, respectively. The dye-labeled nucleotides comprise terminal-phosphate-labeled nucleotides having an alkyl linker with a functional amine group attached to the dye. The stopped-flow techniques for measuring $t_{pol}(1/k_{pol})$ followed the techniques described by M P Roettger (2008 Biochemistry 47:9718-9727; M. Bakhtina 2009 Biochemistry 48:3197-320).

2) B103 Polymerase: Stopped-Flow Measurements of $t_{-1}$

```
Template C sequence:
                                          (SEQ ID NO: 59)
5'-CAGTAACGG AGT TGG TTG GAC GGC TGC GAG GC-3'

Dideoxy-primer sequence:
                                          (SEQ ID NO: 60)
5'-GCC TCG CAG CCG TCC AAC CAA CTC ddC-3'
```

The rate of the nucleotide dissociation ($k_{-1}$) from the ternary complex of [enzyme.DNA.nucleotide] was measured in an Applied Photophysics SX20 stopped-flow spectrometer by monitoring changes in fluorescence from in fluorescence from a duplex Alexa fluor 546 dye-labeled-DNA template following the mixing of the [enzyme.DNA.labeled nucleotide] ternary complex with 50 µM cognate non-labeled deoxynucleoside triphosphate in a buffer containing 50 mM Tris-HCl (pH 7.5), 50 mM NaCl, 4 mM DTT, 0.2% BSA, and 2 mM MnCl$_2$.

The ternary complexes were prepared using: 330 nM polymerase, 100 nM template/primer duplex, and 7 µM terminal phosphate-labeled nucleotides (AF647-C6-dG6P).

The averaged stopped-flow fluorescence traces (>1.5 msec) were fitted with a single exponential equation (2) to extrapolate the rate of the nucleotide dissociation ($k_{-1}$) from the [enzyme.DNA.nucleotide] ternary complex.

$$\text{Fluorescence} = A_1 * e^{-k-1*t} + C \qquad \text{(equation 2)}$$

where $A_1$ represents the corresponding fluorescence amplitude, C is an offset constant, and $k_{-1}$ and the observed rate constants for the fluorescence transition. The stopped-flow techniques for measuring $t_{-1}$ ($1/k_{-1}$) followed the techniques described by M. Bakhtina (2009 Biochemistry 48:3197-3208). The results of the stopped-flow experiments are listed in the table below.

Summary of the $t_{pol}$ and $t_{-1}$ measurements

| Polymerase | $t_{pol}$ | $t_{-1}$ |
|---|---|---|
| B103 (exo-) | 14 | 16 |
| H370R | 17 | 43 |
| H370Y | 15 | 12 |
| E371R | 11 | 17 |
| E371Y | 11 | 7 |
| K372R | 14 | 12 |
| K380R | 783 | 17 |
| D507G | 11 | 13 |
| D507H | 7 | 16 |
| K509Y | 10 | 20 |
| Ph-29 (exo-) | 11 | 27 |
| T373R | 15 | 81 |
| T373Y | 14 | 45 |

What is claimed:

1. A composition, comprising: (i) a modified polymerase linked to an energy transfer donor moiety, (ii) a nucleic acid template molecule, (iii) a nucleic acid primer molecule, and (iv) at least one type of nucleotide having an energy transfer acceptor moiety, wherein the modified polymerase comprises the amino acid sequence of SEQ ID NO: 2.

2. The composition of claim 1, wherein the nucleic acid template molecule or the nucleic acid primer molecule is immobilized to a surface.

3. The composition of claim 1, wherein the energy transfer donor moiety is a nanoparticle or a fluorescent dye.

4. The composition of claim 3, wherein the nanoparticle is an inorganic fluorescent nanoparticle.

5. The composition of claim 3, wherein the nanoparticle is 1-20 nm in its largest dimension.

6. The composition of claim 3, wherein the nanoparticle is a non-blinking nanoparticle.

7. The composition of claim 1, wherein the at least one type of nucleotide comprises 3-10 phosphate groups.

8. The composition of claim 7, wherein a terminal phosphate group of the at least one type of nucleotide is linked to the acceptor moiety.

9. The composition of claim 1, wherein the at least one type of nucleotide is selected from a group consisting of adenosine, guanosine, cytosine, thymidine and uridine.

10. The composition of claim 9, wherein each of the at least one type of nucleotide is linked to a different type of energy transfer acceptor moiety.

11. The composition of claim 1, wherein the energy transfer acceptor moiety is a fluorescent dye.

12. The composition of claim 1, wherein the nucleic acid molecule is DNA or RNA.

* * * * *